US012729386B2

(12) United States Patent
Alkan et al.

(10) Patent No.: US 12,729,386 B2
(45) **Date of Patent: *Sep. 8, 2026**

(54) COMPOSITIONS AND PRODUCTION OF NICKED CLOSED-ENDED DNA VECTORS

(71) Applicant: Generation Bio Co., Cambridge, MA (US)

(72) Inventors: Ozan Alkan, Cambridge, MA (US); Robert Michael Kotin, Cambridge, MA (US); Douglas Anthony Kerr, Cambridge, MA (US); Russell Monds, Cambridge, MA (US); Carolyn Pelletier, Cambridge, MA (US); Matthew Stanton, Cambridge, MA (US)

(73) Assignee: Generation Bio Co., Cambridge, MA (US)

( * ) Notice: Subject to any disclaimer, the term of this patent is extended or adjusted under 35 U.S.C. 154(b) by 890 days.

This patent is subject to a terminal disclaimer.

(21) Appl. No.: 17/617,330

(22) PCT Filed: Jul. 17, 2020

(86) PCT No.: PCT/US2020/042445

§ 371 (c)(1),
(2) Date: Dec. 8, 2021

(87) PCT Pub. No.: WO2021/011840

PCT Pub. Date: Dec. 21, 2021

(65) Prior Publication Data

US 2022/0228171 A1 Jul. 21, 2022

Related U.S. Application Data

(60) Provisional application No. 62/875,262, filed on Jul. 17, 2019.

(51) Int. Cl.
*C12N 15/86* (2006.01)

(52) U.S. Cl.
CPC .... *C12N 15/86* (2013.01); *C12N 2750/14143* (2013.01); *C12N 2800/107* (2013.01); *C12N 2830/001* (2013.01); *C12N 2830/60* (2013.01)

(58) Field of Classification Search
CPC .......... C12N 15/86; C12N 2750/14143; C12N 2800/107; C12N 2830/001; C12N 2830/60
See application file for complete search history.

(56) References Cited

U.S. PATENT DOCUMENTS

| | | | | |
|---|---|---|---|---|
| 2003/0148506 A1 | 8/2003 | Kotin et al. | | |
| 2005/0158834 A1 | 7/2005 | Xu et al. | | |
| 2010/0105110 A1* | 4/2010 | Danthinne | C12N 7/00 | 435/235.1 |
| 2020/0283794 A1 | 9/2020 | Kotin et al. | | |
| 2021/0071197 A1 | 3/2021 | Alkan et al. | | |
| 2022/0220488 A1 | 7/2022 | Alkan et al. | | |

FOREIGN PATENT DOCUMENTS

| | | | |
|---|---|---|---|
| WO | 2012/123430 A1 | 9/2012 | |
| WO | 2017/072330 A2 | 5/2017 | |
| WO | 2017/152149 A1 | 9/2017 | |
| WO | 2018/094110 A2 | 5/2018 | |
| WO | WO-2019051255 A1 * | 3/2019 | C12N 15/66 |
| WO | 2020/097417 A1 | 5/2020 | |
| WO | 2021/011842 A1 | 1/2021 | |

OTHER PUBLICATIONS

U.S. Appl. No. 16/962,005, filed Jul. 14, 2020, 2021-0071197, Published.
U.S. Appl. No. 17/617,332, filed Dec. 8, 2021, 2022-0220488, Published.
New England Biolabs, Common Applications for Exonucleases and Endonucleases. Retrieved online at: https://www.neb.com/en-us/tools-and-resources/selection-charts/common-applications-for-exonucleases-and-endonucleases. 2 pages, retrieved Apr. 8, 2025.
New England Biolabs, Exonuclease V (RecBCD). Retrieved online at: https://www.neb.com/en-us/products/m0345-exonuclease-v-recbcd. 2 pages, retrieved Apr. 8, 2025.
New England Biolabs, T7 Exonuclease. Retrieved online at: https://www.neb.com/en-us/products/m0263-t7-exonuclease. 1 page, retrieved Apr. 8, 2025.
GenBank Accession No. MK801287.1, Cloning vector RS540-AAV-ErbB-RASER1C-OFPBidBH3, complete sequence. 10 pages, May 18, 2019.
International Search Report and Written Opinion for Application No. PCT/US2020/042445, dated Dec. 22, 2020, 15 pages.
International Preliminary Report on Patentability for Application No. PCT/US2020/042445, dated Jan. 27, 2022, 10 pages.
Brister et al., Mechanism of Rep-mediated adeno-associated virus origin nicking. J Virol. Sep. 2000;74(17):7762-71.
Li et al., Production and characterization of novel recombinant adeno-associated virus replicative-form genomes: a eukaryotic source of DNA for gene transfer. PLoS One. Aug. 1, 2013;8(8):e69879, 14 pages.

(Continued)

*Primary Examiner* — Tiffany Nicole Grooms
(74) *Attorney, Agent, or Firm* — McCarter & English, LLP; Marcie B. Clarke

(57) ABSTRACT

The present application discloses methods for synthetic production and cell-free synthesis of DNA vectors, particularly closed-ended linear DNA vectors having one or more gaps (e.g., nicked ceDNA vectors, "neDNA") and adenoassociated-virus (AAV) vector which is single strand DNA having linear and continuous structure, for delivery and expression of a transgene in the host cell. The present invention also relates to an in vitro process for production of closed-ended DNA vectors, corresponding DNA vector products produced by the methods and uses thereof, and oligonucleotides and kits useful in the process of the present invention.

28 Claims, 25 Drawing Sheets

Specification includes a Sequence Listing.

(56) References Cited

OTHER PUBLICATIONS

Smith, The use of exonuclease III for preparing single stranded DNA for use as a template in the chain terminator sequencing method. Nucleic Acids Res. Mar. 1979;6(3):831-48.
International Preliminary Report on Patentability for Application No. PCT/US2020/042449, dated Jan. 27, 2022, 12 pages.
International Search Report and Written Opinion for Application No. PCT/US2020/042449, dated Feb. 12, 2021, 26 pages.
Karu et al., The recBC Deoxyribonuclease of *Escherichia col* K-12. The Journal of Biological Chemistry. Jul. 25, 1973;248(14):4874-4884.
Prell et al., Degradation of Linear and Circular DNA with Gaps by the recBC Enzyme of *Escherichia coli*: Effects of Gap Length and the Presence of Cell-Free Extracts. European Journal of Biochemistry. Mar. 1, 1980;105(1):109-116.

* cited by examiner

Left-wt-ITR for synthesis with wt-AAV2-spacer with gap

RBE partial B B' C C' RBE' TRS'

#1 99bp 5'-phosho-GCTCGCTCACTGAGGCCGCCCGGGCAAAGCCCGGGCGTCGGGCGACCTTTGGTCGCCCGGCCTCAGTGAGCGAGCGAGCGCGCAGAGAGGGAGTGGCCA

#5 45bp 5'-de-phos- GGGGTTCCTGGAGGGGTGGAGTCGTGACGTGAATTACGTCATAGA wtAAV2

#4 85bp 5'-phosho- GGCCTCTATGACGTAATTCACGTCACGACTCCACCCCTCCAGGAACCCCTAGTGATGGAGTTGGCCACTCCCTCTCTGCGCGCTC wtAAV2

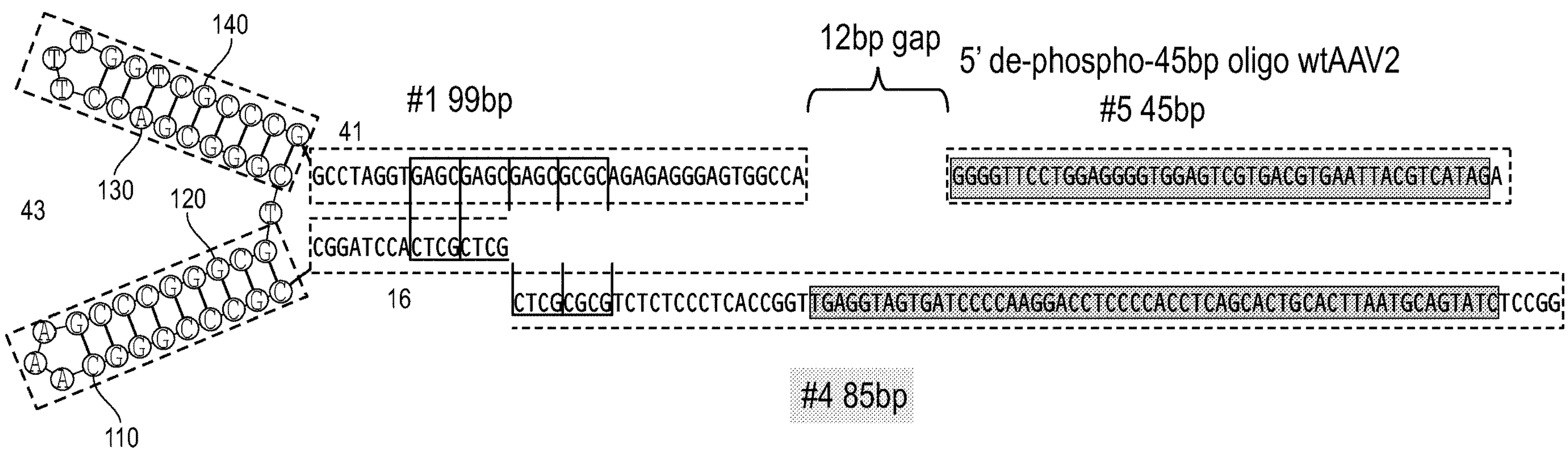

FIG. 8

1) 1kb+ ladder (without NaOH denature step)
2) ssRNA ladder (without NaOH denature step)
3) Synthetic ceDNA, post cut after ligation, no exo, without NaOH
4) Synthetic ceDNA, post cut after ligation, no exo, with NaOH and magnetic bead purification, post wash
5) Synthetic ceDNA, post cut after ligation, no exo, with NaOH and magnetic bead purificaiton, eluate

COMPOSITIONS AND PRODUCTION OF NICKED CLOSED-ENDED DNA VECTORS

RELATED APPLICATIONS

This application is a 35 U.S.C. § 371 national stage filing of International Application No. PCT/US2020/042445, filed on Jul. 17, 2020, which claims priority to U.S. Provisional Application No. 62/875,262, filed on Jul. 17, 2019. The entire contents of each of the aforementioned applications are hereby incorporated by reference in their entireties.

SEQUENCE LISTING

The instant application contains a Sequence Listing which is hereby incorporated by reference in its entirety. Said ASCII copy, created on Jul. 15, 2020, is named 131698-07220_SL.txt and is 29,814 bytes in size.

TECHNICAL FIELD

The present invention relates to the field of gene therapy, including production of viral and non-viral vectors, for the purpose of expressing a therapeutic transgene in a target organism. For example, the present disclosure provides cell-free methods of artificially synthesizing viral and non-viral DNA vectors such as a single stranded AAV or a double stranded closed-ended DNA having one or more gaps.

BACKGROUND

Gene therapy aims to improve clinical outcomes for patients suffering from either genetic disorders or acquired diseases caused by an aberrant gene expression profile. Gene therapy includes treatment or prevention of medical conditions resulting from defective genes or abnormal/aberrant regulation or expression, e.g., under- or over-expression, that can result in a disorder, disease, or malignancy. For example, a disease or disorder caused by a defective gene might be treated by delivery of a corrective genetic material to a patient. The premise of gene therapy is to supply a transcription cassette ("expression cassette") with an active gene product (sometime referred to as a transgene) that can resulting in a gain-of-function effect or a negative loss-of-function effect. Human monogenic disorders can be treated by the delivery and expression of a normal (corrective) gene to the target cells. Delivery and expression of a corrective gene in the patient's target cells can be carried out via numerous methods, including the use of engineered viruses and viral gene delivery vectors. Among the many virus-derived vectors available (e.g., recombinant retrovirus, recombinant lentivirus, recombinant adenovirus, and the like), recombinant adeno-associated virus (rAAV) is gaining acceptance as a versatile as well as relatively safe and reliable vector in gene therapy.

Adeno-associated viruses (AAV) belong to the Parvoviridae family and more specifically constitute the dependoparvovirus genus. Molecular sequences and structural features encoded in the AAV viral genome/vector have evolved to promote episomal stability, viral gene expression and to interact with the host's immune system. AAV vectors contain hairpin DNA structures conserved throughout the AAV family which play critical roles in essential functions of AAV, and provide AAV vectors the ability to tap into the host's genome and replicate themselves while escaping the surveillance system of the host's genome. The linear single-stranded (ss) DNA genome of AAVs form the hairpin structures at its ends through base-pairing of inverted terminal repeats (ITRs), undergoing recombination, often resulting in DNA circles and concatemers after infections.

Vectors derived from AAV (i.e., recombinant AAV (rAVV) or AAV vectors) are attractive for delivering genetic material because (i) they are able to infect ("transduce") a wide variety of dividing as well as non-dividing cell types such as myocytes and neurons; (ii) they are devoid of the virus structural genes, thereby diminishing the host cell responses to virus infection, e.g., interferon-mediated responses; (iii) wild-type AAVs are considered non-pathologic in humans; (iv) in contrast to wild type AAVs, which are capable of integrating into the host cell genome, replication-deficient AAV vectors lack the rep gene and generally persist as an episome, thus greatly limiting the risk of insertional mutagenesis or genotoxicity; and (v) in comparison to other vector systems, AAV vectors are generally considered to be relatively poor immunogens and therefore do not trigger a significant immune response, thus gaining persistence of the vector DNA and potentially, long-term expression of the therapeutic transgenes contained in the vector.

However, there are several major drawbacks and deficiencies in using AAV particles as a gene delivery vector that stem from conventional AAV production from host cells (e.g., Sf9 insect cells in a high scale production setting). One major drawback associated with rAAV is its limited viral packaging capacity of about 4.5 kb of heterologous DNA (Dong et al., 1996; Athanasopoulos et al., 2004; Lai et al., 2010). As a result, the use of AAV vectors has been limited to less than 150 kDa protein coding capacity due to this limitation in viral packaging. A second drawback is related to the capsid immunogenicity that prevents re-administration to patients. The immune system in the patients can respond to the vector which effectively acts as a booster to stimulate the immune system generating high titer anti-AAV antibodies that preclude future treatments. Some recent reports indicate concerns with immunogenicity in high dose situations. Another notable drawback is that the onset of AAV-mediated gene expression is relatively slow, given that single-stranded AAV DNA must be converted to double-stranded DNA prior to heterologous gene expression. More importantly, production of AAV in host cells (e.g., insect cells) in a high scale for the manufacture of the viral genome result in a random mixture of plus (+) and minus (−) stranded vectors. This drastically decreases the strand specificity of a transgene for the much-needed therapeutic expression of the sense strand.

Additionally, conventional AAV virions with capsids are produced by introducing a plasmid or plasmids containing the AAV genome, rep genes, and cap genes (Grimm et al., 1998). However, such encapsidated AAV virus vectors were found to inefficiently transduce certain cell and tissue types and the capsids were also found to induce a severe immune response in hosts. Accordingly, use of adeno-associated virus (AAV) vectors for gene therapy is limited to single administration to patients due to the patient immune response, the limited range of transgene genetic material suitable for delivery in AAV vectors due to minimal viral packaging capacity (about 4.5 kb), and slow AAV-mediated gene expression. Further, the methods of producing such ceDNA vectors have relied greatly upon traditional insect cell dependent production methods. Such methods can be stymied by contaminants from the cells used to produce the vectors which are inconvenient or costly to remove or purify away, and which may pose undesirable side effects if included in a therapeutic formulation.

Accordingly, there is a strong need in the field for a technology that allows for the generation of recombinant viral or non-viral vectors in large quantity and that increases expression level, specificity of AAV strand, and purity while increasing the capacity of a transgene size.

SUMMARY

The invention described herein is drawn to compositions of isolated linear closed-ended duplex nucleic acid having one or more gaps that are nonviral capsid free DNA vectors and to processes and methods of making the vector in a cell free environment. According to some embodiments, the nonviral capsid free vectors disclosed herein are produced synthetically. According to some embodiments, the nonviral capsid free vectors disclosed herein are useful for gene therapy. According to some embodiments, a nick or gap can be introduced near traditional terminal resolution sites (e.g., upstream and/or downstream of an expression cassette) using a set of oligonucleotides as described herein. It is a surprising finding of the present disclosure that the closed-end double stranded DNA having one or more gaps (neDNA) demonstrated expression levels that were equivalent or superior to an AAV vector or a ceDNA vector produced from Sf9 cells that were nucleofected into mammalian host cells and allowed to express a transgene. The results suggest great potential of neDNA as a gene therapy modality.

There are several advantages in producing viral or non-viral vector (e.g., neDNA) synthetically. First, cell-free methods of the present invention minimize contaminants from the cells used to produce the vectors and hence, result in more efficient processing at a high scale, minimizing undesirable side effects related to cellular contaminants. cell-free methods of producing neDNA vectors described in the present disclosure also allow for much greater control over the structure and form of the AAV genome to be synthesized. For instance, in the normal process of AAV replication in a cellular environment, both plus (+) and minus (−) strands of the AAV are made and individually packed into capsids. This product is an uncontrolled heterogeneous mixture of viral particles containing all categories of associated AAV genomes (plus (+) and minus (−) strands monomeric vectors, dimeric vectors and concatemeric vectors). In an application such as gene therapy in which a transgene is carefully designed and constructed for safety and maximum expression in host cells, however, synthesis of one specific strand over the other (e.g., the sense strand over the anti-sense strand) is highly desired as the expression of a sense strand is only therapeutically relevant. Cell-free synthesis methods described herein provide routes to specifically produce one type of AAV genome or vector, either the plus (+) or the minus (−) strand from nicked or gapped closed-ended DNA disclosed herein. Surprisingly, it was discovered that a nicked or gapped closed-ended DNA (neDNA) vector may function as an effective gene therapy vector whose capacity of expression is equivalent or may even greater to than AAV vector or closed-ended DNA. Without wishing to be bound by theory, it is believed that ceDNA having a nick or a gap at 5' cis acting ITR or a spacer between the expression cassette and a 5' ITR can provide increased access to transcriptional enzymes and may lead to a higher expression level. Therefore, the processes and methods disclosed herein in making synthetic ceDNA vectors provide not only novel ways to make viral or nonviral DNA vectors with higher purity and specificity, but also novel compositions of improved ceDNA variants such as synthetic neDNAs that may offer great potential for gene therapy.

According to a first aspect, the disclosure provides an isolated linear duplex nucleic acid molecule comprising a first inverted terminal repeat (ITR), an expression cassette comprising a promoter and a transgene, and optionally a second ITR, wherein said nucleic acid molecule is devoid of AAV capsid protein coding sequences, wherein said promoter is operably linked to the transgene to control expression of the transgene, and wherein said nucleic acid molecule has one or more gaps in a sense strand of said transgene, and wherein said one or more gaps are 5' upstream or 3' downstream of said expression cassette. According to some embodiments, the first ITR has a closed ended hairpin structure comprising one or more loops and an extended stem structure comprising a Rep Binding Elements (RBE). According to some embodiments, the first ITR has a closed-ended stem structure without a loop. According to some embodiments, the stem structure of the first ITR comprises an RBE and is connected to the 5'-end of said expression cassette. According to some embodiments, the gap 5' upstream of said expression cassette is located between said RBE and the 5' end of said expression cassette. According to some embodiments, the gap 5' upstream of said expression cassette is in a junction between said RBE and the 5' end of a promoter sequence in said expression cassette. According to some embodiments, the gap 5' upstream of said expression cassette is located immediately 5' upstream of a promoter in the expression cassette. According to some embodiments, the RBE is connected to the 5'-end of said expression cassette via a spacer sequence. According to some embodiments, the gap 5' upstream of said expression cassette is in the spacer sequence. According to some embodiments, the gap 5' upstream of said expression cassette is in the spacer sequence between said RBE and the 5' end of the expression vector. According to some embodiments, the gap is present 3' downstream of said expression cassette. According to some embodiments, the second ITR has a closed-ended hairpin structure comprising one or more loops and an extended stem structure. According to some embodiments, the second ITR has a closed-ended stem structure without a loop. According to some embodiments, the gap is in the stem structure of the second ITR. According to some embodiments, the first and the second ITRs are substantially symmetrical to each other. According to some embodiments, the first and the second ITRs are asymmetrical to each other. According to some embodiments, the first and the second ITRs are independently selected from the group consisting of wild-type AAV serotypes AAV1, AAV2, AAV3, AAV4, AAV5, AAV6, AAV7, AAV8, AAV9, AAV10, AAV11, and AAV12. According to some embodiments, the first ITR is selected from the group consisting of the 5' WT-ITRs listed in Table 2. According to some embodiments, the second ITR is selected from the group consisting of the 3' WT-ITRs listed in Table 2.

According to some embodiments of the aspects and embodiments herein, the first and the second ITRs are modified ITRs. According to some embodiments, the modified ITRs have a deletion, insertion, and/or substitution in at least one of the ITR regions selected from A, A', B, B', C, C', D and D'. According to some embodiments, the first and the second ITRs are asymmetrical to each other and selected from modified left ITRs for the first ITRs and modified right ITRs for the second ITRs listed in Tables 4A and 4B. According to some embodiments, the first and the second ITRs are symmetrical to each other and selected from the group consisting of modified ITR symmetric pairs listed in Table 5. According to some embodiments, the first ITR is a modified ITR and the second ITR is a wild-type AAV ITR. According to some embodiments, the first ITR is a modified ITR selected from the modified ITRs listed in Table 4B and the second ITR is a wild-type AAV ITR selected from the WT-ITRs listed in Table 2 (right column).

According to some embodiments of the aspects and embodiments herein, the first ITR is a wild-type AAV ITR and the second ITRs is a modified ITR having a deletion, insertion, and/or substitution in at least one of the ITR regions selected from A, A', B, B', C, C' D, and/or D'.

According to some embodiments of the aspects and embodiments herein, the first ITR is a wild-type AAV ITR selected from WT-ITRs listed in Table 2 (left column) and the second ITRs is a modified ITR selected from modified ITRs listed in Table 4A.

According to some embodiments of the aspects and embodiments herein, the gap 5' upstream of said expression cassette or 3' downstream of said expression cassette is 1 base-pair in length.

According to some embodiments of the aspects and embodiments herein, the gap 5' upstream of said expression cassette or 3' downstream of said expression cassette is about 2, about 3, about 4, about 5, about 6, about 7, about 8, about 9, about 10, about 11, about 12, about 13, about 14, about 15, about 16, about 17, about 18, about 19, or about 20 base-pairs in length. According to some embodiments, the gap 5' upstream of said expression cassette or 3' downstream of said expression cassette is about 5 base-pairs in length. According to some embodiments, the gap 5' upstream of said expression cassette or 3' downstream of said expression cassette is about 10 base-pairs in length. According to some embodiments, the gap 5' upstream of said expression cassette or 3' downstream of said expression cassette is about 15 base-pairs in length. According to some embodiments, the gap 5' upstream of said expression cassette or 3' downstream of said expression cassette is about 20 base-pairs in length.

According to some embodiments of any of the aspects or embodiments herein, the gap 5' upstream of said expression cassette or 3' downstream of said expression cassette is 1 to 50 base-pairs in length. According to some embodiments, the gap 5' upstream of said expression cassette is in a stem structure of said first ITR. According to some embodiments, the gap 5' upstream of said expression cassette is located between said RBE and the 5' end of a promoter sequence in said expression cassette.

According to some embodiments of the aspects and embodiments herein, the gap 3' downstream of said expression is in the closed-ended stem structure.

According to some embodiments of the aspects and embodiments herein, the gaps 5' upstream and 3' downstream of said expression cassette are in the stem structures of the first ITR and the second ITR, respectively. According to some embodiments of any of the aspects or embodiments herein, the transgene of the isolated linear duplex nucleic acid molecule comprises a coding sequence encoding a therapeutic protein. According to some embodiments, the therapeutic protein is a lysosomal enzyme. According to some embodiments, the lysosomal enzyme is alpha galactosidase, beta glucocerebrosidase, arylsulfatase A, iduronate-2-sulfatase, hexosaminidase A, lysosomal acid glucosidase, or lysosomal acid lipase. According to some embodiments, the therapeutic protein is Factor VIII, Factor IX or Factor X. According to some embodiments, the therapeutic protein is phenylalanine hydroxylase (PAH). According to some embodiments, the therapeutic protein is CEP290 or ABCA4. According to some embodiments, the transgene comprises a sequence encoding a therapeutic RNA. According to some embodiments, the transgene comprises a sequence for a siRNA. According to some embodiments, the transgene comprises a sequence for an antisense oligonucleotide. According to some embodiments, the transgene comprises noncoding nucleic acid (e.g., RNAi, miR, micro-RNAs, shRNAs, or antagomir). According to some embodiments, the transgene comprises a sequence encoding an immunogenic protein.

According to some aspects, the disclosure provides an isolated linear duplex nucleic acid molecule as described in any of the aspects or embodiments herein, for use in a method for the treatment of a disease in a subject in need thereof, said disease caused by a genetic defect that reduces or eliminates expression of a polypeptide or that results in expression of a nonfunctional or poorly functional polypeptide whose function is directly associated with symptoms of said disease, wherein the isolated linear duplex nucleic acid molecule comprises a transgene encoding a function polypeptide or an oligonucleotide that skip, correct, silences or masks the defect when expressed in said subject, resulting in amelioration or normalization of the symptoms associated with the disease.

According to some aspects, the disclosure provides a pharmaceutical composition comprising an isolated linear duplex nucleic acid molecule of any one of the aspects or embodiments herein. According to some embodiments, the isolated linear duplex nucleic acid molecule is formulated in solution, microemulsion, exosome, or liposome. According to some embodiments, the isolated linear duplex nucleic acid molecule is formulated in liposome comprising one or more lipids selected from: N-(carbonyl-methoxypolyethylene glycol 2000)-1,2-distearoyl-sn-glycero-3-phosphoethanolamine sodium salt, (distearoyl-sn-glycero-phosphoethanolamine), MPEG (methoxy polyethylene glycol)-conjugated lipid, HSPC (hydrogenated soy phosphatidylcholine); PEG (polyethylene glycol); DSPE (distearoyl-sn-glycero-phosphoethanolamine); DSPC (distearoylphosphatidylcholine); DOPC (dioleoylphosphatidylcholine); DPPG (dipalmitoylphosphatidylglycerol); EPC (egg phosphatidylcholine); DOPS (dioleoylphosphatidylserine); POPC (palmitoyloleoylphosphatidylcholine); SM (sphingomyelin); MPEG (methoxy polyethylene glycol); DMPC (dimyristoyl phosphatidylcholine); DMPG (dimyristoyl phosphatidylglycerol); DSPG (distearoylphosphatidylglycerol); DEPC (dierucoylphosphatidylcholine); DOPE (dioleoly-sn-glycero-phophoethanolamine), cholesteryl sulphate (CS), dipalmitoylphosphatidylglycerol (DPPG), DOPC (dioleoly-sn-glycero-phosphatidylcholine) or any combination thereof. According to some embodiments, the isolated linear closed-ended duplex nucleic acid molecule is formulated in liposome comprising one or more neDNA with a polyethylene glycol (PEG) functional group. According to some embodiments, the isolated linear closed-ended duplex nucleic acid molecule is formulated in liposome comprising a ionizable lipid. According to some embodiments, the ionizable lipid is MC3 having the following structure:

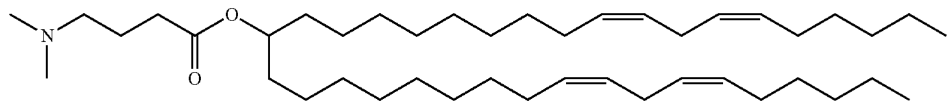
("MC3")

DLin-M-C3-DMA

According to some embodiments, the ionizable lipid is (13Z,16Z)—N,N-dimethyl-3-nonyldocosa-13,16-dien-1-amine. According to some embodiments, the liposome comprises lipid nanoparticles. According to some embodiments, the lipid nanoparticles comprise PEG. According to some embodiments, the lipid nanoparticles comprise one or more compounds which can reduce the immunogenicity or antigenicity. According to some embodiments, the lipid nanoparticles have a mean diameter between about 10 and about 1000 nm.

According to another aspect, the disclosure provides a method of producing a closed-ended DNA vector having a gap comprising providing a double stranded DNA construct comprising an expression cassette, wherein the expression cassette comprises a promoter operably linked to a transgene, wherein at least one end of said double stranded DNA comprises an overhang sequence; providing a first inverted terminal repeat (ITR) comprising an overhang sequence that is a complement to the overhang sequence of one end of the double stranded DNA, wherein the first ITR is closed-ended and is located 5' upstream of said double stranded DNA (5' ITR); providing a second ITR, optionally comprising an overhang sequence that is a complement to a second overhang sequence of the other end of the expression cassette, wherein the second ITR is closed-ended and is located 3' downstream of said double stranded DNA (3' ITR); contacting said double-stranded DNA construct comprising the expression cassette with the first ITR, the second ITR and a ligase, wherein ligation of the first ITR and the second ITR with the double-stranded DNA construct comprising the expression cassette produces a closed-ended DNA vector having at least one gap 5' upstream of the expression cassette, 3' downstream of the expression cassette, or both 5' upstream and 3' downstream of the expression cassette, thereby producing a closed-ended DNA vector having a gap. According to some embodiments, said expression cassette further comprises a polyadenylation sequence. According to some embodiments, said expression cassette comprises a sequence encoding a therapeutic protein. According to some embodiments, said expression cassette comprises a sequence encoding a monoclonal antibody. According to some embodiments, said expression cassette comprises a sequence encoding an immunogenic protein. According to some embodiments, said expression cassette comprises a sequence encoding Factor VIII, Factor IX, or Factor X. According to some embodiments, said expression cassette comprises a sequence encoding CEP290 or ABCA4. According to some embodiments, said expression cassette comprises a sequence encoding phenylalanine hydroxylase (PAH). According to some embodiments, said expression cassette comprises a sequence encoding a therapeutic RNA. According to some embodiments, said expression cassette comprises a sequence for an antisense oligonucleotide. According to some embodiments, said transgene comprises noncoding nucleic acids (e.g., RNAi, miR, micro-RNAs, shRNAs, or antagomir). According to some embodiments, said first ITR and said second ITR are symmetrical to each other. According to some embodiments, said first ITR and said second ITR are asymmetrical to each other. According to some embodiments, said double stranded DNA comprises overhangs on the 5'- and 3'-ends, each overhang comprising a sequence that complements either the first ITR overhang sequence or the second ITR overhang sequence. According to some embodiments, said gap is about one or two base pairs. According to some embodiments, said gap is about five base pair, about ten base pair, about fifteen base pair, or about thirty base pair long in length. According to some embodiments, said gap is 5' upstream of the expression cassette. According to some embodiments, said gap is 3' downstream of the expression cassette. According to some embodiments, said expression cassette comprises a polyadenylation (poly-A) sequence. According to some embodiments, said gap is not within the transgene. According to some embodiments, the presence of said gap enhances expression of the transgene in a host cell. According to some embodiments, the gap is in a spacer sequence between the expression cassette and the first ITR. According to some embodiments, the gap is in a spacer sequence between the expression cassette and a Rep Binding Element (RBE) in the first ITR. According to some embodiments, the gap is present both 5' upstream and 3' downstream of the expression cassette. According to some embodiments, the first ITR or the second ITR is synthesized by annealing a single stranded oligonucleotide that contains a palindromic sequence facilitating self-annealing to form a double stranded hairpin (stem-loop) DNA structure with the overhang. According to some embodiments, the first ITR or second ITR is synthesized by annealing three or more oligonucleotides. According to some embodiments, the first or second ITR produced by annealing said three or more oligonucleotides contains a gap in a stem structure. According to some embodiments, gap is introduced by designing a set of single stranded overhangs in said first and second ITRs and said expression cassette that do not completely cover the resulting double stranded DNA sequence. According to some embodiments, the gap is 3-5 base pairs long. According to some embodiments, the gap is about 5-10 base pairs long. According to some embodiments, the gap is about 10-15 base pair long. According to some embodiments, the gap is about 15-20 base pairs long. According to some embodiments, the gap is about 20-25 base pairs long. According to some embodiments, the gap is about 30-40 base pair long. According to some embodiments, the gap is about 40-50 base pair long. According to some embodiments, the gap is about 50-100 base pairs long. According to some embodiments, the RBE is RPE 78. According to some embodiments, the RBE is devoid of RBE 53. According to some embodiments, the ligase is T4 ligase. According to some embodiments, the method further comprises removing unwanted unligated oligonucleotides and remaining DNA fragments by an exonuclease digestion. According to some embodiments, the first ITR is a wild-type AAV ITR. According to some embodiments, the first ITR is a mutant or a modified AAV ITR. According to some embodiments, the second ITR is a wild-type AAV ITR. According to some embodiments, the second ITR is a mutant or a modified AAV. According to some embodiments, at least one of the first ITR and the second ITR is an AAV ITR. According to some embodiments, at least one of the first ITR and the second ITR is an artificial sequence that form a closed-ended stem structure. According to some embodiments, the expression cassette sequence comprises at least one cis-acting element. According to some embodiments, the cis-acting element is selected from the group consisting of a promoter, an enhancer, a post-transcriptional regulatory element and a polyadenylation sequence. According to some embodiments, the post-transcriptional regulatory element is a Woodchuck hepatitis virus (WHP) post-transcriptional regulatory element (WPRE). According to some embodiments, the promoter is selected from the group consisting of a CAG promoter, an AAT promoter, an LP1 promoter, a CMV promoter and an EF1α promoter. According to some embodiments, the promoter is a tissue specific promoter of a human gene. According to some embodiments, the tissue specific promoter of a human gene is selected from the group consisting of a heart-specific promoter, kidney-specific promoter, liver-specific promoter, pancreas-specific promoter, skeletal-specific promoter, muscle-specific promoter, testis-specific promoter and brain-specific promoter. According to some embodiments, the promoter is a liver specific promoter. According to some embodiments, the liver specific promoter is a human alpha 1-antitrypsin (hAAT) promoter. According to some embodiments, the liver specific promoter is an ApoE/AAT1 chimeric promoter for human hepatocyte expression. According to some embodiments, the promoter is a ubiquitous promoter. According to some embodiments, the promoter is a constitutive promoter. According to some embodiments, the transgene sequence is at least 2 kb, 3 kb, 4 kb, 5 kb, 6 kb in length. According to some embodiments, thee transgene encodes a reporter gene (e.g., luciferase and green fluorescent protein). According to some embodiments, the transgene encodes a gene editing protein. According to some embodiments, the transgene encodes a cytotoxic protein. According to some embodiments, the transgene is a nucleotide sequence encoding a functional wild-type protein. According to some embodiments, at least one of the oligonucleotides integrated into the first or second ITR contains a photocleavable (PC) biotin at the desired location in need of a gap. According to some embodiments, at least of one of the first ITR and the second ITR is produced by ligating at least three or more oligonucleotides.

According to some aspects, the disclosure provides an isolated DNA vector generated by the methods of any of the aspects or embodiments described herein.

According to some aspects, the disclosure provides an isolated DNA vector obtained by or obtainable by a process comprising the steps of the methods of any of the aspects or embodiments described herein.

According to some aspects, the disclosure provides a genetic medicine comprising an isolated linear duplex nucleic acid molecule generated by the methods of any of the aspects or embodiments described herein.

According to some aspects, the disclosure provides a cell comprising the isolated linear duplex nucleic acid molecule of any of the aspects or embodiments herein.

According to another aspect, the disclosure provides a method of delivering a therapeutic protein to a subject, the method comprising: administering to a subject an effective amount a composition comprising a neDNA vector of any of the aspects or embodiments herein, wherein at least one heterologous nucleotide sequence encodes a therapeutic protein.

According to some aspects, the disclosure provides a method of delivering a therapeutic protein to a subject, the method comprising administering to a subject an effective amount of the pharmaceutical composition comprising a nicked closed-ended DNA vector according to any one of the aspects or embodiments herein.

According to another aspect, the disclosure provides a kit for producing a nicked closed-ended DNA vector, comprising a first-single stranded ITR molecule comprising a first ITR, optionally a second single-stranded ITR molecule comprising a second ITR and at least one reagent for ligation of said first-single stranded ITR molecule and optionally said second single-stranded ITR molecule to a double stranded polynucleotide molecule comprising an expression cassette.

According to some embodiments, the disclosure provides a kit for producing nicked closed-ended DNA vector obtained by or obtainable by a process according to any of the aspects or embodiments herein, comprising (1) a double-stranded DNA construct comprising an expression cassette; (2) a first ITR upstream (5'-end) of the expression cassette; (3) a second ITR downstream (3'-end) of the expression cassette, wherein at least two restriction endonuclease cleavage sites flank the ITRs such that restriction digestions by endonucleases are distal to the expression cassette.

According to some embodiments, the expression cassette has a restriction endonuclease site for insertion of a transgene, and (ii) at least one ligation reagent for ligation.

According to some aspects, the disclosure provides a method of producing a closed-ended DNA vector having a gap comprising providing a double stranded DNA construct comprising an expression cassette, wherein the expression cassette comprises a promoter operably linked to a transgene, wherein at least one end of said double stranded DNA comprises an overhang sequence; providing a first inverted terminal repeat (ITR) with an overhang sequence, wherein the first ITR is closed-ended and located 3' downstream of said double stranded DNA (3' ITR); optionally providing a second ITR with an overhang sequence, wherein the second ITR is closed-ended and is located 5' upstream of said double stranded DNA (5' ITR); contacting said double-stranded DNA construct comprising the expression cassette with said first ITR, optionally the second ITR and a ligase, wherein ligation of the first ITR, and optionally the second ITR with the double-stranded DNA construct comprising the expression cassette produces a closed-ended DNA vector having at least one gap, thereby producing a closed-ended DNA vector having a gap.

DESCRIPTION OF DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 1A illustrates an exemplary structure of a neDNA vector comprising asymmetric ITRs. In this embodiment, the exemplary neDNA vector comprises an expression cassette containing CAG promoter, WPRE, and BGHpA. An open reading frame (ORF) encoding a transgene, e.g., a luciferase transgene is inserted into the cloning site (R3/R4) between the CAG promoter and WPRE. The expression cassette is flanked by two inverted terminal repeats (ITRs)—the wild-type AAV2 ITR on the upstream (5'-end) and the modified ITR on the downstream (3'-end) of the expression cassette, therefore the two ITRs flanking the expression cassette are asymmetric with respect to each other. A gap ranging from 1 base pair up to 100 base pairs in length can be present in R2 and/or R5 positions on either the sense or antisense strand. FIG. 1B illustrates an exemplary structure of a neDNA vector comprising asymmetric ITRs with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two inverted terminal repeats (ITRs)—a modified ITR on the upstream (5'-end) and a wild-type ITR on the downstream (3'-end) of the expression cassette. A gap ranging from 1 base pair up to 100 base pairs in length can be present in R2 and/or R5 positions on either the sense or antisense strand. FIG. 1C illustrates an exemplary structure of a neDNA vector comprising asymmetric ITRs, with an expression cassette containing an enhancer/promoter, a transgene, a post transcriptional element (WPRE), and a polyA signal. An open reading frame (ORF) allows insertion of a transgene into the cloning site between CAG promoter and WPRE. The expression cassette is flanked by two inverted terminal repeats (ITRs) that are asymmetrical with respect to each other: a modified ITR on the upstream (5'-end) and a modified ITR on the downstream (3'-end) of the expression cassette, where the 5' ITR and the 3'ITR are both modified ITRs but have different modifications (i.e., they do not have the same modifications). A gap ranging from 1 base pair up to 100 base pairs in length can be present in R2 and/or R5 positions on either the sense or antisense strand. FIG. 1D illustrates an exemplary structure of a neDNA vector comprising symmetric modified ITRs, or substantially symmetrical modified ITRs as defined herein, with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two modified inverted terminal repeats (ITRs), where the 5' modified ITR and the 3' modified ITR are symmetrical or substantially symmetrical. A gap ranging from 1 base pair up to 100 base pairs in length can be present in R2 and/or R5 positions on either the sense or antisense strand. FIG. 1E illustrates an exemplary structure of a neDNA vector comprising symmetric modified ITRs, or substantially symmetrical modified ITRs as defined herein, with an expression cassette containing an enhancer/promoter, a transgene, a post transcriptional element (WPRE), and a polyA signal. An open reading frame (ORF) allows insertion of a transgene into the cloning site between CAG promoter and WPRE. The expression cassette is flanked by two modified inverted terminal repeats (ITRs), where the 5' modified ITR and the 3' modified ITR are symmetrical or substantially symmetrical. A gap ranging from 1 base pair up to 100 base pairs in length can be present in R2 and/or R5 positions on either the sense or antisense strand. FIG. 1F illustrates an exemplary structure of a neDNA vector comprising symmetric WT-ITRs, or substantially symmetrical WT-ITRs as defined herein, with an expression cassette containing CAG promoter, WPRE, and BGHpA. An open reading frame (ORF) encoding a transgene, e.g., a Luciferase transgene is inserted into the cloning site between CAG promoter and WPRE. The expression cassette is flanked by two wild type inverted terminal repeats (WT-ITRs), where the 5' WT-ITR and the 3' WT ITR are symmetrical or substantially symmetrical. A gap ranging from 1 base pair up to 100 base pairs in length can be present in R2 position on either the sense or antisense strand. FIG. 1G illustrates an exemplary structure of a neDNA vector comprising symmetric modified ITRs, or substantially symmetrical modified ITRs as defined herein, with an expression cassette containing an enhancer/promoter, a transgene, a post transcriptional element (WPRE), and a polyA signal. An open reading frame (ORF) allows insertion of a transgene into the cloning site between CAG promoter and WPRE. The expression cassette is flanked by two wild type inverted terminal repeats (WT-ITRs), where the 5' WT-ITR and the 3' WT ITR are symmetrical or substantially symmetrical. A gap ranging from 1 base pair up to 100 base pairs in length can be present in R2 and/or R5 positions on either the sense or antisense strand.

FIG. 2A discloses SEQ ID NO: 81.

FIG. 2B discloses SEQ ID NO: 82.

FIG. 8 depicts a schematic representation of a left ITR (e.g., wild-type AAV2 ITR with a spacer) that can be utilized for cell-free synthetic production of neDNA. When component oligonucleotides are ligated together, a resultant ITR has an overhang sequence at the right-side bottom strand and a gap of 12-base pairs in length at the top strand. The overhang and the gap can be used to create neDNA vector when ligated with an expression cassette of any length. FIG. 8 discloses the "#1" sequences as SEQ ID NOS 72 and 87, the "#5" sequences as SEQ ID NOS 74 and 74 and the "#4" sequences as SEQ ID NOS 73 and 73, all respectively, in order of appearance.

FIG. 9 discloses the "#6.1" sequence as SEQ ID NO: 75, the "#6.2" sequence as SEQ ID NO: 75, the "#8.1 PC and #8.2 Biotin" sequence as SEQ ID NO: 77, the "#12.1 PC and #12.2 Biotin" sequence as SEQ ID NO: 80, the "#7.2" sequence as SEQ ID NO: 76, the "#9" sequence as SEQ ID NO: 78, the "#10" sequence as SEQ ID NO: 79 and the full-length "#9" and "#10" sequence as SEQ ID NO: 76.

FIG. 10 discloses SEQ ID NOS 88-91, respectively, in order of appearance.

DETAILED DESCRIPTION

I. Definitions

Figure 1A:
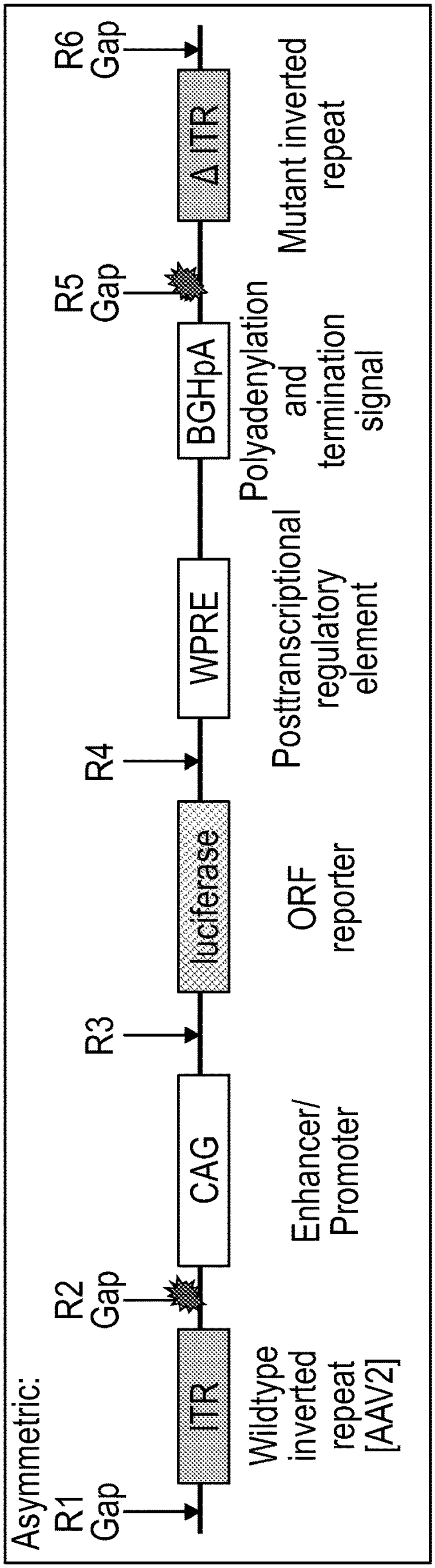
FIGS. 1A, 1B, 1C, 1D, 1E, 1F, and 1G depict structures of neDNA having a gap or nick in various positions in combination with different types of ITRs in the 5' and 3'ends.
Figure 1B:
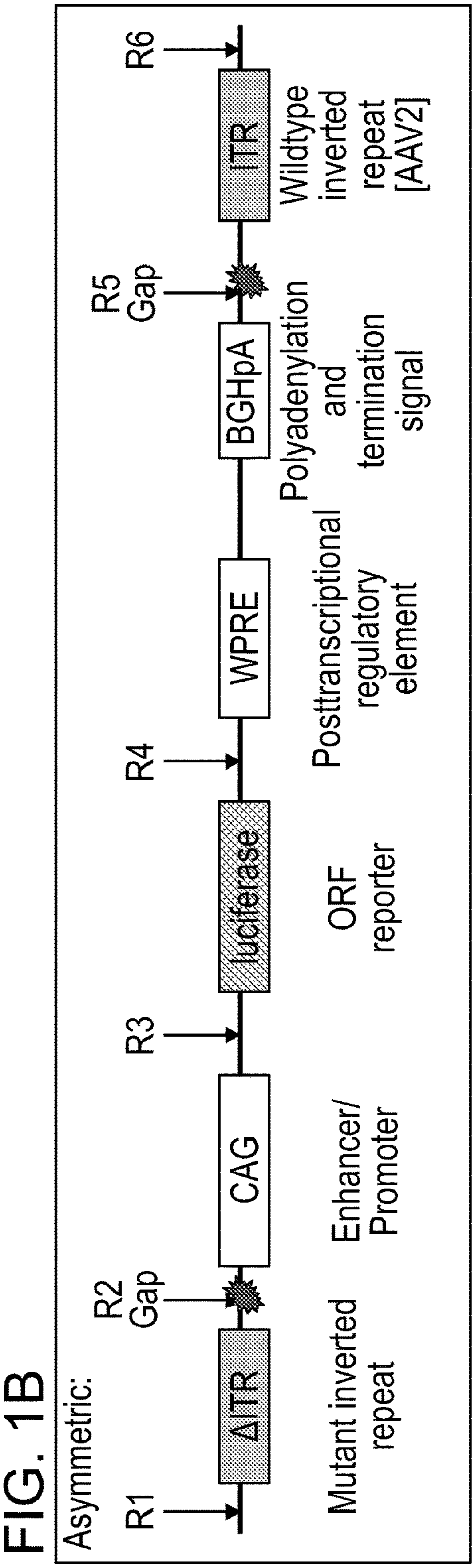
Figure 1C:
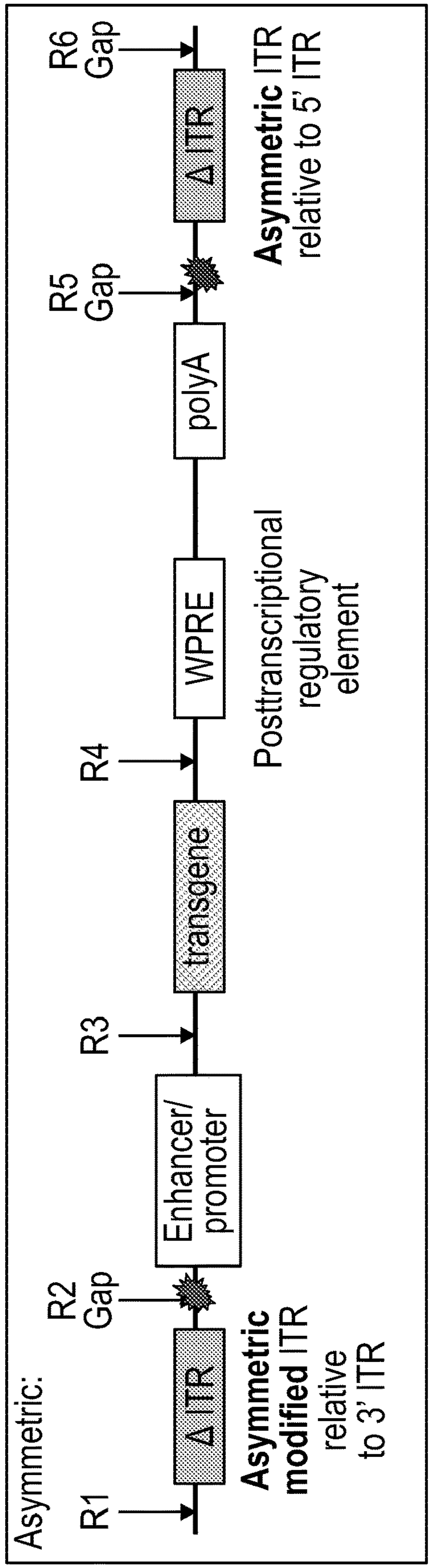
Figure 1D:
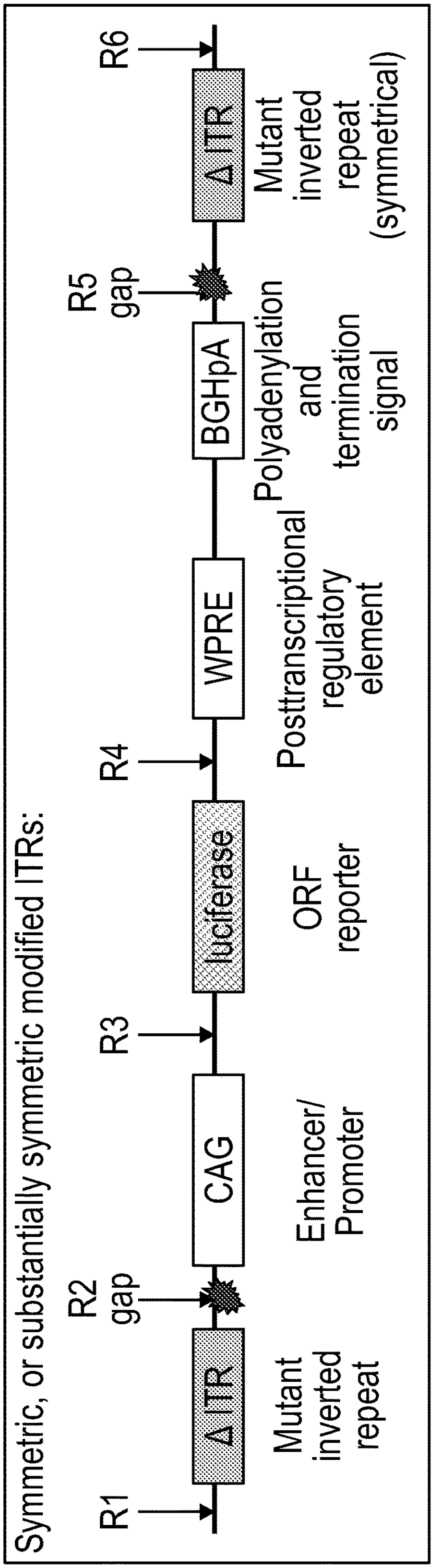
Figure 1E:
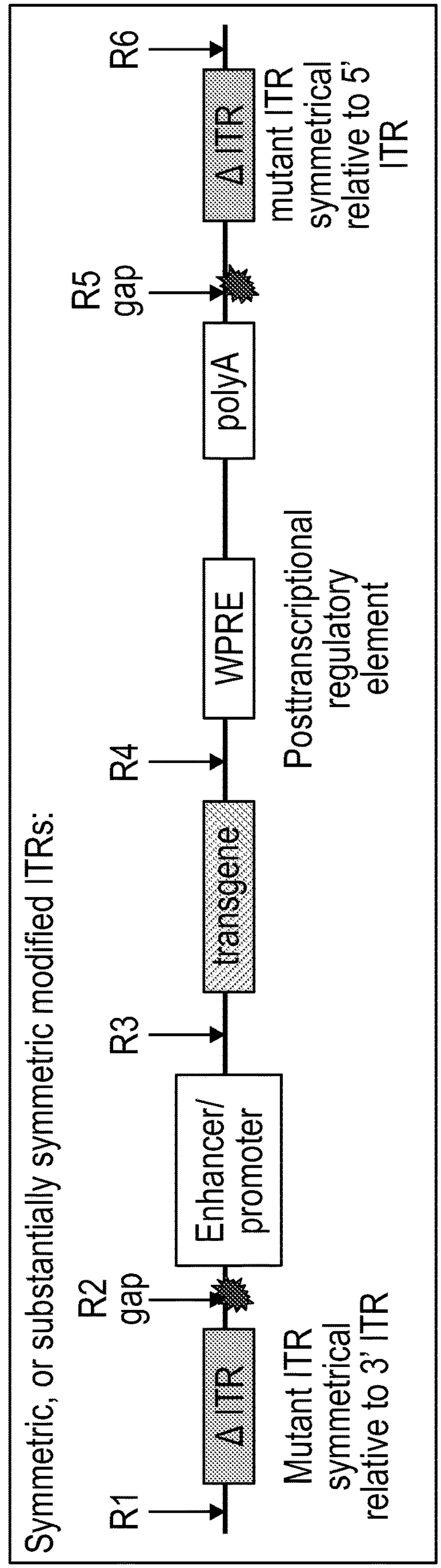

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), Fields Virology, $6^{th}$ Edition, published by Lippincott Williams & Wilkins, Philadelphia, PA, USA (2013), Knipe, D. M. and Howley, P. M. (ed.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the term "synthetic AAV vector" and "synthetic production of AAV vector" refers to an AAV vector and synthetic production methods thereof in an entirely cell-free environment. The production may involve one or more molecules in a manner that does not involve replication or other multiplication of the molecule by or inside of a cell or using a cellular extract. Synthetic production avoids contamination of the produced molecule with cellular contaminants, e.g., cellular proteins or cellular nucleic acid, viral protein or DNA, insect protein or DNA and further avoids unwanted cellular-specific modification of the molecule during the production process, e.g., methylation or glycosylation or other post-translational modification.

As used herein, the term "gap" refers to a discontinued portion of synthetic DNA vector of the present invention, creating a stretch of single stranded DNA portion in otherwise double stranded ceDNA. The gap can be 1 base-pair to 100 base-pair long in length. Typical gaps, designed and created by the methods described herein and synthetic vectors generated by the methods can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 bp long in length. Exemplified gaps in the present disclosure can be 1 bp to 10 bp long, 1 to 20 bp long, 1 to 30 bp long, or any length necessary to nick double stranded DNA to allow for or to maintain efficient transcription of an expression cassette in host cells. According to some embodiments, gaps can be present 5' upstream of an expression cassette. According to some embodiments, gaps can be present 3' downstream of an expression cassette. According to some embodiments, gaps can be present 5' upstream of an expression cassette and 3' downstream of an expression cassette.

As used herein, the term "nick" refers to a discontinuity in a double stranded DNA molecule where there is no phosphodiester bond between adjacent nucleotides of one strand typically through damage or enzyme action. It is understood that one or more nicks allow for the release of torsion in the strand during DNA replication and that nicks are also thought to play a role in facilitating binding of transcriptional machinery.

As used herein, the term "ceDNA" refers to capsid-free closed-ended linear double stranded (ds) duplex DNA for non-viral gene transfer, synthetic or otherwise. Detailed description of ceDNA is described in International application of PCT/US2017/020828, filed Mar. 3, 2017, the entire content of which is incorporated herein by reference. Certain methods for the production of ceDNA comprising various inverted terminal repeat (ITR) sequences and configurations using cell-based methods are described in Example 1 of International applications PCT/US18/49996, filed Sep. 7, 2018, and PCT/US2018/064242, filed Dec. 6, 2018 each of which is incorporated herein in its entirety by reference. Certain methods for the production of synthetic ceDNA vectors comprising various ITR sequences and configurations are described, e.g., in International application PCT/US2019/14122, filed Jan. 18, 2019, the entire content of which is incorporated herein by reference.

As used herein, the term "neDNA", "nicked ceDNA" refers to a closed-ended DNA having a nick or a gap of 1-100 base pairs a stem region or spacer region upstream of an open reading frame (e.g., a promoter and transgene to be expressed).

As used herein, the term "terminal repeat" or "TR" includes any viral or non-viral terminal repeat or synthetic sequence that comprises at least one minimal required origin of replication and a region comprising a palindromic hairpin structure. A Rep-binding sequence ("RBS" or also referred to as Rep-binding element (RBE)) and a terminal resolution site ("TRS") together constitute a "minimal required origin of replication" and thus the TR comprises at least one RBS and at least one TRS. TRs that are the inverse complement of one another within a given stretch of polynucleotide sequence are typically each referred to as an "inverted terminal repeat" or "ITR". In the context of a virus, ITRs plays a critical role in mediating replication, viral particle and DNA packaging, DNA integration and genome and provirus rescue. TRs that are not inverse complement (palindromic) across their full length can still perform the traditional functions of ITRs, and thus, the term ITR is used to refer to a TR in a neDNA vector or an AAV vector that is capable of mediating replication of in the host cell. It will be understood by one of ordinary skill in the art that in complex neDNA vector configurations more than two ITRs or asymmetric ITR pairs may be present.

The "ITR" can be artificially synthesized using a set of oligonucleotides comprising one or more desirable functional sequences (e.g., palindromic sequence, RBS). The ITR sequence can be an artificial AAV ITR, an artificial non-AAV ITR, or an ITR physically derived from a viral AAV ITR (e.g., ITR fragments removed from a viral genome). For example, the ITR can be derived from the family Parvoviridae, which encompasses parvoviruses and dependoviruses (e.g., canine parvovirus, bovine parvovirus, mouse parvovirus, porcine parvovirus, human parvovirus B-19), or the SV40 hairpin that serves as the origin of SV40 replication can be used as an ITR, which can further be modified by truncation, substitution, deletion, insertion and/or addition. Parvoviridae family viruses consist of two subfamilies: Parvovirinae, which infect vertebrates, and Densovirinae, which infect invertebrates. Dependoparvoviruses include the viral family of the adeno-associated viruses (AAV) which are capable of replication in vertebrate hosts including, but not limited to, human, primate, bovine, canine, equine and ovine species. Typically, ITR sequences can be derived not only from AAV, but also from Parvovirus, lentivirus, goose virus, B19, in the configurations of wild-type, "doggy bone" and "dumbbell shape", symmetrical or even asymmetrical ITR orientation. Although the ITRs are typically present in both 5' and 3' ends of the nicked neDNA or synthetic linear AAV, ITR can be present in only one of end of the linear vector. For example, the ITR can be present on the 5' end only. Some other cases, the ITR can be present on the 3' end only in nicked neDNA or synthetic AAV. For convenience herein, an ITR located 5' to ("upstream of") an expression cassette in a nicked neDNA vector or synthetic AAV is referred to as a "5' ITR" or a "left ITR", and an ITR located 3' to ("downstream of") an expression cassette in a neDNA vector or synthetic AAV is referred to as a "3' ITR" or a "right ITR".

As used herein, a "wild-type ITR" or "WT-ITR" refers to the sequence of a naturally occurring ITR sequence in an AAV genome or other dependovirus that remains, e.g., Rep binding activity and Rep nicking ability. The nucleotide sequence of a WT-ITR from any AAV serotype may slightly vary from the canonical naturally occurring sequence due to degeneracy of the genetic code or drift, and therefore WT-ITR sequences encompasses for use herein include WT-ITR sequences as result of naturally occurring changes (e.g., a replication error).

As used herein, the term "substantially symmetrical WT-ITRs" or a "substantially symmetrical WT-ITR pair" refers to a pair of WT-ITRs within a single neDNA vector or synthetic AAV vector that are both wild type ITRs that have an inverse complement sequence across their entire length. For example, an ITR can be considered to be a wild-type sequence, even if it has one or more nucleotides that deviate from the canonical naturally occurring canonical sequence, so long as the changes do not affect the physical and functional properties and overall three-dimensional structure of the sequence (secondary and tertiary structures). In some aspects, the deviating nucleotides represent conservative sequence changes. As one non-limiting example, a sequence that has at least 95%, 96%, 97%, 98%, or 99% sequence identity to the canonical sequence (as measured, e.g., using BLAST® at default settings), and also has a symmetrical three-dimensional spatial organization to the other WT-ITR such that their 3D structures are the same shape in geometrical space. The substantially symmetrical WT-ITR has the same A, C-C' and B-B' loops in 3D space. A substantially symmetrical WT-ITR can be functionally confirmed as WT by determining that it has an operable Rep binding site (RBE or RBE') and terminal resolution site (TRS) that pairs with the appropriate Rep protein. One can optionally test other functions, including transgene expression under permissive conditions.

As used herein, the phrases of "modified ITR" or "mod-ITR" or "mutant ITR" are used interchangeably and refer to an ITR with a mutation in at least one or more nucleotides as compared to the WT-ITR from the same serotype. The mutation can result in a change in one or more of A, C, C', B, B' regions in the ITR, and can result in a change in the three-dimensional spatial organization (i.e. its 3D structure in geometric space) as compared to the 3D spatial organization of a WT-ITR of the same serotype.

As used herein, the term "asymmetric ITRs" also referred to as "asymmetric ITR pairs" refers to a pair of ITRs within a single neDNA genome or neDNA vector that are not inverse complements across their full length. As one non-limiting example, an asymmetric ITR pair does not have a symmetrical three-dimensional spatial organization to their cognate ITR such that their 3D structures are different shapes in geometrical space. Stated differently, an asymmetrical ITR pair have the different overall geometric structure, i.e., they have different organization of their A, C-C' and B-B' loops in 3D space (e.g., one ITR may have a short C-C' arm and/or short B-B' arm as compared to the cognate ITR). The difference in sequence between the two ITRs may be due to one or more nucleotide addition, deletion, truncation, or point mutation. In one embodiment, one ITR of the asymmetric ITR pair may be a wild-type AAV ITR sequence and the other ITR a modified ITR as defined herein (e.g., a non-wild-type or synthetic ITR sequence). In another embodiment, neither ITRs of the asymmetric ITR pair is a wild-type AAV sequence and the two ITRs are modified ITRs that have different shapes in geometrical space (i.e., a different overall geometric structure). In some embodiments, one mod-ITRs of an asymmetric ITR pair can have a short C-C' arm and the other ITR can have a different modification (e.g., a single arm, or a short B-B' arm etc.) such that they have different three-dimensional spatial organization as compared to the cognate asymmetric mod-ITR.

As used herein, the term "symmetric ITRs" refers to a pair of ITRs within a single neDNA genome or neDNA vector that are mutated or modified relative to wild-type dependoviral ITR sequences and are inverse complements across their full length. Neither ITRs are wild type ITR AAV2 sequences (i.e., they are a modified ITR, also referred to as a mutant ITR), and can have a difference in sequence from the wild type ITR due to nucleotide addition, deletion, substitution, truncation, or point mutation. For convenience herein, an ITR located 5' to (upstream of) an expression cassette in a neDNA vector is referred to as a "5' ITR" or a "left ITR", and an ITR located 3' to (downstream of) an expression cassette in a neDNA vector is referred to as a "3' ITR" or a "right ITR".

As used herein, the terms "substantially symmetrical modified-ITRs" or a "substantially symmetrical mod-ITR pair" refers to a pair of modified-ITRs within a single neDNA genome or neDNA vector that are both that have an inverse complement sequence across their entire length. For example, the a modified ITR can be considered substantially symmetrical, even if it has some nucleotide sequences that deviate from the inverse complement sequence so long as the changes do not affect the properties and overall shape. As one non-limiting example, a sequence that has at least 85%, 90%, 95%, 96%, 97%, 98%, or 99% sequence identity to the canonical sequence (as measured using BLAST® at default settings), and also has a symmetrical three-dimensional spatial organization to their cognate modified ITR such that their 3D structures are the same shape in geometrical space. Stated differently, a substantially symmetrical modified-ITR pair have the same A, C-C' and B-B' loops organized in 3D space. In some embodiments, the ITRs from a mod-ITR pair may have different reverse complement nucleotide sequences but still have the same symmetrical three-dimensional spatial organization—that is both ITRs have mutations that result in the same overall 3D shape. For example, one ITR (e.g., 5' ITR) in a mod-ITR pair can be from one serotype, and the other ITR (e.g., 3' ITR) can be from a different serotype, however, both can have the same corresponding mutation (e.g., if the 5'ITR has a deletion in the C region, the cognate modified 3'ITR from a different serotype has a deletion at the corresponding position in the C' region), such that the modified ITR pair has the same symmetrical three-dimensional spatial organization. In such embodiments, each ITR in a modified ITR pair can be from different serotypes (e.g., AAV1, 2, 3, 4, 5, 6, 7, 8, 9, 10, 11, and 12) such as the combination of AAV2 and AAV6, with the modification in one ITR reflected in the corresponding position in the cognate ITR from a different serotype. In one embodiment, a substantially symmetrical modified ITR pair refers to a pair of modified ITRs (mod-ITRs) so long as the difference in nucleotide sequences between the ITRs does not affect the properties or overall shape and they have substantially the same shape in 3D space. As a non-limiting example, a mod-ITR that has at least 95%, 96%, 97%, 98% or 99% sequence identity to the canonical mod-ITR as determined by standard means well known in the art such as BLAST® (Basic Local Alignment Search Tool), or BLASTN® at default settings, and also has a symmetrical three-dimensional spatial organization such that their 3D structure is the same shape in geometric space. A substantially symmetrical mod-ITR pair has the same A, C-C' and B-B' loops in 3D space, e.g., if a modified ITR in a substantially symmetrical mod-ITR pair has a deletion of a C-C' arm, then the cognate mod-ITR has the corresponding deletion of the C-C' loop and also has a similar 3D structure of the remaining A and B-B' loops in the same shape in geometric space of its cognate mod-ITR.

As used herein, the term "flanking" refers to a relative position of one nucleic acid sequence with respect to another nucleic acid sequence. Generally, in the sequence ABC, B is flanked by A and C. The same is true for the arrangement A×B×C. Thus, a flanking sequence precedes or follows a flanked sequence but need not be contiguous with, or immediately adjacent to the flanked sequence. In one embodiment, the term flanking refers to terminal repeats at each end of the linear nicked neDNA vector or single strand synthetic AAV.

As used herein, the term "neDNA genome" or "neDNA vector" refers to an expression cassette that further incorporates at least one inverted terminal repeat region. A neDNA genome/vector may further comprise one or more spacer regions. In some embodiments, the neDNA genome is incorporated as an intermolecular duplex polynucleotide of DNA into a plasmid or viral genome with a gap or nick as described herein.

As used herein, the term "neDNA spacer region" refers to an intervening sequence that separates functional elements in the neDNA vector or neDNA genome. In some embodiments, neDNA spacer regions keep two functional elements at a desired distance for optimal functionality. In some embodiments, neDNA spacer regions provide or add to the genetic stability of the neDNA genome. In some embodiments, neDNA spacer regions facilitate ready genetic manipulation of the neDNA genome by providing a convenient location for cloning sites and a gap of design number of base pair. For example, in certain aspects, an oligonucleotide "polylinker" containing several restriction endonuclease sites, or a non-open reading frame sequence designed to have no known protein (e.g., transcription factor) binding sites can be positioned in the neDNA genome to separate the cis—acting factors, e.g., inserting a 6mer, 12mer, 18mer, 24mer, 48mer, 86mer, 176mer, etc. between the terminal resolution site and the upstream transcriptional regulatory element. Similarly, the spacer may be incorporated between the polyadenylation signal sequence and the 3'-terminal resolution site.

As used herein, the terms "Rep binding site" ("RBS") and "Rep binding element" ("RBE") are used interchangeably and refer to a binding site for Rep protein (e.g., AAV Rep 78 or AAV Rep 68) which upon binding by a Rep protein permits the Rep protein to perform its site-specific endonuclease activity on the sequence incorporating the RBS. An RBS sequence and its inverse complement together form a single RBS. RBS sequences are well known in the art, and include, for example, 5'-GCGCGCTCGCTCGCTC-3' (SEQ ID NO: 1), an RBS sequence identified in AAV2. However, the present invention contemplates utilization of any known RBS sequence, including other known AAV RBS sequences and other naturally known or synthetic RBS sequences. Without being bound by theory it is thought that he nuclease domain of a Rep protein binds to the duplex nucleotide sequence GCTC, and thus the two known AAV Rep proteins bind directly to and stably assemble on the duplex oligonucleotide, 5'-(GCGC)(GCTC)(GCTC)(GCTC)-3' (SEQ ID NO: 1). In addition, soluble aggregated conformers (i.e., undefined number of inter-associated Rep proteins) dissociate and bind to oligonucleotides that contain Rep binding sites. Each Rep protein interacts with both the nitrogenous bases and phosphodiester backbone on each strand. The interactions with the nitrogenous bases provide sequence specificity whereas the interactions with the phosphodiester backbone are non- or less-sequence specific and stabilize the protein-DNA complex.

As used herein, the terms "terminal resolution site" and "TRS" are used interchangeably herein and refer to a region at which Rep forms a tyrosine-phosphodiester bond with the 5' thymidine generating a 3'-OH that serves as a substrate for DNA extension via a cellular DNA polymerase, e.g., DNA pol delta or DNA pol epsilon. Alternatively, the Rep-thymidine complex may participate in a coordinated ligation reaction. In some embodiments, a TRS minimally encompasses a non-base-paired thymidine. In some embodiments, the nicking efficiency of the TRS can be controlled at least in part by its distance within the same molecule from the RBS. When the acceptor substrate is the complementary ITR, then the resulting product is an intramolecular duplex. TRS sequences are known in the art, and include, for example, 5'-GGTTGA-3', the hexanucleotide sequence identified in AAV2. Any known TRS sequence may be used in the embodiments of the invention, including other known AAV TRS sequences and other naturally known or synthetic TRS sequences such as AGTT, GGTTGG, AGTTGG, AGTTGA and other motifs such as RRTTRR.

As used herein, the term "neDNA-plasmid" refers to a plasmid that comprises a neDNA genome as an intermolecular duplex.

As used herein, the term "neDNA-bacmid" refers to an infectious baculovirus genome comprising a neDNA genome as an intermolecular duplex that is capable of propagating in *E. coli* as a plasmid, and so can operate as a shuttle vector for baculovirus.

As used herein, the term "neDNA-baculovirus" refers to a baculovirus that comprises a neDNA genome as an intermolecular duplex within the baculovirus genome.

As used herein, the terms "neDNA-baculovirus infected insect cell" and "neDNA-BIIC" are used interchangeably, and refer to an invertebrate host cell (including, but not limited to an insect cell (e.g., an Sf9 cell)) infected with a neDNA-baculovirus.

As used herein, the terms "neDNA" and "neDNA vector" are used interchangeably and refer to a closed-ended DNA vector having one or more nicks or gaps of 1-100 base pair in length at 5' upstream and 3'dowmstream of an expression cassette, wherein neDNA is a capsid-free DNA vector with at least one covalently closed end and where at least part of the vector has an intramolecular duplex structure.

As used herein, the term "closed-ended DNA vector" refers to a capsid-free DNA vector with at least one covalently closed end and where at least part of the vector has an intramolecular duplex structure.

As used herein, the terms "ceDNA vector" and "ceDNA" are used interchangeably and refer to a closed-ended DNA vector comprising at least one terminal palindrome. In some embodiments, the ceDNA comprises two covalently-closed ends.

As used herein, the terms "sense" and "antisense" refer to the orientation of the structural element on the polynucleotide. The sense and antisense versions of an element are the reverse complement of each other.

As defined herein, "reporters" refer to proteins that can be used to provide detectable read-outs. Reporters generally produce a measurable signal such as fluorescence, color, or luminescence. Reporter protein coding sequences encode proteins whose presence in the cell or organism is readily observed. For example, fluorescent proteins cause a cell to fluoresce when excited with light of a particular wavelength, luciferases cause a cell to catalyze a reaction that produces light, and enzymes such as β-galactosidase convert a substrate to a colored product. Exemplary reporter polypeptides useful for experimental or diagnostic purposes include, but are not limited to β-lactamase, β-galactosidase (LacZ), alkaline phosphatase (AP), thymidine kinase (TK), green fluorescent protein (GFP) and other fluorescent proteins, chloramphenicol acetyltransferase (CAT), luciferase, and others well known in the art.

As used herein, the term "effector protein" refers to a polypeptide that provides a detectable read-out, either as, for example, a reporter polypeptide, or more appropriately, as a polypeptide that kills a cell, e.g., a toxin, or an agent that renders a cell susceptible to killing with a chosen agent or lack thereof. Effector proteins include any protein or peptide that directly targets or damages the host cell's DNA and/or RNA. For example, effector proteins can include, but are not limited to, a restriction endonuclease that targets a host cell DNA sequence (whether genomic or on an extrachromosomal element), a protease that degrades a polypeptide target necessary for cell survival, a DNA gyrase inhibitor, and a ribonuclease-type toxin. In some embodiments, the expression of an effector protein controlled by a synthetic biological circuit as described herein can participate as a factor in another synthetic biological circuit to thereby expand the range and complexity of a biological circuit system's responsiveness.

Transcriptional regulators refer to transcriptional activators and repressors that either activate or repress transcription of a gene of interest. Promoters are regions of nucleic acid that initiate transcription of a particular gene. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators may serve as either an activator or a repressor depending on where they bind and cellular and environmental conditions. Non-limiting examples of transcriptional regulator classes include, but are not limited to homeodomain proteins, zinc-finger proteins, winged-helix (forkhead) proteins, and leucine-zipper proteins.

As used herein, a "repressor protein" or "inducer protein" is a protein that binds to a regulatory sequence element and represses or activates, respectively, the transcription of sequences operatively linked to the regulatory sequence element. Preferred repressor and inducer proteins as described herein are sensitive to the presence or absence of at least one input agent or environmental input. Preferred proteins as described herein are modular in form, comprising, for example, separable DNA-binding and input agent-binding or responsive elements or domains.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutically active substances is well known in the art. Supplementary active ingredients can also be incorporated into the compositions. The phrase "pharmaceutically-acceptable" refers to molecular entities and compositions that do not produce a toxic, an allergic, or similar untoward reaction when administered to a host.

As used herein, an "input agent responsive domain" is a domain of a transcription factor that binds to or otherwise responds to a condition or input agent in a manner that renders a linked DNA binding fusion domain responsive to the presence of that condition or input. In one embodiment, the presence of the condition or input results in a conformational change in the input agent responsive domain, or in a protein to which it is fused, that modifies the transcription-modulating activity of the transcription factor.

As used herein, the term "in vivo" refers to assays or processes that occur in or within an organism, such as a multicellular animal. In some of the aspects described herein, a method or use can be said to occur "in vivo" when a unicellular organism, such as a bacterium, is used. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing of a programmable synthetic biological circuit in a non-cellular system, such as a medium not comprising cells or cellular systems, such as cellular extracts.

As used herein, the term "promoter" refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules can bind, such as RNA polymerase and other transcription factors. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the expression of transgenes in the gapped neDNA vectors or synthetic AAV vectors disclosed herein. A promoter sequence may be bounded at its 3' terminus by the transcription initiation site and extends upstream (5' direction) to include the minimum number of bases or elements necessary to initiate transcription at levels detectable above background.

As used herein, the terms "expression cassette" and "expression unit" are used interchangeably and refer to a heterologous DNA sequence that is operably linked to a promoter or other DNA regulatory sequence sufficient to direct transcription of a transgene of a DNA vector, e.g., neDNA vector or synthetic AAV vector. Suitable promoters include, for example, tissue specific promoters. Promoters can also be of AAV origin.

As used herein, "operably linked" refers to a juxtaposition wherein the components so described are in a relationship permitting them to function in their intended manner. For instance, a promoter is operably linked to a coding sequence if the promoter affects its transcription or expression. A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. An "inverted promoter," as used herein, refers to a promoter in which the nucleic acid sequence is in the reverse orientation, such that what was the coding strand is now the non-coding strand, and vice versa. Inverted promoter sequences can be used in various embodiments to regulate the state of a switch. In addition, in various embodiments, a promoter can be used in conjunction with an enhancer.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., DNA-targeting RNA) or a coding sequence (e.g., site-directed modifying polypeptide, or Cas9/Csn1 polypeptide) and/or regulate translation of an encoded polypeptide.

The term "enhancer" as used herein refers to a cis-acting regulatory sequence (e.g., 50-1,500 base pairs) that binds one or more proteins (e.g., activator proteins, or transcription factor) to increase transcriptional activation of a nucleic acid sequence. Naturally, enhancers can be positioned up to 1,000,000 base pars upstream of the gene start site or downstream of the gene start site that they regulate. An enhancer can be positioned within an intronic region, or in the exonic region of an unrelated gene. A cis-acting enhancer sequence of 20-200 base pairs can be typically used to increase expression of a transgene in AAV vectors.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence. In some embodiments, a coding nucleic acid segment is positioned under the control of a "recombinant promoter" or "heterologous promoter," both of which refer to a promoter that is not normally associated with the encoded nucleic acid sequence that it is operably linked to in its natural environment. Similarly, a "recombinant or heterologous enhancer" refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the synthetic biological circuits and modules disclosed herein (see, e.g., U.S. Pat. Nos. 4,683,202, 5,928,906, each incorporated herein by reference). Furthermore, it is contemplated that control sequences that direct transcription and/or expression of sequences within non-nuclear organelles such as mitochondria, chloroplasts, and the like, can be employed as well.

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be an inducer protein expressed by another component or module), which itself can be under the control or an inducible promoter. In some embodiments, an inducible promoter is induced in the absence of certain agents, such as a repressor. Examples of inducible promoters include but are not limited to, tetracycline, metallothionine, ecdysone, mammalian viruses (e.g., the adenovirus late promoter; and the mouse mammary tumor virus long terminal repeat (MMTV-LTR)) and other steroid-responsive promoters, rapamycin responsive promoters and the like.

The term "subject" as used herein refers to a human or animal, to whom treatment, including prophylactic treatment, with the neDNA vector according to the present invention, is provided. Usually the animal is a vertebrate such as, but not limited to a primate, rodent, domestic animal or game animal. Primates include but are not limited to, chimpanzees, cynomologous monkeys, spider monkeys, and macaques, e.g., Rhesus. Rodents include mice, rats, woodchucks, ferrets, rabbits and hamsters. Domestic and game animals include, but are not limited to, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate or a human. A subject can be male or female. Additionally, a subject can be an infant or a child. In some embodiments, the subject can be a neonate or an unborn subject, e.g., the subject is in utero. Preferably, the subject is a mammal. The mammal can be a human, non-human primate, mouse, rat, dog, cat, horse, or cow, but is not limited to these examples. Mammals other than humans can be advantageously used as subjects that represent animal models of diseases and disorders. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject is already undergoing treatment. In some embodiments, the subject is an embryo, a fetus, neonate, infant, child, adolescent, or adult. In some embodiments, the subject is a human fetus, human neonate, human infant, human child, human adolescent, or human adult. In some embodiments, the subject is an animal embryo, or non-human embryo or non-human primate embryo. In some embodiments, the subject is a human embryo.

As used herein, the term "host cell" includes any cell type that is susceptible to transformation, transfection, transduction, and the like with synthetic AAV vector or nicked neDNA expression vector of the present disclosure. As non-limiting examples, a host cell can be an isolated primary cell, pluripotent stem cells, $CD34^+$ cells, induced pluripotent stem cells, or any of a number of immortalized cell lines (e.g., HepG2 cells). Alternatively, a host cell can be an in situ or in vivo cell in a tissue, organ or organism. Furthermore, a host cell can be a target cell of, for example, a mammalian subject (e.g., human patient in need of gene therapy).

As used herein, the term "exogenous" refers to a substance present in a cell other than its native source. The term "exogenous" when used herein can refer to a nucleic acid (e.g., a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell.

The terms "polynucleotide" and "nucleic acid," used interchangeably herein, refer to a polymeric form of nucleotides of any length, either ribonucleotides or deoxyribonucleotides. Thus, this term includes single, double, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides. DNA may be in the form of, e.g., antisense molecules, plasmid DNA, DNA-DNA duplexes, pre-condensed DNA, PCR products, vectors (P1, PAC, BAC, YAC, artificial chromosomes), expression cassettes, chimeric sequences, chromosomal DNA, or derivatives and combinations of these groups. DNA may be in the form of minicircle, plasmid, bacmid, minigene, ministring DNA (linear covalently closed DNA vector), closed-ended linear duplex DNA (CELiD or ceDNA), doggybone (dbDNA™) DNA, dumbbell shaped DNA, minimalistic immunological-defined gene expression (MIDGE)-vector, viral vector or nonviral vectors. RNA may be in the form of small interfering RNA (siRNA), Dicer-substrate dsRNA, small hairpin RNA (shRNA), asymmetrical interfering RNA (aiRNA), microRNA (miRNA), mRNA, rRNA, tRNA, viral RNA (vRNA), and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs and/or modified residues include, without limitation, phosphorothioates, phosphorodiamidate morpholino oligomer (morpholino), phosphoramidates, methyl phosphonates, chiral-methyl phosphonates, 2'-O-methyl ribonucleotides, locked nucleic acid (LNA™), and peptide nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated.

"Nucleotides" contain a sugar deoxyribose (DNA) or ribose (RNA), a base, and a phosphate group. Nucleotides are linked together through the phosphate groups.

"Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

By "hybridizable" or "complementary" or "substantially complementary" it is meant that a nucleic acid (e.g., RNA) includes a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). For example, G/U base-pairing is partially responsible for the degeneracy (i.e., redundancy) of the genetic code in the context of tRNA anti-codon base-pairing with codons in mRNA. In the context of this disclosure, a guanine (G) of a protein-binding segment (dsRNA duplex) of a subject DNA-targeting RNA molecule is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present disclosure. An "expression cassette" includes a DNA coding sequence operably linked to a promoter.

As used herein, the phrases "nucleic acid therapeutic", "therapeutic nucleic acid" and "TNA" are used interchangeably and refer to any modality of therapeutic using nucleic acids as an active component of therapeutic agent to treat a disease or disorder. As used herein, these phrases refer to RNA-based therapeutics and DNA-based therapeutics. Non-limiting examples of RNA-based therapeutics include mRNA, antisense RNA and oligonucleotides, ribozymes, aptamers, interfering RNAs (RNAi), Dicer-substrate dsRNA, small hairpin RNA (shRNA), asymmetrical interfering RNA (aiRNA), microRNA (miRNA). Non-limiting examples of DNA-based therapeutics include minicircle DNA, minigene, viral DNA (e.g., Lentiviral or AAV genome) or non-viral synthetic DNA vectors, closed-ended linear duplex DNA (ceDNA/CELiD), plasmids, bacmids, doggybone (dbDNA™) DNA vectors, minimalistic immunological-defined gene expression (MIDGE)-vector, nonviral ministring DNA vector (linear-covalently closed DNA vector), or dumbbell-shaped DNA minimal vector ("dumbbell DNA").

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

As used herein, the term "sequence identity" refers to the relatedness between two nucleotide sequences. For purposes of the present disclosure, the degree of sequence identity between two deoxyribonucleotide sequences is determined using the Needleman-Wunsch algorithm (Needleman and Wunsch, 1970, supra) as implemented in the Needle program of the EMBOSS® package (EMBOSS®: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS® version of NCBI NUC4.4) substitution matrix. The output of Needle labeled "longest identity" (obtained using the -nobrief option) is used as the percent identity and is calculated as follows: (Identical Deoxyribonucleotides.times.100)/(Length of Alignment-Total Number of Gaps in Alignment). The length of the alignment is preferably at least 10 nucleotides, preferably at least 25 nucleotides more preferred at least 50 nucleotides and most preferred at least 100 nucleotides.

As used herein, the term "homology" or "homologous" as used herein is defined as the percentage of nucleotide residues in the homology arm that are identical to the nucleotide residues in the corresponding sequence on the target chromosome, after aligning the sequences and introducing gaps, if necessary, to achieve the maximum percent sequence identity. Alignment for purposes of determining percent nucleotide sequence homology can be achieved in various ways that are within the skill in the art, for instance, using publicly available computer software such as BLAST®, BLAST®-2, ALIGN, ClustalW2 or Megalign (DNASTAR®) software. Those skilled in the art can determine appropriate parameters for aligning sequences, including any algorithms needed to achieve maximal alignment over the full length of the sequences being compared. In some embodiments, a nucleic acid sequence (e.g., DNA sequence), for example of a homology arm of a repair template, is considered "homologous" when the sequence is at least 70%, at least 75%, at least 80%, at least 85%, at least 90%, at least 91%, at least 92%, at least 93%, at least 94%, at least 95%, at least 96%, at least 97%, at least 98%, at least 99%, or more, identical to the corresponding native or unedited nucleic acid sequence (e.g., genomic sequence) of the host cell.

As used herein, the term "heterologous," as used herein, means a nucleotide or polypeptide sequence that is not found in the native nucleic acid or protein, respectively. A heterologous nucleic acid sequence may be linked to a naturally occurring nucleic acid sequence (or a variant thereof) (e.g., by genetic engineering) to generate a chimeric nucleotide sequence encoding a chimeric polypeptide. A heterologous nucleic acid sequence may be linked to a variant polypeptide (e.g., by genetic engineering) to generate a nucleotide sequence encoding a fusion variant polypeptide.

As used herein, a "vector" or "expression vector" is a replicon, such as plasmid, bacmid, phage, virus, virion, or cosmid, to which another DNA segment, i.e. an "insert" "transgene" or "expression cassette", may be attached so as to bring about the expression or replication of the attached segment ("expression cassette") in a cell. A vector can be a nucleic acid construct designed for delivery to a host cell or for transfer between different host cells. As used herein, a vector can be viral or non-viral in origin in the final form. However, for the purpose of the present disclosure, a "vector" generally refers to synthetic AAV vector or a nicked ceDNA vector. Accordingly, the term "vector" encompasses any genetic element that is capable of replication when associated with the proper control elements and that can transfer gene sequences to cells. In some embodiments, a vector can be a recombinant vector or an expression vector.

As used herein, the phrase "recombinant vector" means a vector that includes a heterologous nucleic acid sequence, or "transgene" that is capable of expression in vivo. It is to be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the term "expression vector" refers to a vector that directs expression of an RNA or polypeptide from sequences linked to transcriptional regulatory sequences on the vector. The sequences expressed will often, but not necessarily, be heterologous to the host cell. An expression vector may comprise additional elements, for example, the expression vector may have two replication systems, thus allowing it to be maintained in two organisms, for example in human cells for expression and in a prokaryotic host for cloning and amplification, the expression vector may be a recombinant vector.

As used herein, the term "expression" refers to the cellular processes involved in producing RNA and proteins and as appropriate, secreting proteins, including where applicable, but not limited to, for example, transcription, transcript processing, translation and protein folding, modification and processing.

As used herein, the phrase "expression products" include RNA transcribed from a gene (e.g., transgene), and polypeptides obtained by translation of mRNA transcribed from a gene.

As used herein, the term "gene" means the nucleic acid sequence which is transcribed (DNA) to RNA in vitro or in vivo when operably linked to appropriate regulatory sequences. The gene may or may not include regions preceding and following the coding region, e.g., 5' untranslated region (5'UTR) or "leader" sequences and 3' UTR or "trailer" sequences, as well as intervening sequences (introns) between individual coding segments (exons).

The phrase "genetic disease" as used herein refers to a disease, partially or completely, directly or indirectly, caused by one or more abnormalities in the genome, especially a condition that is present from birth and can be treated by neDNA or synthetic AAV described herein. The abnormality may be a mutation, an insertion or a deletion. The abnormality may affect the coding sequence of the gene or its regulatory sequence. The genetic disease may be, but not limited to phenylketonuria (PKU), sickle-cell anemia, melanoma, hemophilia A (clotting factor VIII (FVIII) deficiency)

and hemophilia B (clotting factor IX (FIX) deficiency), cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and mucopolysaccharide storage diseases (e.g., Hurler syndrome (MPS Type I), Scheie syndrome (MPS Type I S), Hurler-Scheie syndrome (MPS Type I H-S), Hunter syndrome (MPS Type II), Sanfilippo Types A, B, C, and D (MPS Types III A, B, C, and D), Morquio Types A and B (MPS IVA and MPS IVB), Maroteaux-Lamy syndrome (MPS Type VI), Sly syndrome (MPS Type VII), hyaluronidase deficiency (MPS Type IX)), Niemann-Pick Disease Types A/B, C1 and C2, Fabry disease, Schindler disease, GM2-gangliosidosis Type II (Sandhoff Disease), Tay-Sachs disease, Metachromatic Leukodystrophy, Krabbe disease, Mucolipidosis Type I, II/III and IV, Sialidosis Types I and II, Glycogen Storage disease Types I and II (Pompe disease), Gaucher disease Types I, II and III, Fabry disease, cystinosis, Batten disease, Aspartylglucosaminuria, Salla disease, Danon disease (LAMP-2 deficiency), Lysosomal Acid Lipase (LAL) deficiency, neuronal ceroid lipofuscinoses (CLN1-8, INCL, and LINCL), sphingolipidoses, galactosialidosis. Also included in genetic disorders are amyotrophic lateral sclerosis (ALS), Parkinson's disease, Alzheimer's disease, Huntington's disease, spinocerebellar ataxia, spinal muscular atrophy, Friedreich's ataxia, Duchenne muscular dystrophy (DMD), Becker muscular dystrophies (BMD), dystrophic epidermolysis bullosa (DEB), ectonucleotide pyrophosphatase 1 deficiency, generalized arterial calcification of infancy (GACI), Leber Congenital Amaurosis (LCA, e.g., LCA10 [CEP290]), Stargardt macular dystrophy (ABCA4), or Cathepsin A deficiency.

As used herein, the term "synthetic AAV vector" and "synthetic production of AAV vector" refers to an AAV vector and synthetic production methods thereof in a cell-free environment.

As used herein the term "comprising" or "comprises" is used in reference to compositions, methods, processes, and respective component(s) thereof, that are essential to the processes, methods or compositions, yet open to the inclusion of unspecified elements, whether essential or not. The use of "comprising" indicates inclusion rather than limitation.

The term "consisting of" refers to compositions, methods, processes, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below.

The abbreviation, "e.g." is derived from the Latin exempli gratia and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

II. Detailed Synthetic Production Methods of neDNA

The technology described herein is directed in general to methods for generating various compositions of closed-ended DNA vectors having a gap or nick 5' upstream and/or 3' downstream of an expression cassette (neDNA), without using cells or cell lines. It is an advantage of the methods described herein that the resulting vectors have fewer impurities than comparable vectors made using conventional cell production methodologies.

A. General Synthetic Production Method

The methods and compositions provided herein are based, in part, on the discovery of synthetic and cell-free production processes and methods useful for generating a closed-ended DNA (ceDNA with ITRs) having one or more gaps located 5' upstream and/or 3' downstream of an expression cassette ("nicked ceDNA" or "neDNA"). The methods and compositions provided herein are also based, in part, on the discovery of synthetic and cell-free production processes and methods useful for generating an AAV vector (a single stranded DNA) with a specific combination of ITRs on 5' and/or 3' ends. neDNA vectors or synthetic AAV created according the present invention have fewer impurities and/or a higher yield of a desired vector construct as compared to DNA vectors produced in a cell culture environment (e.g., an insect cell line such as the Sf9 cell line, yeast cells, or mammalian cell lines, such as HEK 293). The synthetic vectors made according to the production process disclosed herein can be readily streamlined and made more efficient and cost-effective relative to traditional cell-based production, for example, current methods involving baculoviral vectors and Sf9 insect cell lines. Hence, neDNA and synthetic AAV vectors can be synthesized in a large quantity in a highly controlled cell-free environment with improved purity. Furthermore, it is disclosed herein that neDNA compositions can be delivered efficiently into the cell such as human hepatocytes and can stably express a transgene contained therein at a level that is equivalent or superior to ceDNA or AAV produced from Sf9 insect cell-line.

According to some embodiments, the methods and/or production steps of the present disclosure are carried out entirely in a cell-free environment. According to some embodiments, the methods and/or production steps of the present disclosure are carried out partially in a cell-free environment.

In the present invention, it is to be understood that cells are not employed to replicate any of the DNA vectors disclosed herein, and thus the production process of the present invention can be potentially conducted in an entirely cell-free environment if it is desired. However, depending on a starting material, some DNA components can be derived from nucleotide fragments originally prepared in a cell (e.g., plasmid-ceDNA, AAV vectors produced from insect cells). In some embodiments, non-viral nicked ceDNA (neDNA vector having one or more gaps or nicks) can be synthesized according to a cell-free method described herein. In some embodiments, non-viral neDNA can be prepared by introducing a nick or gap at a desired location and length in an existing ceDNA vector produced by cellular replication (e.g., in insect or mammalian cell lines) having a designed sequence of a nicking endonuclease binding site at the stem of an ITR. In other embodiments, synthetic AAV vectors (single stranded DNA expression vector having self-annealed double stranded ITRs with terminal resolution sites on both ends) can also be synthesized in a cell-free method. In some embodiments, provided herein is a method of synthesizing nicked ceDNA vectors (neDNA) without using insect cells. Also provided herein are nicked closed-ended DNA vector compositions produced using the synthetic production methods, including various neDNA vectors with variant ITRs, and the use of such neDNA vectors.

The present invention relates to an in vitro process for production of neDNA vectors, corresponding DNA vector products produced by the methods herein and uses thereof, and oligonucleotides and kits useful in the process of the invention.

Further, the neDNA vectors and synthetic AAV vectors made by the methods described herein are advantageous over other vectors in that they can be used more safely to express a transgene in a cell, tissue or subject. That is, undesirable side effects can potentially be minimized by generating the linear vectors by such cell-free methods since the resulting vectors are free of bacterial or insect cell contaminants. The synthetic production methods may also result in greater purity of the desired vector. The synthetic production method may also be more efficient and/or cost effective than traditional cell-based production methods for such vectors. Furthermore, synthetically produced neDNA can be used as a therapeutic agent as it can be stably transformed or transfected into the cells of a recipient or subject and express a transgene at levels that are equivalent or even superior to those of conventional closed-ended linear duplex DNAs. The vectors synthesized as described herein can express any desired transgene, for example, a transgene to treat or cure a given disease. One of ordinary skill in the art will readily recognize that any transgene used in conventional gene therapy methods with conventional recombinant vectors can be adapted for expression by e.g., neDNA or synthetic AAV vectors made by the synthetic methods described herein, particularly without limitations of the size capacity of a transgene insert.

In some embodiments, disclosed herein is a process for synthesis of neDNA vectors which does not require use of any viral replication steps. In some embodiments, the process allows for synthesis of neDNA vectors in a system using enzymatic cleavage steps using restriction endonucleases and ligases to generate the neDNA vectors. In some embodiments, the synthetic system for DNA vector production is a cell-free system.

It will be appreciated by one of ordinary skill in the art that one or more enzymes for the synthetic production method or one or more of the oligonucleotide components can be produced from a cell and used in the methods of the invention in purified form. Accordingly, in some embodiments, the synthetic production method is a cell-free method, however, a restriction enzyme and/or ligase enzyme can be produced from a cell.

In one embodiment, a restriction endonuclease and/or a ligation-competent protein can be expressed or provided from an expression vector in a cell, e.g., bacterial cell. In one embodiment, a cell, such as a bacterial cell, comprising an expression vector expressing one or more of the restriction endonucleases or the ligase enzymes can be present. Therefore, while the methods disclosed herein are primarily directed to cell-free synthetic methods to generate the DNA vectors disclosed herein, also encompassed in some embodiments are synthetic production methods where a cell, e.g., a bacterial cell, but not an insect cell, is present and can be used to express one or more of the enzymes required in the method. In such embodiments, the cell expressing a restriction endonuclease and/or ligation-competent protein is not an insect cell. In all embodiments where a cell is present and expresses one or more restriction endonucleases or ligation-competent proteins, the cell does not replicate the neDNA vector. Stated differently, the intracellular machinery of the cell does not replicate, or is not involved in the replication of the DNA vector.

In some embodiments, synthesis of neDNA vectors described herein is carried out in an in vitro cell-free process starting from either a double-stranded DNA construct or one or more oligonucleotides. The double-stranded DNA construct or one or more oligonucleotides are cleaved with restriction endonucleases and ligated to form the DNA molecules. In some embodiments, the oligonucleotides are synthesized chemically, thus avoiding use of large starting templates encoding the entirety of the desired sequence which would typically need to be propagated in bacteria. Once a desired DNA sequence is synthesized, it can be cleaved and ligated with other oligonucleotides as disclosed herein. The use of multiple oligonucleotides in the generation of closed-ended DNA vectors using the methods disclosed herein allows for a modular approach to DNA vector generation, enabling tailoring and/or specific selection of the terminal repeats, e.g., ITRs, as well as the spacing of the terminal repeats, the location and length of nicks or gaps and also selection of the heterologous nucleic acid sequence in the synthetically produced neDNA vectors.

B. Synthetic Production of DNA Vectors

Certain methods for the production of a closed-ended DNA vector comprising various ITR configurations using cell-based methods are described in Example 1 of International applications PCT/US18/49996, filed Sep. 7, 2018, and PCT/US2018/064242, filed Dec. 6, 2018 each of which are incorporated herein in their entireties by reference.

In contrast to the cell-based methods, the methods provided herein relate to a synthetic production method, e.g., in some embodiments, a cell-free production method, also referred to herein as "synthetic neDNA vector production" or "synthetic AAV vector production".

In some embodiments, the synthetic production method is a cell-free method, e.g., insect cell-free method. In some embodiments, the synthetic production method occurs in the absence of bacmids, or baculovirus, or both. In alternative embodiments, the synthetic production method can encompass use of cells, e.g., bacterial cells, cells expressing a restriction endonuclease, and/or ligation-competent Rep protein, or the like. In such an embodiment, the cells can be a cell line that has a polynucleotide vector template stably integrated, and can be used to introduce a restriction endonuclease protein and/or a ligase competent protein e.g., such as but not limited to, a Rep protein to the reaction mixture comprising the oligonucleotides used in the synthetic production methods described herein. It is to be understood that, where the synthetic production method encompasses the use of a cell, the cell does not replicate the neDNA vector.

Figure 4:
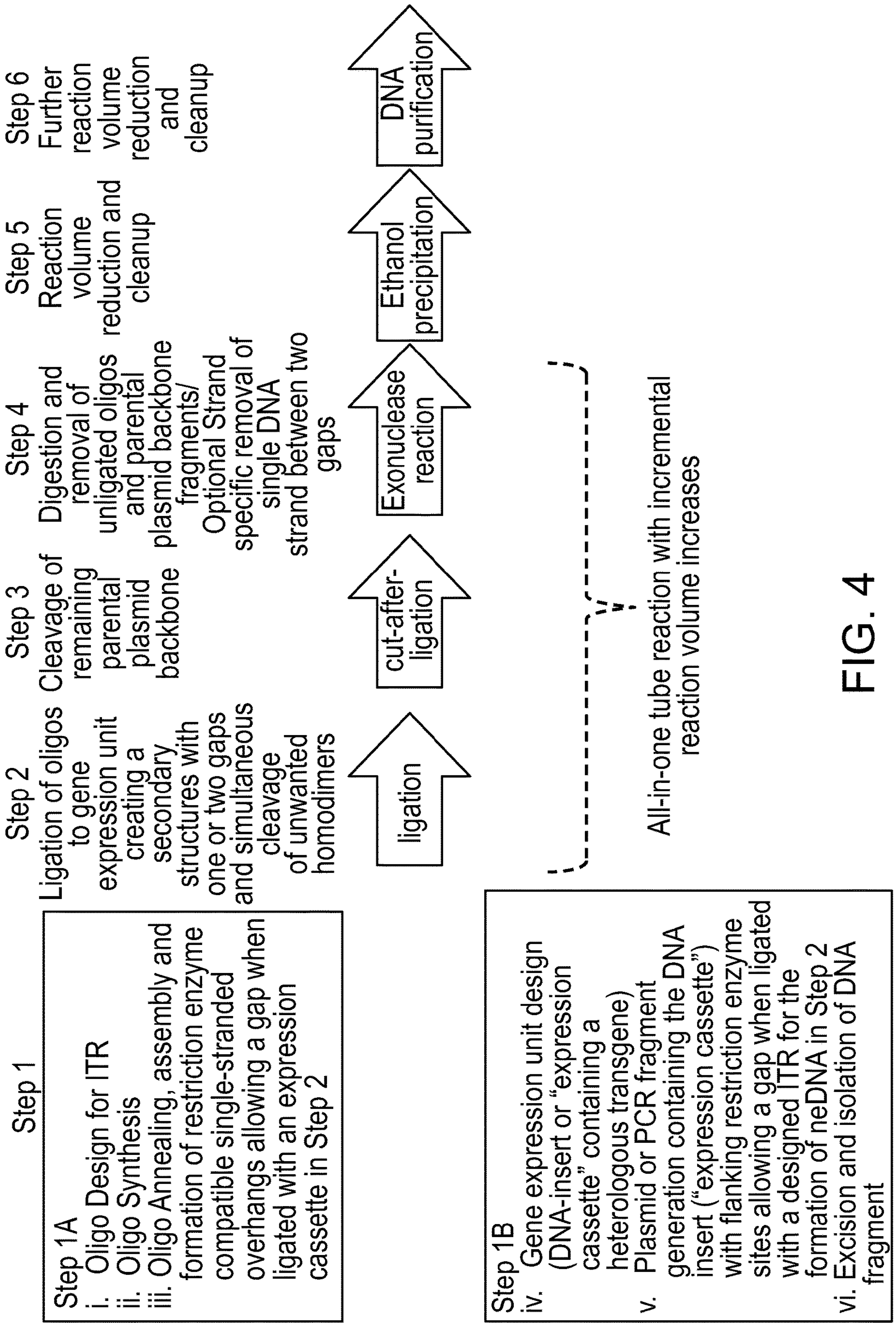
FIG. 4 is a schematic description of an exemplary method used to prepare neDNA vector and AAV vector synthetically.

Examples of the process for generating and isolating neDNA vectors produced using the synthetic production method are exemplified in FIG. 4 and the Examples section below.

According to aspects of the synthetic production methods to generate neDNA vectors as disclosed herein, the ligation step can be a chemical ligation step or an enzymatic ligation step. In some embodiments, ligation can be conducted using a ligation-competent enzyme, e.g., DNA ligase such as T4 ligase, e.g., to ligate 5' and 3' sticky overhangs, or blunt ends. In some embodiments, the ligation enzyme is a ligase enzyme other than a Rep protein. In some embodiments, the ligation enzyme is an AAV Rep protein.

While the methods disclosed herein are primarily directed to cell-free synthetic methods to generate the closed-ended DNA vectors disclosed herein, also encompassed are synthetic production methods where a cell, e.g., a bacterial cell, can be used to express one or more of the DNA fragments used in the method.

(i) Synthetic Production Using 5' and 3' ITR Oligonucleotides

Figure 5:
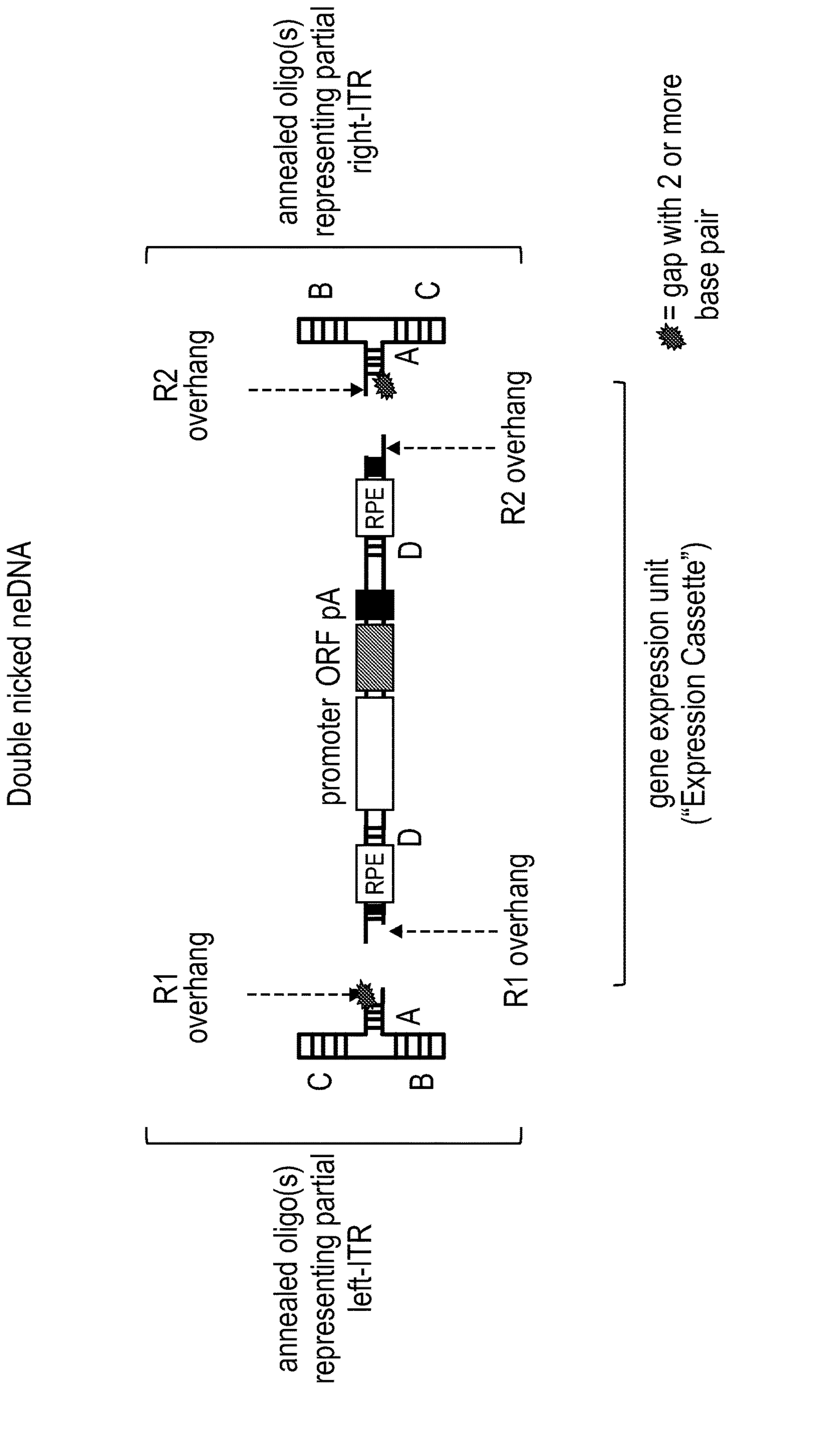
FIG. 5 is a schematic description of neDNA synthesis using two sets of oligonucleotides, one for R-ITR and the other for L-ITR, each of which comprises an overhang sequence and can be ligated with an expression cassette, creating a single gap (1-100 base pair) upon assembly and ligation.
Figure 6:
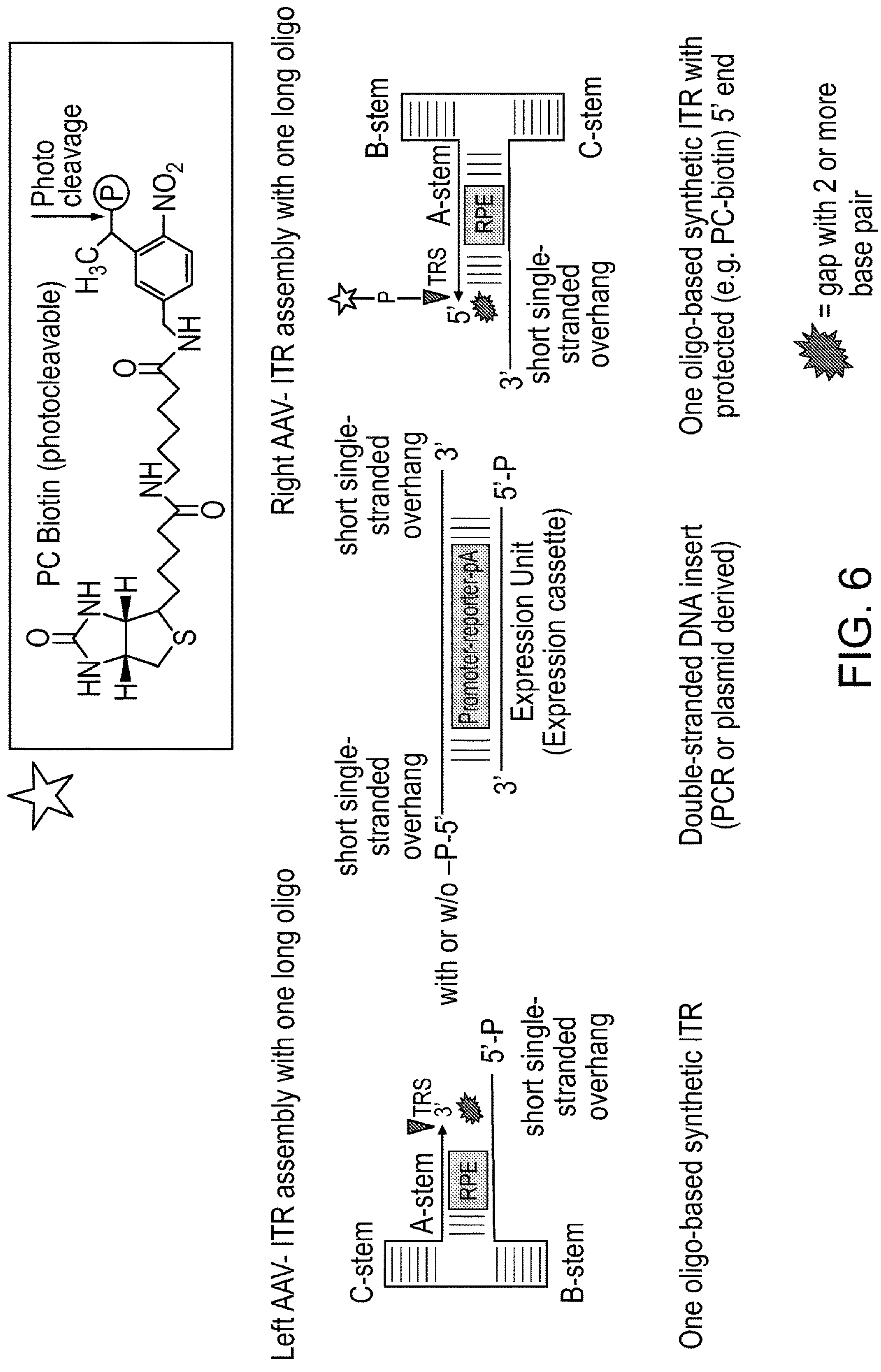
FIG. 6 is a schematic description of neDNA synthesis using two sets of oligonucleotides, one for R-ITR and the other for L-ITR, each of which comprises an overhang sequence and can be ligated with an expression cassette, creating two gaps (each with 1-100 base pair in length) 5' upstream and 3' downstream of the expression cassette upon assembly and ligation.
Figure 7A:
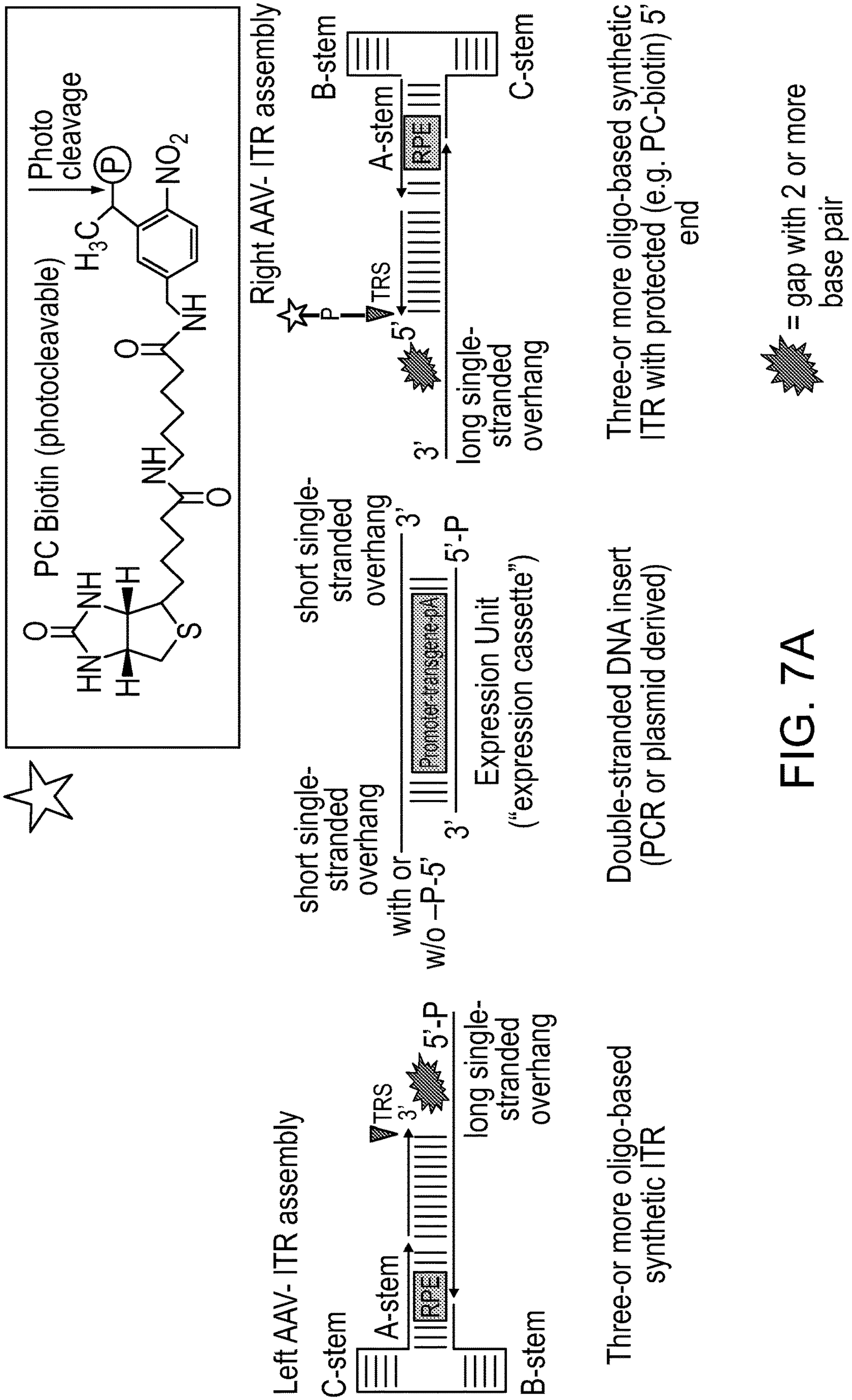
FIG. 7A illustrates a schematic description of neDNA synthesis using three oligonucleotides for each of R-ITR and L-ITR comprising an overhang, and when ligated with an expression vector, they create a gap of 1-100 base pairs.

According to another aspect, the disclosure provides a method or producing a neDNA vector comprising a) synthesizing (and/or providing) a first single-stranded ITR molecule comprising a first ITR; b) synthesizing (and/or providing) a second single-stranded ITR molecule comprising a second ITR; c) providing a double-stranded polynucleotide comprising an expression cassette sequence; and d) ligating the 5' and 3' ends of the first ITR molecule to a first end of the double-stranded molecule and ligating the 5' and 3' ends of the second ITR molecule to the second end of the double stranded molecule to form the neDNA vector. Prior to the ligation step, the ITR molecules and/or the double-stranded polynucleotide can be contacted with restriction enzymes to generate compatible ends, e.g., overhangs to ensure proper ligation at the desired locations. In some embodiments, the three elements are provided as shown in FIGS. 7A and B. The ligations of the each ITR with the double-stranded polynucleotide can be sequential or concurrent. In one embodiment, the ligation step involves ligation of a single stranded 5' to 3' oligonucleotide that forms a hairpin. In such an embodiment, a neDNA vector is produced by synthesizing a 5' and a 3' ITR oligonucleotide, which in some embodiments, are in a hairpin or other three-dimensional configuration (e.g., T- or Y-Holliday junction configuration), and ligating the 5' and 3' ITR oligonucleotides to a double-stranded polynucleotide comprising an expression cassette or heterologous nucleic acid sequence. Optionally, a step is added subjecting the oligo(s) to conditions that facilitate the folding (self-annealing) of the oligonucleotide(s) into a three-dimensional configuration prior to the ligation step. FIGS. 5-7 show an exemplary method of generating a neDNA vector comprising ligating a 5' ITR oligonucleotide and a 3' ITR oligonucleotide to a double-stranded polynucleotide comprising an expression cassette. Exemplary methods of creating a gap by designing various sequence and number of oligonucleotides used in making left and right ITRs with a spacer are described in detail in FIGS. 8 and 9.

In some embodiments, the 5' and 3' ITR with the stem region spacer sequence in the hairpin can be independently prepared by one oligonucleotide for each ITR using the method generally described in FIG. 6. In one embodiment, the 5' ITR with the stem region spacer sequence can be prepared by using one oligonucleotide as shown in FIG. 6. In one embodiment, the 3' ITR with the stem region spacer sequence can be prepared by using one oligonucleotide as shown in FIG. 6.

In some other embodiments, the 5' and 3' ITRs can be independently prepared by more than one oligonucleotide (e.g., two, three, four, five or six oligonucleotides) by the method generally described in FIG. 7A for each of the 5' and 3' ITRs. In one embodiment, the 5' ITR with the stem region spacer sequence can be prepared by three oligonucleotides as in FIG. 7A. In one embodiment, the 3' ITR with the stem region spacer sequence can be prepared by three oligonucleotides as in FIG. 7A.

In these embodiments, it is to be understood that since the 5' and 3' ITRs can be independently prepared and provided sequentially for sequential ligation or simultaneously for one reaction ligation, the present invention contemplates the use of the 5' ITR with a stem region spacer sequence to be independently made out of, e.g., the one oligonucleotide synthesis scheme or the multiple oligonucleotides (e.g., two or three oligonucleotides based) synthesis scheme, and the 3' ITR with a stem region spacer sequence be independently made out of, e.g., one oligo-based synthesis scheme or the multiple oligonucleotides based (e.g., two or three oligonucleotides based) synthesis scheme. One particular example of such asymmetric ITR synthesis method is described in the FIG. 7B. Further, the present invention is not limited by the number of oligonucleotides to be implemented or the length of the gap in the ITR within a stem region spacer sequence as long as the vector can be designed and made in accordance of synthetic methods describe herein and a gap can be introduced.

As such, in some embodiments, the 5' and 3' ITR oligonucleotides are independently 5' and 3' stem loop hairpin oligonucleotides or have a different three-dimensional configuration (e.g., Holliday junction) with respect to each other, and can optionally be provided by in vitro DNA synthesis. In some embodiments, the 5' and a 3' ITR oligonucleotides have been cleaved with a restriction endonuclease to have complementary sticky ends to the double-stranded polynucleotide (e.g., an expression cassette comprising a promoter, transgene and poly-A) that has corresponding restriction endonuclease sticky ends. In some embodiments, the ends of the hairpin of the 5' ITR oligonucleotide having a gap has a sticky end that is complementary to the 5' sense strand and 3' antisense strand of the double-stranded polynucleotide. In some embodiments, the end of the hairpin of the 3' ITR oligonucleotide optionally having a gap has a sticky end that is complementary to the 3' sense strand and 5' antisense strand of the double-stranded polynucleotide (e.g., an expression cassette comprising a promoter, transgene and poly-A). In some embodiments, the gap can be present only in a 5' ITR stem region and not present in 3' ITR oligonucleotide. In some other embodiments, the gap can be present in the 3' ITR stem region only.

In some embodiments, the ends of the hairpin of the 5' ITR oligonucleotide and the 3' ITR oligonucleotide have different restriction endonuclease sticky ends, such that directed ligation to the double-stranded polynucleotide can be achieved (e.g., an expression cassette comprising a promoter, transgene and poly-A). In some embodiments, ligation can be performed sequentially (e.g., a first ligation between 5' ITR with an expression cassette followed by a second ligation of 3' ITR with the ligated product 5'ITR and expression cassette). In some other embodiments, ligation can be performed in one reaction (e.g., ligation of 5' ITR and 3' ITR with an expression cassette). In some embodiments, the ends of one or both of the ITR oligonucleotides do not have overhangs and such ITR oligonucleotides are ligated to the double-stranded polynucleotide by blunt end-joining.

The ITR molecules in the foregoing method can be synthesized and/or ligated by any method known in the art. Various methods of synthesizing oligonucleotides and polynucleotides are known in the art, e.g., PCR, solid-phase DNA synthesis, phosphoramidite DNA synthesis, and etc. The ITR molecules can also be excised from a DNA construct (plasmid) comprising the ITR. Various methods of ligation nucleic acids are well known in the art, e.g., chemical ligation or ligation with ligation-competent protein, e.g., a T4 ligase, AAV Rep, or topoisomerase.

(ii) Synthetic Production Method from a Single-Stranded DNA

Another exemplary method of producing AAV or neDNA vector using the synthetic production method as disclosed herein uses a single-stranded linear DNA with closed ends and comprises two ITRs which flank an expression cassette, first in the sense direction followed by the antisense direction. Accordingly, in some embodiments, the method comprises a) synthesizing a single-stranded molecule containing, from 5' to 3': a sense first ITR; a sense expression cassette sequence; a sense second ITR; an antisense second ITR; an antisense expression cassette sequence; and an antisense first ITR;

b) facilitating the formation of at least one hairpin loop within the single stranded molecule (annealing); and c) ligating the 5' and 3' ends to form the neDNA vector.

Various methods of synthesizing oligonucleotides and polynucleotides are known in the art, e.g., in vitro or in silico synthesis of oligonucleotides and any method known in the art can be used in step a).

As described herein, the neDNA vector is produced by providing a single-stranded linear DNA sequence encoding the expression cassette flanked by sense and antisense ITRs, which is then made closed-ended by ligation. Using the production of a neDNA vector as an exemplary nicked closed-ended DNA vector produced according to embodiments of the disclosure, a single-stranded DNA molecule for production of a neDNA vector comprises, from 5' to 3':

a) a sense first ITR;

b) a 5' gap c) a sense expression cassette sequence;

d) a 3' gap e) a sense second ITR;

f) an antisense second ITR;

g) an antisense expression cassette sequence; and h) an antisense first ITR.

Examples of the process for generating neDNA vectors produced using the synthetic production method as disclosed herein are described in FIGS. 6.

In this exemplary method, the oligonucleotides are ligated in order as shown above, and the antisense first ITR complementary to the sense first ITR, and likewise the antisense second ITR and the antisense expression cassette sequence are complementary to the sense second ITR and the sense expression cassette sequence, respectively. The ligation step joins the free 5' and 3' ends and results in the formation of the closed-ended DNA vector, neDNA.

In all aspects of the synthetic production methods to generate closed-ended DNA vectors as disclosed herein, the ligation step can be a chemical ligation step or an enzymatic ligation step. In some embodiments, ligation can be conducted using a ligation-competent enzyme, e.g., DNA ligase, e.g., to ligate 5' and 3' sticky overhangs. However, upon ligation, it would leave at least a 1 base pair long gap. In some embodiments, the ligation enzyme is a ligase enzyme other than a Rep protein. In some embodiments, the ligation enzyme is an AAV Rep protein.

(iii) Synthetic Production Method not Requiring Ligation

According to some embodiments, the synthetic production of a neDNA vector is by synthesis of a single-stranded sequence comprising at least one ITR having a gap flanking an expression cassette sequence and which also comprises an antisense expression cassette sequence.

In one nonlimiting example, neDNA vector is produced by the method as follows. A single-stranded sequence comprising in order from 5' to 3': a sense first ITR; a sense expression cassette sequence; a sense second ITR; and an antisense expression cassette sequence is provided. In one embodiment the single-stranded sequence may be synthesized directly through any art-known method. In another embodiment, the single-stranded sequence may be constructed by joining by ligation two or more oligonucleotides comprising one or more of the sense first ITR, sense expression cassette sequence, sense second ITR and antisense expression cassette sequence. The single-stranded sequence may be obtained by excision of the sequence from a double-stranded DNA construct with subsequent separation of the strands from the excised double-stranded fragment. More specifically, a double-stranded DNA construct comprising a first restriction site, the sense first ITR, the sense expression cassette sequence, the sense second ITR, the antisense expression cassette sequence, and a second restriction site in 5' to 3' order is provided. The region between the two restriction endonuclease cleavage sites is excised by cleavage with at least one restriction endonuclease recognizing such cleavage site(s). The resulting excised double-stranded DNA fragment is treated such that the sense and antisense strands are separated into the desired single-stranded sequence fragments.

The single-stranded sequence is subjected to an annealing step to facilitate the formation of one or more hairpin loop by the sense first ITR and/or the sense second ITR, and the complementary binding of the sense expression cassette sequence to the antisense expression cassette sequence. The result is a gapped closed-ended structure that did not require ligation to form. Annealing parameters and techniques are well known in the art.

DNA vectors produced by the methods provided herein preferably have a linear and a non-continuous structure, as determined by restriction enzyme digestion assay. While the linear and noncontinuous structure is believed to be stable and facilitate cellular transcription activities by attracting transcriptional enzymes to the gapped site. Thus, vectors in the linear and noncontinuous gapped structure are preferred in some embodiments. The continuous, linear, single strand intramolecular duplex DNA vectors can have a gapped ITR, preferably 5' end stem structure, without sequences encoding AAV capsid proteins. These DNA vectors are structurally distinct from plasmids, which are circular duplex nucleic acid molecules of bacterial origin. The complimentary strands of plasmids may be separated following denaturation whereas these DNA-vectors have complimentary strands and are a single DNA molecule. Preferably, vectors can be produced without DNA base methylation of prokaryotic type unlike plasmids.

(iv) Synthetic Production Method from a Double Stranded DNA Construct Using Nicking Enzymes According to some embodiments, synthetic neDNA can be produced from fully functional ceDNA, whether synthetically produced or replicated from insect or mammalian cell-line, by using an enzyme that hydrolyzes only one strand of the duplex, to produce a nick or gap in ceDNA using one or more nicking enzymes bind to the designed binding sequence in the 5' and/or 3' ITR stem region. Optionally, nucleases such as T7 exo or Exo V can be further employed to remove additional base pairs to create a wider gap or even AAV vector if two nicks (one in the 5' ITR and the other in the 3' ITR) are present to stop to T7 Exo or Exo V nucleases, preventing them from digesting beyond TRS and progressing into the ITR regions (see, FIGS. 12 and 13). The conventional nicks (3'-hydroxyl, 5'-phosphate) can serve as initiation points for variety of enzymatic reaction, such as endonuclease or exonuclease reaction to remove one strand to yield a synthetic AAV vector or creating a short gap desirable in neDNA. Suitable nicking enzymes (nicking endonucleases) include, but are not limited to, BstNBI, BtsI, and BsrDI, which are the large subunits of heterodimeric restriction enzymes that are entirely devoid of small subunits that catalyzes cleavage of the other strand. Thus, this physical property allows for the one-strand specific nicking activity, rather than the double strand cleavage activity. Furthermore, nicking/gapping sites can be readily introduced by introducing nicking enzyme binding sequences into the ITR stem region spacer sequences.

C. Isolating and Purifying neDNA Vectors

Methods to generate and isolate a neDNA vector are described herein. For example, neDNA vector produced by the synthetic methods described herein can be harvested or collected at an appropriate time after the last ligation reaction and can be optimized to achieve a high-yield production of the neDNA vectors. neDNA vectors can be purified by any means known to those of skill in the art for purification of DNA. In one embodiment, neDNA vectors are purified as DNA molecules. Generally, any art-known nucleic acid purification methods can be adopted, as well as commercially available DNA extraction kits.

Purification can be implemented by subjecting a reaction mixture to chromatographic separation. As one non-limiting example, the process can be performed by loading the reaction mixture on an ion exchange column (e.g., SARTOBIND Q®) which retains nucleic acids, and then eluting (e.g., with a 1.2 M NaCl solution) and performing a further chromatographic purification on a gel filtration column (e.g., 6 fast flow GE). The DNA vector, e.g., neDNA vector is then recovered by, e.g., precipitation.

The presence of the neDNA vector can be confirmed by digesting the vector DNA isolated from the cells with a restriction enzyme having a single recognition site on the DNA vector and analyzing both digested and undigested DNA material using gel electrophoresis to confirm the presence of characteristic bands of linear and continuous DNA as compared to linear and non-continuous DNA as known in the art.

In some embodiments, the neDNA vectors produced by the synthetic production methods disclosed herein can be delivered to a target cell in vitro or in vivo by various suitable methods as discussed herein. Vectors alone can be applied or injected. Vectors can be delivered to a cell without the help of a transfection reagent or other physical means. Alternatively, vectors can be delivered using a transfection reagent or other physical means that facilitates entry of DNA into a cell, e.g., liposomes, alcohols, polylysine-rich compounds, arginine-rich compounds calcium phosphate, microvesicles, microinjection, and the like.

D. Other DNA Vectors Produced Using the Synthetic Production Method

Provided herein are various methods of in vitro production of neDNA vectors. In some embodiments, the neDNA vector is, e.g., a dumbbell DNA vector or a dog-bone DNA vector (see e.g., WO2010/0086626, the contents of which is incorporated by reference herein in its entirety) in terms of the physical properties of ITRs.

III. Compositions of neDNA Vector in General

In some embodiments, a nicked/gapped closed-ended DNA vector produced using the synthetic process as described herein is a neDNA vector, including neDNA vectors that can express a transgene stably in a host cell (e.g., mammalian cells). The neDNA vectors described herein are not limited by size, thereby permitting, for example, expression of all of the components necessary for expression of a transgene from a single vector. The neDNA vector is preferably duplex, e.g., self-complementary, over at least a portion of the molecule, such as the expression cassette (e.g., neDNA is not a double stranded circular molecule). The neDNA vector has covalently closed ends on either ends of the linear duplex, but having one or more gaps in the 5' and/or 3' ITR stem region spacer sequences, and thus is sensitive to exonuclease digestion.

In general, a neDNA vector produced using the synthetic process as described herein, comprises in the 5' to 3' direction: a first adeno-associated virus (AAV) inverted terminal repeat (ITR), a nucleotide sequence of interest (for example an expression cassette as described herein) and a second AAV ITR. The ITR sequences selected from any of: (i) at least one WT ITR and at least one modified AAV inverted terminal repeat (mod-ITR) (e.g., asymmetric modified ITRs); (ii) two modified ITRs where the mod-ITR pair have a different three-dimensional spatial organization with respect to each other (e.g., asymmetric modified ITRs), or (iii) symmetrical or substantially symmetrical WT-WT ITR pair, where each WT-ITR has the same three-dimensional spatial organization, or (iv) symmetrical or substantially symmetrical modified ITR pair, where each mod-ITR has the same three-dimensional spatial organization.

The one or more gaps are present in the spacer or stem structure of at least one of 5' and 3' ITRs. The gap can be located 5' upstream and/or 3' downstream of an expression cassette. In some embodiments, the gap is in the terminal resolution site (TRS). In other embodiments, the gap is upstream of a TRS adjacent to 5' of a transgene or down stream of TRS adjacent to 3' end of a transgene.

Encompassed herein are methods and compositions comprising the neDNA vector produced using the synthetic process as described herein, which may further include a delivery system, such as but not limited to, a liposome nanoparticle delivery system. Non-limiting exemplary liposome nanoparticle systems encompassed for use are disclosed herein. In some aspects, the disclosure provides for a lipid nanoparticle comprising neDNA and an ionizable lipid. For example, a lipid nanoparticle formulation that is made and loaded with a neDNA vector obtained by the process is disclosed in International Application PCT/US2018/050042, filed on Sep. 7, 2018, which is incorporated herein.

The neDNA vectors or synthetic AAV produced using the synthetic process as described herein have no packaging constraints imposed by the limiting space within the viral capsid. This permits the insertion of control elements, e.g., regulatory switches as disclosed herein, large transgenes, multiple transgenes etc.

FIG. 1A-1E in general show schematics of non-limiting, exemplary neDNA vectors, or the corresponding sequence of neDNA plasmids. neDNA vectors are capsid-free and can be obtained from synthetic production or a plasmid. neDNA is in general in the order a first ITR with a gap, an expression cassette comprising a transgene and a second ITR optionally with a gap.

A. Expression Cassettes

The expression cassette may comprise a transgene and one or more regulatory sequences that allows and/or controls the expression of the transgene, e.g., where the expression cassette can comprise one or more of, in this order: an enhancer/promoter, an ORF reporter (transgene), a post-transcription regulatory element (e.g., WPRE), and a polyadenylation and termination signal (e.g., BGH polyA). The expression cassette can also comprise an internal ribosome entry site (IRES) and/or a 2A element. The cis-regulatory elements include, but are not limited to, a promoter, a riboswitch, an insulator, a mir-regulatable element, a post-transcriptional regulatory element, a tissue- and cell type-specific promoter and an enhancer. In some embodiments the ITR can act as the promoter for the transgene. In some embodiments, the neDNA vector comprises additional components to regulate expression of the transgene, for example, a regulatory switch, which are described herein in the section entitled "Regulatory Switches" for controlling and regulating the expression of the transgene, and can include if desired, a regulatory switch which is a kill switch to enable controlled cell death of a cell comprising a neDNA vector.

The expression cassette can comprise more than 4000 nucleotides, 5000 nucleotides, 10,000 nucleotides or 20,000 nucleotides, or 30,000 nucleotides, or 40,000 nucleotides or 50,000 nucleotides, or any range between about 4000-10,000 nucleotides or 10,000-50,000 nucleotides, or more than 50,000 nucleotides. In some embodiments, the expression cassette can comprise a transgene in the range of 500 to 50,000 nucleotides in length. In some embodiments, the expression cassette can comprise a transgene in the range of 500 to 75,000 nucleotides in length. In some embodiments, the expression cassette can comprise a transgene which is in the range of 500 to 10,000 nucleotides in length. In some embodiments, the expression cassette can comprise a transgene which is in the range of 1000 to 10,000 nucleotides in length. In some embodiments, the expression cassette can comprise a transgene which is in the range of 500 to 5,000 nucleotides in length. The neDNA vectors do not have the size limitations of encapsidated AAV vectors, thus enable delivery of a large-size expression cassette to provide efficient transgene. In some embodiments, the neDNA vector is devoid of prokaryote-specific methylation.

A neDNA expression cassette can include, for example, an expressible exogenous sequence (e.g., open reading frame) or transgene that encodes a protein that is either absent, inactive, or insufficient activity in the recipient subject or a gene that encodes a protein having a desired biological or a therapeutic effect. The transgene can encode a gene product that can function to correct the expression of a defective gene or transcript. In principle, the expression cassette can include any gene that encodes a protein, polypeptide or RNA that is either reduced or absent due to a mutation or which conveys a therapeutic benefit when overexpressed is considered to be within the scope of the disclosure.

The expression cassette can comprise any transgene useful for treating a disease or disorder in a subject. A neDNA vector produced using the synthetic process as described herein can be used to deliver and express any gene of interest in the subject, which includes but are not limited to, nucleic acids encoding polypeptides, or non-coding nucleic acids (e.g., RNAi, miRs etc.), as well as exogenous genes and nucleotide sequences, including virus sequences in a subjects' genome, e.g., HIV virus sequences and the like. Preferably a neDNA vector disclosed herein is used for therapeutic purposes (e.g., for medical, diagnostic, or veterinary uses) or immunogenic polypeptides. In certain embodiments, a neDNA vector is useful to express any gene of interest in the subject, which includes one or more polypeptides, peptides, ribozymes, peptide nucleic acids, siRNAs, RNAis, antisense oligonucleotides, antisense polynucleotides, or RNAs (coding or non-coding; e.g., siRNAs, shRNAs, micro-RNAs, and their antisense counterparts (e.g., antagoMiR)), antibodies, antigen binding fragments, or any combination thereof.

The expression cassette can also encode polypeptides, sense or antisense oligonucleotides, or RNAs (coding or non-coding; e.g., siRNAs, shRNAs, micro-RNAs, and their antisense counterparts (e.g., antagoMiR)). Expression cassettes can include an exogenous sequence that encodes a reporter protein to be used for experimental or diagnostic purposes, such as β-lactamase, β-galactosidase (LacZ), alkaline phosphatase, thymidine kinase, green fluorescent protein (GFP), chloramphenicol acetyltransferase (CAT), luciferase, and others well known in the art.

Sequences provided in the expression cassette, expression construct of a neDNA vector described herein can be codon optimized for the target host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen®'s GENE FORGE® codon optimization and custom gene synthesis platform (Aptagen®, Inc., 2190 Fox Mill Rd. Suite 300, Herndon, Va. 20171) or another publicly available database.

In some embodiments, a transgene expressed by the neDNA vector is a therapeutic gene. In some embodiments, a therapeutic gene is an antibody, or antibody fragment, or antigen-binding fragment thereof, e.g., a neutralizing antibody or antibody fragment and the like.

In particular, a therapeutic gene is one or more therapeutic agent(s), including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a disease, dysfunction, injury, and/or disorder. Exemplary therapeutic genes are described herein in the section entitled "Method of Treatment".

There are many structural features of neDNA vectors that differ from plasmid-based expression vectors. neDNA vectors produced by the synthetic methods herein may possess one or more of the following features: the lack of original (i.e. not inserted) bacterial DNA, the lack of a prokaryotic origin of replication, being self-containing, i.e., they do not require any sequences other than the two ITRs, including the Rep binding and terminal resolution sites (RBS and TRS), and an exogenous sequence between the ITRs, the presence of ITR sequences that form hairpins, and the absence of bacterial-type DNA methylation or indeed any other methylation associated with production in a given cell type and considered abnormal by a mammalian host. In general, it is preferred for the present vectors not to contain any prokaryotic DNA but it is contemplated that some prokaryotic DNA may be inserted as an exogenous sequence, as a non-limiting example in a promoter or enhancer region. Another important feature distinguishing neDNA vectors from plasmid expression vectors is that neDNA vectors are single-stranded linear DNA having closed ends, while plasmids are always double-stranded DNA.

neDNA vectors produced by the synthetic methods provided herein preferably have a linear non-continuous structure, as determined by restriction enzyme digestion assay. The linear and noncontinuous structure is believed to be stable and equivalent or superior expression capacity in host cells. Thus, a neDNA vector in the linear and noncontinuous "gapped" structure is a preferred embodiment. The continuous, linear, single strand intramolecular duplex neDNA vector can have covalently bound terminal ends, without sequences encoding AAV capsid proteins. These neDNA vectors are structurally distinct from plasmids (including neDNA plasmids), which are circular duplex nucleic acid molecules of bacterial origin. The complimentary strands of plasmids may be separated following denaturation to produce two nucleic acid molecules, whereas in contrast, neDNA vectors, while having complimentary strands, are a single DNA molecule and therefore even if denatured, remain a single molecule. In some embodiments, neDNA vectors as described herein can be produced without DNA base methylation of prokaryotic type, unlike plasmids. Therefore, the neDNA vectors and neDNA-plasmids or ceDNA-plasmid are different both in term of structure (in particular, linear versus circular) and also in view of the methods used for producing and purifying these different objects (see below), and also in view of their DNA methylation which is of prokaryotic type for neDNA-plasmids and of eukaryotic type for the neDNA vector.

There are several advantages of using a neDNA vector as described herein over plasmid-based expression vectors. Such advantages include, but are not limited to: 1) plasmids contain bacterial DNA sequences and are subjected to prokaryotic-specific methylation, e.g., 6-methyl adenosine and 5-methyl cytosine methylation, whereas capsid-free AAV vector sequences are of eukaryotic origin and do not undergo prokaryotic-specific methylation; as a result, capsid-free AAV vectors are less likely to induce inflammatory and immune responses compared to plasmids; 2) while plasmids require the presence of a resistance gene during the production process, neDNA vectors do not; 3) while a circular plasmid is not delivered to the nucleus upon introduction into a cell and requires overloading to bypass degradation by cellular nucleases, neDNA vectors contain viral cis-elements, i.e., ITRs, that confer resistance to nucleases and can be designed to be targeted and delivered to the nucleus. It is hypothesized that the minimal defining elements indispensable for ITR function are a Rep-binding site (RBS; 5'-GCGCGCTCGCTCGCTC-3' (SEQ ID NO: 1) for AAV2) and a terminal resolution site (TRS; 5'-AGTTGG-3' for AAV2) plus a variable palindromic sequence allowing for hairpin formation; and 4) neDNA vectors do not have the over-representation of CpG dinucleotides often found in prokaryote-derived plasmids that reportedly binds a member of the Toll-like family of receptors, eliciting a T cell-mediated immune response. In contrast, transductions with capsid-free AAV vectors disclosed herein can efficiently target cell and tissue-types that are difficult to transduce with conventional AAV virions using various delivery reagent.

B. Inverted Terminal Repeats (ITRs)

As disclosed herein, neDNA vectors contain a transgene or heterologous nucleic acid sequence positioned between two inverted terminal repeat (ITR) sequences, where the ITR sequences can be an asymmetrical ITR pair or a symmetrical- or substantially symmetrical ITR pair, as these terms are defined herein. A neDNA vector as disclosed herein can comprise ITR sequences that are selected from any of: (i) at least one WT ITR and at least one modified AAV inverted terminal repeat (mod-ITR) (e.g., asymmetric modified ITRs); (ii) two modified ITRs where the mod-ITR pair have a different three-dimensional spatial organization with respect to each other (e.g., asymmetric modified ITRs), or (iii) symmetrical or substantially symmetrical WT-WT ITR pair, where each WT-ITR has the same three-dimensional spatial organization, or (iv) symmetrical or substantially symmetrical modified ITR pair, where each mod-ITR has the same three-dimensional spatial organization, where the methods of the present disclosure may further include a delivery system, such as but not limited to a liposome nanoparticle delivery system.

In some embodiments, the ITR sequence can be from viruses of the Parvoviridae family, which includes two subfamilies: Parvovirinae, which infect vertebrates, and Densovirinae, which infect insects. The subfamily Parvovirinae (referred to as the parvoviruses) includes the genus Dependovirus, the members of which, under most conditions, require coinfection with a helper virus such as adenovirus or herpes virus for productive infection. The genus Dependovirus includes adeno-associated virus (AAV), which normally infects humans (e.g., serotypes 2, 3A, 3B, 5, and 6) or primates (e.g., serotypes 1 and 4), and related viruses that infect other warm-blooded animals (e.g., bovine, canine, equine, and ovine adeno-associated viruses). The parvoviruses and other members of the Parvoviridae family are generally described in Kenneth I. Berns, “Parvoviridae: The Viruses and Their Replication,” Chapter 69 in FIELDS VIROLOGY (3d Ed. 1996).

While ITRs exemplified in the specification and Examples herein are AAV2 WT-ITRs, one of ordinary skill in the art is aware that one can as stated above use ITRs from any known parvovirus, for example a dependovirus such as AAV (e.g., AAV1, AAV2, AAV3, AAV4, AAV5, AAV 5, AAV7, AAV8, AAV9, AAV10, AAV 11, AAV12, AAVrh8, AAVrh10, AAV-DJ, and AAV-DJ8 genome. E.g., NCBJ: NC 002077; NC 001401; NC001729; NC001829; NC006152; NC 006260; NC 006261), chimeric ITRs, or ITRs from any synthetic AAV. In some embodiments, the AAV can infect warm-blooded animals, e.g., avian (AAAV), bovine (BAAV), canine, equine, and ovine adeno-associated viruses. In some embodiments the ITR is from B19 parvovirus (GenBank® Accession No: NC 000883), Minute Virus from Mouse (MVM) (GenBank® Accession No. NC 001510); goose parvovirus (GenBank® Accession No. NC 001701); snake parvovirus 1 (GenBank® Accession No. NC 006148). In some embodiments, the 5' WT-ITR can be from one serotype and the 3' WT-ITR from a different serotype, as discussed herein.

An ordinarily skilled artisan is aware that ITR sequences have a common structure of a double-stranded Holliday junction, which typically is a T-shaped or Y-shaped hairpin structure (see e.g., FIG. 2A and FIG. 3A), where each WT-ITR is formed by two palindromic arms or loops (B-B' and C-C') embedded in a larger palindromic arm (A-A'), and a single stranded D sequence, (where the order of these palindromic sequences defines the flip or flop orientation of the ITR). See, for example, structural analysis and sequence comparison of ITRs from different AAV serotypes (AAV1-AAV6) and described in Grimm et al., J. Virology, 2006; 80(1); 426-439; Yan et al., J. Virology, 2005; 364-379; Duan et al., Virology 1999; 261; 8-14. One of ordinary skill in the art can readily determine WT-ITR sequences from any AAV serotype for use in a neDNA vector or neDNA-plasmid based on the exemplary AAV2 ITR sequences provided herein. See, for example, the sequence comparison of ITRs from different AAV serotypes (AAV1-AAV6, and avian AAV (AAAV) and bovine AAV (BAAV)) described in Grimm et al., J. Virology, 2006; 80(1); 426-439; that show the % identity of the left ITR of AAV2 to the left ITR from other serotypes: AAV-1 (84%), AAV-3 (86%), AAV-4 (79%), AAV-5 (58%), AAV-6 (left ITR) (100%) and AAV-6 (right ITR) (82%).

C. Symmetrical and Asymmetrical ITR Pairs

In some embodiments, a neDNA vector as described herein comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are symmetric, or substantially symmetrical with respect to each other—that is, a neDNA vector can comprise ITR sequences that have a symmetrical three-dimensional spatial organization such that their structure is the same shape in geometrical space, or have the same A, C-C' and B-B' loops in 3D space. In such an embodiment, a symmetrical ITR pair, or substantially symmetrical ITR pair can be modified ITRs (e.g., mod-ITRs) that are not wild-type ITRs. A mod-ITR pair can have the same sequence which has one or more modifications from wild-type ITR and are reverse complements (inverted) of each other. In alternative embodiments, a modified ITR pair are substantially symmetrical as defined herein, that is, the modified ITR pair can have a different sequence but have corresponding or the same symmetrical three-dimensional shape. The gaps can be introduced, for example, in the stem regions of the ITRs as described above using single or multiple oligonucleotides per ITR in the synthetic synthesis methods described herein.

(i) Wildtype ITRs

In some embodiments, the symmetrical ITRs, or substantially symmetrical ITRs are wild type (WT-ITRs) as described herein. That is, both ITRs have a wild type sequence, but do not necessarily have to be WT-ITRs from the same AAV serotype. That is, in some embodiments, one WT-ITR can be from one AAV serotype, and the other WT-ITR can be from a different AAV serotype. In such an embodiment, a WT-ITR pair are substantially symmetrical as defined herein, that is, they can have one or more conservative nucleotide modification while still retaining the symmetrical three-dimensional spatial organization.

Accordingly, as disclosed herein, neDNA vectors contain a transgene or heterologous nucleic acid sequence positioned between two flanking wild-type inverted terminal repeat (WT-ITR) sequences, that are either the reverse complement (inverted) of each other, or alternatively, are substantially symmetrical relative to each other—that is a WT-ITR pair have symmetrical three-dimensional spatial organization. In some embodiments, a wild-type ITR sequence (e.g., AAV WT-ITR) comprises a functional Rep binding site (RBS; e.g., 5'-GCGCGCTCGCTCGCTC-3' (SEQ ID NO: 1) for AAV2) and a functional terminal resolution site (TRS; e.g., 5'-AGTT-3').

In one aspect, neDNA vectors are obtainable from a vector polynucleotide that encodes a heterologous nucleic acid operatively positioned between two WT inverted terminal repeat sequences (WT-ITRs) (e.g., AAV WT-ITRs). That is, both ITRs have a wild type sequence, but do not necessarily have to be WT-ITRs from the same AAV serotype. That is, in some embodiments, one WT-ITR can be from one AAV serotype, and the other WT-ITR can be from a different AAV serotype. In such an embodiment, the WT-ITR pair are substantially symmetrical as defined herein, that is, they can have one or more conservative nucleotide modification while still retaining the symmetrical three-dimensional spatial organization. In some embodiments, the 5' WT-ITR is from one AAV serotype, and the 3' WT-ITR is from the same or a different AAV serotype. In some embodiments, the 5' WT-ITR and the 3'WT-ITR are mirror images of each other, that is they are symmetrical. In some embodiments, the 5' WT-ITR and the 3' WT-ITR are from the same AAV serotype.

WT ITRs are well known. In one embodiment the two ITRs are from the same AAV2 serotype. In certain embodiments one can use WT from other serotypes. There are a number of serotypes that are homologous, e.g., AAV2, AAV4, AAV6, AAV8. In one embodiment, closely homologous ITRs (e.g., ITRs with a similar loop structure) can be used. In another embodiment, one can use AAV WT ITRs that are more diverse, e.g., AAV2 and AAV5, and still another embodiment, one can use an ITR that is substantially WT—that is, it has the basic loop structure of the WT but some conservative nucleotide changes that do not alter or affect the properties. When using WT-ITRs from the same viral serotype, one or more regulatory sequences may further be used. In certain embodiments, the regulatory sequence is a regulatory switch that permits modulation of the activity of the neDNA.

In some embodiments, one aspect of the technology described herein relates to a synthetically produced neDNA vector, wherein the neDNA vector comprises at least one heterologous nucleotide sequence, operably positioned between two wild-type inverted terminal repeat sequences (WT-ITRs), wherein the WT-ITRs can be from the same serotype, different serotypes or substantially symmetrical with respect to each other (i.e., have the symmetrical three-dimensional spatial organization such that their structure is the same shape in geometrical space, or have the same A, C-C' and B-B' loops in 3D space). In some embodiments, the symmetric WT-ITRs comprises a functional terminal resolution site and a Rep binding site. In some embodiments, the heterologous nucleic acid sequence encodes a transgene, and wherein the vector is not in a viral capsid.

In some embodiments, the WT-ITRs are the same but the reverse complement of each other. For example, the sequence AACG in the 5' ITR may be CGTT (i.e., the reverse complement) in the 3' ITR at the corresponding site. In one example, the 5' WT-ITR sense strand comprises the sequence of ATCGATCG and the corresponding 3' WT-ITR sense strand comprises CGATCGAT (i.e., the reverse complement of ATCGATCG). In some embodiments, the WT-ITRs neDNA further comprises a terminal resolution site and a replication protein binding site (RPS) (sometimes referred to as a replicative protein binding site), e.g., a Rep binding site.

Exemplary WT-ITR sequences for use in the neDNA vectors comprising WT-ITRs are shown in Table 2 herein, which shows pairs of WT-ITRs (5' WT-ITR and the 3' WT-ITR).

Figure 1F:
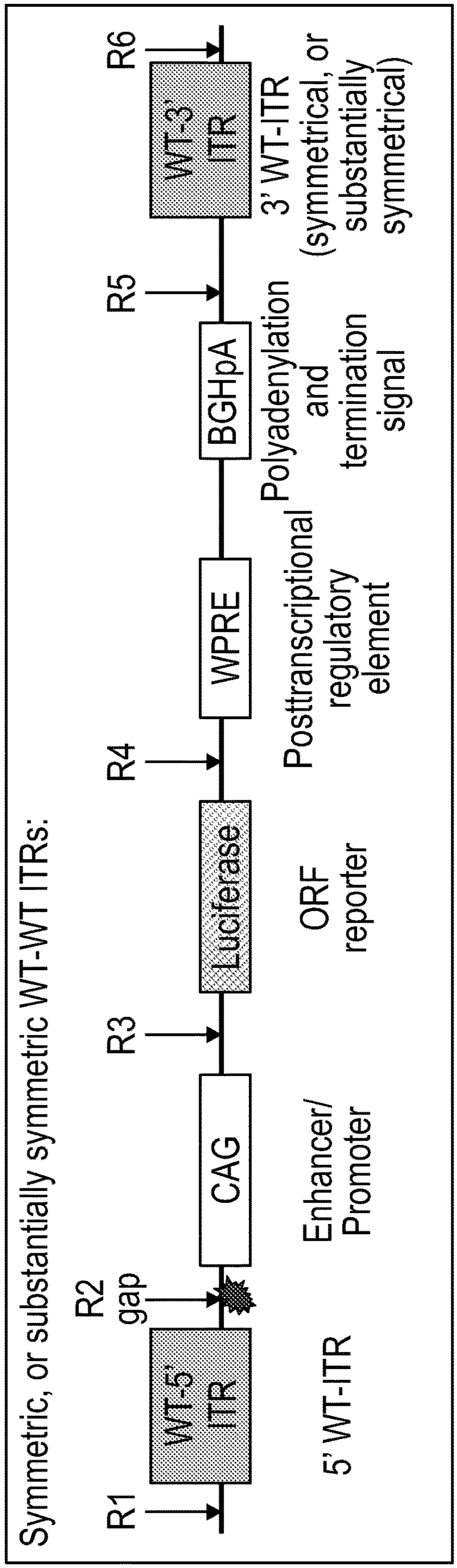
Figure 1G:
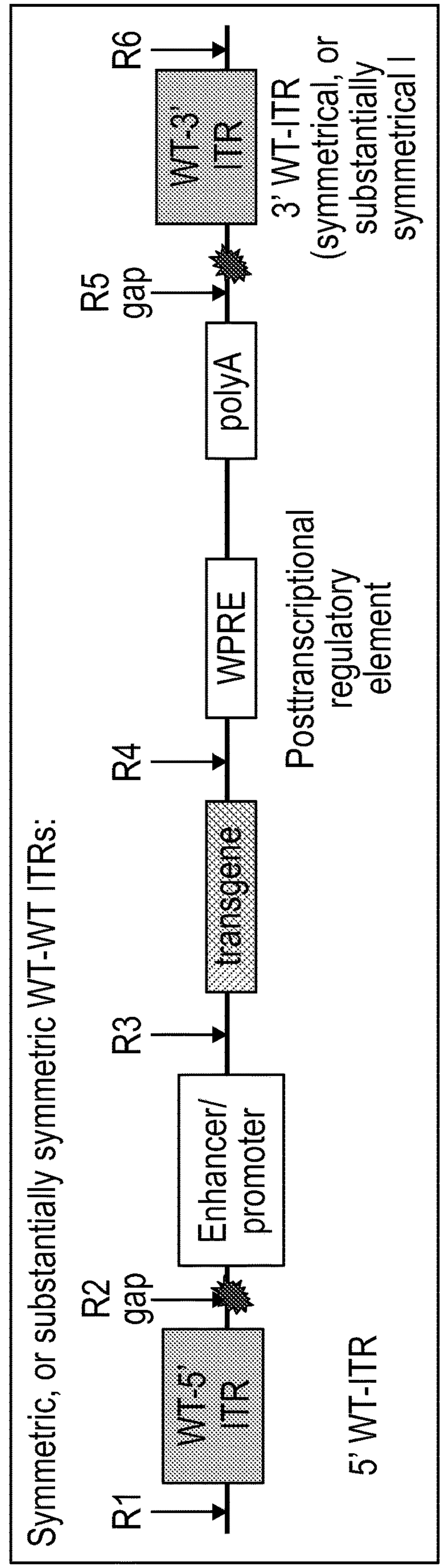

As an exemplary example, the present disclosure provides a synthetically produced neDNA vector comprising a promoter operably linked to a transgene (e.g., heterologous nucleic acid sequence), with or without the regulatory switch, where the neDNA is devoid of capsid proteins and is: (a) produced from a neDNA-plasmid (e.g., see FIGS. 1F-IG) that encodes WT-ITRs, where each WT-ITR has the same number of intramolecularly duplexed base pairs in its hairpin secondary configuration (preferably excluding deletion of any AAA or TTT terminal loop in this configuration compared to these reference sequences), and (b) is identified as neDNA using the assay for the identification of neDNA by agarose gel electrophoresis under native gel and denaturing conditions. The gaps can be introduced, for example, in the stem regions of the ITRs as described above using single or multiple oligonucleotides per ITR in the synthetic synthesis methods described herein.

In some embodiments, the flanking WT-ITRs are substantially symmetrical to each other. In this embodiment the 5' WT-ITR can be from one serotype of AAV, and the 3' WT-ITR from a different serotype of AAV, such that the WT-ITRs are not identical reverse complements. For example, the 5' WT-ITR can be from AAV2, and the 3' WT-ITR from a different serotype (e.g., AAV1, 3, 4, 5, 6, 7, 8, 9, 10, 11, or 12. In some embodiments, WT-ITRs can be selected from two different parvoviruses selected from any to of: AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. In some embodiments, such a combination of WT ITRs is the combination of WT-ITRs from AAV2 and AAV6. In one embodiment, the substantially symmetrical WT-ITRs are when one is inverted relative to the other ITR at least 90% identical, at least 95% identical, at least 96% . . . 97% . . . 98% . . . 99% . . . 99.5% and all points in between and has the same symmetrical three-dimensional spatial organization. In some embodiments, a WT-ITR pair are substantially symmetrical as they have symmetrical three-dimensional spatial organization, e.g., have the same 3D organization of the A, C-C'. B-B' and D arms. In one embodiment, a substantially symmetrical WT-ITR pair are inverted relative to the other, and are at least 95% identical, at least 96% . . . 97% . . . 98% . . . 99% . . . 99.5% and all points in between, to each other, and one WT-ITR retains the Rep-binding site (RBS) of 5'-GCGCGCTCGCTCGCTC-3' (SEQ ID NO: 1) and a terminal resolution site (TRS). In some embodiments, a substantially symmetrical WT-ITR pair are inverted relative to each other, and are at least 95% identical, at least 96% . . . 97% . . . 98% . . . 99% . . . 99.5% and all points in between, to each other, and one WT-ITR retains the Rep-binding site (RBS) of 5'-GCGCGCTCGCTCGCTC-3' (SEQ ID NO: 1) and a terminal resolution site (TRS) and in addition to a variable palindromic sequence allowing for hairpin secondary structure formation. Homology can be determined by standard means well known in the art such as BLAST® (Basic Local Alignment Search Tool), BLASTN® at default setting.

In some embodiments, the structural element of the ITR can be any structural element that is involved in the functional interaction of the ITR with a large Rep protein (e.g., Rep 78 or Rep 68). In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of an A and an A' arm, a B and a B' arm, a C and a C' arm, a D arm, a Rep binding site (RBE) and an RBE' (i.e., complementary RBE sequence), and a terminal resolution sire (TRS).

By way of example only, Table 1 indicates exemplary combinations of WT-ITRs.

Table 1: Exemplary combinations of WT-ITRs from the same serotype or different serotypes, or different parvoviruses. The order shown is not indicative of the ITR position, for example, "AAV1, AAV2" demonstrates that the neDNA can comprise a WT-AAV1 ITR in the 5' position, and a WT-AAV2 ITR in the 3' position, or vice versa, a WT-AAV2 ITR the 5' position, and a WT-AAV1 ITR in the 3' position. Abbreviations: AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12); AAVrh8, AAVrh10, AAV-DJ, and AAV-DJ8 genome (E.g., NCBI: NC 002077; NC 001401; NC001729; NC001829; NC006152; NC 006260; NC 006261), ITRs from warm-blooded animals (avian AAV (AAAV), bovine AAV (BAAV), canine, equine, and ovine AAV), ITRs from B19 parvoviris (GenBank® Accession No: NC 000883), Minute Virus from Mouse (MVM) (GenBank® Accession No. NC 001510); Goose: goose parvovirus (GenBank® Accession No. NC 001701); snake: snake parvovirus 1 (GenBank® Accession No. NC 006148).

TABLE 1

| | | | | |
|---|---|---|---|---|
| AAV1, AAV1 | AAV2, AAV2 | AAV3, AAV3 | AAV4, AAV4 | AAV5, AAV5 |
| AAV1, AAV2 | AAV2, AAV3 | AAV3, AAV4 | AAV4, AAV5 | AAV5, AAV6 |
| AAV1, AAV3 | AAV2, AAV4 | AAV3, AAV5 | AAV4, AAV6 | AAV5, AAV7 |
| AAV1, AAV4 | AAV2, AAV5 | AAV3, AAV6 | AAV4, AAV7 | AAV5, AAV8 |
| AAV1, AAV5 | AAV2, AAV6 | AAV3, AAV7 | AAV4, AAV8 | AAV5, AAV9 |
| AAV1, AAV6 | AAV2, AAV7 | AAV3, AAV8 | AAV4, AAV9 | AAV5, AAV10 |
| AAV1, AAV7 | AAV2, AAV8 | AAV3, AAV9 | AAV4, AAV10 | AAV5, AAV11 |
| AAV1, AAV8 | AAV2, AAV9 | AAV3, AAV10 | AAV4, AAV11 | AAV5, AAV12 |
| AAV1, AAV9 | AAV2, AAV10 | AAV3, AAV11 | AAV4, AAV12 | AAV5, AAVRH8 |
| AAV1, AAV10 | AAV2, AAV11 | AAV3, AAV12 | AAV4, AAVRH8 | AAV5, AAVRH10 |
| AAV1, AAV11 | AAV2, AAV12 | AAV3, AAVRH8 | AAV4, AAVRH10 | AAV5, AAV13 |
| AAV1, AAV12 | AAV2, AAVRH8 | AAV3, AAVRH10 | AAV4, AAV13 | AAV5, AAVDJ |
| AAV1, AAVRH8 | AAV2, AAVRH10 | AAV3, AAV13 | AAV4, AAVDJ | AAV5, AAVDJ8 |
| AAV1, AAVRH10 | AAV2, AAV13 | AAV3, AAVDJ | AAV4, AAVDJ8 | AAV5, AVIAN |
| AAV1, AAV13 | AAV2, AAVDJ | AAV3, AAVDJ8 | AAV4, AVIAN | AAV5, BOVINE |
| AAV1, AAVDJ | AAV2, AAVDJ8 | AAV3, AVIAN | AAV4, BOVINE | AAV5, CANINE |
| AAV1, AAVDJ8 | AAV2, AVIAN | AAV3, BOVINE | AAV4, CANINE | AAV5, EQUINE |
| AAV1, AVIAN | AAV2, BOVINE | AAV3, CANINE | AAV4, EQUINE | AAV5, GOAT |
| AAV1, BOVINE | AAV2, CANINE | AAV3, EQUINE | AAV4, GOAT | AAV5, SHRIMP |
| AAV1, CANINE | AAV2, EQUINE | AAV3, GOAT | AAV4, SHRIMP | AAV5, PORCINE |
| AAV1, EQUINE | AAV2, GOAT | AAV3, SHRIMP | AAV4, PORCINE | AAV5, INSECT |
| AAV1, GOAT | AAV2, SHRIMP | AAV3, PORCINE | AAV4, INSECT | AAV5, OVINE |
| AAV1, SHRIMP | AAV2, PORCINE | AAV3, INSECT | AAV4, OVINE | AAV5, B19 |
| AAV1, PORCINE | AAV2, INSECT | AAV3, OVINE | AAV4, B19 | AAV5, MVM |
| AAV1, INSECT | AAV2, BOVINE | AAV3, B19 | AAV4, MVM | AAV5, GOOSE |
| AAV1, OVINE | AAV2, B19 | AAV3, MVM | AAV4, GOOSE | AAV5, SNAKE |
| AAV1, B19 | AAV2, MVM | AAV3, GOOSE | AAV4, SNAKE | |
| AAV1, MVM | AAV2, GOOSE | AAV3, SNAKE | | |
| AAV1, GOOSE | AAV2, SNAKE | | | |
| AAV1, SNAKE | | | | |
| AAV6, AAV6 | AAV7, AAV7 | AAV8, AAV8 | AAV9, AAV9 | AAV10, AAV10 |
| AAV6, AAV7 | AAV7, AAV8 | AAV8, AAV9 | AAV9, AAV10 | AAV10, AAV11 |
| AAV6, AAV8 | AAV7, AAV9 | AAV8, AAV10 | AAV9, AAV11 | AAV10, AAV12 |
| AAV6, AAV9 | AAV7, AAV10 | AAV8, AAV11 | AAV9, AAV12 | AAV10, AAVRH8 |
| AAV6, AAV10 | AAV7, AAV11 | AAV8, AAV12 | AAV9, AAVRH8 | AAV10, AAVRH10 |
| AAV6, AAV11 | AAV7, AAV12 | AAV8, AAVRH8 | AAV9, AAVRH10 | AAV10, AAV13 |
| AAV6, AAV12 | AAV7, AAVRH8 | AAV8, AAVRH10 | AAV9, AAV13 | AAV10, AAVDJ |
| AAV6, AAVRH8 | AAV7, AAVRH10 | AAV8, AAV13 | AAV9, AAVDJ | AAV10, AAVDJ8 |
| AAV6, AAVRH10 | AAV7, AAV13 | AAV8, AAVDJ | AAV9, AAVDJ8 | AAV10, AVIAN |
| AAV6, AAV13 | AAV7, AAVDJ | AAV8, AAVDJ8 | AAV9, AVIAN | AAV10, BOVINE |
| AAV6, AAVDJ | AAV7, AAVDJ8 | AAV8, AVIAN | AAV9, BOVINE | AAV10, CANINE |
| AAV6, AAVDJ8 | AAV7, AVIAN | AAV8, BOVINE | AAV9, CANINE | AAV10, EQUINE |
| AAV6, AVIAN | AAV7, BOVINE | AAV8, CANINE | AAV9, EQUINE | AAV10, GOAT |
| AAV6, BOVINE | AAV7, CANINE | AAV8, EQUINE | AAV9, GOAT | AAV10, SHRIMP |
| AAV6, CANINE | AAV7, EQUINE | AAV8, GOAT | AAV9, SHRIMP | AAV10, PORCINE |
| AAV6, EQUINE | AAV7, GOAT | AAV8, SHRIMP | AAV9, PORCINE | AAV10, INSECT |
| AAV6, GOAT | AAV7, SHRIMP | AAV8, PORCINE | AAV9, INSECT | AAV10, OVINE |
| AAV6, SHRIMP | AAV7, PORCINE | AAV8, INSECT | AAV9, OVINE | AAV10, B19 |
| AAV6, PORCINE | AAV7, INSECT | AAV8, OVINE | AAV9, B19 | AAV10, MVM |
| AAV6, INSECT | AAV7, OVINE | AAV8, B19 | AAV9, MVM | AAV10, GOOSE |
| AAV6, OVINE | AAV7, B19 | AAV8, MVM | AAV9, GOOSE | AAV10, SNAKE |
| AAV6, B19 | AAV7, MVM | AAV8, GOOSE | AAV9, SNAKE | |
| AAV6, MVM | AAV7, GOOSE | AAV8, SNAKE | | |

TABLE 1-continued

| | | | | |
|---|---|---|---|---|
| AAV6, GOOSE | AAV7, SNAKE | | | |
| AAV6, SNAKE | | | | |
| AAV11, AAV11 | AAV12, AAV12 | AAVRH8, AAVRH8 | AAVRH10, AAVRH10 | AAV13, AAV13 |
| AAV11, AAV12 | AAV12, AAVRH8 | AAVRH8, AAVRH10 | AAVRH10, AAV13 | AAV13, AAVDJ |
| AAV11, AAVRH8 | AAV12, AAVRH10 | AAVRH8, AAV13 | AAVRH10, AAVDJ | AAV13, AAVDJ8 |
| AAV11, AAVRH10 | AAV12, AAV13 | AAVRH8, AAVDJ | AAVRH10, AAVDJ8 | AAV13, AVIAN |
| AAV11, AAV13 | AAV12, AAVDJ | AAVRH8, AAVDJ8 | AAVRH10, AVIAN | AAV13, BOVINE |
| AAV11, AAVDJ | AAV12, AAVDJ8 | AAVRH8, AVIAN | AAVRH10, BOVINE | AAV13, CANINE |
| AAV11, AAVDJ8 | AAV12, AVIAN | AAVRH8, BOVINE | AAVRH10, CANINE | AAV13, EQUINE |
| AAV11, AVIAN | AAV12, BOVINE | AAVRH8, CANINE | AAVRH10, EQUINE | AAV13, GOAT |
| AAV11, BOVINE | AAV12, CANINE | AAVRH8, EQUINE | AAVRH10, GOAT | AAV13, SHRIMP |
| AAV11, CANINE | AAV12, EQUINE | AAVRH8, GOAT | AAVRH10, SHRIMP | AAV13, PORCINE |
| AAV11, EQUINE | AAV12, GOAT | AAVRH8, SHRIMP | AAVRH10, PORCINE | AAV13, INSECT |
| AAV11, GOAT | AAV12, SHRIMP | AAVRH8, PORCINE | AAVRH10, INSECT | AAV13, OVINE |
| AAV11, SHRIMP | AAV12, PORCINE | AAVRH8, INSECT | AAVRH10, OVINE | AAV13, B19 |
| AAV11, PORCINE | AAV12, INSECT | AAVRH8, OVINE | AAVRH10, B19 | AAV13, MVM |
| AAV11, INSECT | AAV12, OVINE | AAVRH8, B19 | AAVRH10, MVM | AAV13, GOOSE |
| AAV11, OVINE | AAV12, B19 | AAVRH8, MVM | AAVRH10, GOOSE | AAV13, SNAKE |
| AAV11, B19 | AAV12, MVM | AAVRH8, GOOSE | AAVRH10, SNAKE | |
| AAV11, MVM | AAV12, GOOSE | AAVRH8, SNAKE | | |
| AAV11, GOOSE | AAV12, SNAKE | | | |
| AAV11, SNAKE | | | | |
| AAVDJ, AAVDJ | AAVDJ8, AVVDJ8 | AVIAN, AVIAN | BOVINE, BOVINE | CANINE, CANINE |
| AAVDJ, AAVDJ8 | AAVDJ8, AVIAN | AVIAN, BOVINE | BOVINE, CANINE | CANINE, EQUINE |
| AAVDJ, AVIAN | AAVDJ8, BOVINE | AVIAN, CANINE | BOVINE, EQUINE | CANINE, GOAT |
| AAVDJ, BOVINE | AAVDJ8, CANINE | AVIAN, EQUINE | BOVINE, GOAT | CANINE, SHRIMP |
| AAVDJ, CANINE | AAVDJ8, EQUINE | AVIAN, GOAT | BOVINE, SHRIMP | CANINE, PORCINE |
| AAVDJ, EQUINE | AAVDJ8, GOAT | AVIAN, SHRIMP | BOVINE, PORCINE | CANINE, INSECT |
| AAVDJ, GOAT | AAVDJ8, SHRIMP | AVIAN, PORCINE | BOVINE, INSECT | CANINE, OVINE |
| AAVDJ, SHRIMP | AAVDJ8, PORCINE | AVIAN, INSECT | BOVINE, OVINE | CANINE, B19 |
| AAVDJ, PORCINE | AAVDJ8, INSECT | AVIAN, OVINE | BOVINE, B19 | CANINE, MVM |
| AAVDJ, INSECT | AAVDJ8, OVINE | AVIAN, B19 | BOVINE, MVM | CANINE, GOOSE |
| AAVDJ, OVINE | AAVDJ8, B19 | AVIAN, MVM | BOVINE, GOOSE | CANINE, SNAKE |
| AAVDJ, B19 | AAVDJ8, MVM | AVIAN, GOOSE | BOVINE, SNAKE | |
| AAVDJ, MVM | AAVDJ8, GOOSE | AVIAN, SNAKE | | |
| AAVDJ, GOOSE | AAVDJ8, SNAKE | | | |
| AAVDJ, SNAKE | | | | |
| EQUINE, EQUINE | GOAT, GOAT | SHRIMP, SHRIMP | PORCINE, PORCINE | INSECT, INSECT |
| EQUINE, GOAT | GOAT, SHRIMP | SHRIMP, PORCINE | PORCINE, INSECT | INSECT, OVINE |
| EQUINE, SHRIMP | GOAT, PORCINE | SHRIMP, INSECT | PORCINE, OVINE | INSECT, B19 |
| EQUINE, PORCINE | GOAT, INSECT | SHRIMP, OVINE | PORCINE, B19 | INSECT, MVM |
| EQUINE, INSECT | GOAT, OVINE | SHRIMP, B19 | PORCINE, MVM | INSECT, GOOSE |
| EQUINE, OVINE | GOAT, B19 | SHRIMP, MVM | PORCINE, GOOSE | INSECT, SNAKE |
| EQUINE, B19 | GOAT, MVM | SHRIMP, GOOSE | PORCINE, SNAKE | |
| EQUINE, MVM | GOAT, GOOSE | SHRIMP, SNAKE | | |
| EQUINE, GOOSE | GOAT, SNAKE | | | |
| EQUINE, SNAKE | | | | |
| OVINE, OVINE | B19, B19 | MVM, MVM | GOOSE, GOOSE | SNAKE, SNAKE |
| OVINE, B19 | B19, MVM | MVM, GOOSE | GOOSE, SNAKE | |
| OVINE, MVM | B19, GOOSE | MVM, SNAKE | | |
| OVINE, GOOSE | B19, SNAKE | | | |
| OVINE, SNAKE | | | | |

By way of example only, Table 2 shows the sequences of exemplary WT-ITRs from AAV1-6 serotypes. ITR sequence information from other viral species mentioned above can be readily found in NCBI database and be employed freely with the methods being described in the present disclosure.

TABLE 2

| AAV serotype | SEQ ID NO: | 5' WT-ITR (LEFT) | SEQ ID NO: | 3' WT-ITR (RIGHT) |
|---|---|---|---|---|
| AAV1 | 2 | 5'-<br>TTGCCCACTCCCTCTCTGCGC<br>GCTCGCTCGCTCGGTGGGGC<br>CTGCGGACCAAAGGTCCGCA<br>GACGGCAGAGGTCTCCTCTG<br>CCGGCCCCACCGAGCGAGCG<br>ACGCGCGCAGAGAGGGAGTG<br>GGCAACTCCATCACTAGGGT<br>AA-3' | 8 | 5'-<br>TTACCCTAGTGATGGAGTTGCCC<br>ACTCCCTCTCTGCGCGCGTCGCT<br>CGCTCGGTGGGGCCGGCAGAGG<br>AGACCTCTGCCGTCTGCGGACCT<br>TTGGTCCGCAGGCCCCACCGAGC<br>GAGCGAGCGCGCAGAGAGGGAG<br>TGGGCAA-3' |
| AAV2 | 3 | CCTGCAGGCAGCTGCGCGCT<br>CGCTCGCTCACTGAGGCCGC | 9 | AGGAACCCCTAGTGATGGAGTT<br>GGCCACTCCCTCTCTGCGCGCTC |

TABLE 2-continued

| AAV serotype | SEQ ID NO: | 5' WT-ITR (LEFT) | SEQ ID NO: | 3' WT-ITR (RIGHT) |
|---|---|---|---|---|
| | | CCGGGCAAAGCCCGGGCGTC GGGCGACCTTTGGTCGCCCG GCCTCAGTGAGCGAGCGAGC GCGCAGAGAGGGAGTGGCCA ACTCCATCACTAGGGGTTCCT | | GCTCGCTCACTGAGGCCGGGCG ACCAAAGGTCGCCCGACGCCCG GGCTTTGCCCGGGCGGCCTCAGT GAGCGAGCGAGCGCGCAGCTGC CTGCAGG |
| AAV3 | 4 | 5'- TTGGCCACTCCCTCTATGCGC ACTCGCTCGCTCGGTGGGGC CTGGCGACCAAAGGTCGCCA GACGGACGTGGGTTTCCACG TCCGGCCCCACCGAGCGAGC GAGTGCGCATAGAGGGAGTG GCCAACTCCATCACTAGAGG TAT-3' | 10 | 5'- ATACCTCTAGTGATGGAGTTGGC CACTCCCTCTATGCGCACTCGCT CGCTCGGTGGGGCCGGACGTGG AAACCCACGTCCGTCTGGCGACC TTTGGTCGCCAGGCCCCACCGAG CGAGCGAGTGCGCATAGAGGGA GTGGCCAA-3' |
| AAV4 | 5 | 5'- TTGGCCACTCCCTCTATGCGC GCTCGCTCACTCACTCGGCCC TGGAGACCAAAGGTCTCCAG ACTGCCGGCCTCTGGCCGGC AGGGCCGAGTGAGTGAGCGA GCGCGCATAGAGGGAGTGGC CAACT-3' | 11 | 5'- AGTTGGCCACATTAGCTATGCGC GCTCGCTCACTCACTCGGCCCTG GAGACCAAAGGTCTCCAGACTG CCGGCCTCTGGCCGGCAGGGCC GAGTGAGTGAGCGAGCGCGCAT AGAGGGAGTGGCCAA-3' |
| AAV5 | 6 | 5'- TCCCCCCTGTCGCGTTCGCTC GCTCGCTGGCTCGTTTGGGG GGGCGACGGCCAGAGGGCCG TCGTCTGGCAGCTCTTTGAGC TGCCACCCCCCCAAACGAGC CAGCGAGCGAGCGAACGCGA CAGGGGGGAGAGTGCCACAC TCTCAAGCAAGGGGGTTTTG TAAG-3' | 12 | 5'- CTTACAAAACCCCCTTGCTTGAG AGTGTGGCACTCTCCCCCCTGTC GCGTTCGCTCGCTCGCTGGCTCG TTTGGGGGGGTGGCAGCTCAAA GAGCTGCCAGACGACGGCCCTCT GGCCGTCGCCCCCCCAAACGAG CCAGCGAGCGAGCGAACGCGAC AGGGGGGA-3' |
| AAV6 | 7 | 5'- TTGCCCACTCCCTCTAATGCG CGCTCGCTCGCTCGGTGGGG CCTGCGGACCAAAGGTCCGC AGACGGCAGAGGTCTCCTCT GCCGGCCCCACCGAGCGAGC GAGCGCGCATAGAGGGAGTG GGCAACTCCATCACTAGGGG TAT-3' | 13 | 5'- ATACCCCTAGTGATGGAGTTGCC CACTCCCTCTATGCGCGCTCGCT CGCTCGGTGGGGCCGGCAGAGG AGACCTCTGCCGTCTGCGGACCT TTGGTCCGCAGGCCCCACCGAGC GAGCGAGCGCGCATTAGAGGGA GTGGGCAA |
| AAV2 | | NONE | 9 | AGGAACCCCTAGTGATGGAGTT GGCCACTCCCTCTCTGCGCGCTC GCTCGCTCACTGAGGCCGGGCG ACCAAAGGTCGCCCGACGCCCG GGCTTTGCCCGGGCGGCCTCAGT GAGCGAGCGAGCGCGCAGCTGC CTGCAGG |
| AAV2 | 3 | CCTGCAGGCAGCTGCGCGCT CGCTCGCTCACTGAGGCCGC CCGGGCAAAGCCCGGGCGTC GGGCGACCTTTGGTCGCCCG GCCTCAGTGAGCGAGCGAGC GCGCAGAGAGGGAGTGGCCA ACTCCATCACTAGGGGTTCCT | | NONE |

In some embodiments, the nucleotide sequence of the WT-ITR sequence can be modified (e.g., by modifying 1, 2, 3, 4 or 5, or more nucleotides or any range therein), whereby the modification is a substitution for a complementary nucleotide, e.g., G for a C, and vice versa, and T for an A, and vice versa.

Figure 2A:
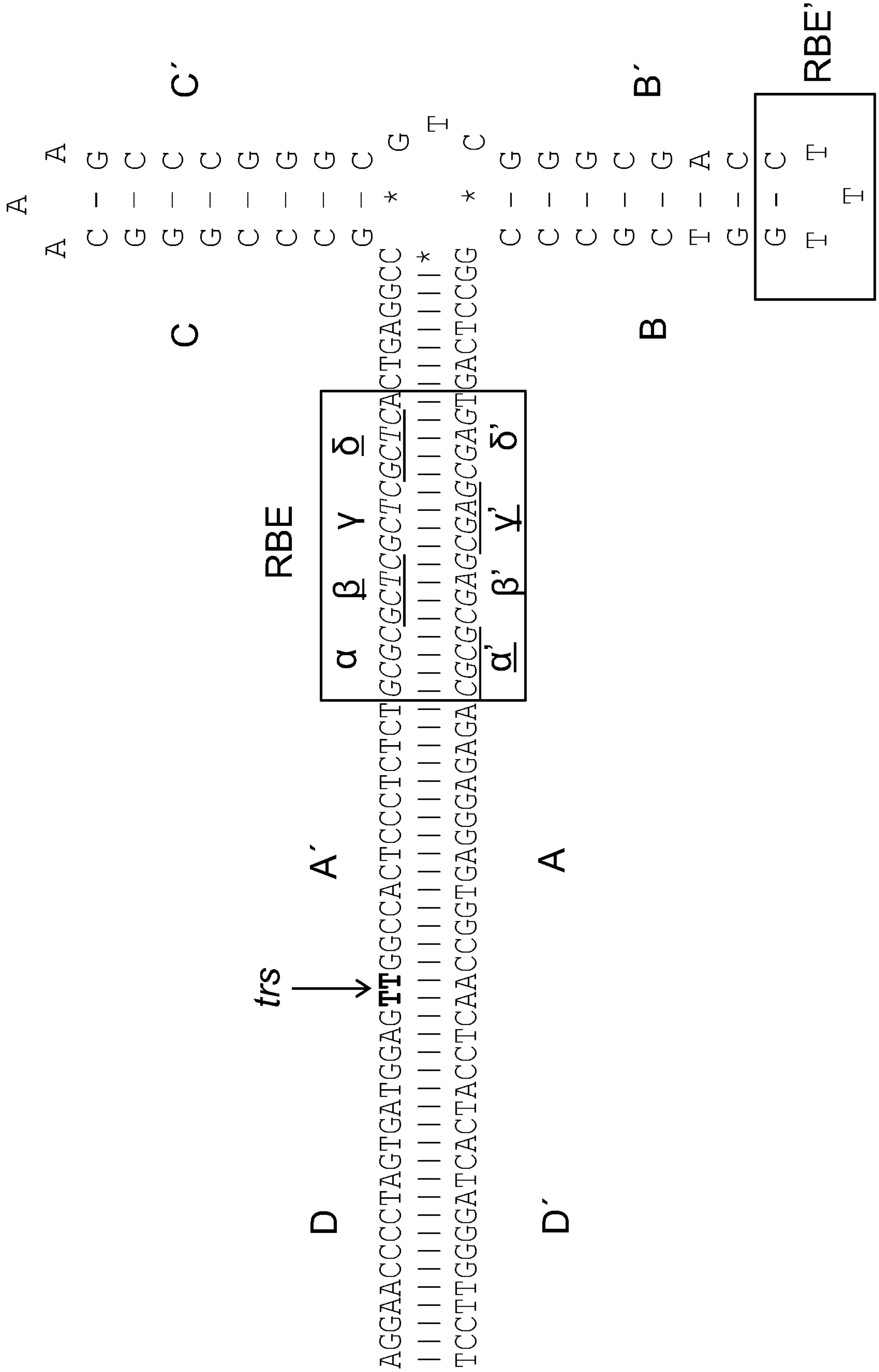
FIG. 2A provides the T-shaped stem-loop structure of a wild-type left ITR of AAV2 with identification of A-A' arm, B-B' arm, C-C' arm, two Rep binding sites (RBE and RBE') and also shows the terminal resolution site (TRS). The RBE contains a series of 4 duplex tetramers that are believed to interact with either Rep 78 or Rep 68. In addition, the RBE' is also believed to interact with Rep complex assembled on the wild-type ITR or mutated ITR in the construct. The D and D' regions contain transcription factor binding sites and other conserved structure.
Figure 2B:
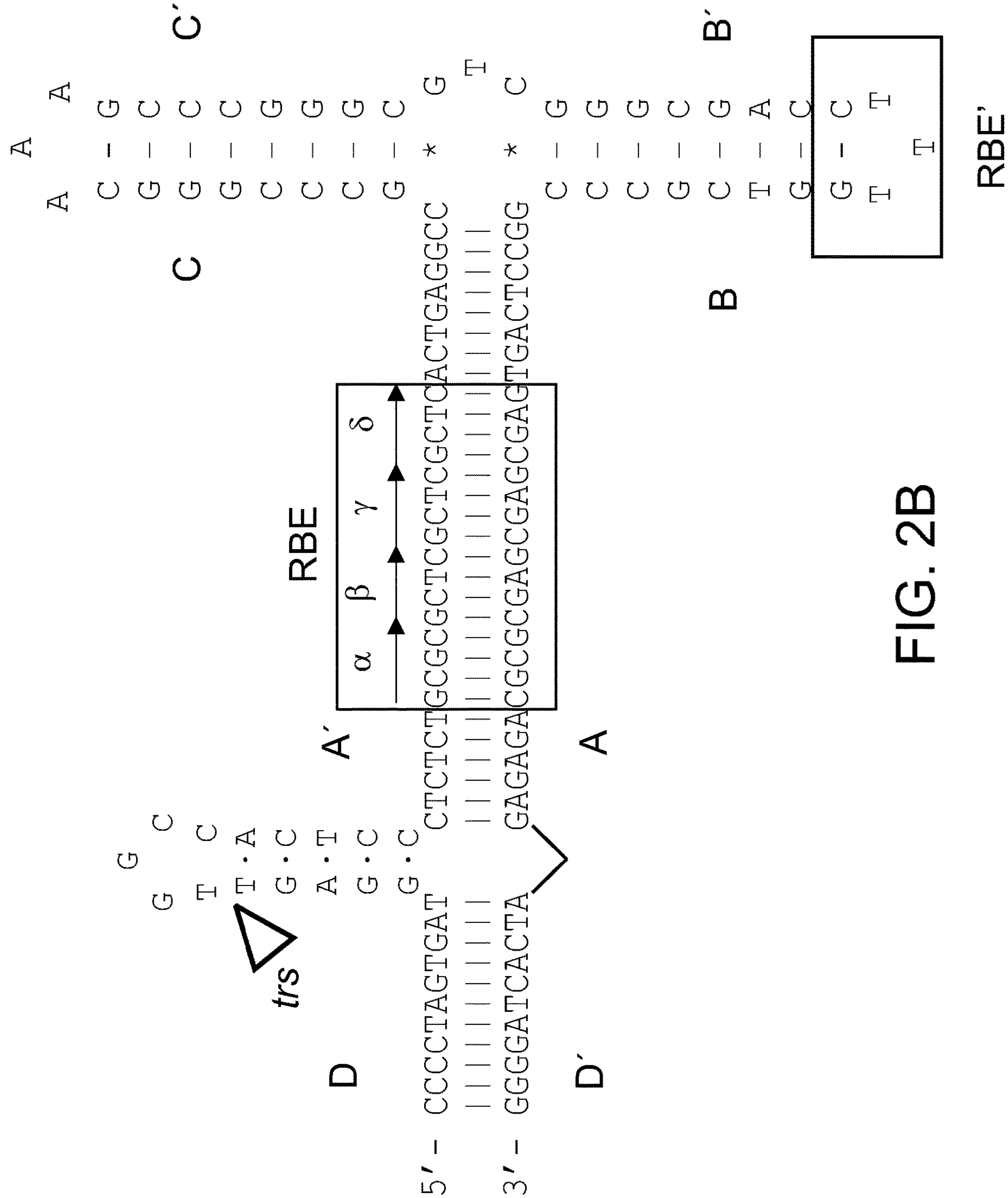
FIG. 2B shows proposed Rep-catalyzed nicking and ligating activities in a wild-type left ITR, including the T-shaped stem-loop structure of the wild-type left ITR of AAV2 with identification of A-A' arm, B-B' arm, C-C' arm, two Rep Binding sites (RBE and RBE') and also shows the terminal resolution site (TRS), and the D and D' region comprising several transcription factor binding sites and other conserved structure.
Figure 3A:
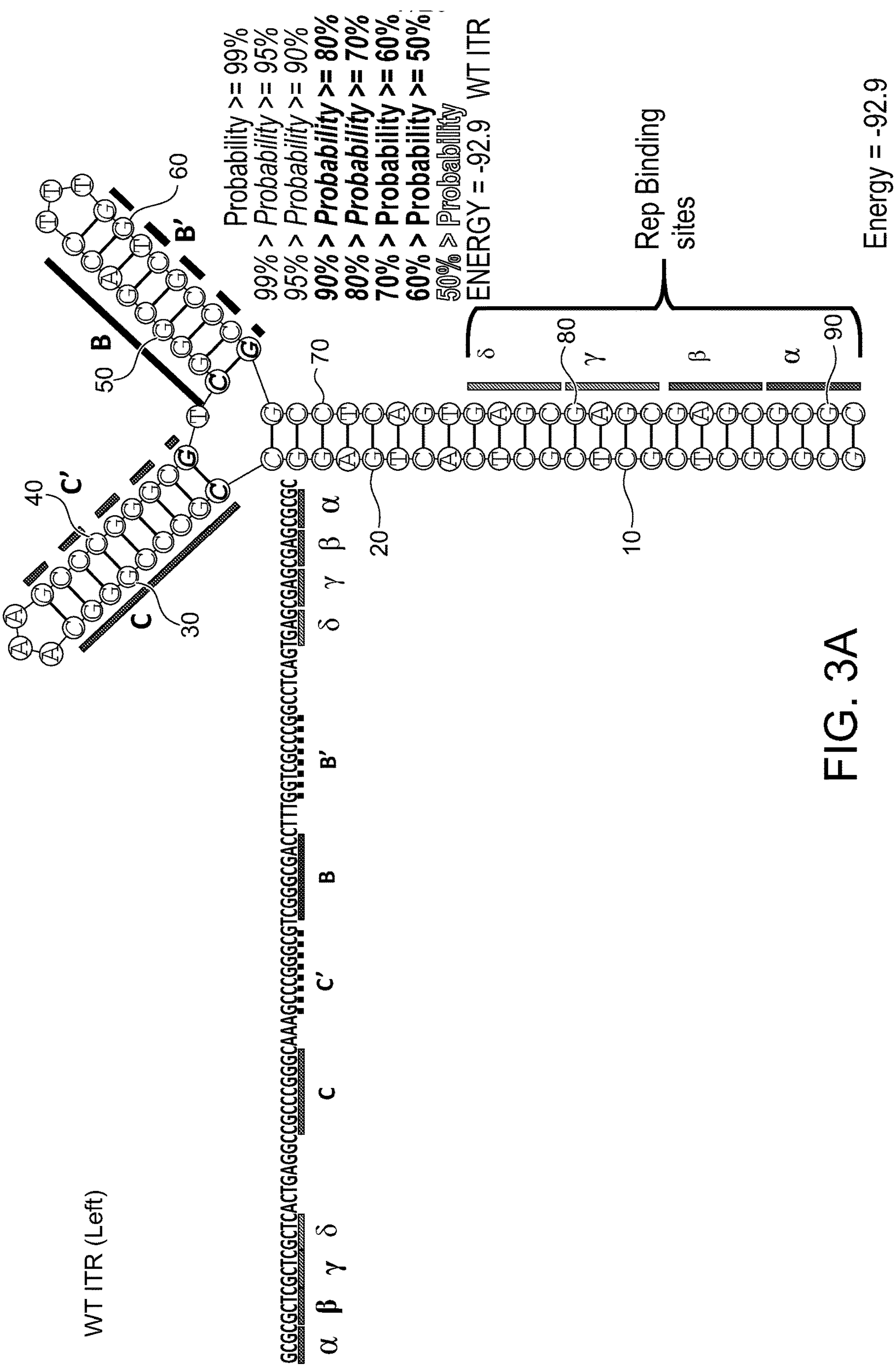
FIG. 3A provides the primary structure (polynucleotide sequence) (left) (SEQ ID NO: 83) and the secondary structure (right) (SEQ ID NO: 83) of the RBE-containing portions of the A-A' arm, and the C-C' and B-B' arm of the wild type left AAV2 ITR.

The neDNA vector described herein can include WT-ITR structures that retains an operable RBE, TRS and RBE' portion. FIG. 2A and FIG. 2B, using wild-type ITRs for exemplary purposes, show one possible mechanism for the operation of a TRS site within a wild type ITR structure portion of a neDNA vector. In some embodiments, the neDNA vector contains one or more functional WT-ITR polynucleotide sequences that comprise a Rep-binding site (RBS; 5'-GCGCGCTCGCTCGCTC-3' (SEQ ID NO: 1) for AAV2) and a terminal resolution site (TRS; 5'-AGTT). In some embodiments, at least one WT-ITR is functional. In alternative embodiments, where a neDNA vector comprises two WT-ITRs that are substantially symmetrical to each other, at least one WT-ITR is functional and at least one WT-ITR is non-functional.

(ii) Modified ITRs (Mod-ITRs) for neDNA Vectors Comprising Asymmetric ITR Pairs or Symmetric ITR Pairs As discussed herein, a synthetically produced neDNA vector can comprise a symmetrical ITR pair or an asymmetrical ITR pair. In both instances, one or both of the ITRs can be modified ITRs—the difference being that in the first instance (i.e., symmetric mod-ITRs), the mod-ITRs have the same three-dimensional spatial organization (i.e., have the same A-A', C-C' and B-B' arm configurations), whereas in the second instance (i.e., asymmetric mod-ITRs), the mod-ITRs have a different three-dimensional spatial organization (i.e., have a different configuration of A-A', C-C' and B-B' arms). The gaps can be introduced, for example, in the stem regions of the ITRs as described above using single or multiple oligonucleotides per ITR in the synthetic synthesis methods described herein.

In some embodiments, a modified ITR is an ITRs that is modified by deletion, insertion, and/or substitution as compared to a wild-type ITR sequence (e.g., AAV ITR). In some embodiments, at least one of the ITRs in the neDNA vector comprises a functional Rep binding site (RBS; e.g., 5'-GCGCGCTCGCTCGCTC-3' (SEQ ID NO: 1) for AAV2) and a functional terminal resolution site (TRS; e.g., 5'-AGTT-3') In one embodiment, at least one of the ITRs is a non-functional ITR. In one embodiment, the different or modified ITRs are not each wild type ITRs from different serotypes.

Specific alterations and mutations in the ITRs are described in detail herein, but in the context of ITRs, "altered" or "mutated" or "modified", it indicates that nucleotides have been inserted, deleted, and/or substituted relative to the wild-type, reference, or original ITR sequence. The altered or mutated ITR can be an engineered ITR. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature.

In some embodiments, a mod-ITR may be synthetic. In one embodiment, a synthetic ITR is based on ITR sequences from more than one AAV serotype. In another embodiment, a synthetic ITR includes no AAV-based sequence. In yet another embodiment, a synthetic ITR preserves the ITR structure described above although having only some or no AAV-sourced sequence. In some aspects, a synthetic ITR may interact preferentially with a wild type Rep or a Rep of a specific serotype, or in some instances will not be recognized by a wild-type Rep and be recognized only by a mutated Rep.

The skilled artisan can determine the corresponding sequence in other serotypes by known means. For example, determining if the change is in the A, A', B, B', C, C' or D region and determine the corresponding region in another serotype. One can use BLAST® (Basic Local Alignment Search Tool) or other homology alignment programs at default status to determine the corresponding sequence. The invention further provides populations and pluralities of neDNA vectors comprising mod-ITRs from a combination of different AAV serotypes—that is, one mod-ITR can be from one AAV serotype and the other mod-ITR can be from a different serotype. Without wishing to be bound by theory, in one embodiment one ITR can be from or based on an AAV2 ITR sequence and the other ITR of the neDNA vector can be from or be based on any one or more ITR sequence of AAV serotype 1 (AAV1), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12).

Any parvovirus ITR can be used as an ITR or as a base ITR for modification. Preferably, the parvovirus is a dependovirus. More preferably AAV. The serotype chosen can be based upon the tissue tropism of the serotype. AAV2 has a broad tissue tropism, AAV1 preferentially targets to neuronal and skeletal muscle, and AAV5 preferentially targets neuronal, retinal pigmented epithelia, and photoreceptors. AAV6 preferentially targets skeletal muscle and lung. AAV8 preferentially targets liver, skeletal muscle, heart, and pancreatic tissues. AAV9 preferentially targets liver, skeletal and lung tissue. In one embodiment, the modified ITR is based on an AAV2 ITR.

More specifically, the ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., A arm, A' arm, B arm, B' arm, C arm, C' arm, D arm, RBE, RBE', and TRS) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the A or A' arm or RBE can be replaced with a structural element from AAV5. In another example, the ITR can be an AAV5 ITR and the C or C' arms, the RBE, and the TRS can be replaced with a structural element from AAV2. In another example, the AAV ITR can be an AAV5 ITR with the B and B' arms replaced with the AAV2 ITR B and B' arms.

By way of example only, Table 3 shows exemplary modifications of at least one nucleotide (e.g., a deletion, insertion and/or substitution) in regions of a modified ITR, where X is indicative of a modification of at least one nucleic acid (e.g., a deletion, insertion and/or substitution) in that section relative to the corresponding wild-type ITR. In some embodiments, any modification of at least one nucleotide (e.g., a deletion, insertion and/or substitution) in any of the regions of C and/or C' and/or B and/or B' retains three sequential T nucleotides (i.e., TTT) in at least one terminal loop. For example, if the modification results in any of: a single arm ITR (e.g., single C-C' arm, or a single B-B' arm), or a modified C—B' arm or C'—B arm, or a two arm ITR with at least one truncated arm (e.g., a truncated C-C' arm and/or truncated B-B' arm), at least the single arm, or at least one of the arms of a two arm ITR (where one arm can be truncated) retains three sequential T nucleotides (i.e., TTT) in at least one terminal loop. In some embodiments, a truncated C-C' arm and/or a truncated B-B' arm has three sequential T nucleotides (i.e., TTT) in the terminal loop.

TABLE 3

Exemplary modifications of at least one nucleotide (e.g., a deletion, insertion and/or substitution) in B, B', C, and C' regions of ITRs

| B region | B' region | C region | C' region |
| --- | --- | --- | --- |
| X | | | |
| | X | | |

TABLE 3-continued

Exemplary modifications of at least one nucleotide (e.g., a deletion, insertion and/or substitution) in B, B', C, and C' regions of ITRs

| B region | B' region | C region | C' region |
|---|---|---|---|
| X | X | | |
| | | X | |
| | | | X |
| | | X | X |
| X | | X | |
| X | | | X |
| | X | X | |
| | X | | X |
| X | X | X | |
| X | X | | X |
| X | | X | X |
| | X | X | X |
| X | X | X | X |

In some embodiments, mod-ITR for use in a synthetically produced neDNA vector comprising an asymmetric ITR pair, or a symmetric mod-ITR pair as disclosed herein can comprise any one of the combinations of modifications shown in Table 3, and also a modification of at least one nucleotide in any one or more of the regions selected from: between A' and C, between C and C', between C' and B, between B and B' and between B' and A. As described above, the gaps can be introduced, for example, in the stem regions of the ITRs using single or multiple oligonucleotides per ITR in the synthetic synthesis methods described herein (see, e.g., FIGS. 6-9)

In some embodiments, any modification of at least one nucleotide (e.g., a deletion, insertion and/or substitution) in the C or C' or B or B' regions, still preserves the terminal loop of the stem-loop. In some embodiments, any modification of at least one nucleotide (e.g., a deletion, insertion and/or substitution) between C and C' and/or B and B' retains three sequential T nucleotides (i.e., TTT) in at least one terminal loop. In alternative embodiments, any modification of at least one nucleotide (e.g., a deletion, insertion and/or substitution) between C and C' and/or B and B' retains three sequential A nucleotides (i.e., AAA) in at least one terminal loop In some embodiments, a modified ITR for use herein can comprise any one of the combinations of modifications shown in Table 3, and also a modification of at least one nucleotide (e.g., a deletion, insertion and/or substitution) in any one or more of the regions selected from: A', A and/or D. For example, in some embodiments, a modified ITR for use herein can comprise any one of the combinations of modifications shown in Table 3, and also a modification of at least one nucleotide (e.g., a deletion, insertion and/or substitution) in the A region. In some embodiments, a modified ITR for use herein can comprise any one of the combinations of modifications shown in Table 3, and also a modification of at least one nucleotide (e.g., a deletion, insertion and/or substitution) in the A' region. In some embodiments, a modified ITR for use herein can comprise any one of the combinations of modifications shown in Table 3, and also a modification of at least one nucleotide (e.g., a deletion, insertion and/or substitution) in the A and/or A' region. In some embodiments, a modified ITR for use herein can comprise any one of the combinations of modifications shown in Table 3, and also a modification of at least one nucleotide (e.g., a deletion, insertion and/or substitution) in the D region.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a modified structural element. In one embodiment, the specific modifications to the ITRs are exemplified herein (e.g., shown in FIG. 7A-7B of PCT/US2018/064242, filed on Dec. 6, 2018 (e.g., SEQ ID Nos: 97-98, 101-103, 105-108, 111-112, 117-134, 545-54 in PCT/US2018/064242). In some embodiments, an ITR can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80%, at least 85%, at least 90%, at least 95%, at least 96%, at least 97%, at least 98%, at least 99%, or more sequence identity with one of the modified ITRs shown in Tables 2-9 of International application PCT/US18/49996, which is incorporated herein in its entirety by reference.

In some embodiments, a modified ITR can have between 1 and 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide deletions relative to a full-length wild-type ITR sequence. In some embodiments, a modified ITR can have between 1 and 30 nucleotide deletions relative to a full-length WT ITR sequence. In some embodiments, a modified ITR has between 2 and 20 nucleotide deletions relative to a full-length wild-type ITR sequence.

Figure 3B:
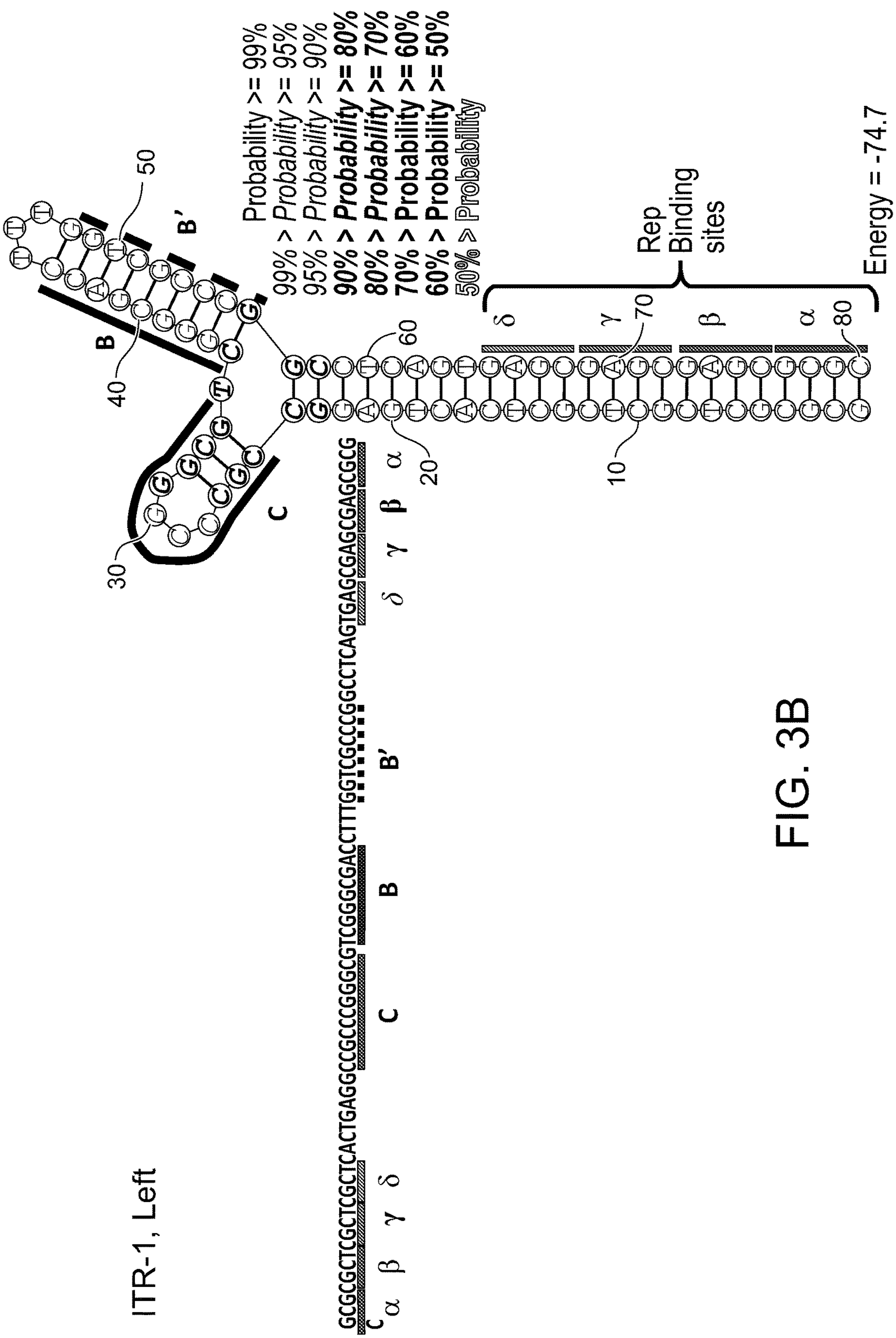
FIG. 3B shows an exemplary mutated ITR (also referred to as a modified ITR) sequence for the left ITR. Shown is the primary structure (left) (SEQ ID NO: 84) and the predicted secondary structure (right) (SEQ ID NO: 84) of the RBE portion of the A-A' arm, the C arm and B-B' arm of an exemplary mutated left ITR (ITR-1, left).
Figure 3C:
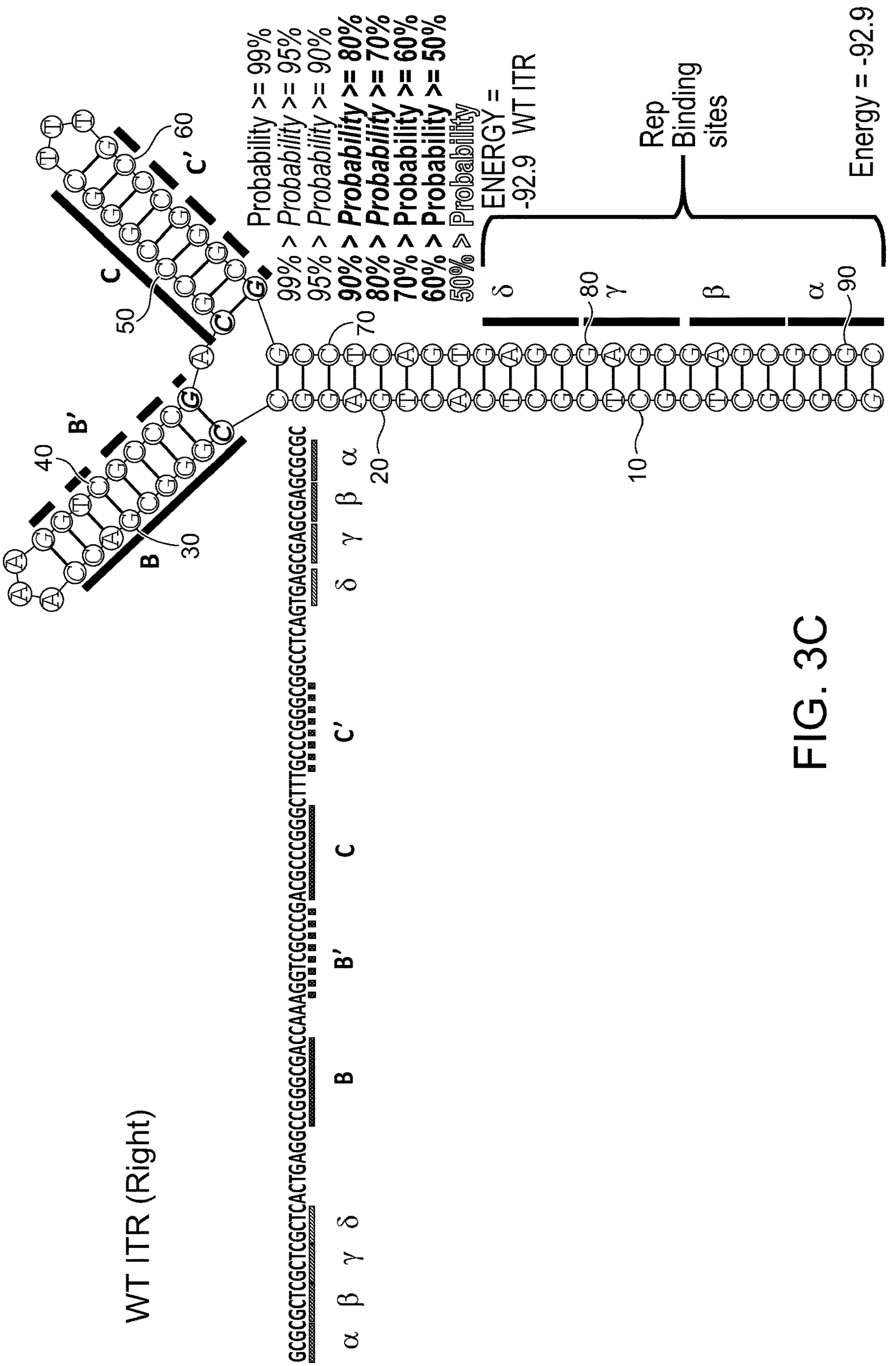
FIG. 3C shows the primary structure (left) (SEQ ID NO: 85) and the secondary structure (right) (SEQ ID NO: 85) of the RBE-containing portion of the A-A' loop, and the B-B' and C-C' arms of wild type right AAV2 ITR.
Figure 3D:
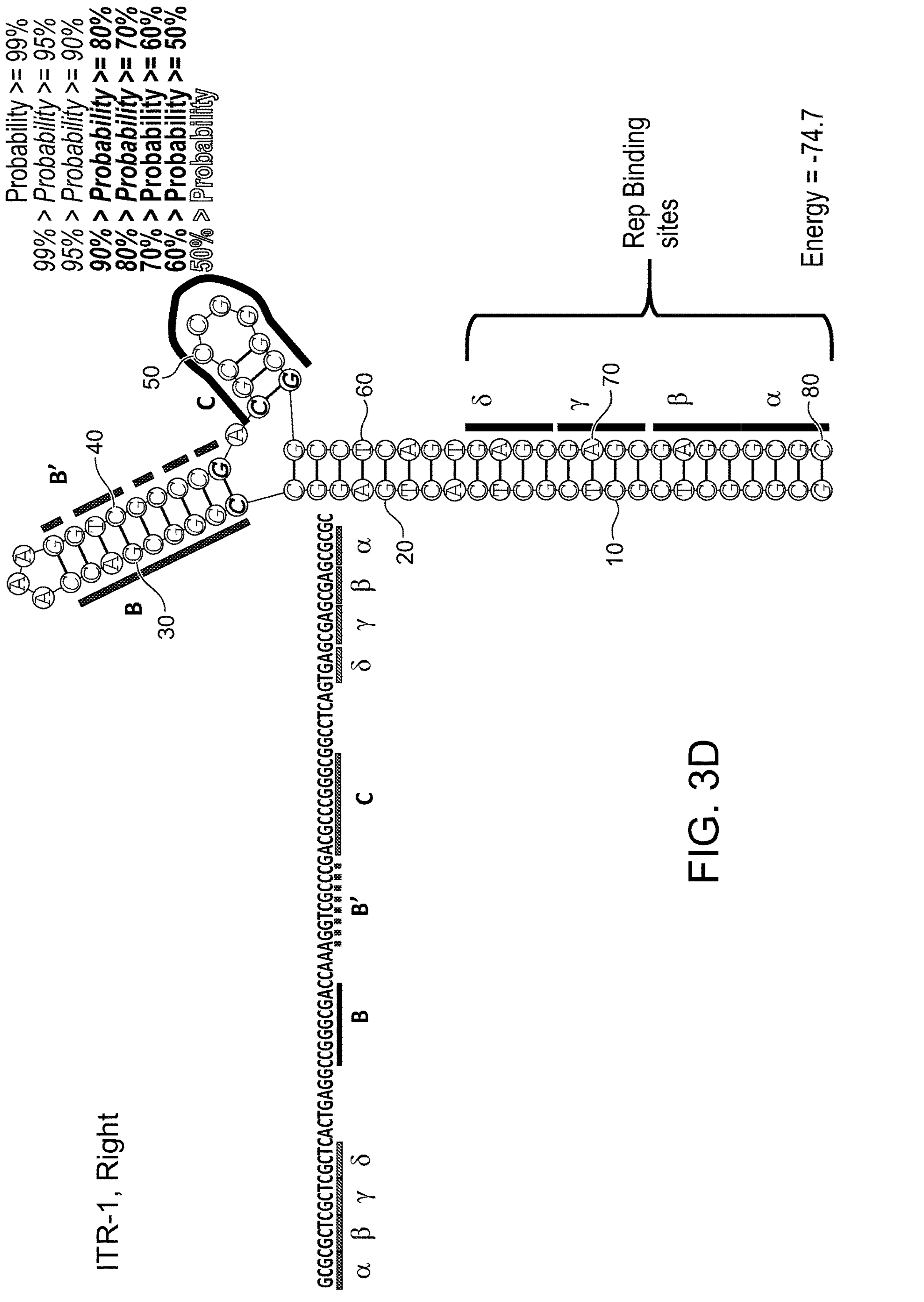
FIG. 3D shows an exemplary right modified ITR. Shown is the primary structure (left) (SEQ ID NO: 86) and the predicted secondary structure (right) (SEQ ID NO: 86) of the RBE containing portion of the A-A' arm, the B-B' and the C arm of an exemplary mutant right ITR (ITR-1, right). Any combination of left and right ITR (e.g., AAV2 ITRs or other viral serotype or synthetic ITRs) can be used as taught herein. Each of FIGS. 3A-3D polynucleotide sequences refers to the sequence used to produce the gapped neDNA as described herein.

In some embodiments, a modified ITR can for example, comprise removal or deletion of all of a particular arm, e.g., all or part of the A-A' arm, or all or part of the B-B' arm or all or part of the C-C' arm, or alternatively, the removal of 1, 2, 3, 4, 5, 6, 7, 8, 9 or more base pairs forming the stem of the loop so long as the final loop capping the stem (e.g., single arm) is still present (e.g., see ITR-21 in FIG. 7A of PCT/US2018/064242, filed on Dec. 6, 2018, the entire content of which is incorporated herein its entirety by reference). In some embodiments, a modified ITR can comprise the removal of 1, 2, 3, 4, 5, 6, 7, 8, 9 or more base pairs from the B-B' arm. In some embodiments, a modified ITR can comprise the removal of 1, 2, 3, 4, 5, 6, 7, 8, 9 or more base pairs from the C-C' arm (see, e.g., ITR-1 in FIG. 3B, or ITR-45 in FIG. 7A of PCT/US2018/064242, filed on Dec. 6, 2018). In some embodiments, a modified ITR can comprise the removal of 1, 2, 3, 4, 5, 6, 7, 8, 9 or more base pairs from the C-C' arm and the removal of 1, 2, 3, 4, 5, 6, 7, 8, 9 or more base pairs from the B-B' arm. Any combination of removal of base pairs is envisioned, for example, 6 base pairs can be removed in the C-C' arm and 2 base pairs in the B-B' arm. As an illustrative example, FIG. 3B shows an exemplary modified ITR with at least 7 base pairs deleted from each of the C portion and the C' portion, a substitution of a nucleotide in the loop between C and C' region, and at least one base pair deletion from each of the B region and B' regions such that the modified ITR comprises two arms where at least one arm (e.g., C-C') is truncated. In some embodiments, the modified ITR also comprises at least one base pair deletion from each of the B region and B' regions, such that the B-B' arm is also truncated relative to WT ITR.

In some embodiments, a modified ITR does not contain any nucleotide deletions in the RBE-containing portion of the A or A' regions, so as not to interfere with DNA replication (e.g., binding to an RBE by Rep protein, or nicking at a terminal resolution site, or extended gap of 10-15 base pairs).

In some embodiments, a modified ITR encompassed for use herein has one or more deletions in the B, B', C, and/or C region as described herein.

In some embodiments, a synthetically produced neDNA vector comprising a symmetric ITR pair or asymmetric ITR pair comprises a regulatory switch as disclosed herein and at least one modified ITR.

In another embodiment, the structure of the structural element can be modified. For example, the structural element a change in the height of the stem and/or the number of nucleotides in the loop. For example, the height of the stem can be about 2, 3, 4, 5, 6, 7, 8, or 9 nucleotides or more or any range therein. In one embodiment, the stem height can be about 5 nucleotides to about 9 nucleotides and functionally interacts with Rep. In another embodiment, the stem height can be about 7 nucleotides and functionally interacts with Rep. In another example, the loop can have 3, 4, 5, 6, 7, 8, 9, or 10 nucleotides or more or any range therein.

In another embodiment, the number of GAGY binding sites or GAGY-related binding sites within the RBE or extended RBE can be increased or decreased. In one example, the RBE or extended RBE, can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as but not limited to the RBE and a hairpin) can be altered (e.g., increased or decreased) to manipulate the functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein. A gap of, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, or 50 base pair in length can be introduced in, e.g., the stem regions of the ITRs as described above using single or multiple oligonucleotides per ITR in the synthetic synthesis methods described herein (see, e.g., FIGS. 6-9).

The synthetically produced neDNA vector described herein can include an ITR structure that is modified with respect to the wild type AAV2 ITR structure disclosed herein, but still retains an operable RBE, TRS and RBE' portion. FIG. 2A and FIG. 2B show one possible mechanism for the operation of a TRS site within a wild type ITR structure portion of a neDNA vector. In some embodiments, the neDNA vector contains one or more functional ITR polynucleotide sequences that comprise a Rep-binding site (RBS; 5'-GCGCGCTCGCTCGCTC-3' (SEQ ID NO: 1) for AAV2) and a terminal resolution site (TRS; 5'-AGTT). In some embodiments, at least one ITR (WT or modified ITR) is functional. In alternative embodiments, where a neDNA vector comprises two modified ITRs that are different or asymmetrical to each other, at least one modified ITR is functional and at least one modified ITR is non-functional.

In some embodiments, the modified ITR for use in a synthetically produced neDNA vector comprising an asymmetric ITR pair, or symmetric mod-ITR pair is selected from any or a combination of those shown in Tables 2, 3, 4, 5, 6, 7, 8, 9 and 10A-10B of International application PCT/US18/49996 which is incorporated herein in its entirety by reference.

Figure 7B:
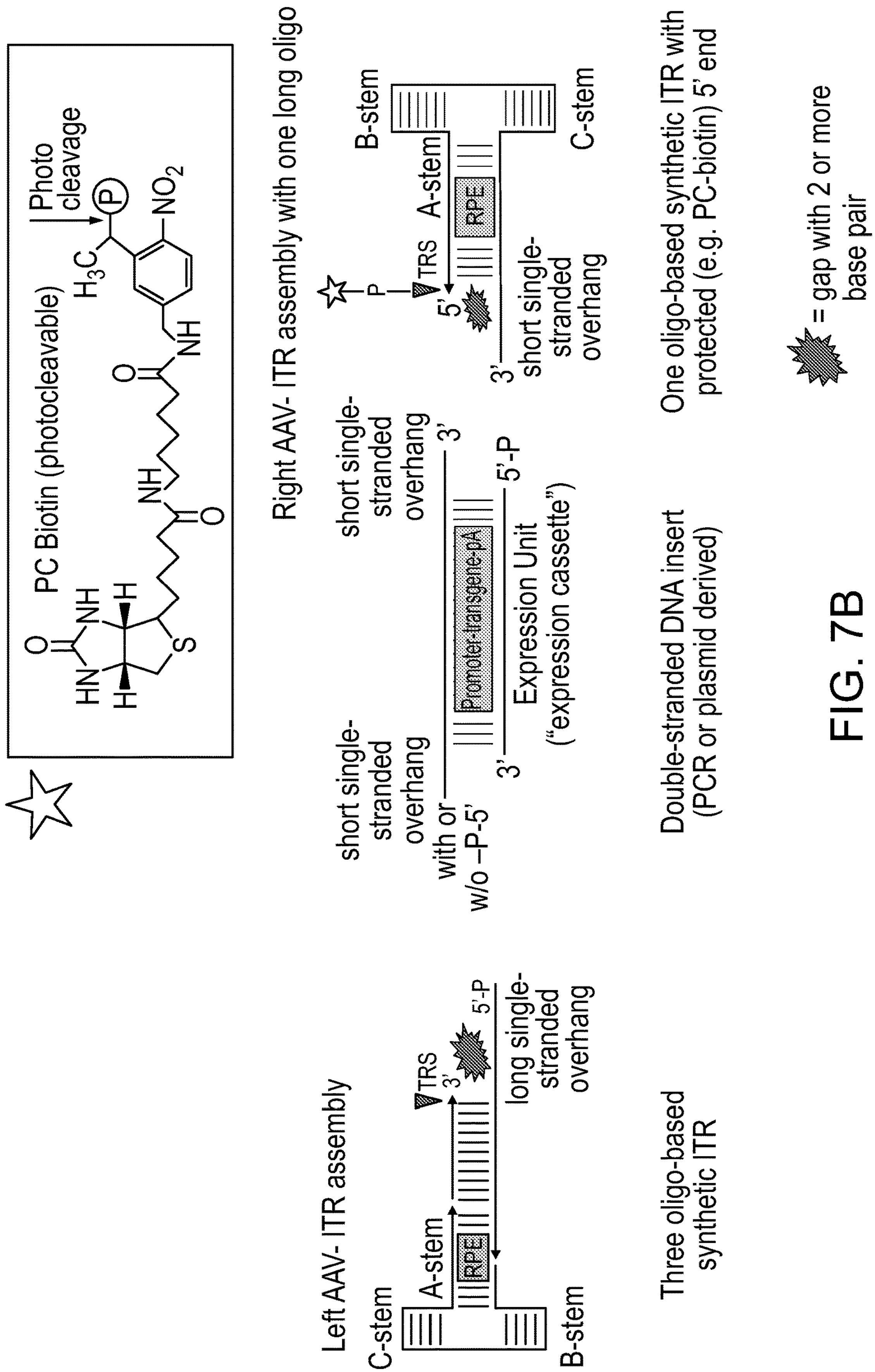
FIG. 7B is a schematic description of neDNA synthesis using asymmetric ITR synthesis, where multiple oligonucleotides (in this case, three oligonucleotides) are used for the L-ITR, and a one oligonucleotide is used for the R-ITR, where each generated ITR comprises an overhang and when ligated with an expression vector, they create a gap of 1-100 base pairs (i.e., long single-stranded overhang).

Additional exemplary modified ITRs for use in a synthetically produced neDNA vector comprising an asymmetric ITR pair, or symmetric mod-ITR pair in each of the above classes are provided in Tables 4A and 4B. The predicted secondary structure of the Right modified ITRs in Table 4A are shown in FIG. 7A of International Application PCT/US2018/064242, filed on Dec. 6, 2018, and the predicted secondary structure of the Left modified ITRs in Table 4B are shown in FIG. 7B of International Application PCT/US2018/064242, filed on Dec. 6, 2018, which is incorporated in its entirety herein.

Table 4A and Table 4B show exemplary right and left modified ITRs. Table 4A lists exemplary modified right ITRs. These exemplary modified right ITRs can comprise the RBE of GCGCGCTCGCTCGCTC-3'(SEQ ID NO: 1), spacer of ACTGAGGC, the spacer complement GCCTCAGT and RBE' (i.e., complement to RBE) of GAGCGAGCGAGCGCGC (SEQ ID NO: 14). A gap can be present between RBE of GCGCGCTCGCTCGCTC-3'(SEQ ID NO: 1) and spacer of ACTGAGGC. Alternatively, the spacer can be discontinued by a gap (e.g., 5'ACTGA---gap---GGC3').

TABLE 4A

Exemplary Right Modified ITRs

| ITR Construct | SEQ ID NO: | Sequence |
|---|---|---|
| ITR-18 Right | 15 | AGGAACCCCTAGTGATGGAGTTGGCCACTCCCTCTCT GCGCGCTCGCTCGCTCACTGAGGCGCACGCCCGGGT TTCCCGGGCGGCCTCAGTGAGCGAGCGAGCGCGCAG CTGCCTGCAGG |
| ITR-19 Right | 16 | AGGAACCCCTAGTGATGGAGTTGGCCACTCCCTCTCT GCGCGCTCGCTCGCTCACTGAGGCCGACGCCCGGGC TTTGCCCGGGCGGCCTCAGTGAGCGAGCGAGCGCGC AGCTGCCTGCAGG |
| ITR-20 Right | 17 | AGGAACCCCTAGTGATGGAGTTGGCCACTCCCTCTCT GCGCGCTCGCTCGCTCACTGAGGCCGGGCGACCAAA GGTCGCCCGACGCCCGGGCGCCTCAGTGAGCGAGCG AGCGCGCAGCTGCCTGCAGG |
| ITR-21 Right | 18 | AGGAACCCCTAGTGATGGAGTTGGCCACTCCCTCTCT GCGCGCTCGCTCGCTCACTGAGGCTTTGCCTCAGTGA GCGAGCGAGCGCGCAGCTGCCTGCAGG |

TABLE 4A-continued

| Exemplary Right Modified ITRs | | |
|---|---|---|
| ITR Construct | SEQ ID NO: | Sequence |
| ITR-22 Right | 19 | AGGAACCCCTAGTGATGGAGTTGGCCACTCCCTCTCT<br>GCGCGCTCGCTCGCTCACTGAGGCCGGGCGACAAAG<br>TCGCCCGACGCCCGGGCTTTGCCCGGGCGGCCTCAGT<br>GAGCGAGCGAGCGCGCAGCTGCCTGCAGG |
| ITR-23 Right | 20 | AGGAACCCCTAGTGATGGAGTTGGCCACTCCCTCTCT<br>GCGCGCTCGCTCGCTCACTGAGGCCGGGCGAAAATC<br>GCCCGACGCCCGGGCTTTGCCCGGGCGGCCTCAGTG<br>AGCGAGCGAGCGCGCAGCTGCCTGCAGG |
| ITR-24 Right | 21 | AGGAACCCCTAGTGATGGAGTTGGCCACTCCCTCTCT<br>GCGCGCTCGCTCGCTCACTGAGGCCGGGCGAAACGC<br>CCGACGCCCGGGCTTTGCCCGGGCGGCCTCAGTGAG<br>CGAGCGAGCGCGCAGCTGCCTGCAGG |
| ITR-25 Right | 22 | AGGAACCCCTAGTGATGGAGTTGGCCACTCCCTCTCT<br>GCGCGCTCGCTCGCTCACTGAGGCCGGGCAAAGCCC<br>GACGCCCGGGCTTTGCCCGGGCGGCCTCAGTGAGCG<br>AGCGAGCGCGCAGCTGCCTGCAGG |
| ITR-26 Right | 23 | AGGAACCCCTAGTGATGGAGTTGGCCACTCCCTCTCT<br>GCGCGCTCGCTCGCTCACTGAGGCCGGGCGACCAAA<br>GGTCGCCCGACGCCCGGGTTTCCCGGGCGGCCTCAG<br>TGAGCGAGCGAGCGCGCAGCTGCCTGCAGG |
| ITR-27 Right | 24 | AGGAACCCCTAGTGATGGAGTTGGCCACTCCCTCTCT<br>GCGCGCTCGCTCGCTCACTGAGGCCGGGCGACCAAA<br>GGTCGCCCGACGCCCGGTTTCCGGGCGGCCTCAGTG<br>AGCGAGCGAGCGCGCAGCTGCCTGCAGG |
| ITR-28 Right | 25 | AGGAACCCCTAGTGATGGAGTTGGCCACTCCCTCTCT<br>GCGCGCTCGCTCGCTCACTGAGGCCGGGCGACCAAA<br>GGTCGCCCGACGCCCGTTTCGGGCGGCCTCAGTGAG<br>CGAGCGAGCGCGCAGCTGCCTGCAGG |
| ITR-29 Right | 26 | AGGAACCCCTAGTGATGGAGTTGGCCACTCCCTCTCT<br>GCGCGCTCGCTCGCTCACTGAGGCCGGGCGACCAAA<br>GGTCGCCCGACGCCCTTTGGGCGGCCTCAGTGAGCG<br>AGCGAGCGCGCAGCTGCCTGCAGG |
| ITR-30 Right | 27 | AGGAACCCCTAGTGATGGAGTTGGCCACTCCCTCTCT<br>GCGCGCTCGCTCGCTCACTGAGGCCGGGCGACCAAA<br>GGTCGCCCGACGCCTTTGGCGGCCTCAGTGAGCGAG<br>CGAGCGCGCAGCTGCCTGCAGG |
| ITR-31 Right | 28 | AGGAACCCCTAGTGATGGAGTTGGCCACTCCCTCTCT<br>GCGCGCTCGCTCGCTCACTGAGGCCGGGCGACCAAA<br>GGTCGCCCGACGCTTTGCGGCCTCAGTGAGCGAGCG<br>AGCGCGCAGCTGCCTGCAGG |
| ITR-32 Right | 29 | AGGAACCCCTAGTGATGGAGTTGGCCACTCCCTCTCT<br>GCGCGCTCGCTCGCTCACTGAGGCCGGGCGACCAAA<br>GGTCGCCCGACGTTTCGGCCTCAGTGAGCGAGCGAG<br>CGCGCAGCTGCCTGCAGG |
| ITR-49 Right | 30 | AGGAACCCCTAGTGATGGAGTTGGCCACTCCCTCTCT<br>GCGCGCTCGCTCGCTCACTGAGGCCGGGCGACCAAA<br>GGTCGCCCGACGGCCTCAGTGAGCGAGCGAGCGCGC<br>AGCTGCCTGCAGG |
| ITR-50 right | 31 | AGGAACCCCTAGTGATGGAGTTGGCCACTCCCTCTCT<br>GCGCGCTCGCTCGCTCACTGAGGCCGGGCGACCAAA<br>GGTCGCCCGACGCCCGGGCGGCCTCAGTGAGCGAGC<br>GAGCGCGCAGCTGCCTGCAGG |

TABLE 4B lists exemplary modified left ITRs. These exemplary modified left ITRs can comprise the RBE of 5'-GCGCGCTCGCTCGCTC-3' (SEQ ID NO: 1), spacer of ACTGAGGC, the spacer complement GCCTCAGT and RBE complement (RBE') of GAGCGAGCGAGCGCGC (SEQ ID NO: 14). A gap can be present between RBE of 5'-GCGCGCTCGCTCGCTC-3'(SEQ ID NO: 1) and spacer of 5'-ACTGAGGC-3'. Alternatively, the spacer in the stem region can be discontinued by a gap (e.g., 5'ACTGA--gap--GGC3').

TABLE 4B

| Exemplary modified left ITRs | | |
|---|---|---|
| ITR-33 Left | (SEQ ID NO: 32) | CCTGCAGGCAGCTGCGCGCTCGCTCGCTCACTGAGGCCGCCCGGGAAACCCGGGCGTGCGCCTCAGTGAGCGAGCGAGCGCGCAGAGAGGGAGTGGCCAACTCCATCACTAGGGGTTCCT |
| ITR-34 Left | (SEQ ID NO: 33) | CCTGCAGGCAGCTGCGCGCTCGCTCGCTCACTGAGGCCGTCGGGCGACCTTTGGTCGCCCGGCCTCAGTGAGCGAGCGAGCGCGCAGAGAGGGAGTGGCCAACTCCATCACTAGGGGTTCCT |
| ITR-35 Left | (SEQ ID NO: 34) | CCTGCAGGCAGCTGCGCGCTCGCTCGCTCACTGAGGCCGCCCGGGCAAAGCCCGGGCGTCGGCCTCAGTGAGCGAGCGAGCGCGCAGAGAGGGAGTGGCCAACTCCATCACTAGGGGTTCCT |
| ITR-36 Left | (SEQ ID NO: 35) | CCTGCAGGCAGCTGCGCGCTCGCTCGCTCACTGAGGCGCCCGGGCGTCGGGCGACCTTTGGTCGCCCGGCCTCAGTGAGCGAGCGAGCGCGCAGAGAGGGAGTGGCCAACTCCATCACTAGGGGTTCCT |
| ITR-37 Left | (SEQ ID NO: 36) | CCTGCAGGCAGCTGCGCGCTCGCTCGCTCACTGAGGCAAAGCCTCAGTGAGCGAGCGAGCGCGCAGAGAGGGAGTGGCCAACTCCATCACTAGGGGTTCCT |
| ITR-38 Left | (SEQ ID NO: 37) | CCTGCAGGCAGCTGCGCGCTCGCTCGCTCACTGAGGCCGCCCGGGCAAAGCCCGGGCGTCGGGCGACTTTGTCGCCCGGCCTCAGTGAGCGAGCGAGCGCGCAGAGAGGGAGTGGCCAACTCCATCACTAGGGGTTCCT |
| ITR-39 Left | (SEQ ID NO: 38) | CCTGCAGGCAGCTGCGCGCTCGCTCGCTCACTGAGGCCGCCCGGGCAAAGCCCGGGCGTCGGGCGATTTTCGCCCGGCCTCAGTGAGCGAGCGAGCGCGCAGAGAGGGAGTGGCCAACTCCATCACTAGGGGTTCCT |
| ITR-40 Left | (SEQ ID NO: 39) | CCTGCAGGCAGCTGCGCGCTCGCTCGCTCACTGAGGCCGCCCGGGCAAAGCCCGGGCGTCGGGCGTTTCGCCCGGCCTCAGTGAGCGAGCGAGCGCGCAGAGAGGGAGTGGCCAACTCCATCACTAGGGGTTCCT |
| ITR-41 Left | (SEQ ID NO: 40) | CCTGCAGGCAGCTGCGCGCTCGCTCGCTCACTGAGGCCGCCCGGGCAAAGCCCGGGCGTCGGGCTTTGCCCGGCCTCAGTGAGCGAGCGAGCGCGCAGAGAGGGAGTGGCCAACTCCATCACTAGGGGTTCCT |
| ITR-42 Left | (SEQ ID NO: 41) | CCTGCAGGCAGCTGCGCGCTCGCTCGCTCACTGAGGCCGCCCGGGAAACCCGGGCGTCGGGCGACCTTTGGTCGCCCGGCCTCAGTGAGCGAGCGAGCGCGCAGAGAGGGAGTGGCCAACTCCATCACTAGGGGTTCCT |
| ITR-43 Left | (SEQ ID NO: 42) | CCTGCAGGCAGCTGCGCGCTCGCTCGCTCACTGAGGCCGCCCGGAAACCGGGCGTCGGGCGACCTTTGGTCGCCCGGCCTCAGTGAGCGAGCGAGCGCGCAGAGAGGGAGTGGCCAACTCCATCACTAGGGGTTCCT |
| ITR 44 Left | (SEQ ID NO: 43) | CCTGCAGGCAGCTGCGCGCTCGCTCGCTCACTGAGGCCGCCCGAAACGGGCGTCGGGCGACCTTTGGTCGCCCGGCCTCAGTGAGCGAGCGAGCGCGCAGAGAGGGAGTGGCCAACTCCATCACTAGGGGTTCCT |
| ITR-45 Left | (SEQ ID NO: 44) | CCTGCAGGCAGCTGCGCGCTCGCTCGCTCACTGAGGCCGCCCAAAGGGCGTCGGGCGACCTTTGGTCGCCCGGCCTCAGTGAGCGAGCGAGCGCGCAGAGAGGGAGTGGCCAACTCCATCACTAGGGGTTCCT |
| ITR-46 Left | (SEQ ID NO: 45) | CCTGCAGGCAGCTGCGCGCTCGCTCGCTCACTGAGGCCGCCAAAGGCGTCGGGCGACCTTTGGTCGCCCGGCCTCAGTGAGCGAGCGAGCGCGCAGAGAGGGAGTGGCCAACTCCATCACTAGGGGTTCCT |
| ITR 47 Left | (SEQ ID NO: 46) | CCTGCAGGCAGCTGCGCGCTCGCTCGCTCACTGAGGCCGCAAAGCGTCGGGCGACCTTTGGTCGCCCGGCCTCAGTGAGCGAGCGAGCGCGCAGAGAGGGAGTGGCCAACTCCATCACTAGGGGTTCCT |
| ITR-48 Left | (SEQ ID NO: 47) | CCTGCAGGCAGCTGCGCGCTCGCTCGCTCACTGAGGCCGAAACGTCGGGCGACCTTTGGTCGCCCGGCCTCAGTGAGCGAGCGAGCGCGCAGAGAGGGAGTGGCCAACTCCATCACTAGGGGTTCCT |

In one embodiment, a synthetically produced neDNA vector comprises, in the 5' to 3' direction: a first adeno-associated virus (AAV) inverted terminal repeat (ITR), a nucleotide sequence of interest (for example an expression cassette as described herein) and a second AAV ITR, where the first ITR (5' ITR) and the second ITR (3' ITR) are asymmetric with respect to each other—that is, they have a different 3D-spatial configuration from one another. As an exemplary embodiment, the first ITR can be a wild-type ITR and the second ITR can be a mutated or modified ITR, or vice versa, where the first ITR can be a mutated or modified ITR and the second ITR a wild-type ITR. In some embodiment, the first ITR and the second ITR are both mod-ITRs, but have different sequences, or have different modifications, and thus are not the same modified ITRs, and have different 3D spatial configurations. Stated differently, a neDNA vector with asymmetric ITRs comprises ITRs where any changes in one ITR relative to the WT-ITR are not reflected in the other ITR; or alternatively, where the asymmetric ITRs have a the modified asymmetric ITR pair can have a different sequence and different three-dimensional shape with respect to each other. Exemplary asymmetric ITRs in the neDNA vector and for use to generate a neDNA-plasmid are shown in Table 4A and 4B.

In an alternative embodiment, a synthetically produced neDNA vector comprises two symmetrical mod-ITRs—that is, both ITRs have the same sequence, but are reverse complements (inverted) of each other. In some embodiments, a symmetrical mod-ITR pair comprises at least one or any combination of a deletion, insertion, or substitution relative to wild type ITR sequence from the same AAV serotype. The additions, deletions, or substitutions in the symmetrical ITR are the same but the reverse complement of each other. For example, an insertion of 3 nucleotides in the C region of the 5' ITR would be reflected in the insertion of 3 reverse complement nucleotides in the corresponding section in the C' region of the 3' ITR. Solely for illustration purposes only, if the addition is AACG in the 5' ITR, the addition is CGTT in the 3' ITR at the corresponding site. For example, if the 5' ITR sense strand is ATCGATCG with an addition of AACG between the G and A to result in the sequence ATCGAACGATCG (SEQ ID NO: 48). The corresponding 3' ITR sense strand is CGATCGAT (the reverse complement of ATCGATCG) with an addition of CGTT (i.e. the reverse complement of AACG) between the T and C to result in the sequence CGATCGTTCGAT (SEQ ID NO: 49) (the reverse complement of ATCGAACGATCG (SEQ ID NO: 48)).

In alternative embodiments, the modified ITR pair are substantially symmetrical as defined herein—that is, the modified ITR pair can have a different sequence but have corresponding or the same symmetrical three-dimensional shape. For example, one modified ITR can be from one serotype and the other modified ITR be from a different serotype, but they have the same mutation (e.g., nucleotide insertion, deletion or substitution) in the same region. Stated differently, for illustrative purposes only, a 5' mod-ITR can be from AAV2 and have a deletion in the C region, and the 3' mod-ITR can be from AAV5 and have the corresponding deletion in the C' region, and provided the 5' mod-ITR and the 3' mod-ITR have the same or symmetrical three-dimensional spatial organization, they are encompassed for use herein as a modified ITR pair.

In some embodiments, a substantially symmetrical mod-ITR pair has the same A, C-C' and B-B' loops in 3D space, e.g., if a modified ITR in a substantially symmetrical mod-ITR pair has a deletion of a C-C' arm, then the cognate mod-ITR has the corresponding deletion of the C-C' loop and also has a similar 3D structure of the remaining A and B-B' loops in the same shape in geometric space of its cognate mod-ITR. By way of example only, substantially symmetrical ITRs can have a symmetrical spatial organization such that their structure is the same shape in geometrical space. This can occur, e.g., when a G-C pair is modified, for example, to a C-G pair or vice versa, or A-T pair is modified to a T-A pair, or vice versa. Therefore, using the exemplary example above of modified 5' ITR as a ATCGAACGATCG (SEQ ID NO: 48), and modified 3' ITR as CGATCGTTCGAT (SEQ ID NO: 49) (i.e., the reverse complement of ATCGAACGATCG (SEQ ID NO: 48)), these modified ITRs would still be symmetrical if, for example, the 5' ITR had the sequence of ATCGAACCATCG (SEQ ID NO: 50), where G in the addition is modified to C, and the substantially symmetrical 3' ITR has the sequence of CGATCGTTCGAT (SEQ ID NO: 49), without the corresponding modification of the T in the addition to a. In some embodiments, such a modified ITR pair are substantially symmetrical as the modified ITR pair has symmetrical stereochemistry.

Table 5 shows exemplary symmetric modified ITR pairs (i.e. a left modified ITRs and the symmetric right modified ITR). The bold (red) portion of the sequences identify partial ITR sequences (i.e., sequences of A-A', C-C' and B-B' loops). These exemplary modified ITRs can comprise the RBE of 5'-GCGCGCTCGCTCGCTC-3' (SEQ ID NO: 1), spacer of ACTGAGGC, the spacer complement GCCTCAGT and RBE' (i.e., complement to RBE) of GAGCGAGCGAGCGCGC (SEQ ID NO: 14). A gap can be present between RBE of 5'-GCGCGCTCGCTCGCTC-3' (SEQ ID NO: 1) and spacer of 5'-ACTGAGGC-3'. Alternatively, the spacer in the stem region can be discontinued by a gap (e.g., 5'ACTGA--gap--GGC3').

TABLE 5

| Exemplary symmetric modified ITR pairs | | | | | |
|---|---|---|---|---|---|
| LEFT modified ITR (modified 5' ITR) | | | Symmetric RIGHT modified ITR (modified 3' ITR) | | |
| ITR-33 left | (SEQ ID NO: 32) | CCTGCAGGCAGCT**GCGCG**<br>**CTCGCTCGCTCACTGAGG**<br>**CCGCCCGGGAAACCCGGG**<br>**CGTGCGCCTCAGTGAGCG**<br>**AGCGAGCGCGC**AGAGAGG<br>GAGTGGCCAACTCCATCA<br>CTAGGGGTTCCT | ITR-18, right | (SEQ ID NO: 15) | AGGAACCCCTAGTGATGG<br>AGTTGGCCACTCCCTCTC<br>**TGCGCGCTCGCTCGCTCA**<br>**CTGAGGCGCACGCCCGGG**<br>**TTTCCCGGGCGGCCTCAG**<br>**TGAGCGAGCGAGCGCGC**A<br>GCTGCCTGCAGG |
| ITR-34 left | (SEQ ID NO: 33) | CCTGCAGGCAGCT**GCGCG**<br>**CTCGCTCGCTCACTGAGG**<br>**CCGTCGGGCGACCTTTGG**<br>**TCGCCCGGCCTCAGTGAG**<br>**CGAGCGAGCGCGC**AGAGA<br>GGGAGTGGCCAACTCCAT<br>CACTAGGGGTTCCT | ITR-51, right | (SEQ ID NO: 30) | AGGAACCCCTAGTGATGG<br>AGTTGGCCACTCCCTCTC<br>**TGCGCGCTCGCTCGCTCA**<br>**CTGAGGCCGGGCGACCAA**<br>**AGGTCGCCCGACGGCCTC**<br>**AGTGAGCGAGCGAGCGCG**<br>**C**AGCTGCCTGCAGG |
| ITR-35 left | (SEQ ID NO: 34) | CCTGCAGGCAGCT**GCGCG**<br>**CTCGCTCGCTCACTGAGG**<br>**CCGCCCGGGCAAAGCCCG**<br>**GGCGTCGGCCTCAGTGAG** | ITR-19, right | (SEQ ID NO: 16) | AGGAACCCCTAGTGATGG<br>AGTTGGCCACTCCCTCTC<br>**TGCGCGCTCGCTCGCTCA**<br>**CTGAGGCCGACGCCCGGG** |

TABLE 5-continued

Exemplary symmetric modified ITR pairs

| LEFT modified ITR (modified 5' ITR) | | | Symmetric RIGHT modified ITR (modified 3' ITR) | | |
|---|---|---|---|---|---|
| | | **CGAGCGAGCGCGC**AGAGA<br>GGGAGTGGCCAACTCCAT<br>CACTAGGGGTTCCT | | | **CTTTGCCCGGGCGGCCTC**<br>**AGTGAGCGAGCGAGCGCG**<br>**C**AGCTGCCTGCAGG |
| ITR-36 left | (SEQ ID NO: 35) | CCTGCAGGCAGCT**GCGCG**<br>**CTCGCTCGCTCACTGAGG**<br>**CGCCCGGGCGTCGGGCGA**<br>**CCTTTGGTCGCCCGGCCT**<br>**CAGTGAGCGAGCGAGCGC**<br>**GC**AGAGAGGGAGTGGCCA<br>ACTCCATCACTAGGGGTT<br>CCT | ITR-20, right | (SEQ ID NO: 17) | AGGAACCCCTAGTGATGG<br>AGTTGGCCACTCCCTCTC<br>**TGCGCGCTCGCTCGCTCA**<br>**CTGAGGCCGGGCGACCAA**<br>**AGGTCGCCCGACGCCCGG**<br>**GCGCCTCAGTGAGCGAGC**<br>**GAGCGCGC**AGCTGCCTGC<br>AGG |
| ITR-37 left | (SEQ ID NO: 36) | CCTGCAGGCAGCT**GCGCG**<br>**CTCGCTCGCTCACTGAGG**<br>**CAAAGCCTCAGTGAGCGA**<br>**GCGAGCGCGC**AGAGAGGG<br>AGTGGCCAACTCCATCAC<br>TAGGGGTTCCT | ITR-21, right | (SEQ ID NO: 18) | AGGAACCCCTAGTGATGG<br>AGTTGGCCACTCCCTCTC<br>**TGCGCGCTCGCTCGCTCA**<br>**CTGAGGCTTTGCCTCAGT**<br>**GAGCGAGCGAGCGCGC**AG<br>CTGCCTGCAGG |
| ITR-38 left | (SEQ ID NO: 37) | CCTGCAGGCAGCT**GCGCG**<br>**CTCGCTCGCTCACTGAGG**<br>**CCGCCCGGGCAAAGCCCG**<br>**GGCGTCGGGCGACTTTGT**<br>**CGCCCGGCCTCAGTGAGC**<br>**GAGCGAGCGCGC**AGAGAG<br>GGAGTGGCCAACTCCATC<br>ACTAGGGGTTCCT | ITR-22 right | (SEQ ID NO: 19) | AGGAACCCCTAGTGATGG<br>AGTTGGCCACTCCCTCTC<br>**TGCGCGCTCGCTCGCTCA**<br>**CTGAGGCCGGGCGACAAA**<br>**GTCGCCCGACGCCCGGGC**<br>**TTTGCCCGGGCGGCCTCA**<br>**GTGAGCGAGCGAGCGCGC**<br>AGCTGCCTGCAGG |
| ITR-39 left | (SEQ ID NO: 38) | CCTGCAGGCAGCT**GCGCG**<br>**CTCGCTCGCTCACTGAGG**<br>**CCGCCCGGGCAAAGCCCG**<br>**GGCGTCGGGCGATTTTCG**<br>**CCCGGCCTCAGTGAGCGA**<br>**GCGAGCGCGC**AGAGAGGG<br>AGTGGCCAACTCCATCAC<br>TAGGGGTTCCT | ITR-23, right | (SEQ ID NO: 20) | AGGAACCCCTAGTGATGG<br>AGTTGGCCACTCCCTCTC<br>**TGCGCGCTCGCTCGCTCA**<br>**CTGAGGCCGGGCGAAAAT**<br>**CGCCCGACGCCCGGGCTT**<br>**TGCCCGGGCGGCCTCAGT**<br>**GAGCGAGCGAGCGCGC**AG<br>CTGCCTGCAGG |
| ITR-40 left | (SEQ ID NO: 39) | CCTGCAGGCAGCT**GCGCG**<br>**CTCGCTCGCTCACTGAGG**<br>**CCGCCCGGGCAAAGCCCG**<br>**GGCGTCGGGCGTTTCGCC**<br>**CGGCCTCAGTGAGCGAGC**<br>**GAGCGCGC**AGAGAGGGAG<br>TGGCCAACTCCATCACTA<br>GGGGTTCCT | ITR-24, right | (SEQ ID NO: 21) | AGGAACCCCTAGTGATGG<br>AGTTGGCCACTCCCTCTC<br>**TGCGCGCTCGCTCGCTCA**<br>**CTGAGGCCGGGCGAAACG**<br>**CCCGACGCCCGGGCTTTG**<br>**CCCGGGCGGCCTCAGTGA**<br>**GCGAGCGAGCGCGC**AGCT<br>GCCTGCAGG |
| ITR-41 left | (SEQ ID NO: 40) | CCTGCAGGCAGCT**GCGCG**<br>**CTCGCTCGCTCACTGAGG**<br>**CCGCCCGGGCAAAGCCCG**<br>**GGCGTCGGGCTTTGCCCG**<br>**GCCTCAGTGAGCGAGCGA**<br>**GCGCGC**AGAGAGGGAGTG<br>GCCAACTCCATCACTAGG<br>GGTTCCT | ITR-25 right | (SEQ ID NO: 22) | AGGAACCCCTAGTGATGG<br>AGTTGGCCACTCCCTCTC<br>**TGCGCGCTCGCTCGCTCA**<br>**CTGAGGCCGGGCAAAGCC**<br>**CGACGCCCGGGCTTTGCC**<br>**CGGGCGGCCTCAGTGAGC**<br>**GAGCGAGCGCGC**AGCTGC<br>CTGCAGG |
| ITR-42 left | (SEQ ID NO: 41) | CCTGCAGGCAGCT**GCGCG**<br>**CTCGCTCGCTCACTGAGG**<br>**CCGCCCGGGAAACCCGGG**<br>**CGTCGGGCGACCTTTGGT**<br>**CGCCCGGCCTCAGTGAGC**<br>**GAGCGAGCGCGC**AGAGAG<br>GGAGTGGCCAACTCCATC<br>ACTAGGGGTTCCT | ITR-26 right | (SEQ ID NO: 23) | AGGAACCCCTAGTGATGG<br>AGTTGGCCACTCCCTCTC<br>**TGCGCGCTCGCTCGCTCA**<br>**CTGAGGCCGGGCGACCAA**<br>**AGGTCGCCCGACGCCCGG**<br>**GTTTCCCGGGCGGCCTCA**<br>**GTGAGCGAGCGAGCGCGC**<br>AGCTGCCTGCAGG |
| ITR-43 left | (SEQ ID NO: 42) | CCTGCAGGCAGCT**GCGCG**<br>**CTCGCTCGCTCACTGAGG**<br>**CCGCCCGGAAACCGGGCG**<br>**TCGGGCGACCTTTGGTCG**<br>**CCCGGCCTCAGTGAGCGA**<br>**GCGAGCGCGC**AGAGAGGG<br>AGTGGCCAACTCCATCAC<br>TAGGGGTTCCT | ITR-27 right | (SEQ ID NO: 24) | AGGAACCCCTAGTGATGG<br>AGTTGGCCACTCCCTCTC<br>**TGCGCGCTCGCTCGCTCA**<br>**CTGAGGCCGGGCGACCAA**<br>**AGGTCGCCCGACGCCCGG**<br>**TTTCCGGGCGGCCTCAGT**<br>**GAGCGAGCGAGCGCGC**AG<br>CTGCCTGCAGG |

TABLE 5-continued

| Exemplary symmetric modified ITR pairs | | | | | |
|---|---|---|---|---|---|
| LEFT modified ITR (modified 5' ITR) | | | Symmetric RIGHT modified ITR (modified 3' ITR) | | |
| ITR-44 left | (SEQ ID NO: 43) | CCTGCAGGCAGCT**GCGCGCTCGCTCGCTCACTGAGGCCGCCCGAAACGGGCGTCGGGCGACCTTTGGTCGCCCGGCCTCAGTGAGCGAGCGAGCGCGC**AGAGAGGGAGTGGCCAACTCCATCACTAGGGGTTCCT | ITR-28 right | (SEQ ID NO: 25) | AGGAACCCCTAGTGATGGAGTTGGCCACTCCCTCTC**TGCGCGCTCGCTCGCTCACTGAGGCCGGGCGACCAAAGGTCGCCCGACGCCCGTTTCGGGCGGCCTCAGTGAGCGAGCGAGCGCGC**AGCTGCCTGCAGG |
| ITR-45 left | (SEQ ID NO: 44) | CCTGCAGGCAGCT**GCGCGCTCGCTCGCTCACTGAGGCCGCCCAAAGGGCGTCGGGCGACCTTTGGTCGCCCGGCCTCAGTGAGCGAGCGAGCGCGC**AGAGAGGGAGTGGCCAACTCCATCACTAGGGGTTCCT | ITR-29, right | (SEQ ID NO: 26) | AGGAACCCCTAGTGATGGAGTTGGCCACTCCCTCTC**TGCGCGCTCGCTCGCTCACTGAGGCCGGGCGACCAAAGGTCGCCCGACGCCCTTTGGGCGGCCTCAGTGAGCGAGCGAGCGCGC**AGCTGCCTGCAGG |
| ITR-46 left | (SEQ ID NO: 45) | CCTGCAGGCAGCT**GCGCGCTCGCTCGCTCACTGAGGCCGCCAAAGGCGTCGGGCGACCTTTGGTCGCCCGGCCTCAGTGAGCGAGCGAGCGCGC**AGAGAGGGAGTGGCCAACTCCATCACTAGGGGTTCCT | ITR-30, right | (SEQ ID NO: 27) | AGGAACCCCTAGTGATGGAGTTGGCCACTCCCTCTC**TGCGCGCTCGCTCGCTCACTGAGGCCGGGCGACCAAAGGTCGCCCGACGCCTTTGGCGGCCTCAGTGAGCGAGCGAGCGCGC**AGCTGCCTGCAGG |
| ITR-47, left | (SEQ ID NO: 46) | CCTGCAGGCAGCT**GCGCGCTCGCTCGCTCACTGAGGCCGCAAAGCGTCGGGCGACCTTTGGTCGCCCGGCCTCAGTGAGCGAGCGAGCGCGC**AGAGAGGGAGTGGCCAACTCCATCACTAGGGGTTCCT | ITR-31, right | (SEQ ID NO: 28) | AGGAACCCCTAGTGATGGAGTTGGCCACTCCCTCTC**TGCGCGCTCGCTCGCTCACTGAGGCCGGGCGACCAAAGGTCGCCCGACGCTTTGCGGCCTCAGTGAGCGAGCGAGCGCGC**AGCTGCCTGCAGG |
| ITR-48, left | (SEQ ID NO: 47) | CCTGCAGGCAGCT**GCGCGCTCGCTCACTGAGGCCGAAACGTCGGGCGACCTTTGGTCGCCCGGCCTCAGTGAGCGAGCGAGCGCGC**AGAGAGGGAGTGGCCAACTCCATCACTAGGGGTTCCT | ITR-32 right | (SEQ ID NO: 29) | AGGAACCCCTAGTGATGGAGTTGGCCACTCCCTCTC**TGCGCGCTCGCTCGCTCACTGAGGCCGGGCGACCAAAGGTCGCCCGACGTTTCGGCCTCAGTGAGCGAGCGAGCGCGC**AGCTGCCTGCAGG |

In some embodiments, a neDNA vector comprising an asymmetric ITR pair can comprise an ITR with a modification corresponding to any of the modifications in ITR sequences or ITR partial sequences shown in any one or more of Tables 4A-4B herein or the sequences shown in FIG. 7A or 7B of International Application PCT/US2018/064242, filed on Dec. 6, 2018, which is incorporated in its entirety herein, or disclosed in Tables 2, 3, 4, 5, 6, 7, 8, 9 or 10A-10B3 of International application PCT/US18/49996 filed Sep. 7, 2018 which is incorporated herein in its entirety by reference.

C. Exemplary neDNA Vectors

As described above, the present disclosure relates to synthetically produced recombinant neDNA expression vectors and neDNA vectors that encode a transgene comprising any one of: an asymmetrical ITR pair, a symmetrical ITR pair, or substantially symmetrical ITR pair as described above. In certain embodiments, the disclosure relates to synthetically produced recombinant neDNA vectors having flanking ITR sequences with a gap and a transgene, where the ITR sequences are asymmetrical, symmetrical or substantially symmetrical relative to each other as defined herein, and the neDNA further comprises a nucleotide sequence of interest (for example an expression cassette comprising the nucleic acid of a transgene) located between the flanking ITRs, wherein said nucleic acid molecule is devoid of viral capsid protein coding sequences.

The synthetically produced neDNA expression vector may be any neDNA vector that can be conveniently subjected to recombinant DNA procedures including nucleotide sequence(s) as described herein, provided at least one ITR is altered. The synthetically produced neDNA vectors of the present disclosure are compatible with the host cell into which the neDNA vector is to be introduced. In certain embodiments, the synthetically produced neDNA vectors may be linear. In certain embodiments, the synthetically produced neDNA vectors may exist as an extrachromosomal entity. In certain embodiments, the synthetically produced neDNA vectors of the present disclosure may contain an element(s) that permits integration of a donor sequence into the host cell's genome.

Referring now to FIGS. 1A-1G, schematics of the functional components of two non-limiting plasmids useful in synthetically producing the neDNA vectors of the present disclosure are shown. FIG. 1A, 1B, 1D, 1F show the construct of neDNA vectors or the corresponding sequences of neDNA plasmids, where the first and second ITR sequences are asymmetrical, symmetrical or substantially symmetrical relative to each other as defined herein. In some embodiments, the expressible transgene cassette includes, as needed: an enhancer/promoter, one or more homology arms, a donor sequence, a post-transcription regulatory element (e.g., WPRE), and a polyadenylation and termination signal (e.g., BGH polyA).

Regulatory Elements

The neDNA vectors as described herein and produced using the synthetic process as described herein can comprise an asymmetric ITR pair or symmetric ITR pair as defined herein, can be further comprise a specific combination of cis-regulatory elements. The cis-regulatory elements include, but are not limited to, a promoter, a riboswitch, an insulator, a mir-regulatable element, a post-transcriptional regulatory element, a tissue- and cell type-specific promoter and an enhancer. In some embodiments, the ITR can act as the promoter for the transgene. In some embodiments, the neDNA vector comprises additional components to regulate expression of the transgene, for example, regulatory switches as described herein, to regulate the expression of the transgene, or a kill switch, which can kill a cell comprising the neDNA vector. Regulatory elements, including Regulatory Switches that can be used in the present invention are more fully discussed in International application PCT/US18/49996, which is incorporated herein in its entirety by reference.

In embodiments, the second nucleotide sequence includes a regulatory sequence, and a nucleotide sequence encoding a nuclease. In certain embodiments the gene regulatory sequence is operably linked to the nucleotide sequence encoding the nuclease. In certain embodiments, the regulatory sequence is suitable for controlling the expression of the nuclease in a host cell. In certain embodiments, the regulatory sequence includes a suitable promoter sequence, being able to direct transcription of a gene operably linked to the promoter sequence, such as a nucleotide sequence encoding the nuclease(s) of the present disclosure. In certain embodiments, the second nucleotide sequence includes an intron sequence linked to the 5' terminus of the nucleotide sequence encoding the nuclease. In certain embodiments, an enhancer sequence is provided upstream of the promoter to increase the efficacy of the promoter. In certain embodiments, the regulatory sequence includes an enhancer and a promoter, wherein the second nucleotide sequence includes an intron sequence upstream of the nucleotide sequence encoding a nuclease, wherein the intron includes one or more nuclease cleavage site(s), and wherein the promoter is operably linked to the nucleotide sequence encoding the nuclease.

The neDNA vectors produced using the synthetic process as described herein can further comprise a specific combination of cis-regulatory elements such as WHP posttranscriptional regulatory element (WPRE) and BGH polyA. Suitable expression cassettes for use in expression constructs are not limited by the packaging constraint imposed by the viral capsid.

(i) Promoters

It will be appreciated by one of ordinary skill in the art that promoters used in the synthetically produced neDNA vectors of the invention should be tailored as appropriate for the specific sequences they are promoting. For example, a guide RNA may not require a promoter at all, since its function is to form a duplex with a specific target sequence on the native DNA to effect a recombination event. In contrast, a nuclease encoded by the neDNA vector would benefit from a promoter so that it can be efficiently expressed from the vector—and, optionally, in a regulatable fashion.

Expression cassettes of the present invention include a promoter, which can influence overall expression levels as well as cell-specificity. For transgene expression, they can include a highly active virus-derived immediate early promoter. Expression cassettes can contain tissue-specific eukaryotic promoters to limit transgene expression to specific cell types and reduce toxic effects and immune responses resulting from unregulated, ectopic expression. In preferred embodiments, an expression cassette can contain a synthetic regulatory element, such as a CAG promoter. The CAG promoter comprises (i) the cytomegalovirus (CMV) early enhancer element, (ii) the promoter, the first exon and the first intron of chicken beta-actin gene, and (iii) the splice acceptor of the rabbit beta-globin gene. Alternatively, an expression cassette can contain an Alpha-1-antitrypsin (AAT) promoter, a liver specific (LP1) promoter, or a Human elongation factor-1 alpha (EFla) promoter. In some embodiments, the expression cassette includes one or more constitutive promoters, for example, a retroviral Rous sarcoma virus (RSV) LTR promoter (optionally with the RSV enhancer), or a cytomegalovirus (CMV) immediate early promoter (optionally with the CMV enhancer). Alternatively, an inducible promoter, a native promoter for a transgene, a tissue-specific promoter, or various promoters known in the art can be used.

Suitable promoters, including those described above, can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., *Nature Biotechnology* 20, 497-500 (2002)), an enhanced U6 promoter (e.g., Xia et al., *Nucleic Acids Res.* 2003 Sep. 1; 31(17)), a human HI promoter (HI), a CAG promoter, a human alpha 1-antitypsin (HAAT) promoter, and the like. In certain embodiments, these promoters are altered at their downstream intron containing end to include one or more nuclease cleavage sites. In certain embodiments, the DNA containing the nuclease cleavage site(s) is foreign to the promoter DNA.

In one embodiment, the promoter used is the native promoter of the gene encoding the therapeutic protein. The promoters and other regulatory sequences for the respective genes encoding the therapeutic proteins are known and have been characterized. The promoter region used may further include one or more additional regulatory sequences (e.g., native enhancers). It is preferred that a gap is located 5' upstream of a promoter.

(ii) Polyadenylation Sequences

A sequence encoding a polyadenylation sequence can be included in the synthetically produced neDNA vector to stabilize an mRNA expressed from the neDNA vector, and to aid in nuclear export and translation. In one embodiment, the synthetically produced neDNA vector does not include a polyadenylation sequence. In other embodiments, the vector includes at least 1, at least 2, at least 3, at least 4, at least 5, at least 10, at least 15, at least 20, at least 25, at least 30, at least 40, least 45, at least 50 or more adenine dinucleotides. In some embodiments, the polyadenylation sequence comprises about 43 nucleotides, about 40-50 nucleotides, about 40-55 nucleotides, about 45-50 nucleotides, about 35-50 nucleotides, or any range there between.

The expression cassettes can include a poly-adenylation sequence known in the art or a variation thereof, such as a naturally occurring sequence isolated from bovine BGHpA or a virus SV40 pA, or a synthetic sequence. Some expression cassettes can also include SV40 late polyA signal upstream enhancer (USE) sequence. In some embodiments, the, USE can be used in combination with SV40 pA or heterologous poly-A signal.

(iii) Nuclear Localization Sequences

In some embodiments, the vector encoding an RNA guided endonuclease comprises one or more nuclear localization sequences (NLSs), for example, 1, 2, 3, 4, 5, 6, 7, 8, 9, 10, or more NLSs. In some embodiments, the one or more NLSs are located at or near the amino-terminus, at or near the carboxy-terminus, or a combination of these (e.g., one or more NLS at the amino-terminus and/or one or more NLS at the carboxy terminus). When more than one NLS is present, each can be selected independently of the others, such that a single NLS is present in more than one copy and/or in combination with one or more other NLSs present in one or more copies. Non-limiting examples of NLSs are shown in Table 6.

TABLE 6

Exemplary Nuclear Localization Sequences (NLS)

| SOURCE | SEQ ID NO: | SEQUENCE |
|---|---|---|
| SV40 virus large T-antigen | 51 | PKKKRKV (encoded by CCCAAGAAGAAGAGGAAGGTG (SEQ ID NO: 52)) |
| nucleoplasmin | 53 | KRPAATKKAGQAKKKK |
| c-myc | 54<br>55 | PAAKRVKLD<br>RQRRNELKRSP |
| hRNPA1 M9 | 56 | NQSSNFGPMKGGNFGGRSSGPYGGGGQYFAKPRNQGGY |
| IBB domain from importin-alpha | 57 | RMRIZFKNKGKDTAELRRRRVEVSVELRKAKKDEQILKRRNV |
| myoma T protein | 58<br>59 | VSRKRPRP<br>PPKKARED |
| human p53 | 60 | PQPKKKPL |
| mouse c-abl IV | 61 | SALIKKKKKMAP |
| influenza virus NS1 | 62<br>63 | DRLRR<br>PKQKKRK |
| Hepatitis virus delta antigen | 64 | RKLKKKIKKL |
| mouse Mx1 protein | 65 | REKKKFLKRR |
| human poly(ADP-ribose) polymerase | 66 | KRKGDEVDGVDEVAKKKSKK |
| steroid hormone receptors (human) glucocorticoid | 67 | RKCLQAGMNLEARKTKK |

The expression cassettes can also include a post-transcriptional element to increase the expression of a transgene. In some embodiments, Woodchuck Hepatitis Virus (WHP) posttranscriptional regulatory element (WPRE) is used to increase the expression of a transgene. Other posttranscriptional processing elements such as the post-transcriptional element from the thymidine kinase gene of herpes simplex virus, or hepatitis B virus (HBV) can be used. Secretory sequences can be linked to the transgenes, e.g., VH-02 and VK-A26 sequences.

D. Additional Components of neDNA Vectors

The neDNA vectors produced using the synthetic process as described herein may contain nucleotides that encode other components for gene expression. For example, to select for specific gene targeting events, a protective shRNA may be embedded in a microRNA and inserted into a recombinant neDNA vector designed to integrate site-specifically into the highly active locus, such as an albumin locus. Such embodiments may provide a system for in vivo selection and expansion of gene-modified hepatocytes in any genetic background such as described in Nygaard et al., *A*

*universal system to select gene-modified hepatocytes in vivo, Gene Therapy*, Jun. 8, 2016. The neDNA vectors of the present disclosure may contain one or more selectable markers that permit selection of transformed, transfected, transduced, or the like cells. A selectable marker is a gene the product of which provides for biocide or viral resistance, resistance to heavy metals, prototrophy to auxotrophs, NeoR, and the like. In certain embodiments, positive selection markers are incorporated into the donor sequences such as NeoR. Negative selections markers may be incorporated downstream the donor sequences, for example a nucleic acid sequence HSV-tk encoding a negative selection marker may be incorporated into a nucleic acid construct downstream the donor sequence.

In embodiments, the neDNA vector produced using the synthetic process as described herein can be used for gene editing, for example, as disclosed in International Application PCT/US2018/064242, filed on Dec. 6, 2018, which is incorporated herein in its entirety by reference, and may include one or more of: a 5' homology arm, a 3' homology arm, a polyadenylation site upstream and proximate to the 5' homology arm. Exemplary homology arms are 5' and 3' albumin homology arms or CCR5 5'- and 3' homology arms.

(i) Regulatory Switches

A molecular regulatory switch is one which generates a measurable change in state in response to a signal. Such regulatory switches can be usefully combined with the neDNA vectors produced using the synthetic process as described herein to control the output of expression of the transgene from the neDNA vector. In some embodiments, the neDNA vector comprises a regulatory switch that serves to fine tune expression of the transgene. For example, it can serve as a biocontainment function of the neDNA vector. In some embodiments, the switch is an "ON/OFF" switch that is designed to start or stop (i.e., shut down) expression of the gene of interest in the neDNA in a controllable and regulatable fashion. In some embodiments, the switch can include a "kill switch" that can instruct the cell comprising the neDNA vector to undergo cell programmed death once the switch is activated. Exemplary regulatory switches encompassed for use in a neDNA vector can be used to regulate the expression of a transgene, and are more fully discussed in International application PCT/US18/49996, which is incorporated herein in its entirety by reference (ii) Binary Regulatory Switches In some embodiments, the neDNA vector produced using the synthetic process as described herein comprises a regulatory switch that can serve to controllably modulate expression of the transgene. For example, the expression cassette located between the ITRs of the neDNA vector may additionally comprise a regulatory region, e.g., a promoter, cis-element, repressor, enhancer etc., that is operatively linked to the gene of interest, where the regulatory region is regulated by one or more cofactors or exogenous agents. By way of example only, regulatory regions can be modulated by small molecule switches or inducible or repressible promoters. Non-limiting examples of inducible promoters are hormone-inducible or metal-inducible promoters. Other exemplary inducible promoters/enhancer elements include, but are not limited to, an RU486-inducible promoter, an ecdysone-inducible promoter, a rapamycin-inducible promoter, and a metallothionein promoter.

(iii) Small Molecule Regulatory Switches

A variety of art-known small-molecule based regulatory switches are known in the art and can be combined with the synthetically produced neDNA vectors disclosed herein to form a regulatory-switch controlled neDNA vector. In some embodiments, the regulatory switch can be selected from any one or a combination of: an orthogonal ligand/nuclear receptor pair, for example retinoid receptor variant/LG335 and GRQCIMFI, along with an artificial promoter controlling expression of the operatively linked transgene, such as that as disclosed in Taylor, et al. BMC Biotechnology 10 (2010): 15; engineered steroid receptors, e.g., modified progesterone receptor with a C-terminal truncation that cannot bind progesterone but binds RU486 (mifepristone) (U.S. Pat. No. 5,364,791); an ecdysone receptor from *Drosophila* and their ecdysteroid ligands (Saez, et al., PNAS, 97(26)(2000), 14512-14517; or a switch controlled by the antibiotic trimethoprim (TMP), as disclosed in Sando R $3^{rd}$; Nat Methods. 2013, 10(11):1085-8. In some embodiments, the regulatory switch to control the transgene or expressed by the neDNA vector is a pro-drug activation switch, such as that disclosed in U.S. Pat. Nos. 8,771,679, and 6,339,070.

(iv) "Passcode" Regulatory Switches

In some embodiments the regulatory switch can be a "passcode switch" or "passcode circuit". Passcode switches allow fine tuning of the control of the expression of the transgene from the synthetically produced neDNA vector when specific conditions occur—that is, a combination of conditions need to be present for transgene expression and/or repression to occur. For example, for expression of a transgene to occur at least conditions A and B must occur. A passcode regulatory switch can be any number of conditions, e.g., at least 2, or at least 3, or at least 4, or at least 5, or at least 6 or at least 7 or more conditions to be present for transgene expression to occur. In some embodiments, at least 2 conditions (e.g., A, B conditions) need to occur, and in some embodiments, at least 3 conditions need to occur (e.g., A, B and C, or A, B and D). By way of an example only, for gene expression from a neDNA to occur that has a passcode "ABC" regulatory switch, conditions A, B and C must be present. Conditions A, B and C could be as follows; condition A is the presence of a condition or disease, condition B is a hormonal response, and condition C is a response to the transgene expression. For example, if the transgene edits a defective EPO gene, Condition A is the presence of Chronic Kidney Disease (CKD), Condition B occurs if the subject has hypoxic conditions in the kidney, Condition C is that Erythropoietin-producing cells (EPC) recruitment in the kidney is impaired; or alternatively, HIF-2 activation is impaired. Once the oxygen levels increase or the desired level of EPO is reached, the transgene turns off again until 3 conditions occur, turning it back on.

In some embodiments, a passcode regulatory switch or "Passcode circuit" encompassed for use in the synthetically produced neDNA vector comprises hybrid transcription factors (TFs) to expand the range and complexity of environmental signals used to define biocontainment conditions. As opposed to a deadman switch which triggers cell death in the presence of a predetermined condition, the "passcode circuit" allows cell survival or transgene expression in the presence of a particular "passcode", and can be easily reprogrammed to allow transgene expression and/or cell survival only when the predetermined environmental condition or passcode is present.

Any and all combinations of regulatory switches disclosed herein, e.g., small molecule switches, nucleic acid-based switches, small molecule-nucleic acid hybrid switches, post-transcriptional transgene regulation switches, post-translational regulation, radiation-controlled switches, hypoxia-mediated switches and other regulatory switches known by persons of ordinary skill in the art as disclosed herein can be used in a passcode regulatory switch as disclosed herein. Regulatory switches encompassed for use are also discussed in the review article Kis et al., J R Soc Interface. 12: 20141000 (2015), and summarized in Table 1 of Kis et al. In some embodiments, a regulatory switch for use in a passcode system can be selected from any or a combination of the switches in Table 11.

(v) Nucleic Acid-Based Regulatory Switches to Control Transgene Expression

In some embodiments, the regulatory switch to control the transgene expressed by the synthetically produced neDNA vector is based on a nucleic-acid based control mechanism. Exemplary nucleic acid control mechanisms are known in the art and are envisioned for use. For example, such mechanisms include riboswitches, such as those disclosed in, e.g., US2009/0305253, US2008/0269258, US2017/0204477, WO2018026762A1, U.S. Pat. No. 9,222,093 and EP application EP288071, and also disclosed in the review by Villa J K et al., Microbiol Spectr. 2018 May; 6(3). Also included are metabolite-responsive transcription biosensors, such as those disclosed in WO2018/075486 and WO2017/147585. Other art-known mechanisms envisioned for use include silencing of the transgene with an siRNA or RNAi molecule (e.g., miR, shRNA). For example, the neDNA vector can comprise a regulatory switch that encodes a RNAi molecule that is complementary to the transgene expressed by the neDNA vector. When such RNAi is expressed even if the transgene is expressed by the neDNA vector, it will be silenced by the complementary RNAi molecule, and when the RNAi is not expressed when the transgene is expressed by the neDNA vector the transgene is not silenced by the RNAi.

In some embodiments, the regulatory switch is a tissue-specific self-inactivating regulatory switch, for example as disclosed in US2002/0022018, whereby the regulatory switch deliberately switches transgene expression off at a site where transgene expression might otherwise be disadvantageous. In some embodiments, the regulatory switch is a recombinase reversible gene expression system, for example as disclosed in US2014/0127162 and U.S. Pat. No. 8,324,436.

(vi) Post-Transcriptional and Post-Translational Regulatory Switches.

In some embodiments, the regulatory switch to control the transgene or gene of interest expressed by the synthetically produced neDNA vector is a post-transcriptional modification system. For example, such a regulatory switch can be an aptazyme riboswitch that is sensitive to tetracycline or theophylline, as disclosed in US2018/0119156, GB201107768, WO2001/064956A3, EP Patent 2707487 and Beilstein et al., ACS Synth. Biol., 2015, 4 (5), pp 526-534; Zhong et al., Elife. 2016 Nov. 2; 5. pii: e18858. In some embodiments, it is envisioned that a person of ordinary skill in the art could encode both the transgene and an inhibitory siRNA which contains a ligand sensitive (OFF-switch) aptamer, the net result being a ligand sensitive ON-switch.

(vii) Other Exemplary Regulatory Switches

Any known regulatory switch can be used in the synthetically produced neDNA vector to control the gene expression of the transgene expressed by the neDNA vector, including those triggered by environmental changes. Additional examples include, but are not limited to; the BOC method of Suzuki et al., Scientific Reports 8; 10051 (2018); genetic code expansion and a non-physiologic amino acid; radiation-controlled or ultra-sound controlled on/off switches (see, e.g., Scott S et al., Gene Ther. 2000 July; 7(13):1121-5; U.S. Pat. Nos. 5,612,318; 5,571,797; 5,770,581; 5,817,636; and WO1999/025385A1. In some embodiments, the regulatory switch is controlled by an implantable system, e.g., as disclosed in U.S. Pat. No. 7,840,263; US2007/0190028A1 where gene expression is controlled by one or more forms of energy, including electromagnetic energy, that activates promoters operatively linked to the transgene in the neDNA vector.

In some embodiments, a regulatory switch envisioned for use in the synthetically produced neDNA vector is a hypoxia-mediated or stress-activated switch, e.g., such as those disclosed in WO1999060142A2, U.S. Pat. Nos. 5,834,306; 6,218,179; 6,709,858; US2015/0322410; Greco et al., (2004) Targeted Cancer Therapies 9, 8368, as well as FROG, TOAD and NRSE elements and conditionally inducible silence elements, including hypoxia response elements (HREs), inflammatory response elements (IREs) and shear-stress activated elements (SSAEs), e.g, as disclosed in U.S. Pat. No. 9,394,526. Such an embodiment is useful for turning on expression of the transgene from the neDNA vector after ischemia or in ischemic tissues, and/or tumors.

E. Kill Switches

Other embodiments of the invention relate to a synthetically produced neDNA vector comprising a kill switch. A kill switch as disclosed herein enables a cell comprising the neDNA vector to be killed or undergo programmed cell death as a means to permanently remove an introduced neDNA vector from the subject's system. It will be appreciated by one of ordinary skill in the art that use of kill switches in the synthetically produced neDNA vectors of the invention would be typically coupled with targeting of the neDNA vector to a limited number of cells that the subject can acceptably lose or to a cell type where apoptosis is desirable (e.g., cancer cells). In all aspects, a "kill switch" as disclosed herein is designed to provide rapid and robust cell killing of the cell comprising the neDNA vector in the absence of an input survival signal or other specified condition. Stated another way, a kill switch encoded by a neDNA vector herein can restrict cell survival of a cell comprising a neDNA vector to an environment defined by specific input signals. Such kill switches serve as a biological biocontainment function should it be desirable to remove the synthetically produced neDNA vector from a subject or to ensure that it will not express the encoded transgene.

Accordingly, kill switches are synthetic biological circuits in the neDNA vector that couple environmental signals with conditional survival of the cell comprising the neDNA vector. In some embodiments different neDNA vectors can be designed to have different kill switches. This permits one to be able to control which transgene expressing cells are killed if cocktails of neDNA vectors are used.

In some embodiments, a neDNA vector can comprise a kill switch which is a modular biological containment circuit. In some embodiments, a kill switch encompassed for use in the neDNA vector is disclosed in WO2017/059245, which describes a switch referred to as a "Deadman kill switch" that comprises a mutually inhibitory arrangement of at least two repressible sequences, such that an environmental signal represses the activity of a second molecule in the construct (e.g., a small molecule-binding transcription factor is used to produce a 'survival' state due to repression of toxin production). In cells comprising a neDNA vector comprising a deadman kill switch, upon loss of the environmental signal, the circuit switches permanently to the 'death' state, where the toxin is now derepressed, resulting in toxin production which kills the cell. In another embodiment, a synthetic biological circuit referred to as a "Passcode circuit" or "Passcode kill switch" that uses hybrid transcription factors (TFs) to construct complex environmental requirements for cell survival, is provided. The Deadman and Passcode kill switches described in WO2017/059245 are particularly useful for use in neDNA vectors, as they are modular and customizable, both in terms of the environmental conditions that control circuit activation and in the output modules that control cell fate. With the proper choice of toxins, including, but not limited to an endonuclease, e.g., a EcoRI, Passcode circuits present in the neDNA vector can be used to not only kill the host cell comprising the neDNA vector, but also to degrade its genome and accompanying plasmids.

Other kill switches known to a person of ordinary skill in the art are encompassed for use in the neDNA vector as disclosed herein, e.g., as disclosed in US2010/0175141; US2013/0009799; US2011/0172826; US2013/0109568, as well as kill switches disclosed in Jusiak et al, Reviews in Cell Biology and molecular Medicine; 2014; 1-56; Kobayashi et al., PNAS, 2004; 101; 8419-9; Marchisio et al., Int. Journal of Biochem and Cell Biol., 2011; 43; 310-319; and in Reinshagen et al., Science Translational Medicine, 2018, 11.

Accordingly, in some embodiments, the neDNA vector can comprise a kill switch nucleic acid construct, which comprises the nucleic acid encoding an effector toxin or reporter protein, where the expression of the effector toxin (e.g., a death protein) or reporter protein is controlled by a predetermined condition. For example, a predetermined condition can be the presence of an environmental agent, such as, e.g., an exogenous agent, without which the cell will default to expression of the effector toxin (e.g., a death protein) and be killed. In alternative embodiments, a predetermined condition is the presence of two or more environmental agents, e.g., the cell will only survive when two or more necessary exogenous agents are supplied, and without either of which, the cell comprising the neDNA vector is killed.

In some embodiments, the neDNA vector is modified to incorporate a kill-switch to destroy the cells comprising the ceDNA vector to effectively terminate the in vivo expression of the transgene being expressed by the neDNA vector (e.g., therapeutic gene, protein or peptide etc). Specifically, the neDNA vector is further genetically engineered to express a switch-protein that is not functional in mammalian cells under normal physiological conditions. Only upon administration of a drug or environmental condition that specifically targets this switch-protein, the cells expressing the switch-protein will be destroyed thereby terminating the expression of the therapeutic protein or peptide. For instance, it was reported that cells expressing HSV-thymidine kinase can be killed upon administration of drugs, such as ganciclovir and cytosine deaminase. See, for example, Dey and Evans, Suicide Gene Therapy by Herpes Simplex Virus-1 Thymidine Kinase (HSV-TK), in Targets in Gene Therapy, edited by You (2011); and Beltinger et al., Proc. Natl. Acad. Sci. USA 96(15):8699-8704 (1999). In some embodiments the neDNA vector can comprise a siRNA kill switch referred to as DISE (Death Induced by Survival gene Elimination) (Murmann et al., Oncotarget. 2017; 8:84643-84658. Induction of DISE in ovarian cancer cells in vivo).

In some aspects, a deadman kill switch is a biological circuit or system rendering a cellular response sensitive to a predetermined condition, such as the lack of an agent in the cell growth environment, e.g., an exogenous agent. Such a circuit or system can comprise a nucleic acid construct comprising expression modules that form a deadman regulatory circuit sensitive to the predetermined condition, the construct comprising expression modules that form a regulatory circuit, the construct including:

i) a first repressor protein expression module, wherein the first repressor protein binds a first repressor protein nucleic acid binding element and represses transcription from a coding sequence comprising the first repressor protein binding element, and wherein repression activity of the first repressor protein is sensitive to inhibition by a first exogenous agent, the presence or absence of the first exogenous agent establishing a predetermined condition;

ii) a second repressor protein expression module, wherein the second repressor protein binds a second repressor protein nucleic acid binding element and represses transcription from a coding sequence comprising the second repressor protein binding element, wherein the second repressor protein is different from the first repressor protein; and iii) an effector expression module, comprising a nucleic acid sequence encoding an effector protein, operably linked to a genetic element comprising a binding element for the second repressor protein, such that expression of the second repressor protein causes repression of effector expression from the effector expression module, wherein the second expression module comprises a first repressor protein nucleic acid binding element that permits repression of transcription of the second repressor protein when the element is bound by the first repressor protein, the respective modules forming a regulatory circuit such that in the absence of the first exogenous agent, the first repressor protein is produced from the first repressor protein expression module and represses transcription from the second repressor protein expression module, such that repression of effector expression by the second repressor protein is relieved, resulting in expression of the effector protein, but in the presence of the first exogenous agent, the activity of the first repressor protein is inhibited, permitting expression of the second repressor protein, which maintains expression of effector protein expression in the "off" state, such that the first exogenous agent is required by the circuit to maintain effector protein expression in the "off" state, and removal or absence of the first exogenous agent defaults to expression of the effector protein.

In some embodiments, the effector is a toxin or a protein that induces a cell death program. Any protein that is toxic to the host cell can be used. In some embodiments the toxin only kills those cells in which it is expressed. In other embodiments, the toxin kills other cells of the same host organism. Any of a large number of products that will lead to cell death can be employed in a deadman kill switch. Agents that inhibit DNA replication, protein translation or other processes or, e.g., that degrade the host cell's nucleic acid, are of particular usefulness. To identify an efficient mechanism to kill the host cells upon circuit activation, several toxin genes were tested that directly damage the host cell's DNA or RNA. The endonuclease ecoRI, the DNA gyrase inhibitor ccdB and the ribonuclease-type toxin mazF were tested because they are well-characterized, are native to *E. coli*, and provide a range of killing mechanisms. To increase the robustness of the circuit and provide an independent method of circuit-dependent cell death, the system can be further adapted to express, e.g., a targeted protease or nuclease that further interferes with the repressor that maintains the death gene in the "off" state. Upon loss or withdrawal of the survival signal, death gene repression is even more efficiently removed by, e.g., active degradation of the repressor protein or its message. As non-limiting examples, mf-Lon protease was used to not only degrade LacI but also target essential proteins for degradation. The mf-Lon degradation tag pdt #1 can be attached to the 3' end of five essential genes whose protein products are particularly sensitive to mf-Lon degradation, and cell viability was measured following removal of ATc. Among the tested essential gene targets, the peptidoglycan biosynthesis gene murC provided the strongest and fastest cell death phenotype (survival ratio $<1\times10^{-4}$ within 6 hours).

As used herein, the term "predetermined input" refers to an agent or condition that influences the activity of a transcription factor polypeptide in a known manner. Generally, such agents can bind to and/or change the conformation of the transcription factor polypeptide to thereby modify the activity of the transcription factor polypeptide. Examples of predetermined inputs include, but are not limited to, environmental input agents that are not required for the survival of a given host organism (i.e., in the absence of a synthetic biological circuit as described herein). Conditions that can provide a predetermined input include, for example temperature, e.g., where the activity of one or more factors is temperature-sensitive, the presence or absence of light, including light of a given spectrum of wavelengths, and the concentration of a gas, salt, metal or mineral. Environmental input agents include, for example, a small molecule, biological agents such as pheromones, hormones, growth factors, metabolites, nutrients, and the like and analogs thereof; concentrations of chemicals, environmental byproducts, metal ions, and other such molecules or agents; light levels; temperature; mechanical stress or pressure; or electrical signals, such as currents and voltages.

In some embodiments, reporters are used to quantify the strength or activity of the signal received by the modules or programmable synthetic biological circuits of the invention. In some embodiments, reporters can be fused in-frame to other protein coding sequences to identify where a protein is located in a cell or organism. Luciferases can be used as effector proteins for various embodiments described herein, for example, measuring low levels of gene expression, because cells tend to have little to no background luminescence in the absence of a luciferase. In other embodiments, enzymes that produce colored substrates can be quantified using spectrophotometers or other instruments that can take absorbance measurements including plate readers. Like luciferases, enzymes like β-galactosidase can be used for measuring low levels of gene expression because they tend to amplify low signals. In some embodiments, an effector protein can be an enzyme that can degrade or otherwise destroy a given toxin. In some embodiments, an effector protein can be an odorant enzyme that converts a substrate to an odorant product. In some embodiments, an effector protein can be an enzyme that phosphorylates or dephosphorylates either small molecules or other proteins, or an enzyme that methylates or demethylates other proteins or DNA.

In some embodiments, an effector protein can be a receptor, ligand, or lytic protein. Receptors tend to have three domains: an extracellular domain for binding ligands such as proteins, peptides or small molecules, a transmembrane domain, and an intracellular or cytoplasmic domain which frequently can participate in some sort of signal transduction event such as phosphorylation. In some embodiments, transporter, channel, or pump gene sequences are used as effector proteins. Non-limiting examples and sequences of effector proteins for use with the kill switches as described herein can be found at the Registry of Standard Biological Parts on the world wide web at parts.igem.org.

As used herein, a "modulator protein" is a protein that modulates the expression from a target nucleic acid sequence. Modulator proteins include, for example, transcription factors, including transcriptional activators and repressors, among others, and proteins that bind to or modify a transcription factor and influence its activity. In some embodiments, a modulator protein includes, for example, a protease that degrades a protein factor involved in the regulation of expression from a target nucleic acid sequence. Preferred modulator proteins include modular proteins in which, for example, DNA-binding and input agent-binding or responsive elements or domains are separable and transferrable, such that, for example, the fusion of the DNA binding domain of a first modulator protein to the input agent-responsive domain of a second results in a new protein that binds the DNA sequence recognized by the first protein, yet is sensitive to the input agent to which the second protein normally responds. Accordingly, as used herein, the term "modulator polypeptide," and the more specific "repressor polypeptide" include, in addition to the specified polypeptides, e.g., "a LacI (repressor) polypeptide," variants, or derivatives of such polypeptides that responds to a different or variant input agent. Thus, for a LacI polypeptide, included are LacI mutants or variants that bind to agents other than lactose or IPTG. A wide range of such agents are known in the art.

Table 7. Exemplary regulatory switches: [b]ON switchability by an effector; other than removing the effector which confers the OFF state. [c]OFF switchability by an effector; other than removing the effector which confers the ON state. [d]A ligand or other physical stimuli (e.g., temperature, electromagnetic radiation, electricity) which stabilizes the switch either in its ON or OFF state. [e] refers to the reference number cited in Kis et al., J R Soc Interface. 12:20141000 (2015), where both the article and the references cited therein are hereby incorporated by reference in their entireties.

TABLE 7

| name | ON switch[b] | OFF switch[c] | origin | effector[d] |
|---|---|---|---|---|
| ABA | yes | no | *Arabidopsis thaliana*, yeast | abscisic acid |
| AIR | yes | no | *Aspergillus nidulans* | acetaldehyde |
| ART | yes | no | *Chlamydia pneumoniae* | 1-arginine |
| BEARON, BEAROFF | yes | yes | *Campylobacter jejuni* | bile acid |
| BirA-tTA | no | yes | *Escherichia coli* | biotin (vitamin H) |
| BIT | yes | no | *Escherichia coli* | biotin (vitamin H) |
| Cry2-CIB1 | yes | no | *Arabidopsis thaliana*, yeast | blue light |
| CTA, CTS | yes | yes | *Comamonas testosteroni*, *Homo sapiens* | food additives (benzoate, vanillate) |

TABLE 7-continued

| name | ON switch[b] | OFF switch[c] | origin | effector[d] |
|---|---|---|---|---|
| cTA, rcTA | yes | yes | *Pseudomonas putida* | cumate |
| Ecdysone | yes | no | *Homo sapiens, Drosophila melanogaster* | Ecdysone |
| EcR:RXR | yes | no | *Homo sapiens, Locusta migratoria* | ecdysone |
| electro-genetic | yes | no | *Aspergillus nidulans* | electricity, acetaldehyde |
| ER-p65-ZF | yes | no | *Homo sapiens,* yeast | 4,4'-dyhydroxybenzil |
| E.REX | yes | yes | *Escherichia coli* | erythromycin |
| EthR | no | yes | *Mycobacterium tuberculosis* | 2-phenylethyl-butyrate |
| GAL4-ER | yes | yes | yeast, *Homo sapiens* | oestrogen, 4-hydroxytamoxifen |
| GAL4-hPR | yes | yes | yeast, *Homo sapiens* | mifepristone |
| GAL4-Raps | yes | yes | yeast, *Homo sapiens* | rapamycin and rapamycin derivatives |
| GAL4-TR | yes | no | yeast, *Homo sapiens* | thyroid hormone |
| GyrB | yes | yes | *Escherichia coli* | coumermycin, novobiocin |
| HEA-3 | yes | no | *Homo sapiens* | 4-hydroxytamoxifen |
| Intramer | no | yes | synthetic SELEX-derived aptamers | theophylline |
| LacI | yes | no | *Escherichia coli* | IPTG |
| LAD | yes | no | *Arabidopsis thaliana*, yeast | blue light |
| LightOn | yes | no | *Neurospora crassa*, yeast | blue light |
| NICE | yes | yes | *Arthrobacter nicotinovorans* | 6-hydroxynicotine |
| PPAR* | yes | no | *Homo sapiens* | rosiglitazone |
| PEACE | no | yes | *Pseudomonas putida* | flavonoids (e.g., phloretin) |
| PIT | yes | yes | *Streptomyces coelicolor* | pristinamycin I, virginiamycin |
| REDOX | no | yes | *Streptomyces coelicolor* | NADH |
| QuoRex | yes | yes | *Streptomyces coelicolor, Streptomyces pristinaespiralis* | butyrolactones (e.g., SCB1) |
| ST-TA | yes | yes | *Streptomyces coelicolor, Escherichia coli, Herpes simplex* | γ-butyrolactone, tetracycline |
| TIGR | no | yes | *Streptomyces albus* | temperature |
| TraR | yes | no | *Agrobacterium tumefaciens* | N-(3-oxo-octanoyl)homoserine lactone |
| TET-OFF, TET-ON | yes | yes | *Escherichia coli, Herpes simplex* | tetracycline, doxycycline |
| TRT | yes | no | *Chlamydia trachomatis* | 1-tryptophan |
| UREX | yes | no | *Deinococcus radiodurans* | uric acid |
| VAC | yes | yes | *Caulobacter crescentus* | vanillic acid |
| ZF-ER, ZF-RXR/EcR | yes | yes | *Mus musculus*, *Homo sapiens Drosophila melanogaster* | 4-hydroxytamoxifen, ponasterone-A |
| ZF-Raps | yes | no | *Homo sapiens* | rapamycin |
| ZF switches | yes | no | *Mus musculus*, *Homo sapiens Drosophila melanogaster* | 4-hydroxytamoxifen, mifepristone |
| ZF(TF)s | yes | no | *Xenopus laevis*, *Homo sapiens* | ethyl-4-hydroxybenzoate, propyl-4-hydroxybenzoate |
| aptamer RNAi | yes | no | synthetic SELEX-derived aptamer | theophylline |
| aptamer RNAi | no | yes | synthetic SELEX-derived aptamer | theophylline |
| aptamer RNAi miRNA | yes | no | synthetic SELEX-derived aptamer | theophylline, tetracycline, hypoxanthine |
| aptamer Splicing | yes | yes | *Homo sapiens*, MS2 bacteriophage | MS2, p65, p50, b-catenin |
| aptazyme | no | yes | synthetic SELEX-derived aptamer, *Schistosoma mansoni* | theophylline |
| replicon CytTS | yes | no | Sindbis virus | temperature |
| TET-OFF-shRNA, TET-ON-shRNA | yes | yes | *Escherichia coli*, *Herpes simplex*, *Homo sapiens* | doxycycline |
| theo aptamer | no | yes | synthetic SELEX-derived aptamer | theophylline |

TABLE 7-continued

| name | ON switch[b] | OFF switch[c] | origin | effector[d] |
|---|---|---|---|---|
| 3' UTR aptazyme | yes | no | synthetic SELEX-derived aptamers, tobacco ringspot virus | theophylline, tetracycline |
| 5' UTR aptazyme | no | yes | synthetic SELEX-derived aptamer, *Schistosoma mansoni* | theophylline |
| Hoechst aptamer | no | yes | synthetic RNA sequence | Hoechst dyes |
| H23 aptamer | no | yes | *Archaeoglobus fulgidus* | L7Ae, L7KK |
| L7Ae aptamer | yes | yes | *Archaeoglobus fulgidus* | L7Ae |
| MS2 aptamer | no | yes | MS2 bacteriophage | MS2 |
| AID | no | yes | *Arabidopsis thaliana*, *Oryza sativa*, *Gossypium hirsutum* | auxins (e.g., IAA) |
| ER DD | no | yes | *Homo sapiens* | CMP8, 4-hydroxytamoxifen |
| FM | yes | no | *Homo sapiens* | AP21998 |
| HaloTag | no | yes | *Rhodococcus* sp. RHA1 | HyT13 |
| HDV-aptazyme | no | yes | hepatitis delta virus | theophylline, guanine |
| PROTAC | no | yes | *Homo sapiens* | proteolysis targeting chimeric molecules (PROTACS) |
| shield DD | yes | no | *Homo sapiens* | shields (e.g., Shld1) |
| shield LID | no | yes | *Homo sapiens* | shields (e.g., Shld1) |
| TMP DD | yes | no | *Escherichia coli* | trimethoprim (TMP) |

IV. Pharmaceutical Compositions Comprising neDNA

In another aspect, pharmaceutical compositions are provided. The pharmaceutical composition comprises a closed-ended DNA vector, e.g., neDNA vector produced using the synthetic process as described herein and a pharmaceutically acceptable carrier or diluent.

A closed-ended DNA vector, including a neDNA vector, produced using the synthetic process as described herein can be incorporated into pharmaceutical compositions suitable for administration to a subject for in vivo delivery to cells, tissues, or organs of the subject. Typically, the pharmaceutical composition comprises a neDNA vector as disclosed herein and a pharmaceutically acceptable carrier. For example, a closed-ended DNA vector, including a neDNA vector, produced using the synthetic process as described herein can be incorporated into a pharmaceutical composition suitable for a desired route of therapeutic administration (e.g., parenteral administration). Passive tissue transduction via high pressure intravenous or intra-arterial infusion, as well as intracellular injection, such as intranuclear microinjection or intracytoplasmic injection, are also contemplated. Pharmaceutical compositions for therapeutic purposes can be formulated as a solution, microemulsion, dispersion, liposomes, or other ordered structure suitable to high synthetically produced closed-ended DNA vector, e.g., neDNA vector concentration. Sterile injectable solutions can be prepared by incorporating the synthetically produced closed-ended DNA vector, e.g., neDNA vector in the required amount in an appropriate buffer with one or a combination of ingredients enumerated above, as required, followed by filtered sterilization including a neDNA vector can be formulated to deliver a transgene in the nucleic acid to the cells of a recipient, resulting in the therapeutic expression of the transgene or donor sequence therein. The composition can also include a pharmaceutically acceptable carrier.

Pharmaceutically active compositions comprising a closed-ended DNA vector, including a neDNA vector, produced using the synthetic process as described herein can be formulated to deliver a transgene for various purposes to the cell, e.g., cells of a subject.

Pharmaceutical compositions for therapeutic purposes typically must be sterile and stable under the conditions of manufacture and storage. The composition can be formulated as a solution, microemulsion, dispersion, liposomes, or other ordered structure suitable to high synthetically produced closed-ended DNA vector, e.g., neDNA vector concentration. Sterile injectable solutions can be prepared by incorporating the synthetically produced closed-ended DNA vector, e.g., neDNA vector in the required amount in an appropriate buffer with one or a combination of ingredients enumerated above, as required, followed by filtered sterilization.

A closed-ended DNA vector, including a neDNA vector, produced using the synthetic process as described herein as disclosed herein can be incorporated into a pharmaceutical composition suitable for topical, systemic, intra-amniotic, intrathecal, intracranial, intra-arterial, intravenous, intralymphatic, intraperitoneal, subcutaneous, tracheal, intra-tissue (e.g., intramuscular, intracardiac, intrahepatic, intrarenal, intracerebral), intrathecal, intravesical, conjunctival (e.g., extra-orbital, intraorbital, retroorbital, intraretinal, subretinal, choroidal, sub-choroidal, intrastromal, intracameral and intravitreal), intracochlear, and mucosal (e.g., oral, rectal, nasal) administration. Passive tissue transduction via high pressure intravenous or intraarterial infusion, as well as intracellular injection, such as intranuclear microinjection or intracytoplasmic injection, are also contemplated.

In some aspects, the methods provided herein comprise delivering one or more closed-ended DNA vector, including a neDNA vector, produced using the synthetic process as described herein to a host cell. Also provided herein are cells produced by such methods, and organisms (such as animals, plants, or fungi) comprising or produced from such cells. Methods of delivery of nucleic acids can include lipofection, nucleofection, microinjection, biolistics, liposomes, immunoliposomes, polycation or lipid:nucleic acid conjugates, naked DNA, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Delivery can be to cells (e.g., in vitro or ex vivo administration) or target tissues (e.g., in vivo administration).

Various techniques and methods are known in the art for delivering nucleic acids to cells. For example, a closed-ended DNA vector, including a neDNA vector, produced using the synthetic process as described herein can be formulated into lipid nanoparticles (LNPs), lipidoids, liposomes, lipid nanoparticles, lipoplexes, or core-shell nanoparticles. Typically, LNPs are composed of nucleic acid (e.g., neDNA) molecules, one or more ionizable or cationic lipids (or salts thereof), one or more non-ionic or neutral lipids (e.g., a phospholipid), a molecule that prevents aggregation (e.g., PEG or a PEG-lipid conjugate), and optionally a sterol (e.g., cholesterol).

Another method for delivering a closed-ended DNA vector, including a neDNA vector, produced using the synthetic process as described herein to a cell is by conjugating the nucleic acid with a ligand that is internalized by the cell. For example, the ligand can bind a receptor on the cell surface and internalized via endocytosis. The ligand can be covalently linked to a nucleotide in the nucleic acid. Exemplary conjugates for delivering nucleic acids into a cell are described, example, in WO2015/006740, WO2014/025805, WO2012/037254, WO2009/082606, WO2009/073809, WO2009/018332, WO2006/112872, WO2004/090108, WO2004/091515 and WO2017/177326.

Nucleic acids and closed-ended DNA vector, including a neDNA vector, produced using the synthetic process as described herein can also be delivered to a cell by transfection. Useful transfection methods include, but are not limited to, lipid-mediated transfection, cationic polymer-mediated transfection, or calcium phosphate precipitation. Transfection reagents are well known in the art and include, but are not limited to, TurboFect® Transfection Reagent (Thermo Fisher Scientific®), Pro-Ject Reagent (Thermo Fisher Scientific®), TRANSPASS™ P Protein Transfection Reagent (New England Biolabs®), CHARIOT™ Protein Delivery Reagent (Active Motif®), PROTEOJUICE™ Protein Transfection Reagent (EMD Millipore), 293fectin, LIPOFECTAMINE™ 2000, LIPOFECTAMINE™ 3000 (Thermo Fisher Scientific®), LIPOFECTAMINE™ (Thermo Fisher Scientific®), LIPOFECTIN™ (Thermo Fisher Scientific®), DMRIE-C, CELLFECTIN™ (Thermo Fisher Scientific®), OLIGOFECTAMINE™ (Thermo Fisher Scientific®), LIPOFECTACE™, FUGENE™ (Roche®, Basel, Switzerland), FUGENE™ HD (Roche®), TRANSFECTAM™ (Transfectam, Promega®, Madison, Wis.), TFX-10™ (Promega®), TFX-20™ (Promega®), TFX-50™ (Promega®), TRANSFECTIN™ (BioRad®, Hercules, Calif.), SILENTFECT™ (Bio-Rad), Effectene™ (Qiagen®, Valencia, Calif.), DC-chol (Avanti Polar Lipids), GENEPORTER™ (Gene Therapy Systems, San Diego, Calif.), DHARMAFECT 1™ (Dharmacon®, Lafayette, Colo.), DHARMAFECT 2™ (Dharmacon®), DHARMAFECT 3™ (Dharmacon®), DHARMAFECT 4™ (Dharmacon®), ESCORT™ III (Sigma, St. Louis, Mo.), and ESCORT™ IV (Sigma Chemical Co.). Nucleic acids, such as neDNA, can also be delivered to a cell via microfluidics methods known to those of skill in the art.

Methods of non-viral delivery of nucleic acids in vivo or ex vivo include electroporation, lipofection (see, U.S. Pat. Nos. 5,049,386; 4,946,787 and commercially available reagents such as Transfectam™ and Lipofectin™), microinjection, biolistics, virosomes, liposomes (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787), immunoliposomes, polycation or lipid:nucleic acid conjugates, naked DNA, and agent-enhanced uptake of DNA. Sonoporation using, e.g., the Sonitron™ 2000 System™ (Rich-Mar®) can also be used for delivery of nucleic acids.

A closed-ended DNA vector, including a neDNA vector, produced using the synthetic process as described herein can also be administered directly to an organism for transduction of cells in vivo. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of a closed-ended DNA vector, including a neDNA vector, produced using the synthetic process as described herein can be delivered into hematopoietic stem cells, for example, by the methods as described, for example, in U.S. Pat. No. 5,928,638.

A closed-ended DNA vector, including a neDNA vector, produced using the synthetic process as described herein can be added to liposomes for delivery to a cell or target organ in a subject. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids. Exemplary liposomes and liposome formulations are disclosed in International Application PCT/US2018/050042, filed on Sep. 7, 2018 and in International application PCT/US2018/064242, filed on Dec. 6, 2018, e.g., see the section entitled "Pharmaceutical Formulations".

In some aspects, the disclosure provides for a liposome formulation that includes one or more compounds with a polyethylene glycol (PEG) functional group (so-called "PEG-ylated compounds") which can reduce the immunogenicity/antigenicity of, provide hydrophilicity and hydrophobicity to the compound(s) and reduce dosage frequency. Or the liposome formulation simply includes polyethylene glycol (PEG) polymer as an additional component. In such aspects, the molecular weight of the PEG or PEG functional group can be from 62 Da to about 5,000 Da.

In some aspects, the disclosure provides for a liposome formulation that will deliver an API with extended release or controlled release profile over a period of hours to weeks. In some related aspects, the liposome formulation may comprise aqueous chambers that are bound by lipid bilayers. In other related aspects, the liposome formulation encapsulates an API with components that undergo a physical transition at elevated temperature which releases the API over a period of hours to weeks.

In some aspects, the liposome formulation comprises sphingomyelin and one or more lipids disclosed herein. In some aspects, the liposome formulation comprises optisomes.

In some aspects, the disclosure provides for a liposome formulation that includes one or more lipids selected from: N-(carbonyl-methoxypolyethylene glycol 2000)-1,2-distearoyl-sn-glycero-3-phosphoethanolamine sodium salt, (distearoyl-sn-glycero-phosphoethanolamine), MPEG (methoxy polyethylene glycol)-conjugated lipid, HSPC (hydrogenated soy phosphatidylcholine); PEG (polyethylene glycol); DSPE (distearoyl-sn-glycero-phosphoethanolamine); DSPC (distearoylphosphatidylcholine); DOPC (dioleoylphosphatidylcholine); DPPG (dipalmitoylphosphatidylglycerol); EPC (egg phosphatidylcholine); DOPS (dioleoylphosphatidylserine); POPC (palmitoyloleoylphosphatidylcholine); SM (sphingomyelin); MPEG (methoxy polyethylene glycol); DMPC (dimyristoyl phosphatidylcholine); DMPG (dimyristoyl phosphatidylglycerol); DSPG (distearoylphosphatidylglycerol); DEPC (dierucoylphosphatidylcholine); DOPE (dioleoly-sn-glycero-phophoethanolamine). cholesteryl sulphate (CS), dipalmitoylphosphatidylglycerol (DPPG), DOPC (dioleoly-sn-glycero-phosphatidylcholine) or any combination thereof.

In some aspects, the disclosure provides for a liposome formulation comprising phospholipid, cholesterol and a PEG-ylated lipid in a molar ratio of 56:38:5. In some aspects, the liposome formulation's overall lipid content is from 2-16 mg/mL. In some aspects, the disclosure provides for a liposome formulation comprising a lipid containing a phosphatidylcholine functional group, a lipid containing an ethanolamine functional group and a PEG-ylated lipid. In some aspects, the disclosure provides for a liposome formulation comprising a lipid containing a phosphatidylcholine functional group, a lipid containing an ethanolamine functional group and a PEG-ylated lipid in a molar ratio of 3:0.015:2 respectively. In some aspects, the disclosure provides for a liposome formulation comprising a lipid containing a phosphatidylcholine functional group, cholesterol and a PEG-ylated lipid. In some aspects, the disclosure provides for a liposome formulation comprising a lipid containing a phosphatidylcholine functional group and cholesterol. In some aspects, the PEG-ylated lipid is PEG-2000-DSPE. In some aspects, the disclosure provides for a liposome formulation comprising DPPG, soy PC, MPEG-DSPE lipid conjugate and cholesterol.

In some aspects, the disclosure provides for a liposome formulation comprising one or more lipids containing a phosphatidylcholine functional group and one or more lipids containing an ethanolamine functional group. In some aspects, the disclosure provides for a liposome formulation comprising one or more: lipids containing a phosphatidylcholine functional group, lipids containing an ethanolamine functional group, and sterols, e.g., cholesterol. In some aspects, the liposome formulation comprises DOPC/DEPC; and DOPE.

In some aspects, the disclosure provides for a liposome formulation further comprising one or more pharmaceutical excipients, e.g., sucrose and/or glycine.

In some aspects, the disclosure provides for a liposome formulation that is wither unilamellar or multilamellar in structure. In some aspects, the disclosure provides for a liposome formulation that comprises multi-vesicular particles and/or foam-based particles. In some aspects, the disclosure provides for a liposome formulation that are larger in relative size to common nanoparticles and about 150 to 250 nm in size. In some aspects, the liposome formulation is a lyophilized powder.

In some aspects, the disclosure provides for a liposome formulation that is made and loaded with neDNA vectors disclosed or described herein, by adding a weak base to a mixture having the isolated neDNA outside the liposome. This addition increases the pH outside the liposomes to approximately 7.3 and drives the API into the liposome. In some aspects, the disclosure provides for a liposome formulation having a pH that is acidic on the inside of the liposome. In such cases the inside of the liposome can be at pH 4-6.9, and more preferably pH 6.5. In other aspects, the disclosure provides for a liposome formulation made by using intra-liposomal drug stabilization technology. In such cases, polymeric or non-polymeric highly charged anions and intra-liposomal trapping agents are utilized, e.g., polyphosphate or sucrose octasulfate.

In other aspects, the disclosure provides for a liposome formulation comprising phospholipids, lecithin, phosphatidylcholine and phosphatidylethanolamine.

Delivery reagents such as liposomes, nanocapsules, microparticles, microspheres, lipid particles, vesicles, and the like, can be used for the introduction of the compositions of the present disclosure into suitable host cells. In particular, the nucleic acids can be formulated for delivery either encapsulated in a lipid particle, a liposome, a vesicle, a nanosphere, a nanoparticle, a gold particle, or the like. Such formulations can be preferred for the introduction of pharmaceutically acceptable formulations of the nucleic acids disclosed herein.

Various delivery methods known in the art or modifications thereof can be used to deliver a closed-ended DNA vector, including a neDNA vector, produced using the synthetic process as described herein in vitro or in vivo. For example, in some embodiments, neDNA vectors are delivered by making transient penetration in cell membrane by mechanical, electrical, ultrasonic, hydrodynamic, or laser-based energy so that DNA entrance into the targeted cells is facilitated. For example, a neDNA vector can be delivered by transiently disrupting cell membrane by squeezing the cell through a size-restricted channel or by other means known in the art. In some cases, a neDNA vector alone is directly injected as naked DNA into skin, thymus, cardiac muscle, skeletal muscle, or liver cells.

In some cases, a neDNA vector is delivered by gene gun. Gold or tungsten spherical particles (1-3 μm diameter) coated with capsid-free AAV vectors can be accelerated to high speed by pressurized gas to penetrate into target tissue cells.

In some embodiments, electroporation is used to deliver neDNA vectors. Electroporation causes temporary destabilization of the cell membrane target cell tissue by insertion of a pair of electrodes into the tissue so that DNA molecules in the surrounding media of the destabilized membrane would be able to penetrate into cytoplasm and nucleoplasm of the cell. Electroporation has been used in vivo for many types of tissues, such as skin, lung, and muscle.

In some cases, a neDNA vector is delivered by hydrodynamic injection, which is a simple and highly efficient method for direct intracellular delivery of any water-soluble compounds and particles into internal organs and skeletal muscle in an entire limb.

In some cases, neDNA vectors are delivered by ultrasound by making nanoscopic pores in membrane to facilitate intracellular delivery of DNA particles into cells of internal organs or tumors, so the size and concentration of plasmid DNA have great role in efficiency of the system. In some cases, ceDNA vectors are delivered by magnetofection by using magnetic fields to concentrate particles containing nucleic acid into the target cells.

In some cases, chemical delivery systems can be used, for example, by using nanomeric complexes, which include compaction of negatively charged nucleic acid by polycationic nanomeric particles, belonging to cationic liposome/micelle or cationic polymers. Cationic lipids used for the delivery method includes, but not limited to monovalent cationic lipids, polyvalent cationic lipids, guanidine containing compounds, cholesterol derivative compounds, cationic polymers, (e.g., poly(ethylenimine), poly-L-lysine, protamine, other cationic polymers), and lipid-polymer hybrid.

Compositions comprising a closed-ended DNA vector, including a neDNA vector, produced using the synthetic process as described herein and a pharmaceutically acceptable carrier are specifically contemplated herein. In some embodiments, the neDNA vector is formulated with a lipid delivery system, for example, liposomes as described herein. In some embodiments, such compositions are administered by any route desired by a skilled practitioner. The compositions may be administered to a subject by different routes including orally, parenterally, sublingually, transdermally, rectally, transmucosally, topically, via inhalation, via buccal administration, intrapleurally, intravenous, intra-arterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gene guns", or other physical methods such as electroporation ("EP"), hydrodynamic methods or ultrasound.

In some cases, a closed-ended DNA vector, including a neDNA vector, produced using the synthetic process as described herein is delivered by hydrodynamic injection, which is a simple and highly efficient method for direct intracellular delivery of any water-soluble compounds and particles into internal organs and skeletal muscle in an entire limb.

In some cases, a closed-ended DNA vector, including a neDNA vector, produced using the synthetic process as described herein is delivered by ultrasound by making nanoscopic pores in membrane to facilitate intracellular delivery of DNA particles into cells of internal organs or tumors, so the size and concentration of the closed-ended DNA vector have a great role in efficiency of the system. In some cases, closed-ended DNA vectors, including a neDNA vector, produced using the synthetic process as described herein are delivered by magnetofection by using magnetic fields to concentrate particles containing nucleic acid into the target cells.

In some cases, chemical delivery systems can be used, for example, by using nanomeric complexes, which include compaction of negatively charged nucleic acid by polycationic nanomeric particles, belonging to cationic liposome/micelle or cationic polymers. Cationic lipids used for the delivery method includes, but not limited to monovalent cationic lipids, polyvalent cationic lipids, guanidine containing compounds, cholesterol derivative compounds, cationic polymers, (e.g., poly(ethylenimine), poly-L-lysine, protamine, other cationic polymers), and lipid-polymer hybrid.

A. Exosomes

In some embodiments, a closed-ended DNA vector, including a neDNA vector, produced using the synthetic process as described herein is delivered by being packaged in an exosome. Exosomes are small membrane vesicles of endocytic origin that are released into the extracellular environment following fusion of multivesicular bodies with the plasma membrane. Their surface consists of a lipid bilayer from the donor cell's cell membrane, they contain cytosol from the cell that produced the exosome, and exhibit membrane proteins from the parental cell on the surface. Exosomes are produced by various cell types including epithelial cells, B and T lymphocytes, mast cells (MC) as well as dendritic cells (DC). Some embodiments, exosomes with a diameter between 10 nm and 1 m, between 20 nm and 500 nm, between 30 nm and 250 nm, between 50 nm and 100 nm are envisioned for use. Exosomes can be isolated for a delivery to target cells using either their donor cells or by introducing specific nucleic acids into them. Various approaches known in the art can be used to produce exosomes containing capsid-free AAV vectors of the present invention.

B. Microparticle/Nanoparticles

In some embodiments, a closed-ended DNA vector, including a neDNA vector, produced using the synthetic process as described herein is delivered by a lipid nanoparticle. Generally, lipid nanoparticles comprise an ionizable amino lipid (e.g., heptatriaconta-6,9,28,31-tetraen-19-yl 4-(dimethylamino)butanoate, DLin-MC3-DMA, a phosphatidylcholine (1,2-distearoyl-sn-glycero-3-phosphocholine, DSPC), cholesterol and a coat lipid (polyethylene glycol-dimyristolglycerol, PEG-DMG), for example as disclosed by Tam et al. (2013). *Advances in Lipid Nanoparticles for siRNA delivery*. Pharmaceuticals 5(3): 498-507.

In some embodiments, a lipid nanoparticle has a mean diameter between about 10 and about 1000 nm. In some embodiments, a lipid nanoparticle has a diameter that is less than 300 nm. In some embodiments, a lipid nanoparticle has a diameter between about 10 and about 300 nm. In some embodiments, a lipid nanoparticle has a diameter that is less than 200 nm. In some embodiments, a lipid nanoparticle has a diameter between about 25 and about 200 nm. In some embodiments, a lipid nanoparticle preparation (e.g., composition comprising a plurality of lipid nanoparticles) has a size distribution in which the mean size (e.g., diameter) is about 70 nm to about 200 nm, and more typically the mean size is about 100 nm or less.

Various lipid nanoparticles known in the art can be used to deliver a closed-ended DNA vector, including a neDNA vector produced using the synthetic process as described herein. For example, various delivery methods using lipid nanoparticles are described in U.S. Pat. Nos. 9,404,127, 9,006,417 and 9,518,272.

In some embodiments, a neDNA vector produced using the synthetic process as described herein is delivered by a gold nanoparticle. Generally, a nucleic acid can be covalently bound to a gold nanoparticle or non-covalently bound to a gold nanoparticle (e.g., bound by a charge-charge interaction), for example as described by Ding et al. (2014). *Gold Nanoparticles for Nucleic Acid Delivery*. Mol. Ther. 22(6); 1075-1083. In some embodiments, gold nanoparticle-nucleic acid conjugates are produced using methods described, for example, in U.S. Pat. No. 6,812,334.

In some embodiments, neDNA described herein can be readily formulated in high concentrations of chitosan-nucleic acid polyplex compositions and administered orally in DNA enteric coated pills described in U.S. Pat. Nos. 8,846,102; 9,404,088; and 9,850,323, each of which is incorporated herein by its entirety.

C. Conjugates

In some embodiments, a closed-ended DNA vector, including a neDNA vector, produced using the synthetic process as described herein as disclosed herein is conjugated (e.g., covalently bound to an agent that increases cellular uptake. An "agent that increases cellular uptake" is a molecule that facilitates transport of a nucleic acid across a lipid membrane. For example, a nucleic acid can be conjugated to a lipophilic compound (e.g., cholesterol, tocopherol, etc.), a cell penetrating peptide (CPP) (e.g., penetratin, TAT, Syn1B, etc.), and polyamines (e.g., spermine). Further examples of agents that increase cellular uptake are disclosed, for example, in Winkler (2013). *Oligonucleotide conjugates for therapeutic applications*. Ther. Deliv. 4(7); 791-809.

In some embodiments, a closed-ended DNA vector, including a neDNA vector, produced using the synthetic process as described herein as disclosed herein is conjugated to a polymer (e.g., a polymeric molecule) or a folate molecule (e.g., folic acid molecule). Generally, delivery of nucleic acids conjugated to polymers is known in the art, for example as described in WO2000/34343 and WO2008/022309. In some embodiments, a neDNA vector as disclosed herein is conjugated to a poly(amide) polymer, for example as described by U.S. Pat. No. 8,987,377. In some embodiments, a nucleic acid described by the disclosure is conjugated to a folic acid molecule as described in U.S. Pat. No. 8,507,455.

In some embodiments, a closed-ended DNA vector, including a neDNA vector, produced using the synthetic process as described herein as disclosed herein is conjugated to a carbohydrate, for example as described in U.S. Pat. No. 8,450,467.

D. Nanocapsule

Alternatively, nanocapsule formulations of a closed-ended DNA vector, including a neDNA vector, produced using the synthetic process as described herein as disclosed herein can be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

E. Liposomes

A closed-ended DNA vector, including a neDNA vector, produced using the synthetic process as described herein can be added to liposomes for delivery to a cell or target organ in a subject. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids.

The formation and use of liposomes is generally known to those of skill in the art. Liposomes have been developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

F. Exemplary Liposome and Lipid Nanoparticle (LNP) Compositions

A closed-ended DNA vector, including a neDNA vector, produced using the synthetic process as described herein can be added to liposomes for delivery to a cell, e.g., a cell in need of expression of the transgene. Liposomes are vesicles that possess at least one lipid bilayer. Liposomes are typical used as carriers for drug/therapeutic delivery in the context of pharmaceutical development. They work by fusing with a cellular membrane and repositioning its lipid structure to deliver a drug or active pharmaceutical ingredient (API). Liposome compositions for such delivery are composed of phospholipids, especially compounds having a phosphatidylcholine group, however these compositions may also include other lipids.

Lipid nanoparticles (LNPs) comprising ceDNA are disclosed in International Application PCT/US2018/050042, filed on Sep. 7, 2018, and International Application PCT/US2018/064242, filed on Dec. 6, 2018, which are each incorporated herein by reference in their entirety and envisioned for use in the methods and compositions as disclosed herein.

In some aspects, the disclosure provides for a liposome formulation that includes one or more compounds with a polyethylene glycol (PEG) functional group (so-called "PEG-ylated compounds") which can reduce the immunogenicity/antigenicity of, provide hydrophilicity and hydrophobicity to the compound(s) and reduce dosage frequency. Or the liposome formulation simply includes polyethylene glycol (PEG) polymer as an additional component. In such aspects, the molecular weight of the PEG or PEG functional group can be from 62 Da to about 5,000 Da.

In some aspects, the disclosure provides for a liposome formulation that will deliver an API with extended release or controlled release profile over a period of hours to weeks. In some related aspects, the liposome formulation may comprise aqueous chambers that are bound by lipid bilayers. In other related aspects, the liposome formulation encapsulates an API with components that undergo a physical transition at elevated temperature which releases the API over a period of hours to weeks.

In some aspects, the liposome formulation comprises sphingomyelin and one or more lipids disclosed herein. In some aspects, the liposome formulation comprises optisomes.

In some aspects, the disclosure provides for a liposome formulation that includes one or more lipids selected from: N-(carbonyl-methoxypolyethylene glycol 2000)-1,2-distearoyl-sn-glycero-3-phosphoethanolamine sodium salt, (distearoyl-sn-glycero-phosphoethanolamine), MPEG (methoxy polyethylene glycol)-conjugated lipid, HSPC (hydrogenated soy phosphatidylcholine); PEG (polyethylene glycol); DSPE (distearoyl-sn-glycero-phosphoethanolamine); DSPC (distearoylphosphatidylcholine); DOPC (dioleoylphosphatidylcholine); DPPG (dipalmitoylphosphatidylglycerol); EPC (egg phosphatidylcholine); DOPS (dioleoylphosphatidylserine); POPC (palmitoyloleoylphosphatidylcholine); SM (sphingomyelin); MPEG (methoxy polyethylene glycol); DMPC (dimyristoyl phosphatidylcholine); DMPG (dimyristoyl phosphatidylglycerol); DSPG (distearoylphosphatidylglycerol); DEPC (dierucoylphosphatidylcholine); DOPE (dioleoly-sn-glycero-phophoethanolamine). cholesteryl sulphate (CS), dipalmitoylphosphatidylglycerol (DPPG), DOPC (dioleoly-sn-glycero-phosphatidylcholine) or any combination thereof.

In some aspects, the disclosure provides for a liposome formulation comprising phospholipid, cholesterol and a PEG-ylated lipid in a molar ratio of 56:38:5. In some aspects, the liposome formulation's overall lipid content is from 2-16 mg/mL. In some aspects, the disclosure provides for a liposome formulation comprising a lipid containing a phosphatidylcholine functional group, a lipid containing an ethanolamine functional group and a PEG-ylated lipid. In some aspects, the disclosure provides for a liposome formulation comprising a lipid containing a phosphatidylcholine functional group, a lipid containing an ethanolamine functional group and a PEG-ylated lipid in a molar ratio of 3:0.015:2 respectively. In some aspects, the disclosure provides for a liposome formulation comprising a lipid containing a phosphatidylcholine functional group, cholesterol and a PEG-ylated lipid. In some aspects, the disclosure provides for a liposome formulation comprising a lipid containing a phosphatidylcholine functional group and cholesterol. In some aspects, the PEG-ylated lipid is PEG-2000-DSPE. In some aspects, the disclosure provides for a liposome formulation comprising DPPG, soy PC, MPEG-DSPE lipid conjugate and cholesterol.

In some aspects, the disclosure provides for a liposome formulation comprising one or more lipids containing a phosphatidylcholine functional group and one or more lipids containing an ethanolamine functional group. In some aspects, the disclosure provides for a liposome formulation comprising one or more: lipids containing a phosphatidylcholine functional group, lipids containing an ethanolamine functional group, and sterols, e.g., cholesterol. In some aspects, the liposome formulation comprises DOPC/DEPC; and DOPE.

In some aspects, the disclosure provides for a liposome formulation further comprising one or more pharmaceutical excipients, e.g., sucrose and/or glycine.

In some aspects, the disclosure provides for a liposome formulation that is either unilamellar or multilamellar in structure. In some aspects, the disclosure provides for a liposome formulation that comprises multi-vesicular particles and/or foam-based particles. In some aspects, the disclosure provides for a liposome formulation that are larger in relative size to common nanoparticles and about 150 to 250 nm in size. In some aspects, the liposome formulation is a lyophilized powder.

In some aspects, the disclosure provides for a liposome formulation that is made and loaded with neDNA vectors disclosed or described herein, by adding a weak base to a mixture having the isolated neDNA outside the liposome. This addition increases the pH outside the liposomes to approximately 7.3 and drives the API into the liposome. In some aspects, the disclosure provides for a liposome formulation having a pH that is acidic on the inside of the liposome. In such cases the inside of the liposome can be at pH 4-6.9, and more preferably pH 6.5. In other aspects, the disclosure provides for a liposome formulation made by using intra-liposomal drug stabilization technology. In such cases, polymeric or non-polymeric highly charged anions and intra-liposomal trapping agents are utilized, e.g., polyphosphate or sucrose octasulfate.

In some aspects, the disclosure provides for a lipid nanoparticle comprising a DNA vector, including a neDNA vector produced using the synthetic process as described herein and an ionizable lipid. For example, a lipid nanoparticle formulation that is made and loaded with neDNA obtained by the process as disclosed in International Application PCT/US2018/050042, filed on Sep. 7, 2018, which is incorporated herein. This can be accomplished by high energy mixing of ethanolic lipids with aqueous neDNA at low pH which protonates the ionizable lipid and provides favorable energetics for neDNA/lipid association and nucleation of particles. The particles can be further stabilized through aqueous dilution and removal of the organic solvent. The particles can be concentrated to the desired level.

Generally, the lipid particles are prepared at a total lipid to neDNA (mass or weight) ratio of from about 10:1 to 30:1. In some embodiments, the lipid to neDNA ratio (mass/mass ratio; w/w ratio) can be in the range of from about 1:1 to about 25:1, from about 10:1 to about 14:1, from about 3:1 to about 15:1, from about 4:1 to about 10:1, from about 5:1 to about 9:1, or about 6:1 to about 9:1. The amounts of lipids and neDNA can be adjusted to provide a desired N/P ratio, for example, N/P ratio of 3, 4, 5, 6, 7, 8, 9, 10 or higher. Generally, the lipid particle formulation's overall lipid content can range from about 5 mg/ml to about 30 mg/mL.

The ionizable lipid is typically employed to condense the nucleic acid cargo, e.g., neDNA at low pH and to drive membrane association and fusogenicity. Generally, ionizable lipids are lipids comprising at least one amino group that is positively charged or becomes protonated under acidic conditions, for example at pH of 6.5 or lower. Ionizable lipids are also referred to as cationic lipids herein.

Exemplary ionizable lipids are described in International PCT patent publications WO2015/095340, WO2015/199952, WO2018/011633, WO2017/049245, WO2015/061467, WO2012/040184, WO2012/000104, WO2015/074085, WO2016/081029, WO2017/004143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO2012/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, and US patent publications US2016/0311759, US2015/0376115, US2016/0151284, US2017/0210697, US2015/0140070, US2013/0178541, US2013/0303587, US2015/0141678, US2015/0239926, US2016/0376224, US2017/0119904, US2012/0149894, US2015/0057373, US2013/0090372, US2013/0274523, US2013/0274504, US2013/0274504, US2009/0023673, US2012/0128760, US2010/0324120, US2014/0200257, US2015/0203446, US2018/0005363, US2014/0308304, US2013/0338210, US2012/0101148, US2012/0027796, US2012/0058144, US2013/0323269, US2011/0117125, US2011/0256175, US2012/0202871, US2011/0076335, US2006/0083780, US2013/0123338, US2015/0064242, US2006/0051405, US2013/0065939, US2006/0008910, US2003/0022649, US2010/0130588, US2013/0116307, US2010/0062967, US2013/0202684, US2014/0141070, US2014/0255472, US2014/0039032, US2018/0028664, US2016/0317458, and US2013/0195920, the contents of all of which are incorporated herein by reference in their entirety.

In some embodiments, the ionizable lipid is MC3 (6Z, 9Z,28Z,31Z)-heptatriaconta-6,9,28,31-tetraen-19-yl-4-(dimethylamino) butanoate (DLin-MC3-DMA or MC3) having the following structure:

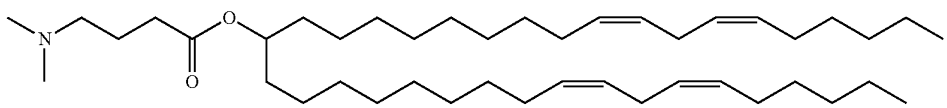

("MC3")

DLin-M-C3-DMA

The lipid DLin-MC3-DMA is described in Jayaraman et al., Angew. Chem. Int. Ed Engl. (2012), 51(34): 8529-8533, content of which is incorporated herein by reference in its entirety.

In some embodiments, the ionizable lipid is the lipid ATX-002 as described in WO2015/074085, content of which is incorporated herein by reference in its entirety.

In some embodiments, the ionizable lipid is (13Z,16Z)—N,N-dimethyl-3-nonyldocosa-13,16-dien-1-amine, as described in WO2012/040184, content of which is incorporated herein by reference in its entirety.

In some embodiments, the ionizable lipid is Compound 6 or Compound 22 as described in WO2015/199952, content of which is incorporated herein by reference in its entirety.

Without limitations, ionizable lipid can comprise 20-90% (mol) of the total lipid present in the lipid nanoparticle. For example, ionizable lipid molar content can be 20-70% (mol), 30-60% (mol) or 40-50% (mol) of the total lipid present in the lipid nanoparticle. In some embodiments, ionizable lipid comprises from about 50 mol % to about 90 mol % of the total lipid present in the lipid nanoparticle.

In some aspects, the lipid nanoparticle can further comprise a non-cationic lipid. Non-ionic lipids include amphipathic lipids, neutral lipids and anionic lipids. Accordingly, the non-cationic lipid can be a neutral uncharged, zwitterionic, or anionic lipid. Non-cationic lipids are typically employed to enhance fusogenicity.

Exemplary non-cationic lipids envisioned for use in the methods and compositions comprising a DNA vector, including a neDNA vector produced using the synthetic process as described herein are described in International Application PCT/US2018/050042, filed on Sep. 7, 2018, and PCT/US2018/064242, filed on Dec. 6, 2018 which is incorporated herein in its entirety.

Exemplary non-cationic lipids are described in International application Publication WO2017/099823 and US patent publication US2018/0028664, the contents of both of which are incorporated herein by reference in their entirety.

The non-cationic lipid can comprise 0-30% (mol) of the total lipid present in the lipid nanoparticle. For example, the non-cationic lipid content is 5-20% (mol) or 10-15% (mol) of the total lipid present in the lipid nanoparticle. In various embodiments, the molar ratio of ionizable lipid to the neutral lipid ranges from about 2:1 to about 8:1.

In some embodiments, the lipid nanoparticles do not comprise any phospholipids. In some aspects, the lipid nanoparticle can further comprise a component, such as a sterol, to provide membrane integrity.

One exemplary sterol that can be used in the lipid nanoparticle is cholesterol and derivatives thereof. Exemplary cholesterol derivatives are described in International application WO2009/127060 and US patent publication US2010/0130588, contents of both of which are incorporated herein by reference in their entirety.

The component providing membrane integrity, such as a sterol, can comprise 0-50% (mol) of the total lipid present in the lipid nanoparticle. In some embodiments, such a component is 20-50% (mol) 30-40% (mol) of the total lipid content of the lipid nanoparticle.

In some aspects, the lipid nanoparticle can further comprise a polyethylene glycol (PEG) or a conjugated lipid molecule. Generally, these are used to inhibit aggregation of lipid nanoparticles and/or provide steric stabilization. Exemplary conjugated lipids include, but are not limited to, PEG-lipid conjugates, polyoxazoline (POZ)-lipid conjugates, polyamide-lipid conjugates (such as *ATTA*-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid. Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a PEGylated phosphatidylethanoloamine (PEG-PE), PEG succinate diacylglycerol (PEGS-DAG) (such as 4-O-(2',3'-di(tetradecanoyloxy)propyl-1-O-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, and US2017/0119904, the contents of all of which are incorporated herein by reference in their entirety.

In some embodiments, a PEG-lipid is a compound disclosed in US2018/0028664, the content of which is incorporated herein by reference in its entirety.

In some embodiments, a PEG-lipid is disclosed in US20150376115 or in US2016/0376224, the content of both of which is incorporated herein by reference in its entirety.

The PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy(polyethylene glycol)-2000]. In some examples, the PEG-lipid can be selected from the group consisting of PEG-DMG, 1,2-dimyristoyl-sn-glycero-3-phosphoethanolamine-N-[methoxy(polyethylene glycol)-2000].

Lipids conjugated with a molecule other than a PEG can also be used in place of PEG-lipid. For example, polyoxazoline (POZ)-lipid conjugates, polyamide-lipid conjugates (such as *ATTA*-lipid conjugates), and cationic-polymer lipid (CPL) conjugates can be used in place of or in addition to the PEG-lipid. Exemplary conjugated lipids, i.e., PEG-lipids, (POZ)-lipid conjugates, *ATTA*-lipid conjugates and cationic polymer-lipids are described in the International patent application publications WO1996/010392, WO1998/051278, WO2002/087541, WO2005/026372, WO2008/147438, WO2009/086558, WO2012/000104, WO2017/117528, WO2017/099823, WO2015/199952, WO2017/004143, WO2015/095346, WO2012/000104, WO2012/000104, and WO2010/006282, US patent application publications US2003/0077829, US2005/0175682, US2008/0020058, US2011/0117125, US2013/0303587, US2018/0028664, US2015/0376115, US2016/0376224, US2016/0317458, US2013/0303587, US2013/0303587, and US20110123453, and US patents U.S. Pat. Nos. 5,885,613, 6,287,591, 6,320,017, and 6,586,559, the contents of all of which are incorporated herein by reference in their entirety.

In some embodiments, the one or more additional compound can be a therapeutic agent. The therapeutic agent can be selected from any class suitable for the therapeutic objective. In other words, the therapeutic agent can be selected from any class suitable for the therapeutic objective. In other words, the therapeutic agent can be selected according to the treatment objective and biological action desired. For example, if the neDNA within the LNP is useful for treating cancer, the additional compound can be an anti-cancer agent (e.g., a chemotherapeutic agent, a targeted cancer therapy (including, but not limited to, a small molecule, an antibody, or an antibody-drug conjugate). In another example, if the LNP containing the neDNA is useful for treating an infection, the additional compound can be an antimicrobial agent (e.g., an antibiotic or antiviral compound). In yet another example, if the LNP containing the neDNA is useful for treating an immune disease or disorder, the additional compound can be a compound that modulates an immune response (e.g., an immunosuppressant, immunostimulatory compound, or compound modulating one or more specific immune pathways). In some embodiments, different cocktails of different lipid nanoparticles containing different compounds, such as a neDNA encoding a different protein or a different compound, such as a therapeutic may be used in the compositions and methods of the invention.

In some embodiments, the additional compound is an immune modulating agent. For example, the additional compound is an immunosuppressant. In some embodiments, the additional compound is immune stimulatory agent.

Also provided herein is a pharmaceutical composition comprising the lipid nanoparticle-encapsulated synthetically produced neDNA vector and a pharmaceutically acceptable carrier or excipient.

In some aspects, the disclosure provides for a lipid nanoparticle formulation further comprising one or more pharmaceutical excipients. In some embodiments, the lipid nanoparticle formulation further comprises sucrose, tris, trehalose and/or glycine.

A closed-ended DNA vector, including a neDNA vector, produced using the synthetic process as described herein can be complexed with the lipid portion of the particle or encapsulated in the lipid position of the lipid nanoparticle. In some embodiments, a DNA vector, including a neDNA vector produced using the synthetic process as described herein can be fully encapsulated in the lipid position of the lipid nanoparticle, thereby protecting it from degradation by a nuclease, e.g., in an aqueous solution. In some embodiments, a DNA vector, including a neDNA vector produced using the synthetic process as described herein in the lipid nanoparticle is not substantially degraded after exposure of the lipid nanoparticle to a nuclease at 37° C. for at least about 20, 30, 45, or 60 minutes. In some embodiments, the neDNA in the lipid nanoparticle is not substantially degraded after incubation of the particle in serum at 37° C. for at least about 30, 45, or 60 minutes or at least about 2, 3, 4, 5, 6, 7, 8, 9, 10, 12, 14, 16, 18, 20, 22, 24, 26, 28, 30, 32, 34, or 36 hours.

In certain embodiments, the lipid nanoparticles are substantially non-toxic to a subject, e.g., to a mammal such as a human. In some aspects, the lipid nanoparticle formulation is a lyophilized powder.

In some embodiments, lipid nanoparticles are solid core particles that possess at least one lipid bilayer. In other embodiments, the lipid nanoparticles have a non-bilayer structure, i.e., a non-lamellar (i.e., non-bilayer) morphology. Without limitations, the non-bilayer morphology can include, for example, three dimensional tubes, rods, cubic symmetries, etc. For example, the morphology of the lipid nanoparticles (lamellar vs. non-lamellar) can readily be assessed and characterized using, e.g., Cryo-TEM analysis as described in US2010/0130588, the content of which is incorporated herein by reference in its entirety.

In some further embodiments, the lipid nanoparticles having a non-lamellar morphology are electron dense. In some aspects, the disclosure provides for a lipid nanoparticle that is either unilamellar or multilamellar in structure. In some aspects, the disclosure provides for a lipid nanoparticle formulation that comprises multi-vesicular particles and/or foam-based particles.

By controlling the composition and concentration of the lipid components, one can control the rate at which the lipid conjugate exchanges out of the lipid particle and, in turn, the rate at which the lipid nanoparticle becomes fusogenic. In addition, other variables including, e.g., pH, temperature, or ionic strength, can be used to vary and/or control the rate at which the lipid nanoparticle becomes fusogenic. Other methods which can be used to control the rate at which the lipid nanoparticle becomes fusogenic will be apparent to those of ordinary skill in the art based on this disclosure. It will also be apparent that by controlling the composition and concentration of the lipid conjugate, one can control the lipid particle size.

The pKa of formulated cationic lipids can be correlated with the effectiveness of the LNPs for delivery of nucleic acids (see Jayaraman et al., Angewandte Chemie, International Edition (2012), 51(34), 8529-8533; Semple et al., Nature Biotechnology 28, 172-176 (2010), both of which are incorporated by reference in their entirety). The preferred range of pKa is ~5 to ~7. The pKa of the cationic lipid can be determined in lipid nanoparticles using an assay based on fluorescence of 2-(p-toluidino)-6-napthalene sulfonic acid (TNS).

V. Methods of Delivering neDNA Vectors

In some embodiments, a closed-ended DNA vector, including a neDNA vector, produced using the synthetic process as described herein can be delivered to a target cell in vitro or in vivo by various suitable methods. A closed-ended DNA vector, including a neDNA vector, produced using the synthetic process as described herein alone can be applied or injected. A closed-ended DNA vector, including a neDNA vector, produced using the synthetic process as described herein can be delivered to a cell without the help of a transfection reagent or other physical means. Alternatively, a closed-ended DNA vector, including a neDNA vector, produced using the synthetic process as described herein can be delivered using any art-known transfection reagent or other art-known physical means that facilitates entry of DNA into a cell, e.g., liposomes, alcohols, polylysine-rich compounds, arginine-rich compounds, calcium phosphate, microvesicles, microinjection, electroporation and the like.

In another embodiment, a closed-ended DNA vector, including a neDNA vector, produced using the synthetic process as described herein is administered to the CNS (e.g., to the brain or to the eye). For example, neDNA vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The neDNA vector may also be administered to different regions of the eye such as the retina, cornea and/or optic nerve. The neDNA vector may be delivered into the cerebrospinal fluid (e.g., by lumbar puncture). The neDNA vector may further be administered intravascularly to the CNS in situations in which the blood-brain barrier has been perturbed (e.g., brain tumor or cerebral infarct).

In some embodiments, a closed-ended DNA vector, including a neDNA vector, produced using the synthetic process as described herein can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In some embodiments, a closed-ended DNA vector, including a neDNA vector, produced using the synthetic process as described herein is administered in a liquid formulation by direct injection (e.g., stereotactic injection) to the desired region or compartment in the CNS. In other embodiments, the synthetically produced neDNA vector can be provided by topical application to the desired region or by intra-nasal administration of an aerosol formulation. Administration to the eye may be by topical application of liquid droplets. As a further alternative, for example, the neDNA vector can be administered as a solid, slow-release formulation (see, e.g., U.S. Pat. No. 7,201,898). In yet additional embodiments, the synthetically produced neDNA vector can be used for retrograde transport to treat, ameliorate, and/or prevent diseases and disorders involving motor neurons (e.g., amyotrophic lateral sclerosis (ALS); spinal muscular atrophy (SMA), etc.). For example, the synthetically produced neDNA vector can be delivered to muscle tissue from which it can migrate into neurons.

VI. Additional Uses of the neDNA Vectors

The compositions and closed-ended DNA vector, including neDNA vectors, produced using the synthetic process as described herein can be used to express a target gene or transgene for various purposes. In some embodiments, the resulting transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease.

In some embodiments, the resulting transgene encodes one or more peptides, polypeptides, or proteins, which are useful for the treatment, prevention, or amelioration of disease states or disorders in a mammalian subject. The resulting transgene can be transferred (e.g., expressed in) to a subject in a sufficient amount to treat a disease associated with reduced expression, lack of expression or dysfunction of the gene.

In some embodiments the resulting transgene can be expressed in a subject in a sufficient amount to treat a disease associated with increased expression, activity of the gene product, or inappropriate upregulation of a gene that the resulting transgene suppresses or otherwise causes the expression of which to be reduced. In yet other embodiments, the resulting transgene replaces or supplements a defective copy of the native gene. It will be appreciated by one of ordinary skill in the art that the transgene may not be an open reading frame of a gene to be transcribed itself; instead it may be a promoter region or repressor region of a target gene, and the neDNA vector may modify such region with the outcome of so modulating the expression of a gene of interest.

In some embodiments, the transgene encodes a protein or functional RNA that is intended to be used to create an animal model of disease. In some embodiments, the transgene encodes one or more peptides, polypeptides, or proteins, which are useful for the treatment or prevention of disease states in a mammalian subject. The transgene can be transferred (e.g., expressed in) to a patient in a sufficient amount to treat a disease associated with reduced expression, lack of expression or dysfunction of the gene.

VII. Methods of Use

A synthetically produced closed-ended DNA vector, e.g., neDNA vector as disclosed herein can also be used in a method for the delivery of a nucleotide sequence of interest (e.g., a transgene) to a target cell (e.g., a host cell). The method may in particular be a method for delivering a transgene to a cell of a subject in need thereof and treating a disease of interest. The invention allows for the in vivo expression of a transgene, e.g., a protein, antibody, nucleic acid such as miRNA etc. encoded in the neDNA vector in a cell in a subject such that therapeutic effect of the expression of the transgene occurs. These results are seen with both in vivo and in vitro modes of closed-ended DNA vector (e.g., neDNA vector) delivery.

In addition, the invention provides a method for the delivery of a transgene in a cell of a subject in need thereof, comprising multiple administrations of the synthetically produced closed-ended DNA vector (e.g., neDNA vector) of the invention comprising said nucleic acid or transgene of interest. Since the neDNA vector of the invention does not induce an immune response like that typically observed against encapsidated viral vectors, such a multiple administration strategy will likely have greater success in a neDNA-based system.

The synthetically produced closed-ended DNA vector (e.g., neDNA vector) nucleic acid(s) are administered in sufficient amounts to transfect the cells of a desired tissue and to provide sufficient levels of gene transfer and expression without undue adverse effects. Conventional and pharmaceutically acceptable routes of administration include, but are not limited to, intravenous (e.g., in a liposome formulation), direct delivery to the selected organ (e.g., intraportal delivery to the liver), intramuscular, and other parental routes of administration. Routes of administration may be combined, if desired.

Closed-ended DNA vector (e.g., neDNA vector) delivery is not limited to delivery gene replacements. For example, the synthetically produced closed-ended DNA vectors (e.g., neDNA vectors) as described herein may be used with other delivery systems provided to provide a portion of the gene therapy. One non-limiting example of a system that may be combined with the synthetically produced neDNA vectors in accordance with the present disclosure includes systems which separately deliver one or more co-factors or immune suppressors for effective gene expression of the transgene.

The invention also provides for a method of treating a disease in a subject comprising introducing into a target cell in need thereof (in particular a muscle cell or tissue) of the subject a therapeutically effective amount of a synthetically produced closed-ended DNA vector (e.g., neDNA vector), optionally with a pharmaceutically acceptable carrier. While the, e.g., synthetically produced neDNA vector can be introduced in the presence of a carrier, such a carrier is not required. For example, the synthetically produced neDNA vector selected comprises a nucleotide sequence of interest useful for treating the disease. In particular, the synthetically produced neDNA vector may comprise a desired exogenous DNA sequence operably linked to control elements capable of directing transcription of the desired polypeptide, protein, or oligonucleotide encoded by the exogenous DNA sequence when introduced into the subject. For example, the synthetically produced neDNA vector can be administered via any suitable route as provided above, and elsewhere herein.

The synthetically produced compositions and vectors provided herein can be used to deliver a transgene for various purposes. In some embodiments, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. In some embodiments, the transgene encodes one or more peptides, polypeptides, or proteins, which are useful for the treatment or prevention of disease states in a mammalian subject. The transgene can be transferred (e.g., expressed in) to a patient in a sufficient amount to treat a disease associated with reduced expression, lack of expression or dysfunction of the gene.

In principle, the expression cassette can include a nucleic acid or any transgene that encodes a protein or polypeptide that is either reduced or absent due to a mutation or which conveys a therapeutic benefit when overexpressed is within the scope of the invention.

A synthetically produced neDNA vector is not limited to one species of neDNA vector. As such, in another aspect, multiple neDNA vectors comprising different transgenes or the same transgene but operatively linked to different promoters or cis-regulatory elements can be delivered simultaneously or sequentially to the target cell, tissue, organ, or subject. Therefore, this strategy can allow for the gene therapy or gene delivery of multiple genes simultaneously. It is also possible to separate different portions of the transgene into separate neDNA vectors (e.g., different domains and/or co-factors required for functionality of the transgene) which can be administered simultaneously or at different times, and can be separately regulatable, thereby adding an additional level of control of expression of the transgene. Delivery can also be performed multiple times and, importantly for gene therapy in the clinical setting, in subsequent increasing or decreasing doses, given the lack of an anti-capsid host immune response due to the absence of a viral capsid. It is anticipated that no anti-capsid response will occur as there is no capsid.

The invention also provides for a method of treating a disease in a subject comprising introducing into a target cell in need thereof (in particular a muscle cell or tissue) of the subject a therapeutically effective amount of a synthetically produced neDNA vector as disclosed herein, optionally with a pharmaceutically acceptable carrier. While the neDNA vector can be introduced in the presence of a carrier, such a carrier is not required. The neDNA vector implemented comprises a nucleotide sequence of interest useful for treating the disease. In particular, the neDNA vector may comprise a desired exogenous DNA sequence operably linked to control elements capable of directing transcription of the desired polypeptide, protein, or oligonucleotide encoded by the exogenous DNA sequence when introduced into the subject. The synthetically produced neDNA vector can be administered via any suitable route as provided above, and elsewhere herein.

VIII. Methods of Treatment

The technology described herein also demonstrates methods for making, as well as methods of using the disclosed synthetically produced neDNA vectors in a variety of ways, including, for example, ex situ, in vitro and in vivo applications, methodologies, diagnostic procedures, and/or gene therapy regimens.

Provided herein is a method of treating a disease or disorder in a subject comprising introducing into a target cell in need thereof (for example, a muscle cell or tissue, or other affected cell type) of the subject a therapeutically effective amount of a synthetically produced neDNA vector, optionally with a pharmaceutically acceptable carrier. While the neDNA vector can be introduced in the presence of a carrier, such a carrier is not required. The synthetically produced neDNA vector implemented comprises a nucleotide sequence of interest useful for treating the disease. In particular, the synthetically produced neDNA vector may comprise a desired exogenous DNA sequence operably linked to control elements capable of directing transcription of the desired polypeptide, protein, or oligonucleotide encoded by the exogenous DNA sequence when introduced into the subject. The synthetically produced neDNA vector can be administered via any suitable route as provided above, and elsewhere herein.

Disclosed herein are neDNA vector compositions and formulations that include one or more of the synthetically produced neDNA vectors of the present invention together with one or more pharmaceutically-acceptable buffers, diluents, or excipients. Such compositions may be included in one or more diagnostic or therapeutic kits, for diagnosing, preventing, treating or ameliorating one or more symptoms of a disease, injury, disorder, trauma or dysfunction. In one aspect the disease, injury, disorder, trauma or dysfunction is a human disease, injury, disorder, trauma or dysfunction.

Another aspect of the technology described herein provides a method for providing a subject in need thereof with a diagnostically- or therapeutically-effective amount of a synthetically produced neDNA vector, the method comprising providing to a cell, tissue or organ of a subject in need thereof, an amount of the synthetically produced neDNA vector as disclosed herein; and for a time effective to enable expression of the transgene from the neDNA vector thereby providing the subject with a diagnostically- or a therapeutically-effective amount of the protein, peptide, nucleic acid expressed by the neDNA vector. In a further aspect, the subject is human.

Another aspect of the technology described herein provides a method for diagnosing, preventing, treating, or ameliorating at least one or more symptoms of a disease, a disorder, a dysfunction, an injury, an abnormal condition, or trauma in a subject. In an overall and general sense, the method includes at least the step of administering to a subject in need thereof one or more of the disclosed synthetically produced neDNA vectors, in an amount and for a time sufficient to diagnose, prevent, treat or ameliorate the one or more symptoms of the disease, disorder, dysfunction, injury, abnormal condition, or trauma in the subject. In a further aspect, the subject is human.

Another aspect is use of the synthetically produced neDNA vector as a tool for treating or reducing one or more symptoms of a disease or disease states. There are a number of inherited diseases in which defective genes are known, and typically fall into two classes: deficiency states, usually of enzymes, which are generally inherited in a recessive manner, and unbalanced states, which may involve regulatory or structural proteins, and which are typically but not always inherited in a dominant manner. For deficiency state diseases, synthetically produced neDNA vectors can be used to deliver transgenes to bring a normal gene into affected tissues for replacement therapy, as well, in some embodiments, to create animal models for the disease using antisense mutations. For unbalanced disease states, synthetically produced neDNA vectors can be used to create a disease state in a model system, which could then be used in efforts to counteract the disease state. Thus, the synthetically produced neDNA vectors and methods disclosed herein permit the treatment of genetic diseases. As used herein, a disease state is treated by partially or wholly remedying the deficiency or imbalance that causes the disease or makes it more severe.

A. Host Cells

In some embodiments, the synthetically produced neDNA vector delivers the transgene into a subject host cell. In some embodiments, the subject host cell is a human host cell, including, for example blood cells, stem cells, hematopoietic cells, $CD34^+$ cells, liver cells, cancer cells, vascular cells, muscle cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a subject for which gene therapy is contemplated. In one aspect, the subject host cell is a human host cell.

The present disclosure also relates to recombinant host cells as mentioned above, including synthetically produced neDNA vectors as described herein. Thus, one can use multiple host cells depending on the purpose as is obvious to the skilled artisan. A construct or synthetically produced neDNA vector including donor sequence is introduced into a host cell so that the donor sequence is maintained as a chromosomal integrant as described earlier. The term host cell encompasses any progeny of a parent cell that is not identical to the parent cell due to mutations that occur during replication. The choice of a host cell will to a large extent depend upon the donor sequence and its source. The host cell may also be a eukaryote, such as a mammalian, insect, plant, or fungal cell. In one embodiment, the host cell is a human cell (e.g., a primary cell, a stem cell, or an immortalized cell line). In some embodiments, the host cell can be administered the synthetically produced neDNA vector ex vivo and then delivered to the subject after the gene therapy event. A host cell can be any cell type, e.g., a somatic cell or a stem cell, an induced pluripotent stem cell, or a blood cell, e.g., T-cell or B-cell, or bone marrow cell. In certain embodiments, the host cell is an allogenic cell. For example, T-cell genome engineering is useful for cancer immunotherapies, disease modulation such as HIV therapy (e.g., receptor knock out, such as CXCR4 and CCR5) and immunodeficiency therapies. MHC receptors on B-cells can be targeted for immunotherapy. In some embodiments, gene modified host cells, e.g., bone marrow stem cells, e.g., $CD34^+$ cells, or induced pluripotent stem cells can be transplanted back into a patient for expression of a therapeutic protein.

B. Exemplary Transgenes and Diseases to be Treated with a neDNA Vector

A closed-ended DNA vector, including a neDNA vector, produced using the synthetic process as described herein are also useful for correcting a defective gene. As a non-limiting example, DMD gene of Duchene Muscular Dystrophy can be delivered using the synthetically produced neDNA vectors as disclosed herein.

A synthetically produced neDNA vector or a composition thereof can be used in the treatment of any hereditary disease. As a non-limiting example, the synthetically produced neDNA vector or a composition thereof e.g., can be used in the treatment of transthyretin amyloidosis (ATTR), an orphan disease where the mutant protein misfolds and aggregates in nerves, the heart, the gastrointestinal system etc. It is contemplated herein that the disease can be treated by deletion of the mutant disease gene (mutTTR) using the synthetically produced neDNA vector systems described herein. Such treatments of hereditary diseases can halt disease progression and may enable regression of an established disease or reduction of at least one symptom of the disease by at least 10%.

In another embodiment, a synthetically produced neDNA vector or a composition thereof can be used in the treatment of ornithine transcarbamylase deficiency (OTC deficiency), hyperammonaemia or other urea cycle disorders, which impair a neonate or infant's ability to detoxify ammonia. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom OTC and/or an improvement in the quality of life for a subject having OTC deficiency. In one embodiment, a nucleic acid encoding OTC can be inserted behind the albumin endogenous promoter for in vivo protein replacement.

In another embodiment, a synthetically produced neDNA vector or a composition thereof can be used in the treatment of phenylketonuria (PKU) by delivering a nucleic acid sequence encoding a phenylalanine hydroxylase enzyme to reduce buildup of dietary phenylalanine, which can be toxic to PKU sufferers. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom of PKU and/or an improvement in the quality of life for a subject having PKU. In one embodiment, a nucleic acid encoding phenylalanine hydroxylase can be inserted behind the albumin endogenous promoter for in vivo protein replacement.

In another embodiment, a synthetically produced neDNA vector or a composition thereof can be used in the treatment of glycogen storage disease (GSD) by delivering a nucleic acid sequence encoding an enzyme to correct aberrant glycogen synthesis or breakdown in subjects having GSD. Non-limiting examples of enzymes that can be delivered and expressed using the synthetically produced neDNA vectors and methods as described herein include glycogen synthase, glucose-6-phosphatase, acid-alpha glucosidase, glycogen debranching enzyme, glycogen branching enzyme, muscle glycogen phosphorylase, liver glycogen phosphorylase, muscle phosphofructokinase, phosphorylase kinase, glucose transporter-2 (GLUT-2), aldolase A, beta-enolase, phosphoglucomutase-1 (PGM-1), and glycogenin-1. As with all diseases of inborn metabolism, it is contemplated herein that even a partial restoration of enzyme activity compared to wild-type controls (e.g., at least 20%, at least 30%, at least 40%, at least 50%, at least 60%, at least 70%, at least 80%, at least 90%, at least 95% or at least 99%) may be sufficient for reduction in at least one symptom of GSD and/or an improvement in the quality of life for a subject having GSD. In one embodiment, a nucleic acid encoding an enzyme to correct aberrant glycogen storage can be inserted behind the albumin endogenous promoter for in vivo protein replacement.

The synthetically produced neDNA vectors described herein are also contemplated for use in the treatment of any of; of Leber congenital amaurosis (LCA), polyglutamine diseases, including polyQ repeats, and alpha-1 antitrypsin deficiency (A1AT). LCA is a rare congenital eye disease resulting in blindness, which can be caused by a mutation in any one of the following genes: GUCY2D, RPE65, SPATA7, AIPLI, LCA5, RPGRIP1, CRX, CRB1, NMNAT1, CEP290, IMPDH1, RD3, RDH12, LRAT, TULPI, KCNJ13, GDF6 and/or PRPH2. It is contemplated herein that the neDNA vectors and compositions and methods as described herein can be adapted for delivery of one or more of the genes associated with LCA in order to correct an error in the gene(s) responsible for the symptoms of LCA. Polyglutamine diseases include, but are not limited to: dentatorubropallidoluysian atrophy, Huntington's disease, spinal and bulbar muscular atrophy, and spinocerebellar ataxia types 1, 2, 3 (also known as Machado-Joseph disease), 6, 7, and 17. A1AT deficiency is a genetic disorder that causes defective production of alpha-1 antitrypsin, leading to decreased activity of the enzyme in the blood and lungs, which in turn can lead to emphysema or chronic obstructive pulmonary disease in affected subjects. Treatment of a subject with an A1AT deficiency is specifically contemplated herein using the neDNA vectors or compositions thereof as outlined herein. It is contemplated herein that a neDNA vector comprising a nucleic acid encoding a desired protein for the treatment of LCA, polyglutamine diseases or A1AT deficiency can be administered to a subject in need of treatment.

In further embodiments, the compositions comprising a synthetically produced neDNA vector as described herein can be used to deliver a viral sequence, a pathogen sequence, a chromosomal sequence, a translocation junction (e.g., a translocation associated with cancer), a non-coding RNA gene or RNA sequence, a disease associated gene, among others.

Any nucleic acid or target gene of interest may be delivered or expressed by a synthetically produced neDNA vector as disclosed herein. Target nucleic acids and target genes include, but are not limited to nucleic acids encoding polypeptides, or non-coding nucleic acids (e.g., RNAi, miRs etc.) preferably therapeutic (e.g., for medical, diagnostic, or veterinary uses) or immunogenic (e.g., for vaccines) polypeptides. In certain embodiments, the target nucleic acids or target genes that are targeted by the synthetically produced neDNA vectors as described herein encode one or more polypeptides, peptides, ribozymes, peptide nucleic acids, siRNAs, RNAis, antisense oligonucleotides, antisense polynucleotides, antibodies, antigen binding fragments, or any combination thereof.

In particular, a gene target or transgene for expression by the synthetically produced neDNA vector as disclosed herein can encode, for example, but is not limited to, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a disease, dysfunction, injury, and/or disorder. In one aspect, the disease, dysfunction, trauma, injury and/or disorder is a human disease, dysfunction, trauma, injury, and/or disorder.

The expression cassette can also encode polypeptides, sense or antisense oligonucleotides, or RNAs (coding or non-coding; e.g., siRNAs, shRNAs, micro-RNAs, and their antisense counterparts (e.g., antagoMiR)). Expression cassettes can include an exogenous sequence that encodes a reporter protein to be used for experimental or diagnostic purposes, such as β-lactamase, β-galactosidase (LacZ), alkaline phosphatase, thymidine kinase, green fluorescent protein (GFP), chloramphenicol acetyltransferase (CAT), luciferase, and others well known in the art.

Sequences provided in the expression cassette, expression construct of a neDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human, by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen®'s Gene Forge® codon optimization and custom gene synthesis platform (Aptagen®, Inc., 2190 Fox Mill Rd. Suite 300, Herndon, Va. 20171) or another publicly available database.

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage (Nakamura, Y., et al. "Codon usage tabulated from the international DNA sequence databases: status for the year 2000" Nucl. Acids Res. 28:292 (2000)).

As noted herein, a synthetically produced neDNA vector as disclosed herein can encode a protein or peptide, or therapeutic nucleic acid sequence or therapeutic agent, including but not limited to one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The synthetically produced neDNA vectors are also useful for ablating gene expression. For example, in one embodiment a neDNA vector can be used to express an antisense nucleic acid or functional RNA to induce knockdown of a target gene. As a non-limiting example, expression of CXCR4 and CCR5, HIV receptors, have been successfully ablated in primary human T-cells, See Schumann et al. (2015), *PNAS* 112(33): 10437-10442, herein incorporated by reference in its entirety. Another gene for targeted inhibition is PD-1, where the synthetically produced neDNA vector can express an inhibitory nucleic acid or RNAi or functional RNA to inhibit the expression of PD-1. PD-1 expresses an immune checkpoint cell surface receptor on chronically active T cells that happens in malignancy. See Schumann et al., supra.

In some embodiments, a synthetically produced neDNA vectors is useful for correcting a defective gene by expressing a transgene that targets the diseased gene. Non-limiting examples of diseases or disorders amenable to treatment by a synthetically produced neDNA vector as disclosed herein, are listed in Tables A-C along with their and their associated genes of U.S. patent publication 2014/0170753, which is herein incorporated by reference in its entirety.

In alternative embodiments, the synthetically produced neDNA vectors are used for insertion of an expression cassette for expression of a therapeutic protein or reporter protein in a safe harbor gene, e.g., in an inactive intron. In certain embodiments, a promoter-less cassette is inserted into the safe harbor gene. In such embodiments, a promoter-less cassette can take advantage of the safe harbor gene regulatory elements (promoters, enhancers, and signaling peptides), a non-limiting example of insertion at the safe harbor locus is insertion into to the albumin locus that is described in Blood (2015) 126 (15): 1777-1784, which is incorporated herein by reference in its entirety. Insertion into Albumin has the benefit of enabling secretion of the transgene into the blood (See e.g., Example 22). In addition, a genomic safe harbor site can be determined using techniques known in the art and described in, for example, Papapetrou, ER & Schambach, A. *Molecular Therapy* 24(4):678-684 (2016) or Sadelain et al. *Nature Reviews Cancer* 12:51-58 (2012), the contents of each of which are incorporated herein by reference in their entirety. It is specifically contemplated herein that safe harbor sites in an adeno associated virus (AAV) genome (e.g., AAVS1 safe harbor site) can be used with the methods and compositions described herein (see e.g., Oceguera-Yanez et al. *Methods* 101:43-55 (2016) or Tiyaboonchai, A et al. *Stem Cell Res* 12(3):630-7 (2014), the contents of each of which are incorporated by reference in their entirety). For example, the AAVS1 genomic safe harbor site can be used with the neDNA vectors and compositions as described herein for the purposes of hematopoietic specific transgene expression and gene silencing in embryonic stem cells (e.g., human embryonic stem cells) or induced pluripotent stem cells (iPS cells). In addition, it is contemplated herein that synthetic or commercially available homology-directed repair donor templates for insertion into an AASV1 safe harbor site on chromosome 19 can be used with the neDNA vectors or compositions as described herein. For example, homology-directed repair templates, and guide RNA, can be purchased commercially, for example, from System Biosciences®, Palo Alto, CA, and cloned into a neDNA vector.

In some embodiments, the synthetically produced neDNA vectors are used for expressing a transgene, or knocking out or decreasing expression of a target gene in a T cell, e.g., to engineer the T cell for improved adoptive cell transfer and/or CAR-T therapies (see, e.g., Example 24). In some embodiments, the neDNA vector as described herein can express transgenes that knock-out genes. Non-limiting examples of therapeutically relevant knock-outs of T cells are described in PNAS (2015) 112(33):10437-10442, which is incorporated herein by reference in its entirety.

C. Additional Diseases for Gene Therapy

In general, the neDNA vector produced by the synthetic methods as disclosed herein can be used to deliver any transgene in accordance with the description above to treat, prevent, or ameliorate the symptoms associated with any disorder related to gene expression. Illustrative disease states include, but are not-limited to: cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Hurler's disease, adenosine deaminase deficiency, metabolic defects, retinal degenerative diseases (and other diseases of the eye), mitochondriopathies (e.g., Leber's hereditary optic neuropathy (LHON), Leigh syndrome, and subacute sclerosing encephalopathy), myopathies (e.g., facioscapulohumeral myopathy (FSHD) and cardiomyopathies), diseases of solid organs (e.g., brain, liver, kidney, heart), and the like. In some embodiments, a neDNA vector produced by the synthetic production methods as described herein can be advantageously used in the treatment of individuals with metabolic disorders (e.g., ornithine transcarbamylase deficiency).

In some embodiments, a neDNA vector produced by the synthetic production methods as described herein can be used to treat, ameliorate, and/or prevent a disease or disorder caused by mutation in a gene or gene product. Exemplary diseases or disorders that can be treated with a neDNA vectors include, but are not limited to, metabolic diseases or disorders (e.g., Fabry disease, Gaucher disease, phenylketonuria (PKU), glycogen storage disease); urea cycle diseases or disorders (e.g., ornithine transcarbamylase (OTC)

deficiency); lysosomal storage diseases or disorders (e.g., metachromatic leukodystrophy (MLD), mucopolysaccharidosis Type II (MPSII; Hunter syndrome)); liver diseases or disorders (e.g., progressive familial intrahepatic cholestasis (PFIC); blood diseases or disorders (e.g., hemophilia (A and B), thalassemia, and anemia); cancers and tumors, and genetic diseases or disorders (e.g., cystic fibrosis).

As still a further aspect, a neDNA vector produced by the synthetic production methods as described herein may be employed to deliver a heterologous nucleotide sequence in situations in which it is desirable to regulate the level of transgene expression (e.g., transgenes encoding hormones or growth factors, as described herein).

Accordingly, in some embodiments, a neDNA vector produced by the synthetic production methods as described herein can be used to correct an abnormal level and/or function of a gene product (e.g., an absence of, or a defect in, a protein) that results in the disease or disorder. The neDNA vector can produce a functional protein and/or modify levels of the protein to alleviate or reduce symptoms resulting from, or confer benefit to, a particular disease or disorder caused by the absence or a defect in the protein. For example, treatment of OTC deficiency can be achieved by producing functional OTC enzyme; treatment of hemophilia A and B can be achieved by modifying levels of Factor VIII, Factor IX, and Factor X; treatment of PKU can be achieved by modifying levels of phenylalanine hydroxylase enzyme; treatment of Fabry or Gaucher disease can be achieved by producing functional alpha galactosidase or beta glucocerebrosidase, respectively; treatment of MLD or MPSII can be achieved by producing functional arylsulfatase A or iduronate-2-sulfatase, respectively; treatment of cystic fibrosis can be achieved by producing functional cystic fibrosis transmembrane conductance regulator; treatment of glycogen storage disease can be achieved by restoring functional G6Pase enzyme function; and treatment of PFIC can be achieved by producing functional ATP8B1, ABCB11, ABCB4, or TJP2 genes.

In alternative embodiments, a neDNA vector produced by the synthetic production methods as described herein can be used to provide an antisense nucleic acid to a cell in vitro or in vivo. For example, where the transgene is a RNAi molecule, expression of the antisense nucleic acid or RNAi in the target cell diminishes expression of a particular protein by the cell. Accordingly, transgenes which are RNAi molecules or antisense nucleic acids may be administered to decrease expression of a particular protein in a subject in need thereof. Antisense nucleic acids may also be administered to cells in vitro to regulate cell physiology, e.g., to optimize cell or tissue culture systems.

In some embodiments, exemplary transgenes encoded by a neDNA vector produced by the synthetic production methods as described herein, include, but are not limited to: X, lysosomal enzymes (e.g., hexosaminidase A, associated with Tay-Sachs disease, or iduronate sulfatase, associated, with Hunter Syndrome/MPS II), erythropoietin, angiostatin, endostatin, superoxide dismutase, globin, leptin, catalase, tyrosine hydroxylase, as well as cytokines (e.g., a interferon, β-interferon, interferon-γ, interleukin-2, interleukin-4, interleukin 12, granulocyte-macrophage colony stimulating factor, lymphotoxin, and the like), peptide growth factors and hormones (e.g., somatotropin, insulin, insulin-like growth factors 1 and 2, platelet derived growth factor (PDGF), epidermal growth factor (EGF), fibroblast growth factor (FGF), nerve growth factor (NGF), neurotrophic factor-3 and 4, brain-derived neurotrophic factor (BDNF), glial derived growth factor (GDNF), transforming growth factor-α and -β, and the like), receptors (e.g., tumor necrosis factor receptor). In some exemplary embodiments, the transgene encodes a monoclonal antibody specific for one or more desired targets. In some exemplary embodiments, more than one transgene is encoded by the neDNA vector. In some exemplary embodiments, the transgene encodes a fusion protein comprising two different polypeptides of interest. In some embodiments, the transgene encodes an antibody, including a full-length antibody or antibody fragment, as defined herein. In some embodiments, the antibody is an antigen-binding domain or an immunoglobulin variable domain sequence, as that is defined herein. Other illustrative transgene sequences encode suicide gene products (thymidine kinase, cytosine deaminase, diphtheria toxin, cytochrome P450, deoxycytidine kinase, and tumor necrosis factor), proteins conferring resistance to a drug used in cancer therapy, and tumor suppressor gene products.

In a representative embodiment, the transgene expressed by a neDNA vector produced by the synthetic production methods as described herein can be used for the treatment of muscular dystrophy in a subject in need thereof, the method comprising: administering a treatment-, amelioration- or prevention-effective amount of neDNA vector described herein, wherein the neDNA vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the synthetically produced neDNA vector can be administered to skeletal, diaphragm and/or cardiac muscle as described elsewhere herein.

In some embodiments, a neDNA vector produced by the synthetic production methods as described herein can be used to deliver a transgene to skeletal, cardiac or diaphragm muscle, for production of a polypeptide (e.g., an enzyme) or functional RNA (e.g., RNAi, microRNA, antisense RNA) that normally circulates in the blood or for systemic delivery to other tissues to treat, ameliorate, and/or prevent a disorder (e.g., a metabolic disorder, such as diabetes (e.g., insulin), hemophilia (e.g., VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid alpha.-glucosidase] or Fabry disease [alpha.-galactosidase A]) or a glycogen storage disorder (such as Pompe disease [lysosomal acid a glucosidase]). Other suitable proteins for treating, ameliorating, and/or preventing metabolic disorders are described above.

In other embodiments, a neDNA vector produced by the synthetic production methods as described herein can be used to deliver a transgene in a method of treating, ameliorating, and/or preventing a metabolic disorder in a subject in need thereof. Illustrative metabolic disorders and transgenes encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art).

Another aspect of the invention relates to a method of treating, ameliorating, and/or preventing congenital heart failure or PAD in a subject in need thereof, the method comprising administering a neDNA vector produced by the synthetic production methods as described herein to a mammalian subject, wherein the neDNA vector comprises a transgene encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β-adrenergic receptor, .beta.2-adrenergic receptor kinase (BARK), PI3 kinase, calsarcan, β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active βARKct, Pim-1, PGC-1α, SOD-1, SOD-2, EC-SOD, kallikrein, HIF, thymosin-β4, mir-1, mir-133, mir-206 and/or mir-208.

In some embodiments, a neDNA vector produced by the synthetic production methods as described herein can be administered to the lungs of a subject by any suitable means, optionally by administering an aerosol suspension of respirable particles comprising the neDNA vectors, which the subject inhales. The respirable particles can be liquid or solid. Aerosols of liquid particles comprising the neDNA vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising a neDNA vector produced by the synthetic production methods as described herein may likewise be produced with any solid particulate medicament aerosol generator, by techniques known in the pharmaceutical art.

In some embodiments, a neDNA vector produced by the synthetic production methods as described herein can be administered to tissues of the CNS (e.g., brain, eye). In a particular embodiment, a neDNA vector produced by the synthetic production methods as described herein may be administered to treat, ameliorate, or prevent diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Ocular disorders that may be treated, ameliorated, or prevented with a neDNA vector produced by the synthetic production methods as described herein include ophthalmic disorders involving the retina, posterior tract, and optic nerve (e.g., retinitis pigmentosa, diabetic retinopathy and other retinal degenerative diseases, uveitis, age-related macular degeneration, glaucoma). Many ophthalmic diseases and disorders are associated with one or more of three types of indications: (1) angiogenesis, (2) inflammation, and (3) degeneration. In some embodiments, a neDNA vector produced by the synthetic production methods as described herein can be employed to deliver anti-angiogenic factors; anti-inflammatory factors; factors that retard cell degeneration, promote cell sparing, or promote cell growth and combinations of the foregoing. Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly. Additional ocular diseases that may be treated, ameliorated, or prevented with the neDNA vectors of the invention include geographic atrophy, vascular or "wet" macular degeneration, Stargardt disease, Leber Congenital Amaurosis (LCA), Usher syndrome, pseudoxanthoma elasticum (PXE), x-linked retinitis pigmentosa (XLRP), x-linked retinoschisis (XLRS), Choroideremia, Leber hereditary optic neuropathy (LHON), Archomatopsia, cone-rod dystrophy, Fuchs endothelial corneal dystrophy, diabetic macular edema and ocular cancer and tumors.

In some embodiments, inflammatory ocular diseases or disorders (e.g., uveitis) can be treated, ameliorated, or prevented by a neDNA vector produced by the synthetic production methods as described herein. One or more anti-inflammatory factors can be expressed by intraocular (e.g., vitreous or anterior chamber) administration of a neDNA vector produced by the synthetic production methods as described herein. In other embodiments, ocular diseases or disorders characterized by retinal degeneration (e.g., retinitis pigmentosa) can be treated, ameliorated, or prevented by the neDNA vectors of the invention. Intraocular (e.g., vitreal administration) of a neDNA vector produced by the synthetic production methods as described herein encoding one or more neurotrophic factors can be used to treat such retinal degeneration-based diseases. In some embodiments, diseases or disorders that involve both angiogenesis and retinal degeneration (e.g., age-related macular degeneration) can be treated with a neDNA vector produced by the synthetic production methods as described herein. Age-related macular degeneration can be treated by administering a neDNA vector produced by the synthetic production methods as described herein encoding one or more neurotrophic factors intraocularly (e.g., vitreous) and/or one or more anti-angiogenic factors intraocularly or periocularly (e.g., in the sub-Tenon's region). Glaucoma is characterized by increased ocular pressure and loss of retinal ganglion cells. Treatments for glaucoma include administration of one or more neuroprotective agents that protect cells from excitotoxic damage using the neDNA vector as disclosed herein. Accordingly, such agents include N-methyl-D-aspartate (NMDA) antagonists, cytokines, and neurotrophic factors, can be delivered intraocularly, optionally intravitreally using a neDNA vector produced by the synthetic production methods as described herein.

In other embodiments, a neDNA vector produced by the synthetic production methods as described herein may be used to treat seizures, e.g., to reduce the onset, incidence or severity of seizures. The efficacy of a therapeutic treatment for seizures can be assessed by behavioral (e.g., shaking, tics of the eye or mouth) and/or electrographic means (most seizures have signature electrographic abnormalities). Thus, a neDNA vector produced by the synthetic production methods as described herein can also be used to treat epilepsy, which is marked by multiple seizures over time. In one representative embodiment, somatostatin (or an active fragment thereof) is administered to the brain using a neDNA vector produced by the synthetic production methods as described herein to treat a pituitary tumor. According to this embodiment, a neDNA vector produced by the synthetic production methods as described herein encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank® Accession No. J00306) and amino acid (e.g., GenBank® Accession No. P01166; contains processed active peptides somatostatin-28 and somatostatin-14) sequences of somatostatins as are known in the art. In particular embodiments, the neDNA vector can encode a transgene that comprises a secretory signal as described in U.S. Pat. No. 7,071,172.

Another aspect of the invention relates to the use of a neDNA vector produced by the synthetic production methods as described herein to produce antisense RNA, RNAi or other functional RNA (e.g., a ribozyme) for systemic delivery to a subject in vivo. Accordingly, in some embodiments, a neDNA vector produced by the synthetic production methods as described herein can comprise a transgene that encodes an antisense nucleic acid, a ribozyme (e.g., as described in U.S. Pat. No. 5,877,022), RNAs that affect spliceosome-mediated trans-splicing (see, Puttaraju et al., (1999) Nature Biotech. 17:246; U.S. Pat. Nos. 6,013,487; 6,083,702), interfering RNAs (RNAi) that mediate gene silencing (see, Sharp et al., (2000) Science 287:2431) or other non-translated RNAs, such as "guide" RNAs (Gorman et al., (1998) Proc. Nat. Acad. Sci. USA 95:4929; U.S. Pat. No. 5,869,248 to Yuan et al.), and the like.

In some embodiments, a neDNA vector produced by the synthetic production methods as described herein can further also comprise a transgene that encodes a reporter polypeptide (e.g., an enzyme such as Green Fluorescent Protein, or alkaline phosphatase). In some embodiments, a transgene that encodes a reporter protein useful for experimental or diagnostic purposes, is selected from any of: β-lactamase, β-galactosidase (LacZ), alkaline phosphatase, thymidine kinase, green fluorescent protein (GFP), chloramphenicol acetyltransferase (CAT), luciferase, and others well known in the art. In some aspects, synthetically produced neDNA vectors comprising a transgene encoding a reporter polypeptide may be used for diagnostic purposes or as markers of the neDNA vector's activity in the subject to which they are administered.

In some embodiments, a neDNA vector produced by the synthetic production methods as described herein can comprise a transgene or a heterologous nucleotide sequence that shares homology with, and recombines with a locus on the host chromosome. This approach may be utilized to correct a genetic defect in the host cell.

In some embodiments, a neDNA vector produced by the synthetic production methods as described herein can comprise a transgene that can be used to express an immunogenic polypeptide in a subject, e.g., for vaccination. The transgene may encode any immunogen of interest known in the art including, but not limited to, immunogens from human immunodeficiency virus, influenza virus, gag proteins, tumor antigens, cancer antigens, bacterial antigens, viral antigens, and the like.

D. Testing for Successful Gene Expression Using a neDNA Vector

Assays well known in the art can be used to test the efficiency of gene delivery by a synthetically produced neDNA vector and can be performed in both in vitro and in vivo models. Knock-in or knock-out of a desired transgene by a synthetically produced neDNA can be assessed by one skilled in the art by measuring mRNA and protein levels of the desired transgene (e.g., reverse transcription PCR, western blot analysis, and enzyme-linked immunosorbent assay (ELISA)). Nucleic acid alterations by synthetically produced neDNA (e.g., point mutations, or deletion of DNA regions) can be assessed by deep sequencing of genomic target DNA. In one embodiment, synthetically produced neDNA comprises a reporter protein that can be used to assess the expression of the desired transgene, for example by examining the expression of the reporter protein by fluorescence microscopy or a luminescence plate reader. For in vivo applications, protein function assays can be used to test the functionality of a given gene and/or gene product to determine if gene expression has successfully occurred. For example, it is envisioned that a point mutation in the cystic fibrosis transmembrane conductance regulator gene (CFTR) inhibits the capacity of CFTR to move anions (e.g., $Cl^-$) through the anion channel, can be corrected by delivering a functional (i.e., non-mutated) CFTR gene to the subject with a neDNA vector. Following administration of a neDNA vector, one skilled in the art can assess the capacity for anions to move through the anion channel to determine if the CFTR gene has been delivered and expressed. One skilled will be able to determine the best test for measuring functionality of a protein in vitro or in vivo.

It is contemplated herein that the effects of gene expression of the transgene from the neDNA vector in a cell or subject can last for at least 1 month, at least 2 months, at least 3 months, at least four months, at least 5 months, at least six months, at least 10 months, at least 12 months, at least 18 months, at least 2 years, at least 5 years, at least 10 years, at least 20 years, or can be permanent.

In some embodiments, a transgene in the expression cassette, expression construct, or neDNA vector described herein can be codon optimized for the host cell. As used herein, the term "codon optimized" or "codon optimization" refers to the process of modifying a nucleic acid sequence for enhanced expression in the cells of the vertebrate of interest, e.g., mouse or human (e.g., humanized), by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen®'s Gene Forge® codon optimization and custom gene synthesis platform (Aptagen®, Inc.) or another publicly available database.

IX. Administration of Compositions Comprising neDNA

In particular embodiments, more than one administration (e.g., two, three, four or more administrations) may be employed to achieve the desired level of gene expression over a period of various intervals, e.g., daily, weekly, monthly, yearly, etc.

Exemplary modes of administration of a closed-ended DNA vector, including a neDNA vector, produced using the synthetic process as described herein includes oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration of a neDNA vector produced using the synthetic process as described herein can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye. Administration of the synthetically produced neDNA vector can also be to a tumor (e.g., in or near a tumor or a lymph node). The most suitable route in any given case will depend on the nature and severity of the condition being treated, ameliorated, and/or prevented and on the nature of the particular neDNA vector that is being used. Additionally, a neDNA vector produced using the synthetic process as described herein permits one to administer more than one transgene in a single vector, or multiple neDNA vectors (e.g., a neDNA cocktail).

Administration of a neDNA vector produced using the synthetic process as described herein can be to skeletal muscle according to the present invention and include but is not limited to administration to skeletal muscle in the limbs (e.g., upper arm, lower arm, upper leg, and/or lower leg), back, neck, head (e.g., tongue), thorax, abdomen, pelvis/perineum, and/or digits. The synthetically produced neDNA vector can be delivered to skeletal muscle by intravenous administration, intra-arterial administration, intraperitoneal administration, limb perfusion, (optionally, isolated limb perfusion of a leg and/or arm; see, e.g., Arruda et al., (2005) Blood 105: 3458-3464), and/or direct intramuscular injection. In particular embodiments, the neDNA vector as disclosed herein is administered to a limb (arm and/or leg) of a subject (e.g., a subject with muscular dystrophy such as DMD) by limb perfusion, optionally isolated limb perfusion, e.g., by intravenous or intra-articular administration. In certain embodiments, a DNA vector, including a neDNA vector produced using the synthetic process as described herein can be administered without employing 'hydrodynamic" techniques.

In some embodiments, neDNA described herein can be readily formulated in high concentrations of chitosan-nucleic acid polyplex compositions and administered orally in DNA enteric coated pills described in U.S. Pat. Nos. 8,846,102; 9,404,088; and 9,850,323, each of which is incorporated herein by reference in its entirety.

In some embodiments, neDNA vector produced using the synthetic process as described herein can be administered to cardiac muscle including the left atrium, right atrium, left ventricle, right ventricle and/or septum. The synthetically produced neDNA vector as described herein can be delivered to cardiac muscle by intravenous administration, intra-arterial administration such as intra-aortic administration, direct cardiac injection (e.g., into left atrium, right atrium, left ventricle, right ventricle), and/or coronary artery perfusion. Administration to diaphragm muscle can be by any suitable method including intravenous administration, intra-arterial administration, and/or intra-peritoneal administration. Administration to smooth muscle can be by any suitable method including intravenous administration, intra-arterial administration, and/or intra-peritoneal administration. In one embodiment, administration can be to endothelial cells present in, near, and/or on smooth muscle.

In some embodiments, a DNA vector, including a neDNA vector produced using the synthetic process as described herein is administered to skeletal muscle, diaphragm muscle and/or cardiac muscle (e.g., to treat, ameliorate and/or prevent muscular dystrophy or heart disease (e.g., PAD or congestive heart failure).

A. Ex Vivo Treatment

In some embodiments, cells are removed from a subject, a neDNA vector produced using the synthetic process as described herein is introduced therein, and the cells are then replaced back into the subject. Methods of removing cells from subject for treatment ex vivo, followed by introduction back into the subject are known in the art (see, e.g., U.S. Pat. No. 5,399,346; the disclosure of which is incorporated herein in its entirety). Alternatively, a closed-ended DNA vector, including a neDNA vector, produced using the synthetic process as described herein is introduced into cells from another subject, into cultured cells, or into cells from any other suitable source, and the cells are administered to a subject in need thereof.

Cells transduced with a neDNA vector, produced using the synthetic process as described herein are preferably administered to the subject in a "therapeutically-effective amount" in combination with a pharmaceutical carrier. Those of ordinary skill in the art will appreciate that the therapeutic effects need not be complete or curative, as long as some benefit is provided to the subject.

In some embodiments, a neDNA vector produced using the synthetic process as described herein can encode a transgene that is any polypeptide that is desirably produced in a cell in vitro, ex vivo, or in vivo. For example, in contrast to the use of the neDNA vectors in a method of treatment as previously discussed herein, in some embodiments a neDNA vector produced using the synthetic process as described herein may be introduced into cultured cells and the expressed gene product isolated therefrom, e.g., for the production of antigens or vaccines.

A neDNA vector produced using the synthetic process as described herein can be used in both veterinary and medical applications. Suitable subjects for ex vivo gene delivery methods as described above include both avians (e.g., chickens, ducks, geese, quail, turkeys and pheasants) and mammals (e.g., humans, bovines, ovines, caprines, equines, felines, canines, and lagomorphs), with mammals being preferred. Human subjects are most preferred. Human subjects include neonates, infants, juveniles, and adults.

One aspect of the technology described herein relates to a method of delivering a transgene to a cell. Typically, for in vitro methods, a neDNA vector produced using the synthetic process as described herein may be introduced into the cell using the methods as disclosed herein, as well as other methods known in the art. A neDNA vector produced using the synthetic process as described herein disclosed herein are preferably administered to the cell in a biologically-effective amount. If a neDNA vector produced using the synthetic process as described herein is administered to a cell in vivo (e.g., to a subject), a biologically-effective amount of the neDNA vector is an amount that is sufficient to result in transduction and expression of the transgene in a target cell.

B. Dose Ranges

In vivo and/or in vitro assays can optionally be employed to help identify optimal dosage ranges for use of the synthetically produced neDNA vector. The precise dose to be employed in the formulation will also depend on the route of administration, and the seriousness of the condition, and should be decided according to the judgment of the person of ordinary skill in the art and each subject's circumstances. Effective doses can be extrapolated from dose-response curves derived from in vitro or animal model test systems.

A neDNA vector produced using the synthetic process as described herein is administered in sufficient amounts to transfect the cells of a desired tissue and to provide sufficient levels of gene transfer and expression without undue adverse effects. Conventional and pharmaceutically acceptable routes of administration include, but are not limited to, those described above in the "Administration" section, such as direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration can be combined, if desired.

The dose of the amount of a synthetically produced neDNA vector required to achieve a particular "therapeutic effect," will vary based on several factors including, but not limited to: the route of nucleic acid administration, the level of gene or RNA expression required to achieve a therapeutic effect, the specific disease or disorder being treated, and the stability of the gene(s), RNA product(s), or resulting expressed protein(s). One of skill in the art can readily determine a synthetically produced neDNA vector dose range to treat a patient having a particular disease or disorder based on the aforementioned factors, as well as other factors that are well known in the art.

Dosage regime can be adjusted to provide the optimum therapeutic response. For example, the oligonucleotide can be repeatedly administered, e.g., several doses can be administered daily or the dose can be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

A "therapeutically effective dose" will fall in a relatively broad range that can be determined through clinical trials and will depend on the particular application (neural cells will require very small amounts, while systemic injection would require large amounts). For example, for direct in vivo injection into skeletal or cardiac muscle of a human subject, a therapeutically effective dose will be on the order of from about 1 μg to 100 g of the neDNA vector. If exosomes or microparticles are used to deliver a DNA vector, including a neDNA vector produced using the synthetic process as described herein, then a therapeutically effective dose can be determined experimentally, but is expected to deliver from 1 μg to about 100 g of vector. Moreover, a therapeutically effective dose is an amount neDNA vector that expresses a sufficient amount of the transgene to have an effect on the subject that results in a reduction in one or more symptoms of the disease, but does not result in significant off-target or significant adverse side effects.

Formulation of pharmaceutically-acceptable excipients and carrier solutions is well-known to those of skill in the art, as is the development of suitable dosing and treatment regimens for using the particular compositions described herein in a variety of treatment regimens.

For in vitro transfection, an effective amount of a closed-ended DNA vector, including a neDNA vector, produced using the synthetic process as described herein to be delivered to cells ($1\times10^6$ cells) will be on the order of 0.1 to 100 μg neDNA vector, preferably 1 to 20 μg, and more preferably 1 to 15 μg or 8 to 10 μg. Larger neDNA vectors will require higher doses. If exosomes or microparticles are used, an effective in vitro dose can be determined experimentally but would be intended to deliver generally the same amount of the neDNA vector.

Treatment can involve administration of a single dose or multiple doses. In some embodiments, more than one dose can be administered to a subject; in fact multiple doses can be administered as needed, because the synthetically produced neDNA vector elicits does not elicit an anti-capsid host immune response due to the absence of a viral capsid, and its formulation does not contain unwanted cellular contaminants due to its synthetic production. As such, one of skill in the art can readily determine an appropriate number of doses. The number of doses administered can, for example, be on the order of 1-100, preferably 2-20 doses.

Without wishing to be bound by any particular theory, the lack of typical anti-viral immune response elicited by administration of a synthetically produced neDNA vector as described by the disclosure (i.e., the absence of capsid components) allows the synthetically produced neDNA vector to be administered to a host on multiple occasions. In some embodiments, the number of occasions in which a heterologous nucleic acid is delivered to a subject is in a range of 2 to 10 times (e.g., 2, 3, 4, 5, 6, 7, 8, 9, or 10 times). In some embodiments, a synthetically produced neDNA vector is delivered to a subject more than 10 times.

In some embodiments, a dose of a synthetically produced neDNA vector is administered to a subject no more than once per calendar day (e.g., a 24-hour period). In some embodiments, a dose of a synthetically produced neDNA vector is administered to a subject no more than once per 2, 3, 4, 5, 6, or 7 calendar days. In some embodiments, a dose of a synthetically produced neDNA vector is administered to a subject no more than once per calendar week (e.g., 7 calendar days). In some embodiments, a dose of a synthetically produced neDNA vector is administered to a subject no more than bi-weekly (e.g., once in a two calendar week period). In some embodiments, a dose of a synthetically produced neDNA vector is administered to a subject no more than once per calendar month (e.g., once in 30 calendar days). In some embodiments, a dose of a synthetically produced neDNA vector is administered to a subject no more than once per six calendar months. In some embodiments, a dose of a synthetically produced neDNA vector is administered to a subject no more than once per calendar year (e.g., 365 days or 366 days in a leap year).

C. Unit Dosage Forms

In some embodiments, the pharmaceutical compositions can conveniently be presented in unit dosage form. A unit dosage form will typically be adapted to one or more specific routes of administration of the pharmaceutical composition. In some embodiments, the unit dosage form is adapted for administration by inhalation. In some embodiments, the unit dosage form is adapted for administration by a vaporizer. In some embodiments, the unit dosage form is adapted for administration by a nebulizer. In some embodiments, the unit dosage form is adapted for administration by an aerosolizer. In some embodiments, the unit dosage form is adapted for oral administration, for buccal administration, or for sublingual administration. In some embodiments, the unit dosage form is adapted for intravenous, intramuscular, or subcutaneous administration. In some embodiments, the unit dosage form is adapted for intrathecal or intracerebroventricular administration. In some embodiments, the pharmaceutical composition is formulated for topical administration. The amount of active ingredient which can be combined with a carrier material to produce a single dosage form will generally be that amount of the compound which produces a therapeutic effect.

X. Various Applications

The compositions comprising a neDNA vector produced using the synthetic process as described herein can be used to deliver a transgene for various purposes as described above. In some embodiments, a transgene can encode a protein or be a functional RNA, and in some other embodiments, it can be a protein or functional RNA modified for research purposes, e.g., to create a somatic transgenic animal model harboring one or more mutations or a corrected gene sequence, e.g., to study the function of the target gene. In another example, the transgene encodes a protein or functional RNA to create an animal model of disease.

In some embodiments, the transgene encodes one or more peptides, polypeptides, or proteins, which are useful for the treatment, amelioration, or prevention of disease states in a mammalian subject. The transgene expressed by the synthetically produced neDNA vector is administered to a patient in a sufficient amount to treat a disease associated with an abnormal gene sequence, which can result in any one or more of the following: reduced expression, lack of expression or dysfunction of the target gene.

In some embodiments, a neDNA vector produced using the synthetic process as described herein are envisioned for use in diagnostic and screening methods, whereby a transgene is transiently or stably expressed in a cell culture system, or alternatively, a transgenic animal model.

Another aspect of the technology described herein provides a method of transducing a population of mammalian cells. In an overall and general sense, the method includes at least the step of introducing into one or more cells of the population, a composition that comprises an effective amount of one or more of the synthetically produced neDNA disclosed herein.

Additionally, the present invention provides compositions, as well as therapeutic and/or diagnostic kits that include one or more of the neDNA vector compositions, produced using the synthetic process as described herein, formulated with one or more additional ingredients, or prepared with one or more instructions for their use.

A cell to be administered with a neDNA vector produced using the synthetic process as described herein may be of any type, including but not limited to neural cells (including cells of the peripheral and central nervous systems, in particular, brain cells), lung cells, retinal cells, epithelial cells (e.g., gut and respiratory epithelial cells), muscle cells, dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

EXAMPLES neDNA vectors and AAV vectors having various serotype ITRs can be synthetically synthesized by the methods described in the present disclosure.

A single-stranded break ("nick") in DNA can be formed by the hydrolysis and subsequent removal of a phosphate group within the helical backbone. The advantage of a neDNA with a gap in the junction between the ITR and expression cassette includes: (1) the nicked or gapped sequence can better facilitate binding of transcriptional enzymes by decreasing torsion of the double strand and thus, resulting in increased expression level in the host cells; and (2) the nicked or gapped sequence allows for the exonuclease (T7 or Exo V) activity by providing a binding site for these enzymes and leading to designed removal of one strand that has a nick or gap at 5' upstream and 3' downstream of an expression vector. Hence, this exonuclease activity effectively leads to creation of a single stranded closed-ended DNA vector like an AAV vector. In this way, an AAV vector can be synthesized synthetically with a specific design to yield only one type of single stranded AAV over the other (e.g., either plus (+) or minus (−) strand) depending of the location and strand of the designed nick. Therefore, the methods disclosed herein allow for heightened levels of manufacturing control which are highly desired in production of therapeutic grades of AAV vectors.

Example 1. Production of Synthetic ITRs and an Expression Cassette

AAV's terminal repeats that are the inverse complement of one another within a given stretch of polynucleotide sequence are typically each referred to as an inverted terminal repeat or ITR.

In the context of a virus, ITRs plays a critical role in mediating replication, viral particle and DNA packaging, DNA integration and genome and provirus rescue. As such, the ITR is an important structural feature of the neDNA and AAV vector for transgene expression, vector persistence and vector-host protein interactions (e.g., host immune response).

As exemplified in throughout Examples, the ITR can be artificially synthesized using a set of oligonucleotides comprising one or more desirable functional sequences (e.g., palindromic sequence, Rep protein Binding sequence). The ITR sequence can be an artificial AAV WT-ITR, an artificial non-AAV Modified ITR, or an ITR physically derived from a viral AAV ITR (e.g., ITR fragments removed from a viral genome).

FIG. 6 depicts generation of neDNA using single fragment of oligonucleotide per ITR. In such a case, the inverse complement sequence is present within the oligonucleotide molecule in order to facilitate the formation of a hairpin loop structure during the annealing step. In this process, the synthetic ITR are designed to produce an overhang with sequence for specific ligation with the expression cassette. The overhang sequence will complement with an overhang sequence with the double strand expression cassette.

FIGS. 7A and 7B depicts generation of neDNA using multiple oligonucleotide molecules per ITR. In a preferred embodiment, two oligonucleotide molecules per ITR are implemented. In another preferred embodiment, three oligonucleotide molecules per ITR are implemented. Regardless of single or multiple oligos, the design entails creation of one or more gaps in the double stranded linear structure of ceDNA. Depending on the structural preference, single oligonucleotide or multiple oligonucleotides per ITR can be utilized to generate ITR synthetically (e.g., via DNA oligonucleotide assembly).

Once a desired ITR were produced by annealing oligonucleotides, designed overhangs can be ligated with a double stranded DNA preferably containing an expression cassette sequence with a complement overhang structure to the overhang sequence the ITR. The overhang by design does not provide complete coverage of the single strand on the single strand oligo, such that when ligation is completed, it results in creation of a desire gap of a specific length in the DNA structure, thereby resulting in a nicked ("gapped") closed-ended double stranded DNA vector.

Wild-type AAV and/or modified ITRs can be used for synthesis of neDNA or AAV DNA vectors. As discussed herein, a synthetically produced DNA vector can comprise a symmetrical ITR pair or an asymmetrical ITR pair. In both instances, one or both of the ITRs can be modified ITRs—the difference being that in the first instance (i.e., symmetric mod-ITRs), the mod-ITRs have the same three-dimensional spatial organization (i.e., have the same A-A', C-C' and B-B' arm configurations), whereas in the second instance (i.e., asymmetric mod-ITRs), the mod-ITRs have a different three-dimensional spatial organization (i.e., have a different configuration of A-A', C-C' and B-B' arms). See, FIGS. 6, 7A and 7B for symmetrical and asymmetrical ITR designs by various oligonucleotides.

1) Cell Free Synthesis of neDNA with One Oligonucleotide for Each ITR

The following procedure describes a method for producing neDNA using a different oligo to generate each of the two closed-ended synthetic ITRs.

Synthetic ITR and Transgene Expression Cassette Design

Oligonucleotides were designed such that intramolecular annealing generated AAV2 ITR structures (inclusive of A, B, C, and D stems as well as conserved Rep Binding Elements (RBE)). In addition, oligos were designed to generate cohesive overhangs compatible with ligation to restriction sites flanking the transgene insert. Restriction sites were selected to generate unique cohesive overhangs to facilitate directional ligation to the left and right ITR.

Left full length ITR oligo with BamHI compatible overhang: wt-L-oligo-20

Right full length ITR oligo with XhoI compatible overhang: wt-L-oligo-21

In the example provided, restriction sites utilized are BamHI and XhoJ, but in theory any cohesive end restriction enzyme would be compatible if it did not cleave inside the transgene insert.

ITR oligonucleotides were also modified to prevent reformation of the transgene restriction site upon ligation. Where possible, base substitutions in the ITR were introduced to generate a new restriction site in the event of homodimerization.

Generation of a neDNA vector is directed by omission of the 5' phosphate from one or both the ITR oligonucleotides or by enzymatic removal of the 5' phosphate from one or both cohesive overhangs on the transgene cassette. Absence of a 5'-phosphate at any of these locations will prevent ligation with the juxtaposed 3'OH that is derived from annealing of compatible overhangs. Sequential treatment with restriction enzymes and phosphatase allows control over which of the transgene termini get dephosphorylated.

Figure 11A:
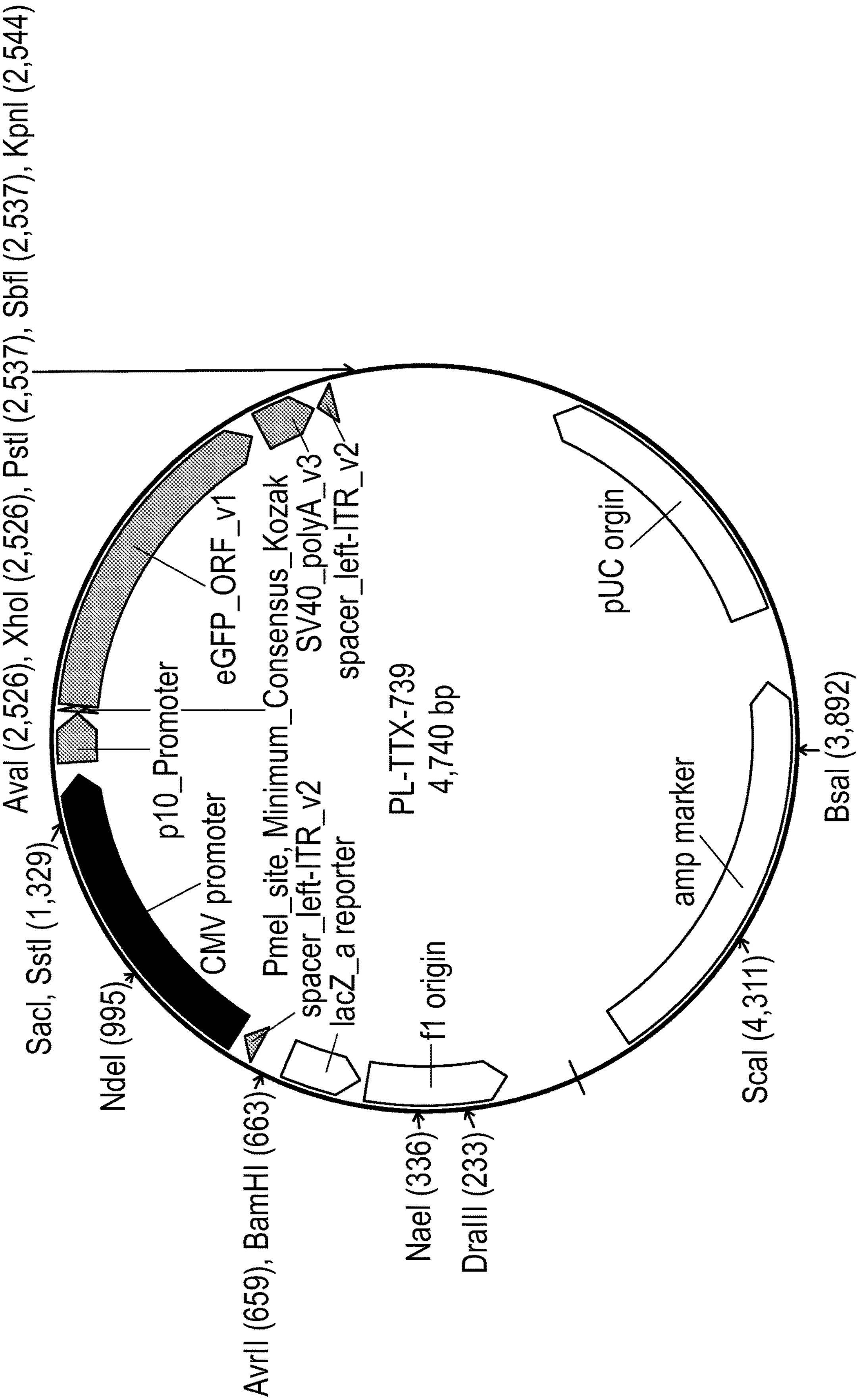
FIGS. 11A and 11B illustrate exemplary circular plasmids containing an expression cassette comprising a promoter, a transgene, and polyadenylation sequence. These plasmids can be used to derive a double stranded expression cassette with overhang sequences.

Additionally, a gap of more than a base pair, instead of a nick of one base pair, can be introduced at the junctions by engineering a larger overhang into the ITR fragment such that when annealed to its compatible cohesive overhang a gap is introduced upon strand specific ligation (see, FIGS. 6-9; FIG. 11A)

Methods of oligonucleotides synthesis and purification are known in the art and available commercially. Formation of ITR duplexes was achieved by denaturation of a 100 μM oligo stock solution at 95° C. for 2 mins, followed by rapid cooling in an ice bath. Aliquots of the annealed ITR stocks were aliquoted and kept frozen until use.

The transgene expression cassette with appropriate flanking restriction sites was cloned into a pUC based high-copy vector to generate PL-TTX-739 (FIG. 11A) and purified from *E. coli* using standard techniques. In this example, the expression cassette included the CMV promoter, green fluorescent protein (GFP) CDS, SV40 polyadenylation sequences (SV40 polyA). The cassette was also flanked by restriction enzymes compatible for ligation of synthetic ITR fragments. In the examples, BamHI and XhoI were used. This plasmid served as the source of the transgene expression cassette for subsequent steps.

Restriction/Ligation One Step Reaction to Form neDNA

The transgene expression cassette was released from the plasmid backbone by restriction digest using BamHI and XhoI enzyme (see, FIG. 11A). The reaction was performed in a 100 μL volume combining 20 pmol of plasmid with 3% v/v of each restriction enzymes BamHI and XhoJ. The reaction was incubated for 4 hours at 37° C.

ITR were ligated to the transgene expression cassette by adding 160 pmol of both left and right pre-annealed ITR fragments, 2% v/v T4 DNA ligase, 10% v/v of ATP containing ligase buffer and 2% v/v of restriction enzymes BamHI, XhoI, BglII and SalI to the 100 μL of digested transgene expression cassette plasmid. The reaction was made up to 400 μL with water and was incubated at 4 to 16 hours at 22° C., followed by heat inactivation at 65° C. for 20 min. Addition of restriction enzymes served to prevent unwanted ligated products. First, BamHI and XhoI prevented re-ligation of the transgene cassette back to the plasmid backbone. Importantly, since ligation of ITR fragments does not reform BamHI and XhoI restriction sites, the desired product (neDNA) will be unaffected. Second, BglII and SalI cleave the homodimer ligation products of left and right ITRs, respectively. Neither BglII or SalI cleave inside the transgene expression cassette or neDNA.

To remove remaining plasmid backbone, the 400 μL ligation reaction is supplemented with 3% v/v DraIII, 5% v/v BsaI and 10% v/v of the manufacturer recommended buffer. The reaction was adjusted to a total volume of 1 mL and incubated at 37° C. for 1-2 hours. Both enzymes further fragment the vector backbone, while not cleaving the desired product neDNA.

Open ended fragments derived from the plasmid backbone, un-ligated transgene cassette ITR fragments were degraded with addition of 3% v/v of ExoV exonuclease, 10% ExoV buffer and 10% v/v ATP. The reaction was brought to a final volume of 5 mL and incubated at 37° C. for 1-4 hours. Importantly, ExoV cleaves single stranded a double stranded linear DNA, but not closed-ended DNA (ceDNA) or DNA or closed-ended nicked DNA (neDNA).

neDNA was concentrated by ethanol precipitation followed by purification using a silica spin column to remove any residual enzymes and small DNA fragments.

The result of this procedure is a selective enrichment and purification of the desired end product, neDNA—a closed-ended DNA duplex with terminal ITR structures derived from AAV that possess one or more nicks or gaps in regions distal to the transgene expression cassette.

2) Cell Free Synthesis of neDNA Using Engineered ITRs and Short Oligonucleotides The following procedure describes a method of producing neDNA using a different oligonucleotide to generate each of the two closed-ended synthetic ITRs (two oligos in total). In contrast to Example 1, oligonucleotides are much shorter in length, <100 bp. The benefit of this modification is two-fold: 1) shorter oligos are easier and cheaper to synthesize to high purity; and 2) intra-molecular annealing of shorter oligos is more efficient and less likely to produce undesired end-products. In this example, reforming the full length ITR structure using shorter oligonucleotides requires that the dsDNA insert contain the A stem, Rep Binding Elements (RBE) and the D stem regions flanking the transgene expression cassette. Additionally, compatible restriction sites must be engineered between the RBEs and the B/C stems of the AAV2 ITRs to direct ligation with synthetic ITR fragments.

Synthetic ITR and Trans-Gene Expression Cassette Design

Oligonucleotides were designed, such that intramolecular annealing generated AAV2 ITR structures (inclusive of A, B, C and D stems as well as conserved Rep Binding Elements (RBE). In addition, oligonucleotides were designed to generate cohesive overhangs compatible with ligation to restriction sites flanking the transgene insert. Restrictions sites were selected to generate unique cohesive overhangs to facilitate directional ligation to the left and right ITR. wt-L-oligo-14 and wt-R-oligo-16 oligonucleotides were used to generate left and right ITR fragments, respectively.

```
wt-L-oligo-20 Left one oligo-full length ITR
                                   (SEQ ID NO: 68)
/5Phos/GATCTAGGAACCCCTAGTGATGGAGTTGGCCACTCCCTCTCTG

CGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAG

TGGCCAACTCCATCACTAGGGGTTCCTA

wt-R-oligo-21 Right one oligo-full length ITR
                                   (SEQ ID NO: 69)
TCGACAGGAACCCCTAGTGATGGAGTTGGCCACTCCCTCTCTGCGCGCTC

GCTCGCTCACTGAGGCCGGGCGACCAAAGGTCGCCCGACGCCCGGGCTTT

GCCCGGGCGGCCTCAGTGAGCGAGCGAGCGCGCAGAGAGGGAGTGGCCAA

CTCCATCACTAGGGGTTCCTG

wt-L-oligo-14 Left one oligo-engineered ITR
                                   (SEQ ID NO: 70)
/5Phos/CTAGCTGAGGCCGCCCGGGCAAAGCCCGGGCGTCGGGCGACCT

TTGGTCGCCCGGCCTCAG

wt-R-oligo-16 Right one oligo-engineered
                                   (SEQ ID NO: 71)
ITRCTGAGGCCGCCCGGGCAAAGCCCGGGCGTCGGGCGACCTTTGGTCGC

CCGGCCTCAGTGCA
```

The Left ITR oligo anneals to generate an AvrII compatible overhang, whereas the Right ITR oligos anneal to generate a SbfI compatible overhang. In theory any cohesive end restriction enzyme would be compatible with this method if it does not cleave within the transgene insert.

ITR oligonucleotides were also modified to prevent reformation of the transgene restriction site upon ligation. Where possible, base substitutions in the ITR were introduced to generate a new restriction site in the event of homo-dimerization.

Generation of a Nicked close-ended DNA was directed by omission of the 5' phosphate from one or both the ITR oligonucleotides or by enzymatic removal of the 5' phosphate from one or both cohesive overhangs on the trans-gene cassette. Absence of a 5'-phosphate at any of these locations prevented ligation with the juxtaposed 3'OH that is derived from annealing of compatible overhangs. Sequential treatment with restriction enzymes and phosphatase allowed control over which of the trans-gene termini were dephosphorylated.

Additionally, gaps instead of nicks could be introduced at the junctions by engineering a larger overhang into the ITR fragment such that when annealed to its compatible cohesive overhang a gap would be introduced upon strand-specific ligation.

Methods of oligonucleotide synthesis and purification are known in the art and routinely available from third party service providers. Formation of ITR duplexes was achieved by denaturation of a 100 μM oligo stock solution at 95° C. for 2 mins, followed by rapid cooling in an ice bath. Aliquots of the annealed ITR stocks were aliquoted and kept frozen until use.

In this example, the expression cassette included the CAG promoter, green fluorescent protein CDS (GFP), WPRE 5' UTR and bovine growth hormone poly Adenylation sequence (bGH polyA).

Figure 11B:
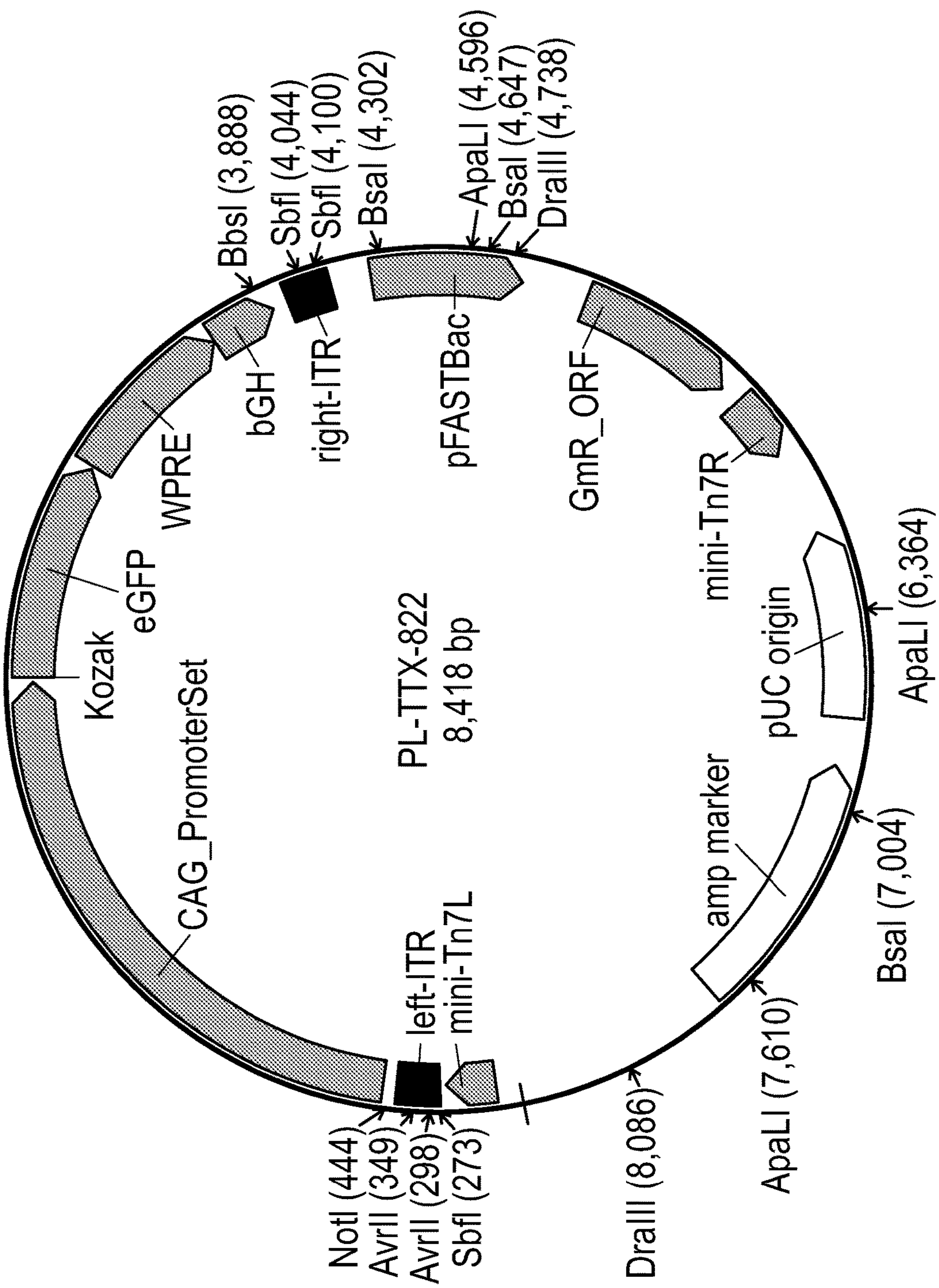
Figure 11C:
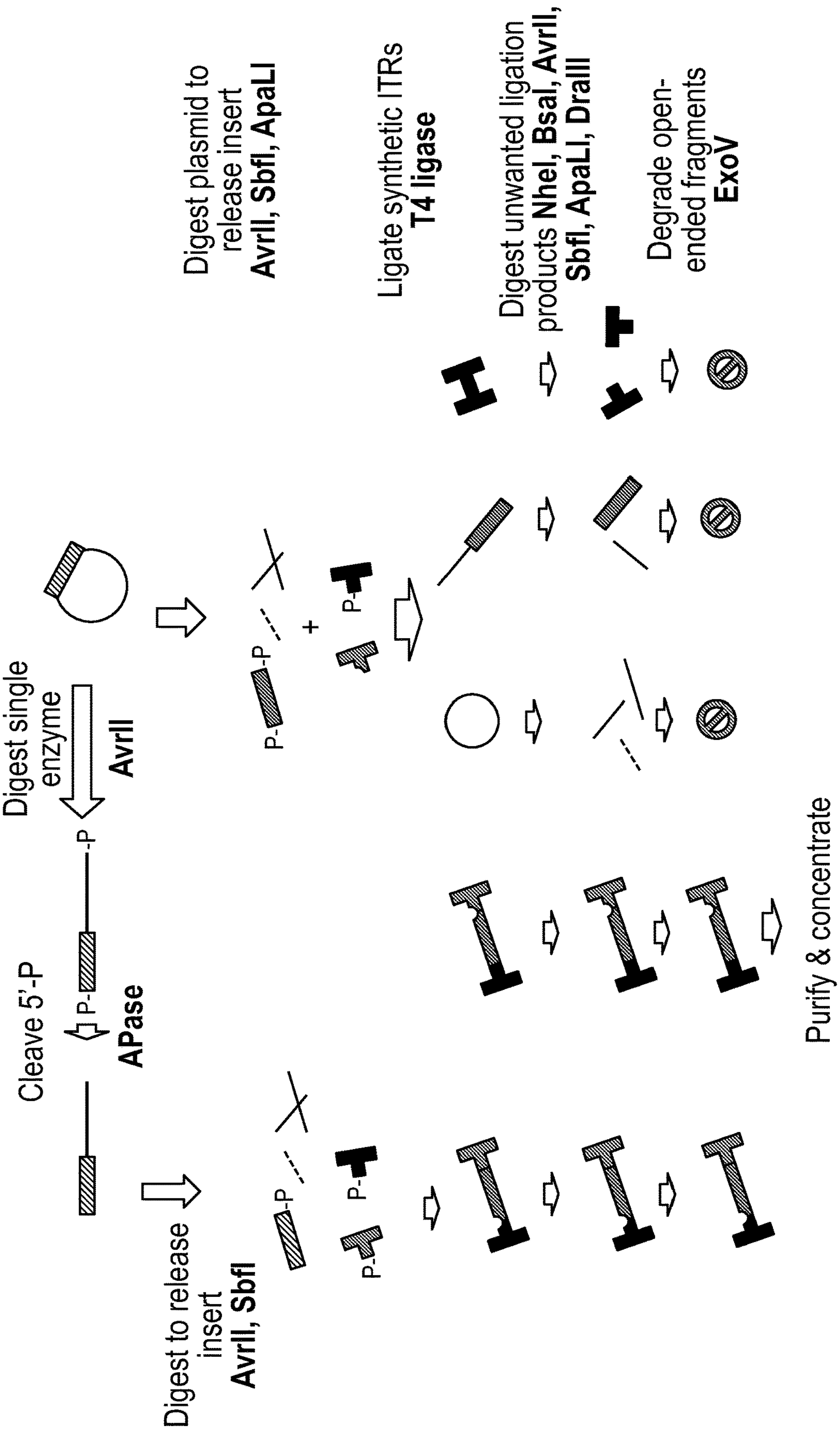
FIG. 11C is a schematic description of neDNA synthesis starting from a neDNA-plasmid.
Figure 11D:
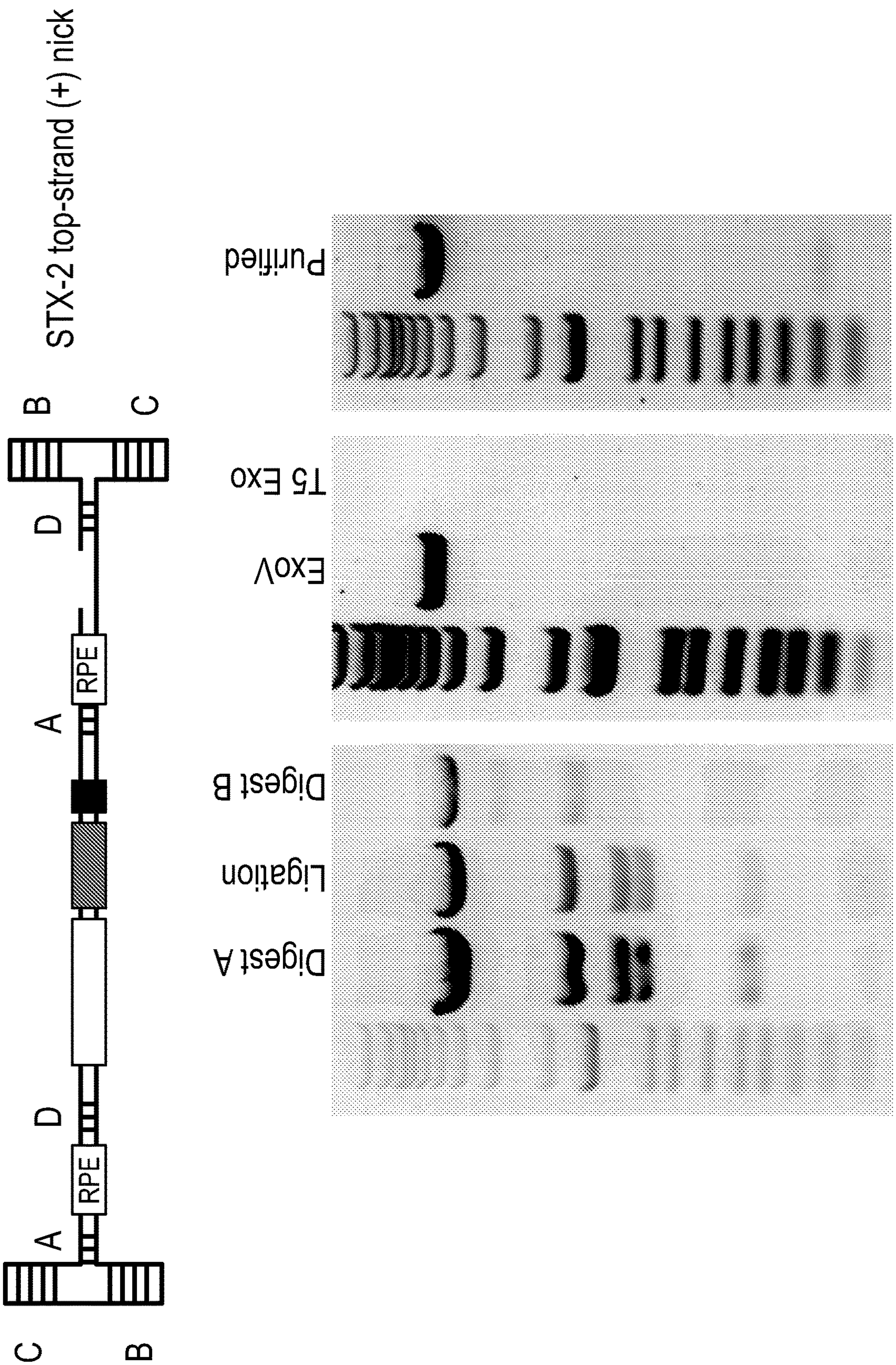
FIG. 11D depicts a gel image showing expected outcome for distinct steps in the process of making neDNA in FIG. 11C.

The transgene expression cassette was cloned into a vector harboring engineered ITR sequences (see PL-TTX-822; FIG. 11B). Specifically, the left ITR was mutated to introduce an AvrII site in between the B/C stem and the RBEs, whereas the right ITR was engineered to include a SbfI site in between the B/C stem and the RBEs both the X and X stem. Engineering of restriction sites into the ITRs was required to facilitate reformation of the full ITR sequence when using the shorter oligonucleotides described in section 3 below.

Restriction/Ligation in Single Reaction to Form neDNA

The transgene expression cassette was release from the plasmid backbone by restriction digest, in this example, using AvrII and SbfI enzymes. The reaction was performed in a 100 μL volume combining 20 pmol of plasmid with 3% v/v of each restriction enzymes AvrII, SbfI and ApaLI. The reaction was incubated for 4 hrs at 37° C. ApaLI enzyme cuts the plasmid backbone, but does not cut inside the transgene expression cassette.

ITRs were ligated to the trans-gene expression cassette by adding 160 pmol of both left and right pre-annealed ITR fragments, 2% v/v T4 DNA ligase, 10% v/v of ATP containing ligase buffer and 2% v/v of restriction enzymes AvrII, SbfI, ApaLI and NheI to the 100 μL of digested transgene expression cassette plasmid. The reaction was made up to 400 μL with water and was incubated at 4 to 16 hours at 22° C., followed by heat inactivation at 65° C. for 20 min. Addition of restriction enzymes served to prevent unwanted ligation product because SbfI and AvrII prevent re-ligation of the transgene cassette back to the plasmid backbone. Importantly, since ligation of ITR fragments does not reform SbfI and AvrII restriction sites, the desired product (neDNA) was unaffected. Second, NheI and ApaLI cleave the homodimer ligation products of left and right ITRs, respectively. Neither NheI or ApaLI cleave inside the transgene expression cassette or neDNA.

To remove remaining plasmid backbone, the 400 uL ligation reaction was supplemented with 3% v/v DraIII, 5% v/v BsaI and 10% v/v of the manufacturer recommended buffer. The reaction was adjusted to a total volume of 1 mL and incubated at 37° C. for 1-2 hrs. Both enzymes further fragment the vector backbone, while not cleaving the desired product neDNA.

Open ended fragments derived from the plasmid backbone, un-ligated trans-gene cassette and ITR fragments were degraded with addition of 3% v/v ExoV exonuclease, 10% ExoV v/v buffer and 10% v/v ATP. The reaction was brought up to a final volume of 5 mL and incubated at 37° C. for 1-4 hours. Importantly. ExoV cleaves ssDNA and dsDNA linear DNA but does not cleave close-ended DNA (ceDNA) or DNA or close-ended nicked DNA (neDNA).

neDNA was concentrated by ethanol precipitation followed by purification using a silica spin column to remove any residual enzymes and small DNA fragments. Both procedures are well known in the art.

The result of this procedure was a selective enrichment and purification of the desired end product, neDNA—a closed-ended DNA duplex with terminal ITR structures derived from AAV that possessed one or more nicks or gaps in regions distal to the transgene expression cassette.

3) Cell Free Synthesis of neDNA with Multiple Oligonucleotides Per ITR

The following procedure describes a method for producing neDNA using 3 or more different oligos to generate each of the two closed-ended synthetic ITRs. The use of multiple oligos to recapitulate the full ITR sequence benefits from the ability to use shorter oligonucleotides as in Example 2, but also allows maintenance of the WT-ITR sequence. Additionally, there is much greater flexibility in the positioning of the nick or gaps. For example, this method allows a nick to be generated at the native TRS site of AAV mimicking a structural intermediate in the AAV replication cycle.

Synthetic ITR and Trans-Gene Expression Cassette Design

Oligonucleotides were designed, such that intramolecular annealing generated AAV2 ITR structures (inclusive of A, B, C and D stems as well as conserved Rep Binding Elements (RBE). In addition, oligos were designed to generate cohesive overhangs compatible with ligation to restriction sites flanking the trans gene insert. Restrictions sites were selected to generate unique cohesive overhangs to facilitate directional ligation to the left and right ITR.

The following primers were used to generate ITR fragments:

- Left ITR (FIG. 8): Primer No. 1, Primer No. 4, and Primer No. 5;
- RIGHT ITR (FIG. 9) (3 oligo version): Primer No. 6, Primer No. 7, and Primer No. 8;
- RIGHT ITR (FIG. 9) (4 oligo version): Primer No. 6, Primer No. 8, Primer No. 9, and Primer No. 10.

Variations in primer modifications, such as biotinylation and phosphorylation are denoted by sub-numbering (i.e. 8.1, 8.2). See, below for details.

```
Primer No. 1 Left three oligo-full length ITR
                                    (SEQ ID NO: 72)
/5Phos/GCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAG

TGGCCA

Primer No. 4 Left three oligo-full length ITR
                                    (SEQ ID NO: 73)
/5Phos/GGCCTCTATGACGTAATTCACGTCACGACTCCACCCCTCCAGG

AACCCCTAGTGATGGAGTTGGCCACTCCCTCTCTGCGCGCTC
```

-continued

```
Primer No. 5 Left three oligo-full length ITR
                                    (SEQ ID NO: 74)
GGGGTTCCTGGAGGGGTGGAGTCGTGACGTGAATTACGTCATAGA

Primer No. 6.1 Left three & four oligo-full length
ITR
                                    (SEQ ID NO: 75)
/5Phos/TAGCAGGCATGCTGGGGATGCGGTGGGCTCTATGGCTCTAGAG

CATGGCTACGTAGATAAGTAGCATGGCGGGTTAATCATTAACTACACCTG

CAGG

Primer No. 6.2 Left three & four oligo-full length
ITR
                                    (SEQ ID NO: 75)
/5Phos/TAGCAGGCATGCTGGGGATGCGGTGGGCTCTATGGCTCTAGAG

CATGGCTACGTAGATAAGTAGCATGGCGGGTTAATCATTAACTACACCTG

CAGG/3Phos/

Primer No. 7 Left three oligo-full length ITR
                                    (SEQ ID NO: 76)
/5Phos/GAGCGCGCAGAGAGGGAGTGGCCAACTCCATCACTAGGGGTTC

CTCCTGCAGGTGTAGTTAATGATTAACCCGCCATGCTACTTATCTACGTA

GCCATGCTCTAGAGCCATAGAGCCCACCGCATCCCCAGCATGCCT

Primer No. 8.1 Left three & four oligo-full length
ITR
                                    (SEQ ID NO: 77)
/5PCBio/TGGCCACTCCCTCTCTGCGCGCTCGCTCGCTCACTGAGGCCG

GGCGACCAAAGGTCGCCCGACGCCCGGGCTTTGCCCGGGCGGCCTCAGTG

AGCGAGC

Primer No. 8.2 Left three & four oligo-full length
ITR
                                    (SEQ ID NO: 77)
/5Biotin/TEG/TGGCCACTCCCTCTCTGCGCGCTCGCTCGCTCACTGA

GGCCGGGCGACCAAAGGTCGCCCGACGCCCGGGCTTTGCCCGGGCGGCCT

CAGTGAGCGAGC

Primer No. 9 Left four oligo-full length ITR
                                    (SEQ ID NO: 78)
/5Phos/CGCCATGCTACTTATCTACGTAGCCATGCTCTAGAGCCATAGA

GCCCACCGCATCCCCAGCATGCCT

Primer No. 10 Left four oligo-full length
                                    (SEQ ID NO: 79)
ITR/5Phos/GAGCGCGCAGAGAGGGAGTGGCCAACTCCATCACTAGGGG

TTCCTCCTGCAGGTGTAGTTAATGATTAACC

Primer No. 12.1 Right three & four oligo-full
length ITR
                                    (SEQ ID NO: 80)
/5PBio/TGGCCACTCCCTCTCTGCGCGCTCGCTCGCTCACTGAGGCAAA

GCCTCAGTGAGCGAGC

Primer No. 12.2 Right three & four oligo-full
length ITR
                                    (SEQ ID NO: 80)
/5BiotinTEG/TGGCCACTCCCTCTCTGCGCGCTCGCTCGCTCACTGAG

GCAAAGCCTCAGTGAGCGAGC
```

Left ITR oligonucleotides annealed to generate a NotI compatible overhang, whereas the Right ITR oligos anneal to generate a BbsI compatible overhang. In the example given, restriction sites utilized were NotI (Left ITR) and BbsI (Right ITR), but any cohesive end restriction enzyme would be compatible as long as it did not also cleave within the transgene insert.

ITR oligonucleotides were also modified to prevent reformation of the transgene restriction site upon ligation. Where possible, base substitutions in the ITR were introduced to generate a new restriction site in the event of homo-dimerization.

Generation of a nicked close-ended DNA ("neDNA") was directed by omission of the 5' phosphate from one or more of the ITR oligonucleotides or by enzymatic removal of the 5' phosphate from one or both cohesive overhangs on the transgene cassette. Absence of a 5'-phosphate at any of these locations prevented ligation with the juxtaposed 3'OH that is derived from annealing of compatible overhangs. Sequential treatment with restriction enzymes and phosphatase allowed control over which of the transgene termini get dephosphorylated.

Additionally, gaps, instead of nicks, can be introduced at the junctions by engineering oligonucleotides to generate longer or shorter overhangs. In this way, gaps between 3' and 5' termini can be generated either during intramolecular annealing to form the ITR fragment and/or during ligation of the ITR's to transgene (see FIGS. 6-9)

Figure 9:
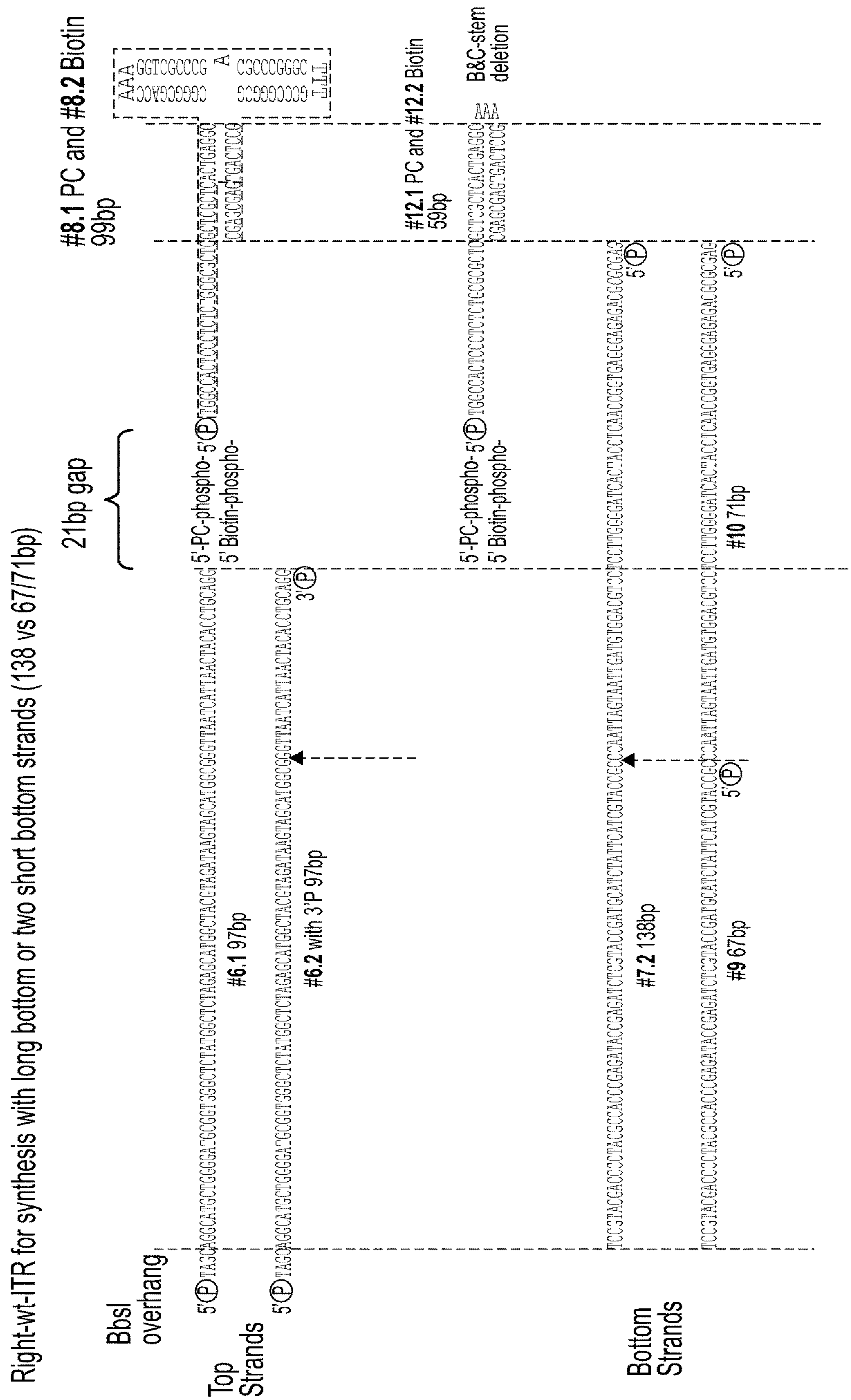
FIG. 9 depicts a schematic representation of a right ITR (e.g., synthetic modified ITR or a semi-blunt (e.g., B and C stem deleted) with a spacer) that can be used for cell-free synthesis of neDNA. 5'-photocleavable-phosphate or 5'biotin-phosphate can be used on the closed end 99 base pair structure to facilitate a gap. Two different options for the bottom sequence (i.e., a long sequence with 138 bp and short sequence with either 67 or 71 bp) having phosphates on the 5' end and two different potential top strands, each with an overhang (i.e., one with phosphates on both 5' and 3' ends and the other with one phosphate on the 5' end only). When assembled and ligated, this ITR contains a gap of 21 base pairs in length on the top strand and can be used to create neDNA or synthetic AAV vector when ligated with an expression cassette.
Figure 10:
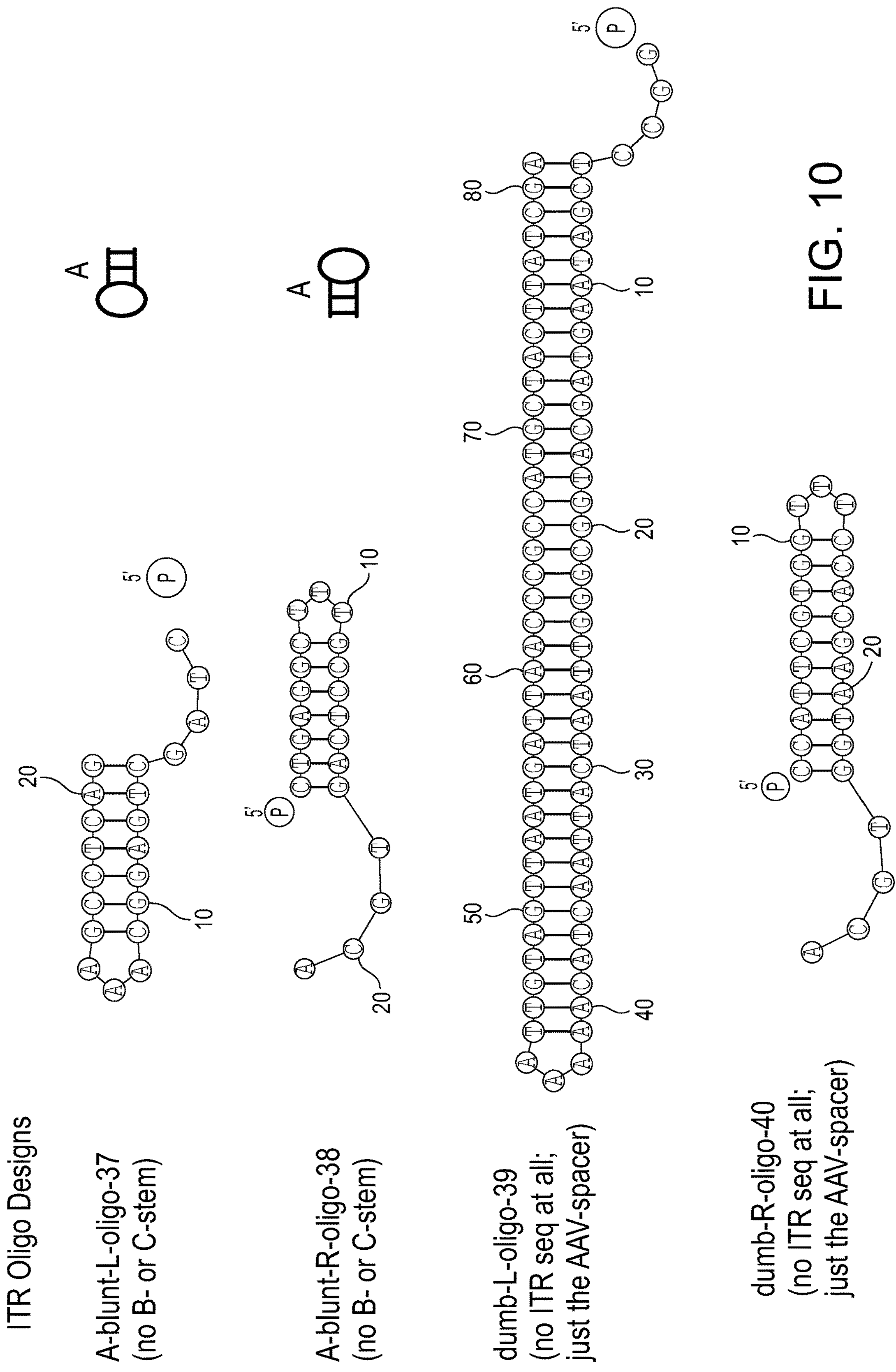
FIG. 10 depicts ITR variants that can be used in synthetic synthesis of neDNA and AAV vectors. Shown are blunt ended (no B or C stem in the left or right ITR) and dumbbell structures (spacer sequence with a closed end without ITR sequence) and various nicks and/or gaps that can be created in accordance with the methods described in FIG. 6 or 9.

In the current example, a 12 bp gap was introduced in the Left ITR by reducing the length of Primer No. 5 at the 5'end to generate a larger overhang when annealed with Primer No. 4 (FIG. 8). Similarly, a 21-bp gap was introduced into the right ITR by reducing the length of Primer No. 6 at the 3' end to generate a larger overhang when annealed with Primer No. 7.2 or Primer No.10 (FIG. 9). Note that this method of introducing gaps, instead of nicks, obviates the need to control ligation by removal of 5' phosphates, at least with respect to junction spanning the gap.

Methods and reagents involved in oligonucleotide synthesis and purification are well known in the art and readily available commercially. Formation of ITR duplexes was achieved by mixing 100 μM stock solutions of oligonucleotides in equal parts, boiling for 2 mins followed by annealing in a water bath during slow cooling to room temperature. Aliquots of the annealed ITR stocks were aliquoted and kept frozen until use.

Restriction/Ligation One-Pot Reaction to Form neDNA

The expression cassette comprising a CAG promoter, transgene and bGH poly A was released from a plasmid backbone by restriction digest, using NotI and BbsI enzymes, which flank the CAG promoter and the bGH polyA sequence. The reaction was performed in a 100 μL volume combining 20 pmol of plasmid with 3% v/v of each restriction enzymes NotI, BbsI and ApaLI. The reaction was incubated for 4 hrs at 37° C. ApaLI enzyme cleaves the plasmid backbone, but does not cut inside the trans-gene expression cassette.

ITRs were ligated to the transgene expression cassette by adding 160 pmol of both left and right pre-annealed ITR fragments, 2% v/v T4 DNA ligase, 10% v/v of ATP containing ligase buffer and 2% v/v of restriction enzymes NotI, BbsI and ApaLI to the 100 μL of digested transgene expression cassette plasmid. The reaction was made up to 400 μL with water and was incubated at 4 to 16 hours at 22° C., followed by heat inactivation at 65° C. for 20 min. Addition of restriction enzymes served to prevent unwanted ligation products. First, NotI and BbsI prevented re-ligation of the transgene cassette back to the plasmid backbone. Since ligation of ITR fragments does not reform NotI and BbsI restriction sites, the desired product (neDNA) would not be unaffected. Second, ApaLI cleaved religation of vector backbone fragments.

To remove remaining plasmid backbone, the 400 uL ligation reaction was supplemented with 3% v/v DraIII, 5% v/v BsaI and 10% v/v of the manufacturer recommended buffer. The reaction was adjusted to a total volume of 1 mL and incubated at 37° C. for 1-2 hrs. Both enzymes further fragment the vector backbone, while not cleaving the desired product neDNA.

Open ended fragments derived from the plasmid backbone, un-ligated trans-gene cassette and ITR fragments were degraded with addition of 3% v/v ExoV exonuclease, 10% ExoV buffer and 10% v/v ATP. The reaction was brought up to a final volume of 5 mL and incubated at 37° C. for 1-4 hours. Importantly. ExoV cleaves ssDNA and dsDNA linear DNA, but does not cleave close-ended DNA (ceDNA) or DNA or close-ended nicked DNA (neDNA).

neDNA was concentrated by ethanol precipitation followed by purification using a silica spin column to remove any residual enzymes and small DNA fragments. Both procedures are well known in the art.

Example 2. Synthetic Production of neDNA from ceDNA

In this method, a process and method for generating nicked ceDNA from double strand ceDNA using a nicking enzyme (nicking endonuclease) is exemplified. A nicking enzyme is an enzyme that nicks one strand of a double stranded DNA at a specific nucleotide sequence (i.e., restriction site for nicking enzyme). Nicking is achieved by hydrolyzing the backbone phosphodiester bond of one strand of the DNA duplex producing DNA molecules that are nicked at a specific site, rather than complete cleavage. In one embodiment, the nicking enzyme can create a series of gaps. The restriction/target site for the nickase can be designed and incorporated into the ceDNA during production by introducing the sequence into one or more oligonucleotides of the ITRs as described above, or included in sequences flanking the trans-gene cassette. For example, a programmable nickase, such as CRISPR/Cas9 can be effectively used in vitro to introduce a single strand break in the double stranded duplex of intact ceDNA to yield neDNA. Other nicking enzymes may include, but are not limited to, BspQI, CviPII, BstNBI, BsrDI, BtsI, Alwl, BbvCI, BsmI, BssSI, BsmAI. It is possible to use any sequence specific enzyme that can cleave only one strand of DNA on a double-stranded DNA substrate.

Example 3. Synthetic neDNA Stably Expresses a Transgene in Human Cells

Figure 12:
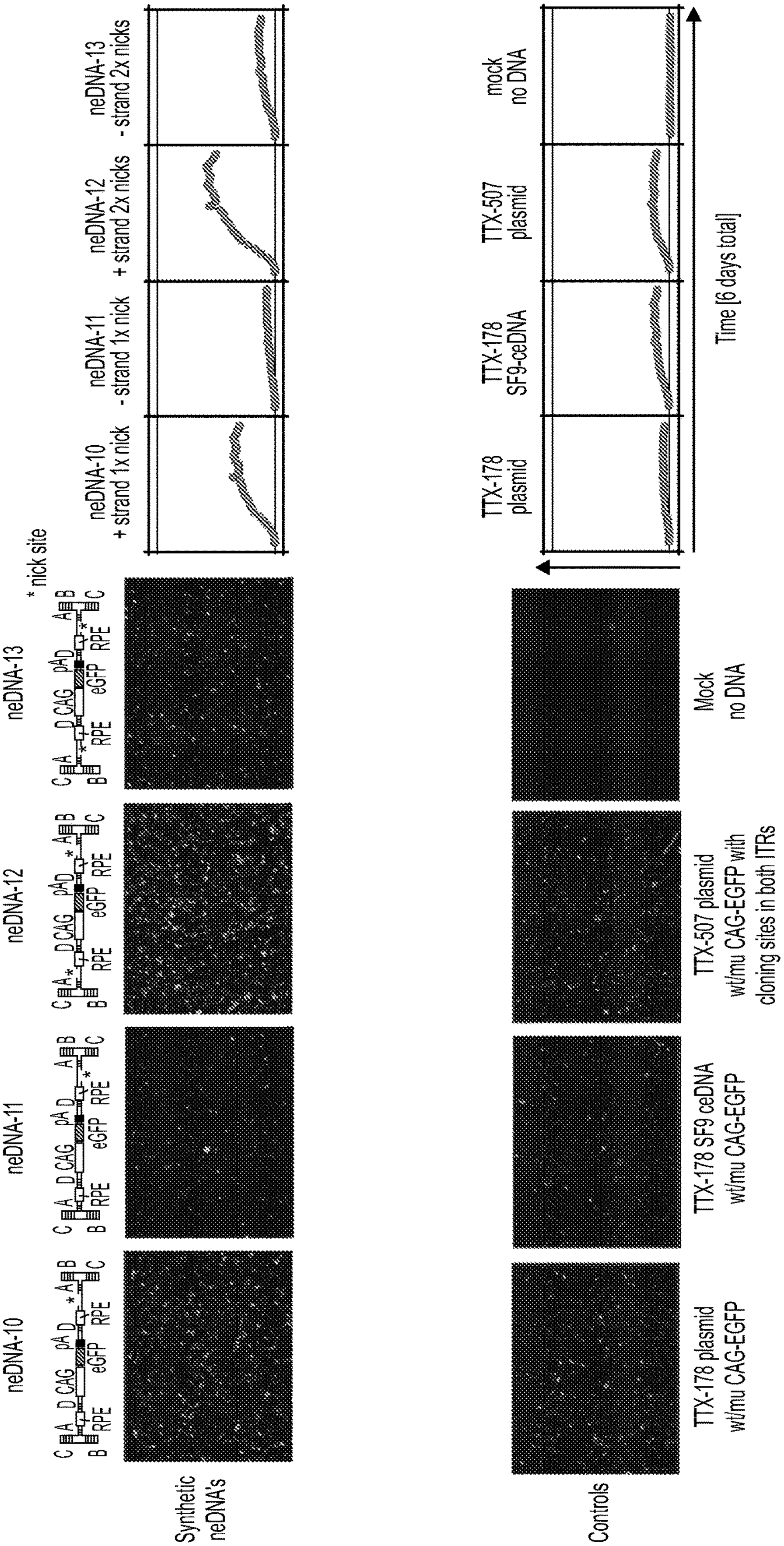
FIG. 12 depicts the results of the in vitro cell expression assays set forth in Example 3 comparing expression of a transgene (eGFP) from synthetically produced neDNA to that from traditionally Sf9-produced ceDNA vectors and plasmid DNA in HepaRG cells. A schematic representation of each construct used is set forth immediately above the fluorescence microscopy image for the cells transfected with corresponding DNA vector. Images were taken 6 days after introduction of the indicated vector by nucleofection. Graphs depict the time course of GFP expression through 6 days, as measured using IncuCyte®.

To assess whether the synthetically produced neDNA vectors were able to express transgene similarly to traditionally Sf9-produced ceDNA vectors and ceDNA construct in a plasmid, the expression of four different neDNA vectors in cultured cells was measured by the degree of fluorescent protein (GFP) production and fluorescence emission.

neDNA-10: wt/wt ITRs, containing point-mutations in the A-stem for cloning, single-nicked at right & top (+) strand neDNA-11: wt/wt ITRs, containing point-mutations in the A-stem for cloning, single-nicked at right & bottom (−) strand neDNA-12: wt/wt ITRs, containing point-mutations in the A-stem for cloning, double-nicked at left & right top (+) strands neDNA-13: wt/wt ITRs, containing point-mutations in the A-stem for cloning, double-nicked at left & right top (+) strands Human hepatic cells (HepaRG cell line, Lonza®) were plated at a concentration of $7.5\times10^4$ cells/mL. The four different neDNA vectors (neDNA No. 10-13) were introduced to the cultured cells using a commercially available device (Nucleofector™, Lonza®) according to the manufacturer's protocols. A 16-well strip containing 150 ng/well of each construct was nucleofected in a volume of 20 μL. Nucleofected samples were grown in a well of a 96-well plate for a final volume in each well of 100 μL. The media was changed 24 hours post nucleofection, and subsequently replaced twice per week. ceDNA produced from Sf9 cells and plasmids comprising ceDNA vector were used as control as shown in FIG. 12. The fluorescence intensity of each culture was measured 6 days after nucleofection using the Essen Bioscience IncuCyte® live cell imaging microscope. This system was positioned inside an incubator and automatically takes time lapse phase and fluorescence photos of cells over the desired timeframe.

As shown in FIG. 12, expression of GFP appeared as bright white spots. Cells treated with the Sf9-produced ceDNA vector with WT/mutant ITRs had similar expression of GFP as seen in the plasmid-treated cells. Two of the synthetically produced neDNA vectors (i.e., the plus strand having one gap and two gaps) demonstrated greater fluorescence intensity and number of spots than either the plasmid control or the traditionally Sf9-produced ceDNA vector. This relative increase in fluorescence may be at least partially due to the greater purity of the synthetically produced material to that of the traditionally produced material and the presence of one or more gaps that facilitates transcription. The results illustrated that the synthetically produced neDNA vector indeed stably expressed the encoded transgene and possibly greater than the traditionally Sf9-produced ceDNA vector or plasmid-ceDNA. Thus, the synthetically produced neDNA having one or more gaps not only possessed functional expression capacity, but also has potential to be a greater expression vector useful for gene therapy.

Example 4. Production of Synthetic AAV Vector from neDNA

In general, cell-free synthesis neDNA is achieved by intra-molecular annealing of oligonucleotides to form ITR structures followed by their strand-specific ligation to double-stranded expression cassette with compatible cohesive overhangs. Omission of the 5' phosphate from one or both ITR oligonucleotides prevents ligation to the corresponding 3'-OH of the compatible cohesive overhang. The products of this reaction contain sequence specified nicks and/or gaps in the neDNA vector. Alternatively, or in combination, the 5' phosphate can be enzymatically removed from one or both ends of the expression cassette to generate nicks/gaps on the opposite strand to that which is generated via modification of the ITR-oligonucleotide. In the latter method, sequential digestion of the expression cassette enables differential protection and/or cleavage of the 5' end phosphate associated with each ITR compatible overhang. Various methods are described to remove unwanted ligation by products and enrich for desired molecular end-product. Together, this method and its variants (as described below) allow cell free production ceDNA with one or more nicks/gaps at sequence specified location on either strand and/or end of the expression cassette. The product of this reaction is collectively referred to as neDNA (Nicked closed-end DNA)

Figure 13:
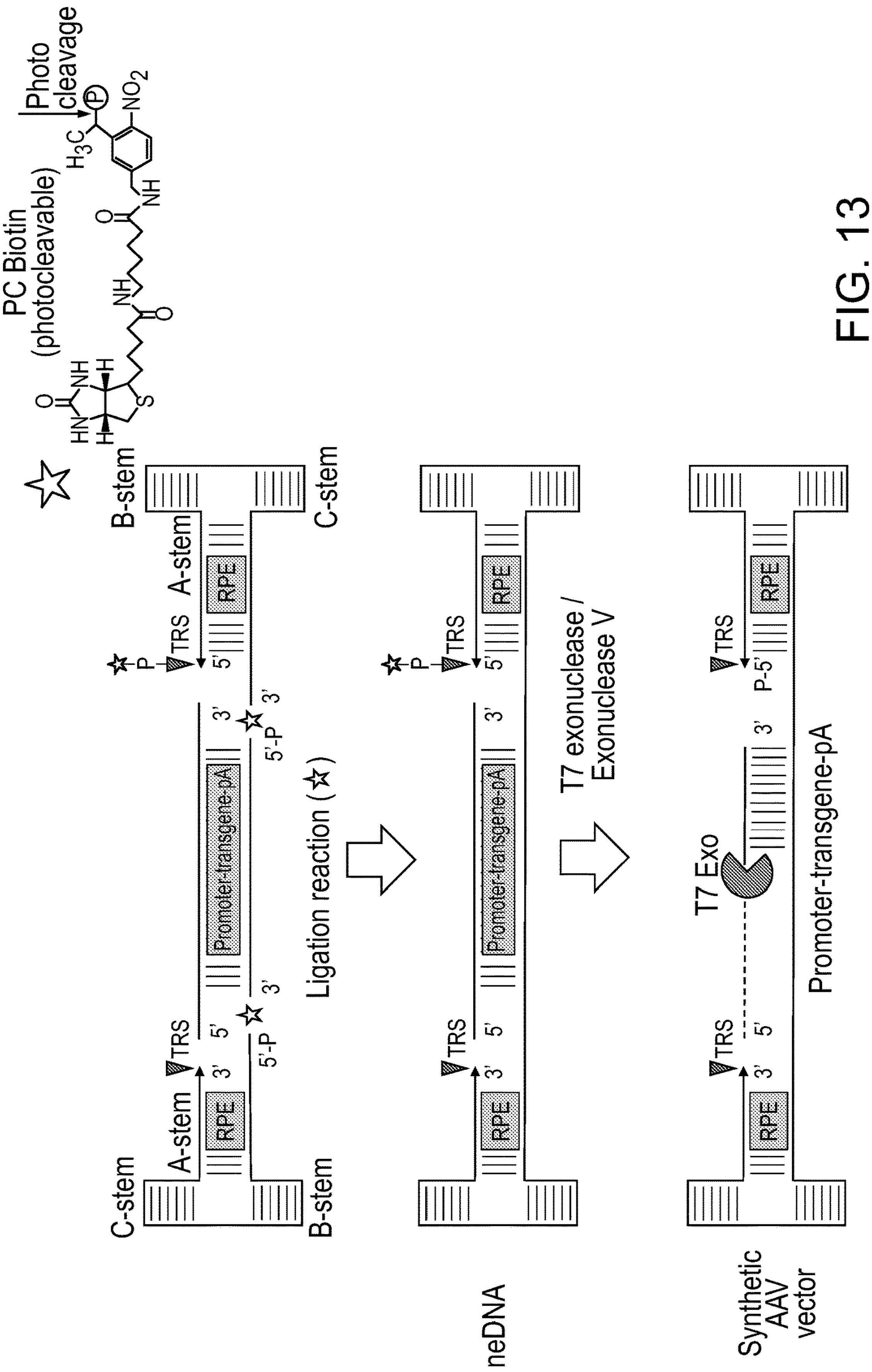
FIG. 13 depicts a schematic showing single strand (ss) DNA molecule generation by stepwise removal of one strand from a neDNA that has two gaps flanking the transgene cassette on the plus strand. In this example, T7-Exo selectively degrades the nicked template from the 5'-termini. The PC-Biotin group inhibits exo degradation, ensuring protection of the AAV vector. 5' overhangs and photo-induced removal of the biotin group allows designing a gap of preferably 1-100 base pairs in length on the 5' and 3'-ends. Biotin-streptavidin-based extraction of ligation product followed by photo-induced removal of the biotin group will ensure the 5'-end with phosphate, for example, on the right ITR. Using T7 Exo or optionally ExoV, one strand of the expression cassette comprising a promoter, transgene and poly-A sequence can be removed, resulting in a synthetic AAV vector.

In this method, a single stranded AAV vector having one or two ITR can be produced from nicked ceDNA. As illustrated in FIG. 13, starting from neDNA, one can obtain ssAAV vector by employing a strand-specific exonuclease which can initiate at a nick/and or gap region engineered at the TRS site. Subsequent removal of the nicked strand, from either the 3' or the 5' end generates a ssDNA region spanning the transgene. Examples of suitable exonucleases include, but is not limited to, ExoV and T7 exonuclease. Importantly, the structure of neDNA must enable both accurate initiation/termination of strand degradation to generate an equivalent synthetic AAV vector. For this purpose, it is preferable for neDNA to possess a nick and/or gap both 5' and 3' of the trans gene expression cassette. The exonuclease must also be prevented from unwanted initiation on free 3' and/or 5' ends generated by constructing neDNA that would result in degradation of the AAV vector. This can be achieved by selective protection of 3' or 5' termini by covalent modification of the ITR oligonucleotide. FIG. 13 demonstrates the use of T7-exo to selectively remove the (+) strand, initiating at the 5' nick/and or gap outside the left ITR TRS and terminating at the nick/and or gap at the right ITR TRS. In this example, the 5' end of the right-ITR is protected from exonuclease by covalent addition of biotin/or photo-cleavable (PC) biotin during synthesis of the oligonucleotide. Such modifications are standard and commercially available. The use of PC-biotin is of note as it allows subsequent removal of the biotin from the AAV vector. Use of 3' to 5' exonuclease like ExoV is also possible and would require protection of the 3' end of the left ITR with a suitable covalent modification to inhibit exonuclease initiation (e.g., biotin).

As an alternative method to above, displacement and removal of the dual-nicked strand encoding the transgene insert can be achieved by disassociation of the DNA duplex, followed by strand specific capture of the AAV vector using the covalently attached PC-biotin. Disassociation can be achieved by a variety of methods, denaturation via increased temperature or buffer pH. Because trans gene cassette is flanked by nicks/and or gaps on the same strand, it will freely diffuse and can be physically separated using known chromatographic techniques (e.g., magnetic beads coated with streptavidin, affinity columns using immobilized streptavidin).

Enzymes known as helicases can also be used to separate and displace DNA strands. Polymerases have varying degrees of strand-displace activity and could also be utilized for removal of the nicked trans gene plus strand. Enzymatic routes to strand separation and labelling are of particular utility as they provide options to recover a specific strand without use of harsh abiotic conditions. In one embodiment, dCas9 is used in conjunction with a helicase to dissociate and capture specific ssDNA molecules. For this purpose, dCas9 is targeted to a user determined sequence(s) to bind but not cut the target sequence. Affinity purification of Cas9 will recover the bound DNA. Alternatively, Cas9 nickase could be targeted to cleave the plus strand insert into small fragments that are easier to dissociate and prevent reannealing than the full length insert. ssDNA binding proteins (e.g., SSB) could also be utilized to maintain strand separation after dissociation by treatment with helicase.

Figure 14:
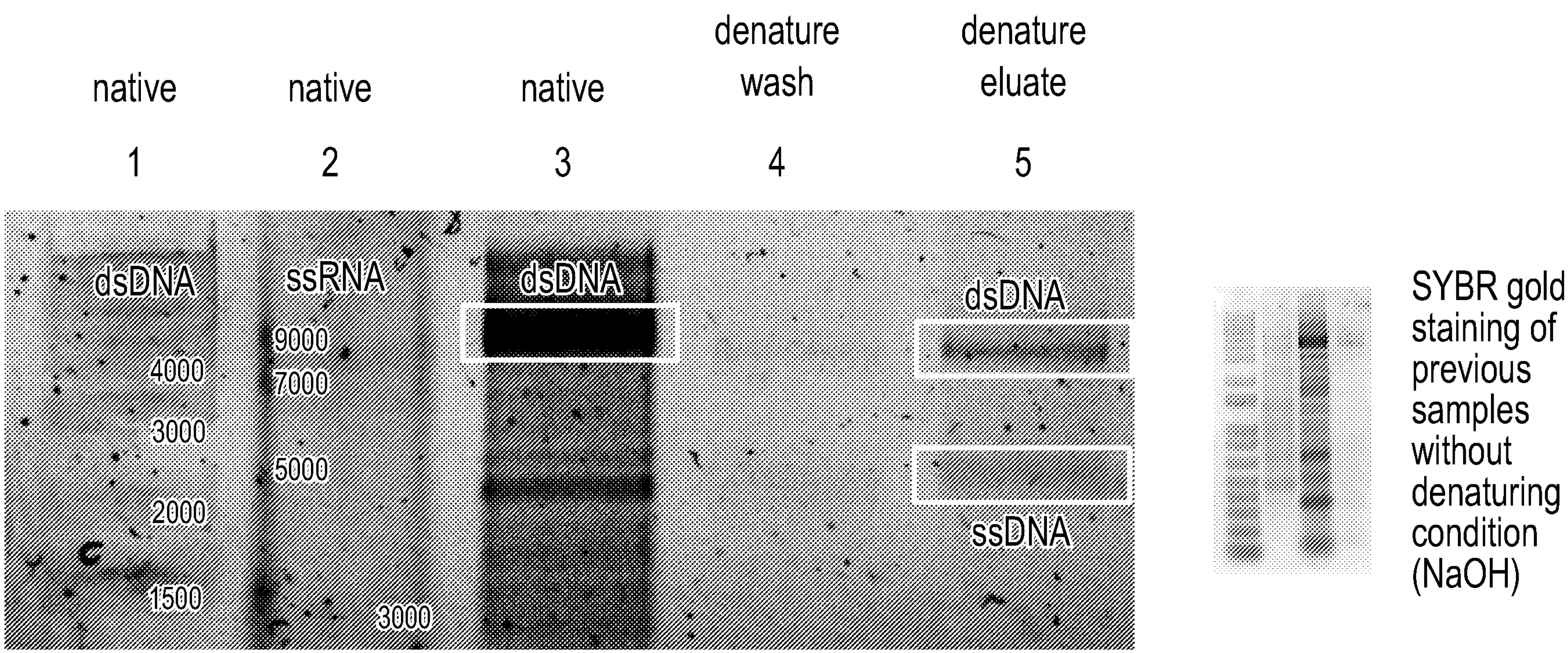
FIG. 14 depicts the successful enrichment of ssDNA representing a synthetic AAV vector.

FIG. 14 demonstrates the successful enrichment of ssDNA representing a synthetic AAV vector. In this example, neDNA with gaps flanking the transgene plus strand (see FIGS. 7, 8 and 9) was denatured in NaOH resulting in disassociation and release of the trans-gene plus strand fragment. Subsequently the synthetic AAV ssDNA-tagged with Biotin was recovered using magnetic beads coated with streptavidin. Subsequent washing and elution resulted in enrichment of a ssDNA species relative to the dsDNA neDNA input material. The ssDNA nature of the recovered product was confirmed by showing that it was resistant to cleavage by a restriction enzyme known to cut the dsDNA neDNA molecule (e.g., PacI).

In general, the ability to generate nicks and or gaps at sequence specified locations through the production of neDNA allows unprecedented control over the sequence and structure of the AAV vector. Moreover, either method can be used to exclusively generate the plus or minus version of the AAV vector, which is not possible using cell-based methods to produce AAV.

REFERENCES

All publications and references, including but not limited to patents and patent applications, cited in this specification and Examples herein are incorporated by reference in their entirety as if each individual publication or reference were specifically and individually indicated to be incorporated by reference herein as being fully set forth. Any patent application to which this application claims priority is also incorporated by reference herein in the manner described above for publications and references.

What is claimed is:

1. A method of producing a closed-ended DNA vector having one or more gaps (neDNA) comprising:
   - providing a double-stranded DNA construct comprising an expression cassette, wherein the expression cassette comprises a promoter linked to a transgene, wherein a 3' end and a 5' end of said double-stranded DNA construct each comprise an overhang sequence;
   - providing a first inverted terminal repeat (ITR) comprising an overhang sequence that comprises a complement to at least a portion of the overhang sequence of the 5' end of the double-stranded DNA construct, wherein the first ITR is closed-ended (5' ITR);
   - providing a second ITR comprising an overhang sequence that comprises a complement to at least a portion of the overhang sequence of the 3' end of the double-stranded DNA construct, wherein the second ITR is closed-ended (3' ITR);

contacting said double-stranded DNA construct comprising the expression cassette with the first ITR, the second ITR, and a ligase, wherein ligation of the first ITR and the second ITR with the double-stranded DNA construct comprising the expression cassette produces (i) the closed-ended DNA vector having one or more gaps in a sense or antisense strand 5' upstream of the expression cassette, or 3' downstream of the expression cassette, or (ii) the closed-ended DNA vector having one or more gaps in a sense or antisense strand both 5' upstream and 3' downstream of the expression cassette.

2. The method of claim 1, wherein the method is performed in a cell-free environment.

3. The method of claim 1, wherein ligation of the first ITR and the second ITR with the double-stranded DNA construct comprising the expression cassette produces a closed-ended DNA vector having one or more gaps in the sense strand.

4. The method of claim 1, wherein ligation of the first ITR and the second ITR with the double-stranded DNA construct comprising the expression cassette produces a closed-ended DNA vector having one or more gaps in the antisense strand.

5. The method of claim 1, wherein the transgene encodes a protein selected from the group consisting of a therapeutic protein, a reporter protein, a cytotoxic protein, and a gene editing protein.

6. The method of claim 5, wherein the therapeutic protein is selected from the group consisting of an antibody, an immunogenic protein, Factor VIII, Factor IX, Factor X, CEP290, ABCA4, and phenylalanine hydroxylase (PAH).

7. The method of claim 5, wherein the reporter protein is selected from the group consisting of luciferase and green fluorescent protein.

8. The method of claim 1, wherein the transgene encodes a therapeutic RNA and/or a noncoding nucleic acid.

9. The method of claim 8, wherein said noncoding nucleic acid is selected from the group consisting of an siRNA, a microRNA, an shRNA, an antisense oligonucleotide (ASO), and an antagomir.

10. The method of claim 1, wherein:
   - said first ITR and said second ITR are symmetric or substantially symmetric with respect to each other; or
   - said first ITR and said second ITR are asymmetric with respect to each other.

11. The method of claim 1, wherein:
   - the gap is about one or two base pairs in length;
   - the gap is about five base pairs, about ten base pairs, about fifteen base pairs, or about thirty base pairs in length; and/or
   - the gap is about 1 base-pair to 100 base-pairs in length.

12. The method of claim 11, wherein:
   - the gap is about 3-5 base pairs in length;
   - the gap is about 5-10 base pairs in length;
   - the gap is about 10-15 base pairs in length;
   - the gap is about 15-20 base pairs in length;
   - the gap is about 20-25 base pairs in length;
   - the gap is about 25-30 base pairs in length;
   - the gap is about 30-40 base pairs in length;
   - the gap is about 40-50 base pairs in length; and/or
   - the gap is about 50-100 base pairs in length.

13. The method of claim 1, wherein:
   - the gap is 5' upstream of the expression cassette;
   - the gap is 3' downstream of the expression cassette the gap is not within the transgene;
   - the gap is in a spacer sequence between the expression cassette and the first ITR;
   - the gap is in a spacer sequence between the expression cassette and a Rep Binding Element (RBE) in the first ITR;
   - the one or more gaps are present both 5' upstream and 3' downstream of the expression cassette; and/or
   - the presence of said gap enhances expression of the transgene in a host cell.

14. The method of claim 1, wherein:
   - the first ITR and/or the second ITR are produced by annealing a single-stranded oligonucleotide that contains a palindromic sequence facilitating self-annealing to form a double-stranded stem-loop DNA structure with the overhang;
   - the first ITR and/or second ITR are produced by annealing and/or ligating three or more oligonucleotides; and/or
   - the one or more gaps are introduced by designing a set of single-stranded overhangs in said first and second ITRs and said expression cassette that do not completely cover the resulting double-stranded DNA sequence.

15. The method of claim 14, wherein the first ITR and/or the second ITR produced by annealing said three or more oligonucleotides contain a gap in a stem structure.

16. The method of claim 14, wherein at least one of the oligonucleotides used to produce the first and/or second ITR comprises a photocleavable (PC) biotin.

17. The method of claim 1, wherein said ligase is T4 ligase.

18. The method of claim 1, further comprising removing unligated oligonucleotides and remaining DNA fragments by an exonuclease digestion.

19. The method of claim 1, wherein:
   - said first ITR is a wild-type AAV ITR;
   - said first ITR is mutant or modified AAV ITR;
   - said second ITR is a wild-type AAV ITR;
   - said second ITR is a mutant or modified AAV;
   - at least one of the first ITR and the second ITR is an AAV ITR; and/or at least one of the first ITR and the second ITR is an artificial sequence that forms a closed-ended stem-loop structure.

20. The method of claim 1, wherein the expression cassette comprises at least one cis-acting element.

21. The method of claim 20, wherein the cis-acting element is selected from the group consisting of a promoter, an enhancer, a post-transcriptional regulatory element, and a polyadenylation sequence.

22. The method of claim 21, wherein the promoter is a tissue-specific promoter, a ubiquitous promoter, or a constitutive promoter.

23. The method of claim 22, wherein:

the constitutive or ubiquitous promoter is selected from the group consisting of a CAG promoter, a CMV promoter, and an EF1α promoter; or the tissue-specific promoter is selected from the group consisting of a heart-specific promoter, a kidney-specific promoter, a liver-specific promoter, a pancreas-specific promoter, a skeletal-specific promoter, a muscle-specific promoter, a testis-specific promoter, and a brain-specific promoter.

24. The method of claim 23, wherein the liver-specific promoter is selected from the group consisting of a human alpha 1-antitrypsin (hAAT) promoter, an LP1 promoter, and an ApoE/AAT1 chimeric promoter.

25. The method of claim 1, wherein the transgene is at least 2 kb, 3 kb, 4 kb, 5 kb, or 6 kb in length.

26. The method of claim 1, wherein the first ITR comprises an overhang sequence that comprises a complete complement to the overhang sequence of the 5' end of the double-stranded DNA construct.

27. The method of claim 1, wherein the second ITR comprises an overhang sequence that comprises a complete complement to the overhang sequence of the 3' end of the double-stranded DNA construct.

28. The method of claim 1, wherein ligation of the first ITR and the second ITR with the double-stranded DNA construct comprising the expression cassette produces a closed-ended DNA vector having one or more gaps in the sense strand and one or more gaps in the antisense strand.

* * * * *

SEQUENCE LISTING

```
<160> NUMBER OF SEQ ID NOS: 91

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gcgcgctcgc tcgctc                                                    16


<210> SEQ ID NO 2
<211> LENGTH: 143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

ttgcccactc cctctctgcg cgctcgctcg ctcggtgggg cctgcggacc aaaggtccgc     60

agacggcaga ggtctcctct gccggcccca ccgagcgagc gacgcgcgca gagagggagt    120

gggcaactcc atcactaggg taa                                           143


<210> SEQ ID NO 3
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc t                                             141


<210> SEQ ID NO 4
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 4
ttggccactc cctctatgcg cactcgctcg ctcggtgggg cctggcgacc aaaggtcgcc 60
agacggacgt gggtttccac gtccggcccc accgagcgag cgagtgcgca tagagggagt 120
ggccaactcc atcactagag gtat 144

<210> SEQ ID NO 5
<211> LENGTH: 127
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
ttggccactc cctctatgcg cgctcgctca ctcactcggc cctggagacc aaaggtctcc 60
agactgccgg cctctggccg gcagggccga gtgagtgagc gagcgcgcat agagggagtg 120
gccaact 127

<210> SEQ ID NO 6
<211> LENGTH: 166
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6 tccccccctgt cgcgttcgct cgctcgctgg ctcgtttggg ggggcgacgg ccagagggcc 60
gtcgtctggc agctctttga gctgccaccc ccccaaacga gccagcgagc gagcgaacgc 120
gacagggggg agagtgccac actctcaagc aagggggttt tgtaag 166

<210> SEQ ID NO 7
<211> LENGTH: 144
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
ttgcccactc cctctaatgc gcgctcgctc gctcggtggg gcctgcggac caaaggtccg 60
cagacggcag aggtctcctc tgccggcccc accgagcgag cgagcgcgca tagagggagt 120
gggcaactcc atcactaggg gtat 144

<210> SEQ ID NO 8
<211> LENGTH: 143
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
ttaccctagt gatggagttg cccactccct ctctgcgcgc gtcgctcgct cggtggggcc 60
ggcagaggag acctctgccg tctgcggacc tttggtccgc aggccccacc gagcgagcga 120
gcgcgcagag agggagtggg caa 143

<210> SEQ ID NO 9
<211> LENGTH: 141

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag g 141

<210> SEQ ID NO 10
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atacctctag tgatggagtt ggccactccc tctatgcgca ctcgctcgct cggtggggcc 60
ggacgtggaa acccacgtcc gtctggcgac ctttggtcgc caggccccac cgagcgagcg 120
agtgcgcata gagggagtgg ccaa 144

<210> SEQ ID NO 11
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11
agttggccac attagctatg cgcgctcgct cactcactcg gccctggaga ccaaaggtct 60
ccagactgcc ggcctctggc cggcagggcc gagtgagtga gcgagcgcgc atagagggag 120
tggccaa 127

<210> SEQ ID NO 12
<211> LENGTH: 166
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
cttacaaaac ccccttgctt gagagtgtgg cactctcccc cctgtcgcgt tcgctcgctc 60
gctggctcgt ttgggggggt ggcagctcaa agagctgcca gacgacggcc ctctggccgt 120 cgcccccccca aacgagccag cgagcgagcg aacgcgacag gggga 166

<210> SEQ ID NO 13
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
atacccctag tgatggagtt gcccactccc tctatgcgcg ctcgctcgct cggtggggcc 60
ggcagaggag acctctgccg tctgcggacc tttggtccgc aggccccacc gagcgagcga 120
gcgcgcatta gagggagtgg gcaa 144

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
gagcgagcga gcgcgc 16

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
aggaacccct agtgatggag ttggccactc cctctctgcg cgctcgctcg ctcactgagg 60
cgcacgcccg ggtttcccgg gcggcctcag tgagcgagcg agcgcgcagc tgcctgcagg 120

<210> SEQ ID NO 16
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16
aggaacccct agtgatggag ttggccactc cctctctgcg cgctcgctcg ctcactgagg 60
ccgacgcccg ggctttgccc gggcggcctc agtgagcgag cgagcgcgca gctgcctgca 120
gg 122

<210> SEQ ID NO 17
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
aggaacccct agtgatggag ttggccactc cctctctgcg cgctcgctcg ctcactgagg 60
ccgggcgacc aaaggtcgcc cgacgcccgg gcgcctcagt gagcgagcga gcgcgcagct 120
gcctgcagg 129

<210> SEQ ID NO 18
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18
aggaacccct agtgatggag ttggccactc cctctctgcg cgctcgctcg ctcactgagg 60
ctttgcctca gtgagcgagc gagcgcgcag ctgcctgcag g 101

```
<210> SEQ ID NO 19
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

aggaacccct agtgatggag ttggccactc cctctctgcg cgctcgctcg ctcactgagg     60

ccgggcgaca aagtcgcccg acgcccgggc tttgcccggg cggcctcagt gagcgagcga    120

gcgcgcagct gcctgcagg                                                 139


<210> SEQ ID NO 20
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

aggaacccct agtgatggag ttggccactc cctctctgcg cgctcgctcg ctcactgagg     60

ccgggcgaaa atcgcccgac gcccgggctt tgcccgggcg gcctcagtga gcgagcgagc    120

gcgcagctgc ctgcagg                                                   137


<210> SEQ ID NO 21
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

aggaacccct agtgatggag ttggccactc cctctctgcg cgctcgctcg ctcactgagg     60

ccgggcgaaa cgcccgacgc ccgggctttg cccgggcggc ctcagtgagc gagcgagcgc    120

gcagctgcct gcagg                                                     135


<210> SEQ ID NO 22
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

aggaacccct agtgatggag ttggccactc cctctctgcg cgctcgctcg ctcactgagg     60

ccgggcaaag cccgacgccc gggctttgcc cgggcggcct cagtgagcga gcgagcgcgc    120

agctgcctgc agg                                                       133


<210> SEQ ID NO 23
<211> LENGTH: 139
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
```

```
aggaacccct agtgatggag ttggccactc cctctctgcg cgctcgctcg ctcactgagg     60

ccgggcgacc aaaggtcgcc cgacgcccgg gtttcccggg cggcctcagt gagcgagcga    120

gcgcgcagct gcctgcagg                                                 139


<210> SEQ ID NO 24
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

aggaacccct agtgatggag ttggccactc cctctctgcg cgctcgctcg ctcactgagg     60

ccgggcgacc aaaggtcgcc cgacgcccgg tttccgggcg gcctcagtga gcgagcgagc    120

gcgcagctgc ctgcagg                                                   137


<210> SEQ ID NO 25
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

aggaacccct agtgatggag ttggccactc cctctctgcg cgctcgctcg ctcactgagg     60

ccgggcgacc aaaggtcgcc cgacgcccgt ttcgggcggc ctcagtgagc gagcgagcgc    120

gcagctgcct gcagg                                                     135


<210> SEQ ID NO 26
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

aggaacccct agtgatggag ttggccactc cctctctgcg cgctcgctcg ctcactgagg     60

ccgggcgacc aaaggtcgcc cgacgcccttt tgggcggcct cagtgagcga gcgagcgcgc    120

agctgcctgc agg                                                       133


<210> SEQ ID NO 27
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

aggaacccct agtgatggag ttggccactc cctctctgcg cgctcgctcg ctcactgagg     60

ccgggcgacc aaaggtcgcc cgacgccttt ggcggcctca gtgagcgagc gagcgcgcag    120

ctgcctgcag g                                                         131


<210> SEQ ID NO 28
<211> LENGTH: 129
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 28
aggaacccct agtgatggag ttggccactc cctctctgcg cgctcgctcg ctcactgagg 60
ccgggcgacc aaaggtcgcc cgacgctttg cggcctcagt gagcgagcga gcgcgcagct 120
gcctgcagg 129

<210> SEQ ID NO 29
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
aggaacccct agtgatggag ttggccactc cctctctgcg cgctcgctcg ctcactgagg 60
ccgggcgacc aaaggtcgcc cgacgtttcg gcctcagtga gcgagcgagc gcgcagctgc 120
ctgcagg 127

<210> SEQ ID NO 30
<211> LENGTH: 122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
aggaacccct agtgatggag ttggccactc cctctctgcg cgctcgctcg ctcactgagg 60
ccgggcgacc aaaggtcgcc cgacggcctc agtgagcgag cgagcgcgca gctgcctgca 120
gg 122

<210> SEQ ID NO 31
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
aggaacccct agtgatggag ttggccactc cctctctgcg cgctcgctcg ctcactgagg 60
ccgggcgacc aaaggtcgcc cgacgcccgg gcggcctcag tgagcgagcg agcgcgcagc 120
tgcctgcagg 130

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cctgcaggca gctgcgcgct cgctcgctca ctgaggccgc ccgggaaacc cgggcgtgcg 60
cctcagtgag cgagcgagcg cgcagagagg gagtggccaa ctccatcact aggggttcct 120

<210> SEQ ID NO 33
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33
cctgcaggca gctgcgcgct cgctcgctca ctgaggccgt cgggcgacct ttggtcgccc 60
ggcctcagtg agcgagcgag cgcgcagaga gggagtggcc aactccatca ctaggggttc 120
ct 122

<210> SEQ ID NO 34
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34
cctgcaggca gctgcgcgct cgctcgctca ctgaggccgc ccgggcaaag cccgggcgtc 60
ggcctcagtg agcgagcgag cgcgcagaga gggagtggcc aactccatca ctaggggttc 120
ct 122

<210> SEQ ID NO 35
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
cctgcaggca gctgcgcgct cgctcgctca ctgaggcgcc cgggcgtcgg gcgacctttg 60
gtcgcccggc ctcagtgagc gagcgagcgc gcagagaggg agtggccaac tccatcacta 120
ggggttcct 129

<210> SEQ ID NO 36
<211> LENGTH: 101
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
cctgcaggca gctgcgcgct cgctcgctca ctgaggcaaa gcctcagtga gcgagcgagc 60
gcgcagagag ggagtggcca actccatcac taggggttcc t 101

<210> SEQ ID NO 37
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 37
cctgcaggca gctgcgcgct cgctcgctca ctgaggccgc ccgggcaaag cccgggcgtc 60
gggcgacttt gtcgcccggc ctcagtgagc gagcgagcgc gcagagaggg agtggccaac 120
tccatcacta ggggttcct 139

<210> SEQ ID NO 38
<211> LENGTH: 137
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 38
cctgcaggca gctgcgcgct cgctcgctca ctgaggccgc ccgggcaaag cccgggcgtc 60
gggcgatttt cgcccggcct cagtgagcga gcgagcgcgc agagagggag tggccaactc 120
catcactagg ggttcct 137

<210> SEQ ID NO 39
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 39
cctgcaggca gctgcgcgct cgctcgctca ctgaggccgc ccgggcaaag cccgggcgtc 60
gggcgtttcg cccggcctca gtgagcgagc gagcgcgcag agagggagtg gccaactcca 120
tcactagggg ttcct 135

<210> SEQ ID NO 40
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 40
cctgcaggca gctgcgcgct cgctcgctca ctgaggccgc ccgggcaaag cccgggcgtc 60
gggctttgcc cggcctcagt gagcgagcga gcgcgcagag agggagtggc caactccatc 120
actaggggtt cct 133

<210> SEQ ID NO 41
<211> LENGTH: 139
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
cctgcaggca gctgcgcgct cgctcgctca ctgaggccgc ccgggaaacc cgggcgtcgg 60
gcgacctttg gtcgcccggc ctcagtgagc gagcgagcgc gcagagaggg agtggccaac 120
tccatcacta ggggttcct 139

<210> SEQ ID NO 42
<211> LENGTH: 137
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
cctgcaggca gctgcgcgct cgctcgctca ctgaggccgc ccggaaaccg ggcgtcgggc 60
gacctttggt cgcccggcct cagtgagcga gcgagcgcgc agagagggag tggccaactc 120
catcactagg ggttcct 137

<210> SEQ ID NO 43
<211> LENGTH: 135
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
cctgcaggca gctgcgcgct cgctcgctca ctgaggccgc ccgaaacggg cgtcgggcga 60
cctttggtcg cccggcctca gtgagcgagc gagcgcgcag agagggagtg gccaactcca 120
tcactagggg ttcct 135

<210> SEQ ID NO 44
<211> LENGTH: 133
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
cctgcaggca gctgcgcgct cgctcgctca ctgaggccgc ccaaagggcg tcgggcgacc 60
tttggtcgcc cggcctcagt gagcgagcga gcgcgcagag agggagtggc caactccatc 120
actaggggtt cct 133

<210> SEQ ID NO 45
<211> LENGTH: 131
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45
cctgcaggca gctgcgcgct cgctcgctca ctgaggccgc caaaggcgtc gggcgacctt 60
tggtcgcccg gcctcagtga gcgagcgagc gcgcagagag ggagtggcca actccatcac 120
taggggttcc t 131

<210> SEQ ID NO 46
<211> LENGTH: 129
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 46
cctgcaggca gctgcgcgct cgctcgctca ctgaggccgc aaagcgtcgg gcgacctttg 60
gtcgcccggc ctcagtgagc gagcgagcgc gcagagaggg agtggccaac tccatcacta 120
ggggttcct 129

<210> SEQ ID NO 47
<211> LENGTH: 127
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 47
cctgcaggca gctgcgcgct cgctcgctca ctgaggccga aacgtcgggc gacctttggt 60
cgcccggcct cagtgagcga gcgagcgcgc agagagggag tggccaactc catcactagg 120
ggttcct 127

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
atcgaacgat cg 12

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
cgatcgttcg at 12

<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
atcgaaccat cg 12

<210> SEQ ID NO 51
<211> LENGTH: 7
<212> TYPE: PRT
<213> ORGANISM: Simian virus 40

<400> SEQUENCE: 51

Pro Lys Lys Lys Arg Lys Val
1 5

<210> SEQ ID NO 52
<211> LENGTH: 21
<212> TYPE: DNA
<213> ORGANISM: Simian virus 40

<400> SEQUENCE: 52
cccaagaaga agaggaaggt g 21

<210> SEQ ID NO 53
<211> LENGTH: 16

-continued

```
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 53

Lys Arg Pro Ala Ala Thr Lys Lys Ala Gly Gln Ala Lys Lys Lys Lys
1               5                   10                  15


<210> SEQ ID NO 54
<211> LENGTH: 9
<212> TYPE: PRT
<213> ORGANISM: Unknown
<220> FEATURE:
<223> OTHER INFORMATION: Description of Unknown:
      C-myc NLS sequence

<400> SEQUENCE: 54

Pro Ala Ala Lys Arg Val Lys Leu Asp
1               5


<210> SEQ ID NO 55
<211> LENGTH: 11
<212> TYPE: PRT
<213> ORGANISM: Unknown
<220> FEATURE:
<223> OTHER INFORMATION: Description of Unknown:
      C-myc NLS sequence

<400> SEQUENCE: 55

Arg Gln Arg Arg Asn Glu Leu Lys Arg Ser Pro
1               5                   10


<210> SEQ ID NO 56
<211> LENGTH: 38
<212> TYPE: PRT
<213> ORGANISM: Homo sapiens

<400> SEQUENCE: 56

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35


<210> SEQ ID NO 57
<211> LENGTH: 42
<212> TYPE: PRT
<213> ORGANISM: Unknown
<220> FEATURE:
<223> OTHER INFORMATION: Description of Unknown:
      IBB domain from importin-alpha sequence

<400> SEQUENCE: 57

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40


<210> SEQ ID NO 58
<211> LENGTH: 8
```

<212> TYPE: PRT
<213> ORGANISM: Unknown
<220> FEATURE:
<223> OTHER INFORMATION: Description of Unknown:
Myoma T protein sequence

<400> SEQUENCE: 58

Val Ser Arg Lys Arg Pro Arg Pro
1 5

<210> SEQ ID NO 59
<211> LENGTH: 8
<212> TYPE: PRT
<213> ORGANISM: Unknown
<220> FEATURE:
<223> OTHER INFORMATION: Description of Unknown:
Myoma T protein sequence

<400> SEQUENCE: 59

Pro Pro Lys Lys Ala Arg Glu Asp
1 5

<210> SEQ ID NO 60
<211> LENGTH: 8
<212> TYPE: PRT
<213> ORGANISM: Homo sapiens

<400> SEQUENCE: 60

Pro Gln Pro Lys Lys Lys Pro Leu
1 5

<210> SEQ ID NO 61
<211> LENGTH: 12
<212> TYPE: PRT
<213> ORGANISM: Mus musculus

<400> SEQUENCE: 61

Ser Ala Leu Ile Lys Lys Lys Lys Lys Met Ala Pro
1 5 10

<210> SEQ ID NO 62
<211> LENGTH: 5
<212> TYPE: PRT
<213> ORGANISM: Influenza virus

<400> SEQUENCE: 62

Asp Arg Leu Arg Arg
1 5

<210> SEQ ID NO 63
<211> LENGTH: 7
<212> TYPE: PRT
<213> ORGANISM: Influenza virus

<400> SEQUENCE: 63

Pro Lys Gln Lys Lys Arg Lys
1 5

<210> SEQ ID NO 64
<211> LENGTH: 10
<212> TYPE: PRT
<213> ORGANISM: Hepatitis delta virus

<400> SEQUENCE: 64

Arg Lys Leu Lys Lys Lys Ile Lys Lys Leu
1 5 10

<210> SEQ ID NO 65
<211> LENGTH: 10
<212> TYPE: PRT
<213> ORGANISM: Mus musculus

<400> SEQUENCE: 65

```
Arg Glu Lys Lys Lys Phe Leu Lys Arg Arg
1               5                   10
```

<210> SEQ ID NO 66
<211> LENGTH: 20
<212> TYPE: PRT
<213> ORGANISM: Homo sapiens

<400> SEQUENCE: 66

```
Lys Arg Lys Gly Asp Glu Val Asp Gly Val Asp Glu Val Ala Lys Lys
1               5                   10                  15

Lys Ser Lys Lys
            20
```

<210> SEQ ID NO 67
<211> LENGTH: 17
<212> TYPE: PRT
<213> ORGANISM: Homo sapiens

<400> SEQUENCE: 67

```
Arg Lys Cys Leu Gln Ala Gly Met Asn Leu Glu Ala Arg Lys Thr Lys
1               5                   10                  15

Lys
```

<210> SEQ ID NO 68
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gatctaggaa cccctagtga tggagttggc cactccctct ctgcgcgctc gctcgctcac     60

tgaggccgcc cgggcaaagc ccgggcgtcg ggcgaccttt ggtcgcccgg cctcagtgag    120

cgagcgagcg cgcagagagg gagtggccaa ctccatcact aggggttcct a             171
```

<210> SEQ ID NO 69
<211> LENGTH: 171
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
tcgacaggaa cccctagtga tggagttggc cactccctct ctgcgcgctc gctcgctcac     60

tgaggccggg cgaccaaagg tcgcccgacg cccgggcttt gcccgggcgg cctcagtgag    120

cgagcgagcg cgcagagagg gagtggccaa ctccatcact aggggttcct g             171
```

<210> SEQ ID NO 70
<211> LENGTH: 61
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 70
ctagctgagg ccgcccgggc aaagcccggg cgtcgggcga cctttggtcg cccggcctca 60
g 61

<210> SEQ ID NO 71
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
ctgaggccgc ccgggcaaag cccgggcgtc gggcgacctt tggtcgcccg gcctcagtgc 60
a 61

<210> SEQ ID NO 72
<211> LENGTH: 99
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
gctcgctcac tgaggccgcc cgggcaaagc ccgggcgtcg ggcgaccttt ggtcgcccgg 60
cctcagtgag cgagcgagcg cgcagagagg gagtggcca 99

<210> SEQ ID NO 73
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
ggcctctatg acgtaattca cgtcacgact ccacccctcc aggaacccct agtgatggag 60
ttggccactc cctctctgcg cgctc 85

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
ggggttcctg gaggggtgga gtcgtgacgt gaattacgtc ataga 45

<210> SEQ ID NO 75
<211> LENGTH: 97
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
tagcaggcat gctggggatg cggtgggctc tatggctcta gagcatggct acgtagataa 60
gtagcatggc gggttaatca ttaactacac ctgcagg 97

<210> SEQ ID NO 76
<211> LENGTH: 138
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
gagcgcgcag agagggagtg gccaactcca tcactagggg ttcctcctgc aggtgtagtt 60
aatgattaac ccgccatgct acttatctac gtagccatgc tctagagcca tagagcccac 120
cgcatcccca gcatgcct 138

<210> SEQ ID NO 77
<211> LENGTH: 99
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
tggccactcc ctctctgcgc gctcgctcgc tcactgaggc cgggcgacca aaggtcgccc 60
gacgcccggg ctttgcccgg gcggcctcag tgagcgagc 99

<210> SEQ ID NO 78
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
cgccatgcta cttatctacg tagccatgct ctagagccat agagcccacc gcatccccag 60
catgcct 67

<210> SEQ ID NO 79
<211> LENGTH: 71
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
gagcgcgcag agagggagtg gccaactcca tcactagggg ttcctcctgc aggtgtagtt 60
aatgattaac c 71

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
tggccactcc ctctctgcgc gctcgctcgc tcactgaggc aaagcctcag tgagcgagc 59

-continued

<210> SEQ ID NO 81
<211> LENGTH: 165
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 81
aggaacccct agtgatggag ttggccactc cctctctgcg cgctcgctcg ctcactgagg 60
ccgcccgggc aaagcccggg cgtcgggcga cctttggtcg cccggcctca gtgagcgagc 120
gagcgcgcag agagggagtg gccaactcca tcactagggg ttcct 165

<210> SEQ ID NO 82
<211> LENGTH: 140
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82
cccctagtga tggagttggc cactccctct ctgcgcgctc gctcgctcac tgaggccgcc 60
cgggcaaagc ccgggcgtcg ggcgaccttt ggtcgcccgg cctcagtgag cgagcgagcg 120
cgcagagaga tcactagggg 140

<210> SEQ ID NO 83
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
gcgcgctcgc tcgctcactg aggccgcccg ggcaaagccc gggcgtcggg cgacctttgg 60
tcgcccggcc tcagtgagcg agcgagcgcg c 91

<210> SEQ ID NO 84
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 84
gcgcgctcgc tcgctcactg aggccgcccg ggcgtcgggc gacctttggt cgcccggcct 60
cagtgagcga gcgagcgcgc 80

<210> SEQ ID NO 85
<211> LENGTH: 91
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 85
gcgcgctcgc tcgctcactg aggccgggcg accaaaggtc gcccgacgcc cgggctttgc 60
ccgggcggcc tcagtgagcg agcgagcgcg c 91

<210> SEQ ID NO 86
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 86
gcgcgctcgc tcgctcactg aggccgggcg accaaaggtc gcccgacgcc cgggcggcct 60
cagtgagcga gcgagcgcgc 80

<210> SEQ ID NO 87
<211> LENGTH: 99
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 87
gctcgctcac ctaggccgcc cgggcaaagc ccgggcgtcg ggcgaccttt ggtcgcccgg 60
cctaggtgag cgagcgagcg cgcagagagg gagtggcca 99

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 88
ctagctgagg caaagcctca g 21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 89
ctgaggcttt gcctcagtgc a 21

<210> SEQ ID NO 90
<211> LENGTH: 81
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 90
ggcctcgata agtagcatgg cgggttaatc attaactaca aaaattgtag ttaatgatta 60
acccgccatg ctacttatcg a 81

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 91

```
ccattcgtgg tttccacgaa tggtgca                                  27
```